US005830670A

United States Patent [19]
de la Monte et al.

[11] Patent Number: 5,830,670
[45] Date of Patent: Nov. 3, 1998

[54] NEURAL THREAD PROTEIN GENE EXPRESSION AND DETECTION OF ALZHEIMER'S DISEASE

[75] Inventors: Suzanne de la Monte, Cambridge; Jack R. Wands, Waban, both of Mass.

[73] Assignee: The General Hospital Corporation, Boston, Mass.

[21] Appl. No.: 454,557

[22] Filed: May 30, 1995

Related U.S. Application Data

[60] Division of Ser. No. 340,426, Nov. 14, 1994, which is a continuation-in-part of Ser. No. 230,139, Apr. 20, 1994, abandoned, and Ser. No. 55,778, May 3, 1993, abandoned, which is a continuation of Ser. No. 451,975, Dec. 20, 1989, abandoned, which is a continuation-in-part of Ser. No. 287,207, Dec. 21, 1988, abandoned, said Ser. No. 230,139, is a continuation-in-part of Ser. No. 50,559, Apr. 20, 1993, abandoned.

[51] Int. Cl.$^6$ .......................... G01N 33/53; G01N 33/48; C12Q 1/08
[52] U.S. Cl. .......................... 435/7.2; 435/7.1; 435/7.92; 435/40.52; 436/63
[58] Field of Search ................................. 435/6, 7.1, 7.2, 435/7.92, 40.52, 7.23; 436/63, 64, 813; 514/44

[56] References Cited

U.S. PATENT DOCUMENTS

| | | | |
|---|---|---|---|
| 4,394,448 | 7/1983 | Szoka, Jr. et al. | 435/172 |
| 4,624,846 | 11/1986 | Goldenberg | 424/1.1 |
| 4,666,829 | 5/1987 | Glenner et al. | 435/6 |
| 4,735,210 | 4/1988 | Goldenberg | 128/654 |
| 4,816,388 | 3/1989 | Sipe et al. | 435/6 |
| 4,866,042 | 9/1989 | Neuwelt | 514/44 |
| 4,897,355 | 1/1990 | Eppstein et al. | 435/240.2 |
| 5,168,053 | 12/1992 | Altman et al. | 435/91 |
| 5,436,169 | 7/1995 | Iovanna et al. | 436/518 |

FOREIGN PATENT DOCUMENTS

| | | |
|---|---|---|
| 0 263 740 | 4/1988 | European Pat. Off. . |
| WO 89/03849 | 5/1989 | WIPO . |
| WO 90/06993 | 6/1990 | WIPO . |
| WO 90/09180 | 8/1990 | WIPO . |
| WO 91/06626 | 5/1991 | WIPO . |
| WO 92/06693 | 4/1992 | WIPO . |
| WO 92/07065 | 4/1992 | WIPO . |
| WO 92/10590 | 6/1992 | WIPO . |

OTHER PUBLICATIONS

Abraham, C.R. et al., "Immunochemical Identification of the Serine Protease Inhibitor $\alpha_1$–Antichymotrypsin in the Brain Amyloid Deposits of Alzheimer's Disease," *Cell* 52:487–501 (Feb. 1988).

Chong, J. et al., "Detection and Measurement of Neural Thread Protein (NTP) in Cerebrospinal Fluid (CSF): A Potential Antemortem Marker for Alzheimer's Disease," *Soc. Neurosci. 17—Abstracts from the 21st Annual Meeting*:1259, Abstract No. 498.7 (1991).

Chong, J.K. et al., "Automated Microparticle Enzyme Immunoassay for Neural Thread Protein in Cerebrospinal Fluid from Alzheimer's Disease Patients," *J. Clin. Lab. Anal.* 6:379–383 (1992).

de la Monte, S.M. and J.R. Wands, "Neuronal Thread Protein: A Potential Marker for Alzheimer's Disease," *J. Neuropathol. Exp. Neurol.* 50:316, Abstract No. 83 (May 1991).

de la Monte, S.M. and J.R. Wands, "Elevated Neuronal Thread Protein Levels in Ventricular Fluid and Temporal Cortex of Alzheimer's Disease," *Neurobiol Aging 13, Suppl. 1*:S26, Abstract No. 103 (1992).

Figarella, C. et al., "Pancreatic Stone Protein, Protein X, and Thread Protein," *Lancet 1(8526)*; 222–223 (Jan. 1987).

Glenner, G.G. et al., "Alzheimer's Disease: Initial Report of the Purification and Characterization of a Novel Cerebrovascular Amyloid Protein," *Biochem. Biophys Res. Comm.* 120(3):885–890 (May 1984).

Goldgaber, D. et al., "Characterization and Chromosomal Localization of a cDNA Encoding Brain Amyloid of Alzheimer's Disease," *Science* 235:877–880 (Feb. 1987).

Joachim, C.L. et al., "Amyloid β–protein deposition in tissues other than brain in Alzheimer's disease," *Nature* 341:226–230 (Sep. 1989).

Johnson, S.A. et al., "Relation of Neuronal APP–751/APP–695 mRNA Ratio and Neuritic Plaque Density in Alzheimer's Disease," *Science* 248:854–857 (May 1990).

Kang, J. et al., "The precursor of Alzheimer's disease amyloid A4 protein resembles a cell–surface receptor," *Nature* 325:733–736 (Feb. 1987).

Manetto, V. et al., "Ubiquitin is associated with abnormal cytoplasmic filaments characteristic of neurodegenerative diseases," *Proc. Natl. Acad. Sci. USA* 85:4501–4505 (Jun. 1988).

Masters, C.L. et al., "Amyloid plaque core protein in Alzheimer disease and Down syndrome," *Proc. Natl. Acad. Sci. USA* 82:4245–4249 (Jun. 1985).

Schmiegel, W.–H. et al., "Pancreatic Stone Protein in Serum of Patients with Pancreatitis," *Lancet 2(8508)*:686–687 (Sep. 1986).

(List continued on next page.)

*Primary Examiner*—Sheela Huff
*Assistant Examiner*—Yvonne Eyler
*Attorney, Agent, or Firm*—Sterne, Kessler, Goldstein & Fox P.L.L.C.

[57] ABSTRACT

The present invention is directed to recombinant hosts expressing novel proteins associated with Alzheimer's Disease, neuroectodermal tumors, malignant astrocytomas, and glioblastomas. This invention is specifically directed to the recombinant hosts and vectors which contain the genes coding for the neuronal thread proteins. This invention is also directed to substantially pure neural thread protein, immunodiagnostic and molecular diagnostic methods to detect the presence of neural thread proteins, and the use of nucleic acid sequences which code for neural thread proteins in gene therapy.

25 Claims, 52 Drawing Sheets

OTHER PUBLICATIONS

St. George–Hyslop, P.H. et al., "The Genetic Defect Causing Familial Alzheimer's Disease Maps on Chromosome 21," *Science* 235:885–890 (Feb. 1987).

Tanzi, R.E. et al., "Amyloid β Protein Gene: cDNA, mRNA Distribution, and Genetic Linkage Near the Alzheimer Locus," *Science* 235:880–884 (Feb. 1987).

Van Broeckhoven, C. et al., "Failure of familial Alzheimer's disease to segregate with the A4–amyloid gene in several European families," *Nature* 329:153–155 (Sep. 1987).

Wischik, C.M. et al., "Structural characterization of the core of the paired helical filament of Alzheimer disease," *Proc. Natl. Acad. Sci. USA* 85:4884–4888 (Jul. 1988).

Ghanbari, H. et al., "Detection and Measurement of Alzheimer's Disease Associated Protein (ADAP) in Cerebrospinal Fluid (CSF): An Antemortem Marker for Alzheimer's Disease," *Soc. Neurosci. 17—Abstracts from the 21st Annual Meeting*:1259, Abstract No. 498.8 (1991).

Abe, M., et al., "Production and Immunodiagnostic Applications of Antihuman Light Chain Monoclonal Antibodies," *Am. J. Clin. Pathol.* 100:67–74 (Jul. 1993).

Bahmanyar, S., et al., "Localization of Amyloid β Protein Messenger RNA in Brains from Pathents with Alzheimer's Disease," *Science* 237:77–80 (Jul. 3, 1987).

Denman, R.B., et al., "Ribozyme Mediated Degradation of β–amyloid Peptide Precursor mRNA in COS–7 Cells," *Nucl. Acids Res.* 22(12):2375–2382 (Jun. 25, 1994).

Ponte, P., et al., "A New A4 Amyloid mRNA Contains a Domain Homologous to Serine Proteinase Inhibitors," *Nature* 331:525–527 (Feb. 11, 1988).

A copy of the International Search Report for the corresponding PCT application, International Application No. PCT/US95/17111. (1995).

Benowitz, L.I. and Lewis, E.R., "Increased Transport of 44,000– to 49,000–Dalton Acidic Proteins During Regeneration of the Goldfish Optic Nerve: A Two–Dimensional Gel Analysis," *J. Neurosci.* 3(11):2153–2163 (1983).

de la Monte, S.M. and Wands, J.R. "Neuronal thread protein over–expression in brains with Alzheimer's disease lesions," *J. Neurol. Sci.* 113:152–164 (Dec. 1992).

de la Monte et al., "Enhanced Expression of an Exocrine Pancreatic Protein in Alzheimer's Disease and the Developing Human Brain," *J. Clin. Invest.* 86:1004–1013 (1990).

de la Monte et al., "Increased Levels of Neuronal Thread Protein in Cerebrospinal Fluid of Patients with Alzheimer's Disease," *Ann. Neurol.* 32:733–742 (Jun. 1992).

De Caro et al., "Characterization of a Protein Isolated From Pancreatic Calculi of Men Suffering From Chronic Calcifying Pancreatitis," *Biochem. Biophys. Res. Comm.* 87(4):1176–1182 (1979).

De Caro et al., "Complete amino acid sequence of an immunoreactive form of human pancreatic stone protein isolated from pancreatic juice," *Eur. J. Biochem.* 168:201–207 (1987).

De Caro et al., "The molecular characteristics of a human pancreatic acidic phosphoprotein that inhibits calcium carbonate crystal growth," *Biochem. J.* 222:669–677 (1984).

De Graan et al., "Phosphoprotein B–50 in Nerve Growth Cones from Fetal Rat Brain," *Neurosci. Lett.* 61:235–241 (1985).

DePamphilis, M.L., "Origins of DNA Replication in Metazoan Chromosomes," *J. Biol. Chem.* 268(1):1–4 (Jan. 1993).

Forstner et al., "Selective Precipitation of 14 kDa Stone/Thread Proteins by Concentration of Pancreaticobiliary Secretions: Relevance to Pancreatic Ductal Obstruction, Pancreatic Failure, and CF," *J. Pediatric Gastroenterology and Nutrition* 8:313–320 (1989).

Gross et al., "Isolation, Characterization, and Distribution of an Unusual Pancreatic Human Secretory Protein," *J. Clin. Invest.* 76:2115–2126 (1985).

Gross et al., "An unusual bovine pancreatic protein exhibiting pH–dependent globule–fibril transformation and unique amino acid sequence," *PNAS USA* 82:5627–5631 (1985).

Guy–Crotte et al., "Characterization and N–Terminal Sequence of a Degradation Product of 14,000 Molecular Weight Isolated From Human Pancreatic Juice," *Biochem. Biophys. Res. Comm.* 125(2) :516–523 (1984).

Ishii et al., "Presence of Neurofilament Protein in Alzheimer's Neurofibrillary Tangles (ANT), An Immunofluorescent Study," *Acta Neuropathol. (Berl.)* 48:105–112 (1979).

Kalil, K. and Skene, J.H.P., "Elevated Synthesis of an Axonally Transported Protein Correlates with Axon Outgrowth in Normal and Injured Pyramidal Tracts,"0 *J. Neurosci.* 6(9) :2563–2570 (1986).

Lasserre et al., "A Novel Gene (HIP) Activated in Human Primary Liver Cancer," *Cancer Res.* 52:5089–5095 (Sep. 1992).

Lathe, R., "Synthetic Oligonucleotide Probes Deduced from Amino Acid Sequence Data, Theoretical and Practical Considerations," *J. Molec. Biol.* 183:1–12 (1985).

Ozturk et al., "Elevated levels of an exocrine pancreatic secretory protein in Alzheimer disease brain," *PNAS USA* 86:419–423 (1989).

Perry et al., "Alteration of the Neurofilament–Microtubule Network in Alzheimer Disease and Other Neurogenerative Disorders," in: Alterations of the Neuronal Cytoskeleton in Alzheimer's Disease, Plenum Press, pp. 137–149 (1987).

Sano et al., "Immuno–PCR: Very Sensitive Antigen Detection by Means of Specific Antibody–DNA Conjugates," *Science* 258:120–122 (Oct. 1992).

Sano et al., "A Streptavidin–Protein A Chimera That Allows One–Step Production of a Variety of Specific Antibody Conjugates," *Bio/Technology* 9:1378–1381 (1991).

Selkoe, D.J., "Altered Structural Proteins in Plagues and Tangles: What Do They Tell Us About the Bioloby of Alzheimer's Disease?" *Neurobiology of Aging* 7:425–432 (1986).

Terazono et al., "A Novel Gene Activated in Regenerating Islets," *J. Biol. Chem.* 263(5):2111–2114 (1988).

Watanabe et al., "Complete Nucleotide Sequence of Human reg Gene and Its Expression in Normal and Tumoral Tissues," *J. Biol. Chem.* 265(13):7432–7439 (1990).

Wischik et al., "Structural Characterization of the Core of the Paired Helical Filament of Alzheimer Disease," *PNAS USA* 85:4884–4888 (1988).

Wolozin et al., "A Neuronal Antigen in the Brains of Alzheimer Patients," *Science* 232:648–650 (1986).

Gutierrez et al., "Gene therapy for cancer," *The Lancet* 339:715–721 (Mar. 1992).

 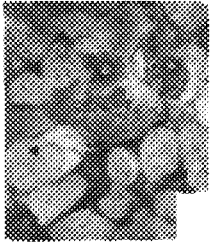 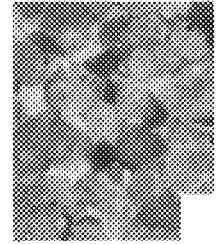 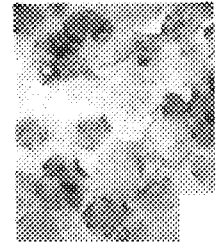 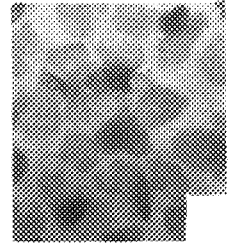
 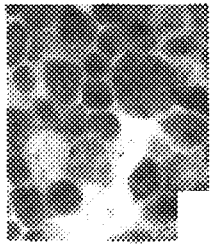 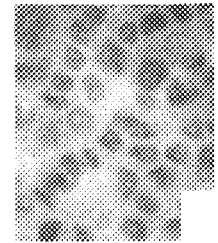 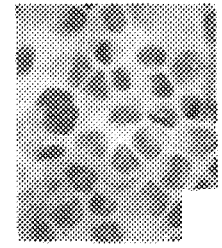 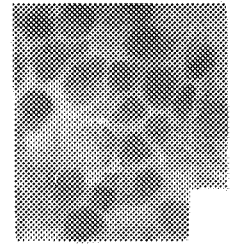

1-9a T7 SEQUENCE

Sequence Range: 1 to 1442

| | | | | | | | | | | |
|---|---|---|---|---|---|---|---|---|---|---|
|CGCTG|CGCCC|AGGCT|GGCTC|TGGAA|AGCCT|GTGCG|GTCCT|GGCAG|GAAGC|CCGGC CCGTG 60|
|GAGCA|GGTTT|TCGTT|CTGCT|TCAGC|AATAA|ATAAG|GGTGA|CCACA|GGGAC|TTTGC TTTTG 120|
|GTTTC|CTTTC|CTGTG|AAAAG|GTTGG|TTTTA|AAGTG|AGATA|CACTT|TTCCG|TAGAA CAAGT 180|
|GTTCT|ATCTT|TAAAA|ACCCA|AATTG|CAGCA|CCGTG|GATTA|CTGGT|CTCAG|AACAA CTCAT 240|
|TGCGC|ATCAG|ATTTG|ACTCT|CTGAT|TTTCT|GTCTA|TTGGC|CAAAT|TGCCC|TTTAA CTGCA 300|
|CCTGA|ATCCT|TTGTG|TACTG|ATGCC|TTTGA|GCTGG|GCACC|TTGGG|AGAGT|GTTGT GTTGC 360|
|TGTTT|ACGGT|TCTTC|CTTCC|CCTTG|CTAAT|TACAG|TCTCT|GGTGC|CCAGC|AAGCC CCTTT 420|
|GGCTT|CCTTC|CGTGA|CTGGT|CACGT|TGTCT|GCCTG|GGCTC|AGCGT|GGACC|TGCCC CATGC 480|
|TGCAG|AACCT|GGCCT|CACCT|GGACT|TTTAC|TAGAA|TTGCC|AGCTT|CTCAA|CTTAG CAGAT 540|
|CATCA|CTCAT|GCGGG|CACAA|GCAAA|GATCA|ACACT|TTCTT|TTTTG|GTAAG|CTTGA GTTTT 600|
|ACAAG|TTATT|TTTTG|GTGAT|GCGTA|AGACA|TTGCA|GTGGG|AAACC|ATTCA|ACTTG AGTTT 660|
|ATTGG|AGTTT|GCTGT|TGTAG|CAGGT|TTTAA|CTCAG|GAACA|ACTCT|TGTCT|GATCT CTCGC 720|
|CCCTC|TGCCG|GGACT|ACATT|ACTGT|CTCTC|GGAGC|CGGTA|GCGTT|GCTGT|CGAGT CCCAG 780|
|GACTA|TCTCT|GCAGA|CTGCT|ATGCT|CAGAT|CGAAG|TATTT|CACAA|GAATA|CTTGT GTTTT 840|
|TAACA|GCCCT|TCCCC|TGGAC|GGTGC|GCCAT|GAGGG|CCTCA|TGTTA|CGCAT|TGCCT TTTCT 900|
|TTCTG|TGGAT|CCAGT|ATCTT|CCTCG|GCTTT|TTAGG|GAGCA|GGAAA|AATGC|GTCTG AGAGC 960|
|AACTC|TTTTT|AAAAA|CCTGC|CCTGT|TGTAT|ATAAC|TGTGT|CTGTT|TCACC|GTGTG ACCTC 1020|
|CAAGG|GGGTG|GGAAC|TTGAT|ATAAA|CGTTT|AAAGG|GGCCA|CGATT|TGCCC|GAGGG TTACT 1080|
|CCTTT|GCTCT|CACCT|TGTAT|GGATG|AGGAG|ATGAA|GCCAT|TTCTT|ATCCT|GTAGA TGTGA 1140|
|AGCAC|TTTCA|GTTTT|CAGCG|ATGTT|GGAAT|GTAGC|ATCAG|AAGCT|CGTTC|CTTCA CACTC 1200|
|AGTGG|CGTCT|GTGCT|TGTCC|ACATG|CGCTG|GGCGT|CTGGA|CCTTG|AATGC|CTGCC CTGGT 1260|
|TGTGT|GGACT|CCTTA|ATGCC|AATCA|TTTCT|TCACT|TCTCT|GGACA|CCCAG|GGCGC CTGTT 1320|
|GACAA|GTGTG|GAGAA|ACTCC|TAATT|TAAAT|GTCAC|AGACA|ATGTC|CTAGT|GTTGA CTACT 1380|
|ACAAT|GTTGA|TGCTA|CACTG|TTGTA|ATTAT|TAAAC|TGATT|ATTTT|TCTTA|TGTCA AAAAA 1440|
|AAA| | | | | | | | | | |

FIG.9

WP5' SEQUENCE

Sequence Range: 1 to 313

GATCC CGTTT GACAG GTGTA CCGCC CCAGT CAAAC TCCCC ACCTG GCACT GTCCC CGGAG
CGGTC GCGCC CGCGC GACCA GGAGC TCTG GGCGC CAGAA GCGAG AGCCC CTCGC TGCCC
CCCGC CTCAC CGGGT AGTGA AAAAA CGATG AGAGT AGTGG TATTT CACCG GCGGC CCGCG
AGGAC CCCCG CCCGA CCCAG TGCGG AACGG GGG

FIG.9A

```
9A*1-T7                                                          5    10   15   20
[ 386 ]     ─────────────────────────────────────────────────CAcc GtgGa TtA-C tgGtC>
Human-PTP                                                    CATT GCAGC TCAGC ATGGC 9A*1-T7     25   30   35   40   45   50   55   60   65   70   75
[ 386 ]     TCAGA oCAoC TCATt gcgCA T-CoG ATtTo CTctC TGAtt TTTCT GTCTo ttgGC CAttG>
Human-PTP   TCAGA CCAGC TCATA CTTCA TGCTG ATCTC CTGCC TGATG TTTCT GTCTC AGAGC CAAGG 9A*1-T7     85   90   95   100  105  110  115       125  130  135  140
[ 386 ]     CCctt tooCt gcocC tGA-o TcCtt tgtGt oCtGA TCctt TGogC tG--G GCACC -tTG->
Human-PTP   CCAAG AGGCC CAGAC AGAGT TGCCC CAGGC CCGGA TCAGC TGCCC AGAAG GCACC AATGC 9A*1-T7     145  150  155  160  165  170  175  180  185  190  195
[ 386 ]     ggAgo G-T-g TtgTG ttgCT -gTTT AcgGt tcttC cT-tc cCCTt GcToo ttoCA G-TCT>
Human-PTP   CTATC GCTCC TACTG CTACT ACTTT AATGA AGACC GTGAG ACCTG GGTTG ATGCA GATCT 9A*1-T7     200  205  210  215  220  225  230  235  240  245  250  255
[ 386 ]     CTggT GCCAG cA-Ag ccccT ttGGC ttCCT tccGT gocTG gTCAC gttGt CtGcc tGgGC>
Human-PTP   CTATT GCCAG AACAT GAATT CGGGC AACCT GGTGT CTGTG CT Q C CCAGG CCGAG GGTGC 9A*1-T7     260  270  275  280       285  290       300  305  310  315
[ 386 ]     CogcG TGGCC cCA-T GcTgc A-GAo ccTGG C-CTc AgGAC TTttc ocT-o GoATT GcCCT>
Human-PTP   CTTTG TGGCC TCACT GATTA AGGAG AGTGG CACTG ATGAC TTCAA TGTCT GGATT GGCCT 9A*1-T7     325  330  335  340  345  350  355  360  365  370  375
[ 386 ]     tCcTc A-oCt tAgcA GAtCo ttCoC Tcotg CgGGc oCA-o Gcooo goTco oCoCt TtC-t>
Human-PTP   CCATG ACCCC AAAAA GAACC GCCGC TGGCA CTGGA GCAGT GGGTC CCTGG TCTCC TACAA 9o-t7                      10   15   20   25   30   35   40   45
[ 180 ]     ───────────TT ttCCT AgA-A cA-oG -gGtT cTotC T-TTA A---AA -Accc ooATT>
H REG GENE              TT CTCCT ATAGA GATTG TTGAT TTGCC TCTTA AGCAA GAGAT TCATT 9o-t7       50   55   65   70   75   80   85   90   95   100  105  110
[ 180 ]     GCAGC oCcGC tgGtC TCAGA oCAoC TCATt gcgCA T-CoG ATtTo CTctC TGAtt TTTCT>
H REG GENE  GCAGC TCAGC ATGGC TCAGA CCAGC TCATA CTTCA TGCTG ATCTC CTGCC TGATG TTTCT 9o-t7       115  120  125  130  135  140  145  150  155
[ 180 ]     GTCTo tttGg CcAoo T-tGc cCT-T TToaC tgCAc CtgAo TCTTT>
H REG GENE  GTCTC AGAGC CAAGG TAAGA TCTCT TTTCC ACCAA CCAAC TCTTT
```

FIG.10

```
9A•1-T7                        5     10    15    20    25    30
[ 130 ]   ————————————————————CAc cGtgG aTtA- CtgGt CTCAG AaCAa>
EXON2                          CAT TGCAG CTCAG CATGG CTCAG ACCAG

9A•1-T7   35    40    45    50    55    60    65    70    75    80
[ 130 ]   CTCAT tgcgC AT-Ca GATtT aCTct CTGAT tTTTC TGTCT attgG CCAA>
EXON2     CTCAT ACTTC ATGCT GATCT CCTGC CTGAT GTTTC TGTCT CAGAG CCAA H REG GENE                 5     10    15    20    25    30    35    40    45
[ 136 ]   ————————G aAtTc cTGgg cTCAa GtgAt CCTC- TCatG caGTC TCC-- CA-oA gT-GC>
WP03-4 T7         G GACTT TTGTC ATCAG GCCAG CCTCA TCCCC AGGTC TCCTC CACCA TTGGC H REG GENE 50    55    60    65    70    75    80    85    95    100
[ 136 ]    tG-gG atgaC AGGcT -tGaG C-CAC C-AcA ---ccA ggCCC aT-Ca TCAGt ttatA TAAAG>
WP03-4 T7  CGTAG CCAGC AGGTT CAGTG CTCAC CGAAA GTAAA ATCCC CTCCT TCAGC AAGAA TAAAG H REG GENE 105   110   115   120   125   130
[ 136 ]    aAAaA aAaAC CTTAa aaT-t gtTAg GcAA- ATA>
WP03-4 T7  CAATA TACAC CTTAG GTTCC ACTAA GTAAC ATA WP03 8SP    120   115   110   105   100   95    90    85    80    75
[ 108 ]   ————<GTT-c TgTGa gTCTc AAttt gttcc TTCtT gGaAG CT--G tcTGG -TgA- AtCtG
EXON2          GTTGA TTTGC CTCTT AAGCA AGAGA TTCAT TGCAG CTCAG CATGG CTCAG ACCAG WP03 8SP   70    65    60    55    50    45    40    35    30
[ 108 ]    <tTggT cCcTC tgtCT GcTaT tCTGt CTG-T cTgTa TGTCT ---G-t CCAtG
EXON2      CTCAT ACTTC ATGCT GATCT CCTGC CTGAT GTTTC TGTCT CAGAG CCAAG
```

FIG.10A

```
AD3-4-296                 260   255   250   245   240   235   230
[ 112 ]        ----------<ACtA CcaAa C-CT- -GCat tA-AA --aAa tttCg gTtG- -GtCg
WP5' 4/93                 ACCA CGGAG CTCTG GGCGC CAGAA GCGAG AGCCC CTCGC TGCCC AD3-4-296      225   220   215   210   205   200   195   190   185   180   175   170
[ 112 ]        <aCCtC -ggAg C-aGa AcccA Acctc CGAgc AGtac A-TGc TAaga CttCa cCaGt CaaaG
WP5' 4/93      CCCGC CTCAC CGGGT AGTGA AAAAA CGATG AGAGT AGTGG TATTT CACCG GCGGC CCGCG AD3-4-296       165   160   155   150   145   140   135   130   125   120   115
[ 112 ]         <-cGA- aCgta CtatA CtCAa T--tG AtCca ataAc TtGaC CaacG Gaaca AgTTA ccCTA
WP5' 4/93       AGGAC CCCCG CCCGA CCCAG TGCGG AACGG GGGAG TAGTC CCGGG GGCTC ACTTA TTCTA AD3-4-296       105   100   95    90    85    80   75 70   65    60    55    50
[ 112 ]         <tAacA G-CgC Aatcc tAttC TAGAG TCcAt aTCAA CAGGG TtTaC gacCt CGaTG -TTgg
WP5' 4/93       CATTA GTCTC ACGTG CAGAC TAGAC TCAAG CTCAA CAGGG TCTTC TTTCC CGCTG ATTCC AD3-4-296       45    40
[ 112 ]         <atCAg GaC
WP5' 4/93       GCCAA GTC AD2 SP6F         10    15    20    25    30    35    40    45    50    55    60    65
[ 504 ]         AG-Tt TCaCT CTGTt gCCCA GGCTG gAGTG CAaTG GCaCA ATCct GGCTC ACTGC aAcCT>
1-9AT7-3 3      AGATC TCGCT CTGTC ACCCA GGCTG AAGTG CAGTG GCCCA ATCTC GGCTC ACTGC GAGCT AD2 SP6F         70    75    80    85    90    95   100   105   110   115
[ 504 ]         CCgCC TCCCG aGcTC Aagca ATTCT CCTGC CTCA- -GCCT C-G-- --TGA GccGC TGGGA>
1-9AT7-3 3      CCACC TCCCG GGTTC ACTTC ATTCT CCTGC CTCAC TGCCT CAGCC TCTGA GTAGC TGGGA
```

FIG.10B

HB4-SEQ SEQUENCE

```
GAGGC GTATT ATACC ATGCT CCATC TGCCT ACGAC AAACA GACCT AAAAT CGCTC ATTGC   60
ATACT CTTCA ATCAG CCACA TAGCC CTCGT AGTAA CAGCC ATTCT CATCC AAACC CCCTG  120
AAGCT TCACC GGCGC AGTCA TTCTC ATAAT CGCCC ACGGG CTTAC ATCCT CATTA CTATT  180
CTGCC TAGCA AACTC AAACT ACGAA CGCAC TCACA GTCGC ATCAT AATCC TCTCT CAAGG  240
ACTTC AAACT CTACT CCCAC TAATA GCTTT TTGAT GACTT CTAGC AAGCC TCGCT AACCT  300
CGCCT TACCC CCCAC TATTA ACCTA CTGGG AGAAC TCTCT GTGCT AGTAA CCACG TTCTC  360
CTGAT CAAAT ATCAC TCTCC TACTT ACAGG ACTCA ACATA CTAGT CACAG CCCTA TACTC  420
CCTCT ACATA TTTAC CACAA CACAA TGGGG CTCAC TCACC CACCA CATTA ACAAC ATAAA  480
ACCCT CATTC ACACG AGAAA ACACC CTCAT GTTCA TACAC CTATC CCCCA TTCTC CTCCT  540
ATCCC TCAAC CCCGA CATCA TTACC GGGTT TTCCT CTTAA AAAAA AAAAA AAAA        590
```

HB4 PROTEIN

```
EAYYT MLHLP TTNRP KIAHC ILFNQ PHSPR SNSHS HPNPL KLHRR SHSHN RPRAY ILITI   60
LPSKL KLRTH SQSHH NPLSR TSNST PTNSF LMTSS KPR                            95
```

FIG. 11A

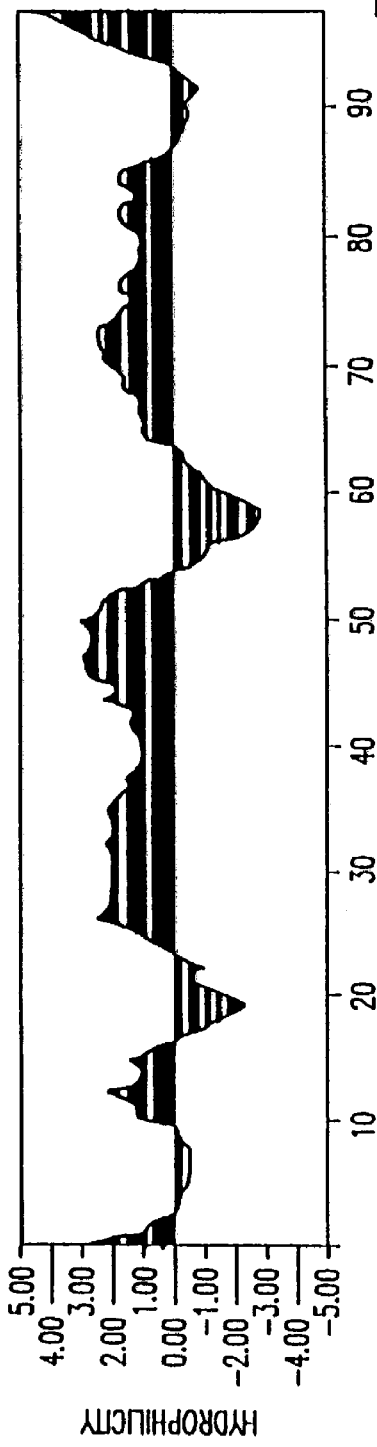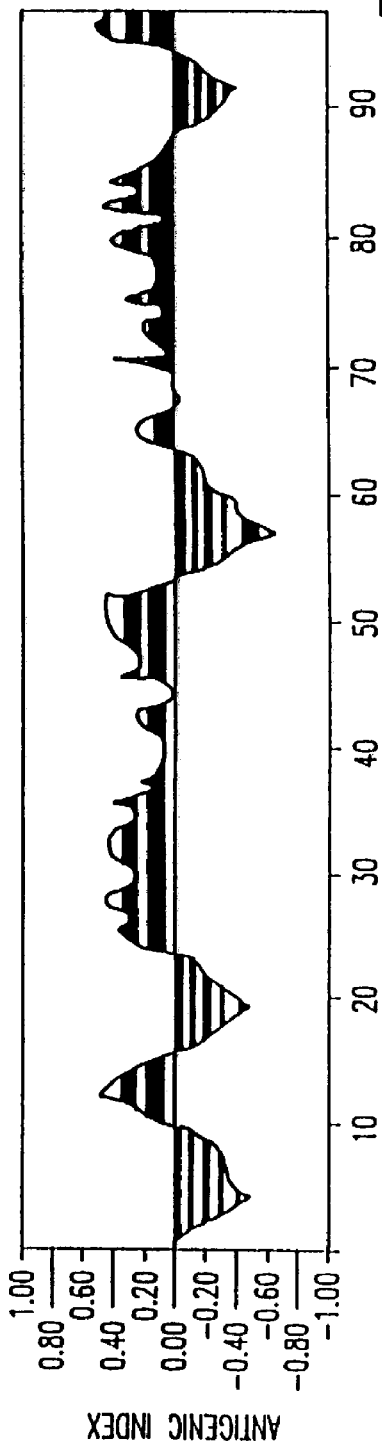

```
HB4 SEQ
[ 440 ]                                                              ——ATaC>
Human-PTP                                                              ATGC HB4-SEQ  15    20    25    30    35    40    45    50    55    60    65
[ 440 ]  C-AT- GCTCC alCTG C—CT  ACgac AA-ac AGACC -T-A- AaaTc GcTca LTGCA lA-CT>
Human-PTP CTATC GCTCC TACTG CTACT ACTTT AATGA AGACC GTGAG ACCTG GGTTG ATGCA GATCT HB4-SEQ       70    75    80    85    90    95    100   105   110   115   120
[ 440 ]  CTtca alCAG cACAT -Agcc ClcG- lAgla acaG- CcaTl CTCAl CCAaa CCccc lGaag>
Human-PTP CTATT GCCAG AACAT GAATT CGGGC AACCT GGTGT CTGTG CTCAC CCAGG CCGAG GGTGC HB4-SEQ  125   130   135   140   145   150   155   160   165   170   175
[ 440 ]  CTTca ccGgC gCAgT cATT- clcAl AaTcG C-Cca cgGgC TTacA T-cCT -cATT aclaT>
Human-PTP CTTTG TGGCC TCACT GATTA AGGAG AGTGG CACTG ATGAC TTCAA TGTCT GGATT GGCCT HB4-SEQ  180   185   190   195   200   205   210   215   220   225 230   235
[ 440 ]  lC-TG cCaqC AAAcl cAAaC laCGa acGCA CT-cA -CAGT cGcal CaTaa TCTCl clCAA>
Human-PTP CCATG ACCCC AAAAA GAACC GCCGC TGGCA CTGGA GCAGT GGGTC CCTGG TCTCC TACAA HB4-SEQ  240   245   250   255   265 270 275   280   285   290   295   300   305
[ 440 ]  GgaCT -lcaa AcTcl AcLCC CAAGC lLTGT gAcTl CTaGC aACcl cGclA aCCTc gCCTl>
Human-PTP GTCCT GGGGC ATTGG AGCCC CAAGC AGTGT TAATC CTGGC TACTG TGTGA GCCTG ACCTC HB4-SEQ  310   315   320   325   330   340   345   350   355   360365 370
[ 440 ]  AccCc CAclA TTaac clAcT GGgAG aATGT G-CTa GT-AA -cCAc GTTCT CCTTc aaaTa>
Human-PTP AAGCA CAGGA TTCCA GAAAT GGAAG GATGT GCCTT GTGAA GACAA GTTCT ccTTT CTCTG HB4-SEQ        375 380 385   390        395   400   405 410   415   420   425
[ 440 ]  lcAcT clccl AclTA cAGG- A-CT- cAAcA TACla GTCcA GccCT -AToC lcCcl cTACA>
Human-PTP CAAGT TCAAA AACTA GAGGC AGCTG GAAAA TACAT GTCTA GAACT GATCC AGCAA TTACA HB4-SEQ  430   435   440   445   450   455   460   465   470 475   480   485
[ 440 ]  lallL acCAc AAcac AAlgg GGclC A-CTC aCCcA C-CAc aTlAA CCala AaACc CTCaT>
Human-PTP ACGGA GTCAA AAATT AAACC GGACC ATCTC TCCAA CTCAA CTCAA CCTGG ACACT CTCTT HB4-SEQ  490   495   500   505   510   515   520        525   530        540   545
[ 440 ]  -TCac acGAG -aaaa Caccc TcATg TTC-A TAcac cTA— TcCCC CAlTC TTccl AlCCc>
Human-PTP CTCTG CTGAG TTTGC CTTGT TAATC TTCAA TAGTT TTACC TACCC CAGTC TTTGG AACCT HB4-SEQ        550   555   560 565   570   575   580   585   590
[ 440 ]  TcAAc cccgA cAlcA AcCgg GTTTC CLCTl AAAAA AAAAA AAAAA A>
Human-PTP TAAAT AATAA AAATA AACAT GTTTC CACTA AAAAA AAAAA AAAAA A
```

FIG.11D

```
H REG GENE        2260  2265  2270  2275  2280  2285  2290   2295  2300 2305
[ 284 ]       ——C tTcTT -TttC AgGC- CaAga gGCCc A-GAC AgAgt tgCC- ccAgg CcCgg ATcag>
HB4-SEQ         C GTATT ATACC ATGCT CCATC TGCCT ACGAC AAACA GACCT AAAAT CGCTC ATTGC H REG GEN2310 2315  2320  2322330  2335  2340   2345  2350  2355  2360  2365  2370
[ 284 ]       cTgCc CagaA ggCAc CaACc TAtCg CTCcT AcT-g CtaCt AcTtT aATga AgACC gCgaG>
HB4-SEQ       ATACT CTTCA ATCAG CCACA TAGCC CTCGT AGTAA CAGCC ATTCT CATCC AAACC CCCTG H REG GENE        2375  2380  23852390 2395  2400 2405  2410  2415  2420  2425   2430
[ 284 ]       -AcCT gggtt GatGC AGTgt gagTg AggAg aGCgt gtGGG aaggg AgaCT CATgA -aggg>
HB4-SEQ       AAGCT T QCC GGCGC AGTCA TTCTC ATAAT CGCCC ACGGG CTTAC ATCCT CATTA CTATT H REG GENE        2435  2440   2445    2450  2455  2460  2465 2470  2475   2480  2485
[ 284 ]       agGgg aAGC- tgC-C AcTCT -CcAg tGtgt TCAgt GgCGC Aatga gAT-g agaCT gAAcc>
HB4-SEQ       CTGCC TAGCA AACTC AAACT ACGAA CGCAC TCACA GTCGC ATCAT AATCC TCTCT CAAGG H REG GENE 24902495  2500  2505  2510   2515  2520    2525   2530  2535  2540
[ 284 ]       cCTTt AtACT aTcaT CagcC ccA-A aCTTT ccaAT ——CTa CT—t tAtCC -CatT AttCa>
HB4-SEQ       ACTTC AAACT CTACT CCCAC TAATA GCTTT TTGAT GACTT CTAGC AAGCC TCGCT AACCT H REG GENE2545  2550  2555  2560  2565  2570    2580  2585   2590  2595  2600
[ 284 ]       gcaCa TtCCC agCAC aAagA ACCTg gTGGG tG-AC agcaT catC- AcggA Catta cTCTg>
HB4-SEQ       CGCCT TACCC CCCAC TATTA ACCTA CTGGG AGAAC TCTCT GTGCT AGTAA CCACG TTCTC H REG GEN2605  2610  2612620 2625   2630  2635  2640  2645  2650  2655  2665  2670
[ 284 ]       CTG-T CcttT tTCAC cCTCC T-CTT ggAGG ACTCA gtATA tccGT CACAa CCCTc cACTg>
HB4-SEQ       CTGAT CAAAT ATCAC TCTCC TACTT ACAGG ACTCA ACATA CTAGT CACAG CCCTA TACTC H REG GENE  2675 2680   2685    2690   2695  2700   2705 2710  2715   2720
[ 284 ]       agTCT cCAT- TTT-C ttC— tgCAA ca—G CTCta T-tgC CAgaA CATgA A-ttC gggcA>
HB4-SEQ       CCTCT ACATA TTTAC CACAA CACAA TGGGG CTCAC TCACC CACCA CATTA ACAAC ATAAA H REG GENE 2725   2730   2735     2740
[ 284 ]       A-CCT -ggTg tC-tG tG—c tCACC C>
HB4-SEQ       ACCCT CATTC ACACG AGAAA ACACC C
```

```
GTTCT TAGTC TATCT CTTGT ACAAA CGATG TGCTT TGAAG ATGTT AGTGT ATAAC AATTG    60
ATGTT TGTTT TCTGT TTGAT TTTAA ACAGA GAAAA AATAA AAGGG GGTAA TAGCT CCTTT   120
TTTCT TCTTT CTTTT TTTTT TTCAT TTCAA AATTG CTGCC AGTGT TTTCA ATGTA GGACA   180
ACAGA GGGAT ATGCT GTAGA GTGTT TTTAT TGCCT AGTTG ACAAA GCTGC TTTTG AATGC   240
TGGTG GTTCT ATTCC TTTGC ACATC ACGAC ATTTT ATAAT CATAG TTAAA TCGTA TATGA   300
CAAAA ATGCT CTGAT CTGAT GCCAA AGGTC AATTC AGTGT ATATA ACCTG AACAC ACTCA   360
TCCAT TGCGT TT                                                           372
```

AD2-2 T7 PEP

```
MFVFC LILNR EKIKG GNSSF FLLSF FFSFQ NCCQC FQCRT TEGYA VECFY CLVDK AAFEC    60
WWFYS FDT
```

```
ACTGT CTCCC CCTTT GATAG GGACA CTAAA GTGGT CTGTA CTTGG GTAGA GGATG GCAAG    60
TTAAG AATTA AAATC GTCTG GGTGC GGTCT GCACG CTTGT AATCC CAGCA CTTTG GGAGG   120
CTGAG GCGGG CGGAT CACCT GAGGT CAGGA GTTCG ACACC AGCCT GATGA ACATG GAGAA   180
ACCCC ATCTC TACTA AAAAT ACAAA TATTA GCTGG GCGTT GTCGC GCGCC TGTAA TCCCA   240
GCGGC TCACG AGGCT GAGGC AGGAG AATTG CTTGA GCTCG GGATG GCGGA GGTTG CAGTG   300
AGCCA GGATT GTGCC ATTGC ACTCC AGCCT GGGCA CAAG AGTGA AACTC TGTCT CAAAA   360
AAAAA AAAAA AAAAA AA                                                    377
```

FIG.16D

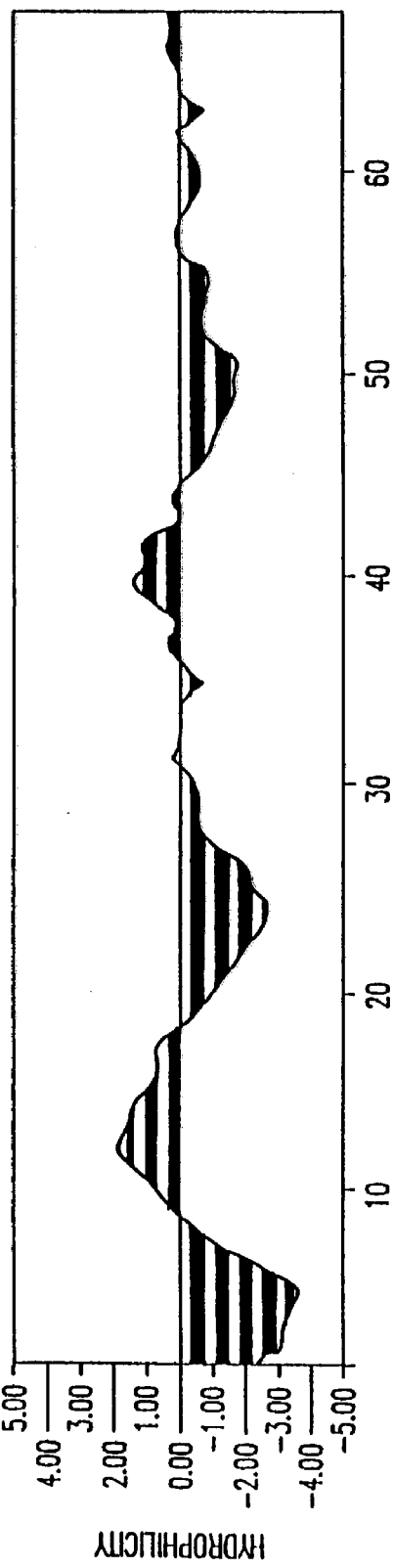
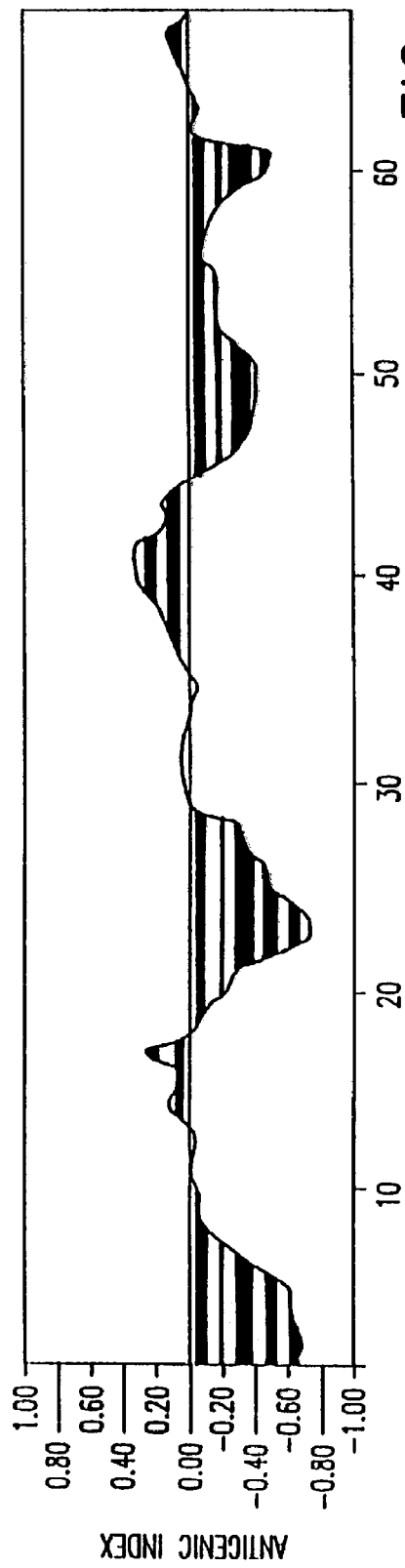

AD2-2 SEQUENCE

```
GCGTAAACAC ATTTTTGTTC TTAGTCTATC TCTTGTACAA ACGATGTGCT TTGAAGATGT   60
TAGTGTATAA CAATTGATGT TTGTTTTCTG TTTGATTTTA AACAGAGAAA AAATAAAAGG  120
GGGTAATAGC TCCTTTTTTC TTCTTTCTTT GATTTTAAAC AGAGAAAAAA TAAAACGGGG  180
TAATAGCTCC TTTTTCTTC TTTCTTTTTT TTTTTTCATT TCAAAATTCC TGCCAGTGTT  240
TTCAATGATG GACAACAGAG GGATATGCTG TAGAGTGTTT TATTGCCTAG TTGACAAAGC  300
TGCTTTGAAT GCTGGTGGTT CTATTCCTTT GACACTACGC ACTTTTATAA TACATGTTAA  360
TGCTATAGGA CAAGATGCTC TGATTCCTGA GTGCCAGAGG TTCAATTCAG TGTATATAAC  420
TGAACACACT CATCCATTTG TGCTTTTGTT TTTTTTATGG TGGCTTAAAG GTAAAGAGCC  480
CATCCTTTGC AAGTCATCCA TGTTGTTACT TAGGCATTTT ATCTTGGCTC AAATTGTTGG  540
AAGAATGGTG GCTTGTTTCA TGGTTTTTGT ATTTGTGTCT AATGCACGTT TTAACATGAT  600
AGACGCAATG CATTGTGTAG CTACTTTTCT GGAAAAGTCA ACTCTTTTAG GAATTGTTTT  660
TCAGATCTTC AATAAATTTT TTCTTTAAAT TTCAAAGAAC AATGTGCTTG TGTTGATGCC  720
TTACAAAAAC CATTGTATAT TTGTGTATTC CTTCTTGTAT TTAGACAGTG GTTTTTCAGG  780
TGCCTGCTTT GTTTTCTGGT ATGGCCTTTA TGGAATGAGA CGCTTTAGCT TTGGTACGTA  840
GCGCTAATCC ATAGCAGCTT TGGCAGTTTC GTGTCTTGAC TCTTAGCTAA AAAGTTAGAA  900
GTTTACATGA CTGTTTTTTT TATTTTCCCT AAATTATTAC TTACTCTGAG CATTAATTAA  960
GGGCATTTTC ACCTGTGTAA AATTATGGTC AGCTTTTTTC TGTCTATAAT TGTTTACTTT 1020
TGTGGGTTTA CTCTAGAAAC ATGAGCCAAA AATGTCAATA GACAACACAG TATTAAAATA 1080
ACCCAAAAGT TGTAAAGGGC AACGTTTCTC CCCTTTGATA GGGACACTAA AGTGGTCTGT 1140
ACTTGGGTAG AGGATGGCAG ACGTTAAGAA TTAAAATGCC TCTGGGTGCG GTCTCACGCT 1200
TGTAATCCCA GCACTTTGGG AGGCTGAGGC GGGCGGATCA CCTGAGGTCA GGAGTTCGAC 1260
ACCAGCCTGA TGAACATGGA GAAACCCCAT CTCTACTAAA AATACAAATA TTAGCTGGGC 1320
GTTGTCGCGC GCCTGTAATC CCAGCGGCTC ACGAGGCTGA GGCAGGAGAA TTGCTTGAGC 1380
TCGGCATGGC GGAGGTTGCA GTGAGCCAGG ATTGTGCCAT TGCACTCCAG CCTGGGCAAC 1440
AAGAGTGAAA CTCTGTCTCA AAAAAAAAAA AAAAAAAAA                        1480
```

FIG.16E

AD3-4 SEQUENCE

```
                                                         ttgggtgggtgga
ATGAT GGTCT GTTGG AATCG GTTTG GTAAA TGGGT TTATT TCATA TCCGC TATCT TTAAC    60
TTTGG ACCGC GTTAT CTATA TCATG GCGTT CCTTT CTACT TTTTA ATATT GGTTC GTATT   120
ATATC GTTCC TGATT GGGGA TATGG AAGAC GTATT ACTTA ATTGT ACTTT ATTGA AACGT   180
TCCTC TCGGT TTCGA TTCTG GGGGC TTTGG TCTGC TCGAT GGATT CTTGT CGATT TTCTC   240
GTGTG GCAGT AACAT ACCGT TTTAT CACCC TTCTA AATAT CCCAT CTCCC GCTGT TTGGT   300
AGGCT CGGAA CACTA TCGAC CAACA GGTTC TATCT AGAAT CAAGT TGGAA ATTAA ACGGT   360
GTCTT GG                                                                 367
```

AD3-4 PROTEIN

```
MMVCW NRFGK WVYFI SAIFN FGPRY LYHGV PFYFL ILVRI ISFLI GDMED VLLNC TLLKR    60
SSRFR FWGAL VCSMD SCRFS RVAVT YRFIT LLNIP SPAVW MARNT IDQQV LSRIK LEIKR   120
CL                                                                      122
```

```
CCCAC AGGTC CTAAA CTACC AAACC TGCAT TAAAA AATTT CGGTT GGTCG ACCTC GGAGC  1180
AGAAC CCAAC CTCCG AGCAG TACAT GCTAA GACTT CACCA GTCAA GCGA ACGTA CTATA   1240
CTCAA TTGAT CCAAT AACTT GACCA ACGGA ACAAG TTACC CTAGG GATAA CAGCG CAATC  1300
CTATT CTAGA GTCCA TATCA ACAAT AGGGT TTACG ACCTC GATGT TGGAT CAGGA CATCC  1360
CGATG GTGCA GCCGC TATTA AAGGT TCGTT TGTTC AAACG ATTAA AGTCC TCGTG TCTGA  1420
GTTCA GACCG AAGTA ATCCA GGTCG GTTTC TATCT TCTTC AAATT CCTCC CTGTA CCGAA  1480
AGGAC TAATG AGAAA TAAGG CCTAC TTCAC AAAGC GGCCT TCCCC CGTAA TGATA TCATC  1540
TCAAC TTAGT ATTAT ACCCA CACCC ACCCA AGAAC AGGGT TTGTT AAAAA AAAAA AAAAA  1600
```

FIG.16I

AD3-4SP SEQUENCE

```
AACCCACTCC ACCTTACTAC CAGACAACCT TAGCCAAACC ATTTACCCAA ATAAAGTATA   60
GGCGATAGAA ATTGAAACCT GGCGCAATAG ATATAGTACC GCAAGGAAAG ATGAAAAATT  120
ATAACCAAGC ATAATATAGC AAGGACTAAC CCCTATACCT TCTGCATAAT GAATTAACAT  180
GAAATAACTT TGCAAGGAGA GCCAAAGCTA AGACCCCCGA AACCAGACGA GCTACCTAAG  240
AACAGCTAAA AGAGCACACC GTCATTGTAT GGCAAAATAG TGGGAAGATT TATAGGGTAG  300
AGGGCGACAA ACCATCCGAG CCTTGTGATA GCTGGTTGTC CAAGATAGAT CTTAGTTCAA  360
CCTTTAATTT GCCACAGAAC C                                            381
```

FIG.16J

AD3-4T7 SEQUENCE

```
TTTTTTTTTT TTTTTAACAA ACCCTGTTCT TGGGTGGGTG TGGGTATAAT ACTAAGTTGA   60
GATGATATCA TTACGGGGGA AGGCCGCTTT GTGAAGTAGG CCTTATTTCT CATTAGTCCT  120
TTCGGTACAG GGAGGAATTT GAAGAAGATA GAAACCGACC TGGATTACTT CGGTCTGAAC  180
TCAGACACGA GGACTTTAAT CGTTTGAACA AACGAACCTT TAATAGCGGC TGCACCATCG  240
GGATGTCCTG ATCCAACATC GAGGTCGTAA ACCCTATTGT TGATATGGAC TCTAGAATAG  300
GATTGCGCTG TTATCCCTAG GGTAACTTGT TCCGTTGGTC AAGTTATTGG ATCAATTGAG  360
TTTAGTAGTC CGCTTGGAGT GGTGAAGTCT AGAATGTCCT GTTCGGGGGT TGGTTTCTGC  420
TCCCAGGTCG CCCCAACCGA ATTTTTTATT GAAGGTTGGG TAGTTTAGCA CCTGTGGGTT  480
GGTAAGGTAC TGTTGGAATT AATAAATTAA AGCTCCATAG GGTCTCCTCG TCTTGTTGTC  540
TAATGCCCCC CTCTCCACGG GAAGGTCAAT TCCACTGGTT AAAAGTAAGA GAAAGCTGAA  600
CCCTCGGGGA GCCATCCATA CAGGTCCCC                                    629
```

FIG.16K

AD4-4 SP6 SEQUENCE

Sequence Range: 1 to 256

```
GCGGG TAAAT TGGTT TGTTA TTTTT TAAAA AAAAC TTGCA TGTTT AAAAA AAAGT TGATT   60
GCTTC AAATT TCTGC TACTA ACTTC AAGCT ATGGG AGTTT GGCAG TAGTC ACTTG AGGAT  120
TTTTT TTCCA ATTCT TTTCT TTTTG TTGTT AAAGC TGTAC TTCAG TGAAC AGAAA AATTG  180
CCAAG CAAAC TAATG GACTA TAAAG CGTAA TTTGA CTGTG TGGGA CTAAA CTACA GAGCC  240
TACTT GACCA GTGGA T                                                     256
```

FIG.16L

AD4-4 T7F SEQUENCE

Sequence Range: 1 to 270

```
CATGT TTAAA AAAAA GTTGA TTGCT TCAAA TTACT GCTAC TAACT TCAAG CTATG GGAGT  60
TTGGC AGTAG TCACT TGAGG ATTTT TTTTC CAATT CGTTT TCATT TTTGT TGTTA AAGCT 120
CGTAC TTCAG TGAGA CAGAA AAATT GCCAA GCTAA ACTAA TGGTC TATAA AAGCG TAATT 180
TGCAT GTGTG GGCAA AAACT ACAGA GCCTC AATTG CCACT GAGGT ATAGT ACAAA GTTTT 240
AATAC ATTTT GTAAA TCAAA TTGAA AGAAA                                    270
```

FIG.16M

AD4-4 SEQUENCE

```
CATGTTTAAA AAAAAGTTGA TTGCTTCAAA TTACTGCTAC TAACTTCAAG CTATGGGAGT  60
TTGGCAGTAG TCACTTGAGG ATTTTTTTTC CAATTCGTTT TCATTTTTGT TGTTAAAGCT 120
CGTACTTCAG TGAGACAGAA AAATTGCCAA GCTAAACTAA TGGTCTATAA AAGCGTAATT 180
TGCATGTGTG GGCAAAAACT ACAGAGCCTC AATTGCCACT GAGGTATAGT ACAAAGTTTT 240
AATACATTTT GTAAATCAAA TTGAAAGAAA                                   270
```

FIG.16N

AD16c-T7 SEQUENCE

```
TCTGC CCAGG CTGGT CTGAA ATTCC TGGGC TGAAG TGATC CTCCA GTCTT GGCCT CCCAA  60
AGTGC TGGGA TTACA GGCAT GAGCT ACTGA GCCTA GCCTT AATGA TTAAT TTTAG AGTGA 120
TGGCT TGTAC CTTCA AGACA CATAT AGATT GAGAC AGAAA ATTTC CATCG TCCCC GAGAA 180
AACT                                                                   184
```

AD16c-T7 PEP

```
       5    10    15    20    25    30    35    40    45    50    55    60
    SSSLG LPKCW DYRHE LLSLA LMINF RVMAC TFKQH IELRQ KISIV PRKLC CMGPV CPVKI 65    70    75
    ALLTI NGHCT WLPAS
```

FIG.16O

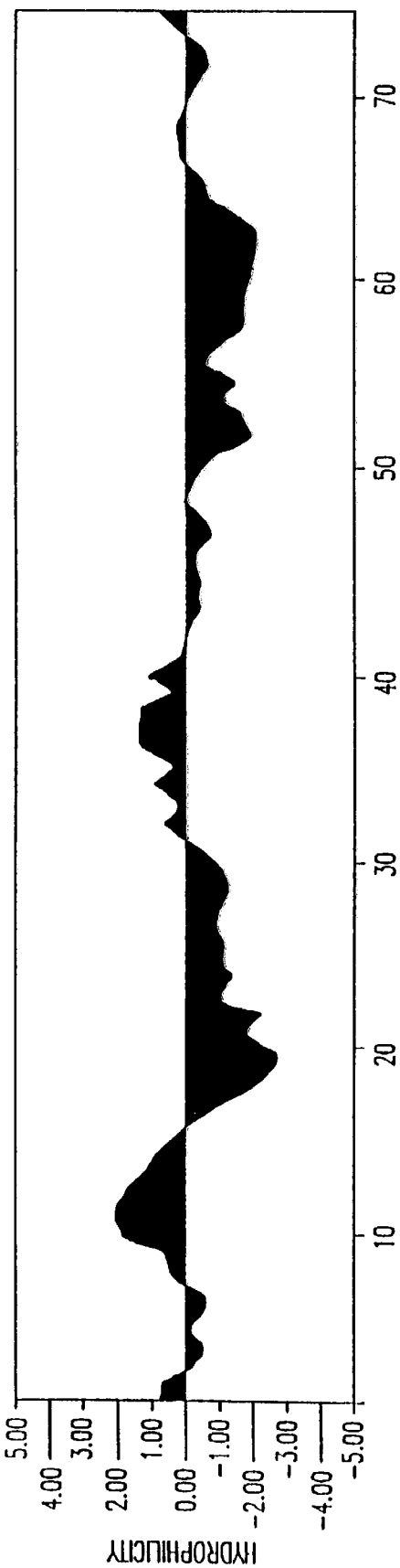
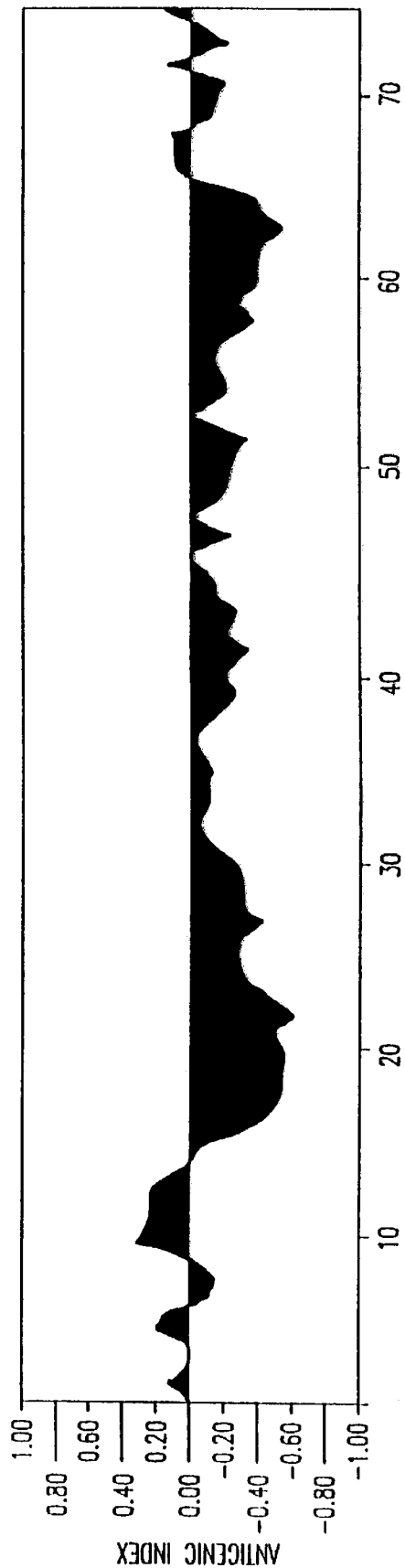

```
TTTTTTTTTT TGAGATGGAG TTTTCGCTCT TGTTGCCCAG GCTGGAGTGC AATGGCGCAA      60
TCTCAGCTCA CCGCAACCTC CGCCTCCCGG GTTCAAGCGA TTCTCCTGCC TCAGCCTCCC     120
CAGTAGCTGG GATTACAGGC ATGTGCACCC ACGCTCGGCT AATTTTGTAT TTTTTTTTAG     180
TAGAGATGGA GTTTCTCCAT GTTGGTCAGG CTGGTCTCGA ACTCCCGACC TCAGATGATC     240
CCTCCGTCTC GGCCTCCCAA AGTGCTAGAT ACAGGACTGG CCACCATGCC CGGCTCTGCC     300
TGGCTAATTT TTGTGGTAGA AACAGGGTTT CACTGATGTG CCCAAGCTGG TCTCCTGAGC     360
TCAAGCAGTC CACCTGCCTC AGCCTCCCAA AGTGCTGGGA TTACAGGCGT GCAGCCGTGC     420
CTGGCCTTTT TATTTTATTT TTTTAAGAC ACAGGTGTCC CACTCTTACC CAGGATGAAG      480
TGCAGTGGTG TGATCACAGC TCACTGCAGC CTTCAACTCC TGAGATCAAG CATCCTCCTG     540
CCTCAGCCTC CCAAGTAGCT GGGACCAAAG ACATGCACCA CTACACCTGG CTAATTTTTA     600
TTTTTATTTT TAATTTTTTG AGACAGAGTC TCAACTCTGT CACCCAGGCT GGAGTGCAGT     660
GGCGCAATCT TGGCTCACTG CAACCTCTGC CTCCCGGGTT CAAGTTATTC TCCTGCCCCA     720
GCCTCCTGAG TAGCTGGGAC TACAGGCGCC CACCACGCCT AGCTAATTTT TTTGTATTTT     780
TAGTAGAGAT GGGGTTCACC ATGTTCGCCA GGTTGATCTT GATCTCTGGA CCTTGTGATC     840
TGCCTGCCTC GGCCTCCCAA AGTGCTGGGA TTACAGGCGT GAGCCACCAC GCCCGGCTTA     900
TTTTTAATTT TTGTTTGTTT GAAATGGAAT CTCACTCTGT TACCCAGGCT GGAGTGCAAT     960
GGCCAAATCT CGGCTCACTG CAACCTCTGC CTCCCGGGCT CAAGCGATTC TCCTGTCTCA    1020
GCCTCCCAAG CAGCTGGGAT TACGGGCACC TGCCACCACA CCCCGCTAAT TTTTGTATTT    1080
TCATTAGAGG CGGGGTTTCA CCATATTTGT CAGGCTGGTC TCAAACTCCT GACCTCAGGT    1140
GACCCACCTG CCTCAGCCTT CCAAAGTGCT GGGATTACAG GCGTGAGCCA CCTCACCCAG    1200
CCGGCTAATT TAGATAAAAA AATATGTAGC AATGGGGGGT CTTGCTATGT TGCCCAGGCT    1260
GGTCTCAAAC TTCTGGCTTC ATGCAATCCT TCCAAATGAG CCACAACACC CAGCCAGTCA    1320
CATTTTTTAA ACAGTTACAT CTTTATTTTA GTATACTAGA AAGTAATACA ATAAACATGT    1380
CAAACCTGCA AATTCAGTAG TAACAGAGTT CTTTTATAAC TTTTAAACAA AGCTTTAGAG    1440
CA                                                                  1442
```

FIG.16R

AD16c-SEQUENCE

```
CCATTGTTAG GTTGTCTCTT ACCTGTTAAA ATCAGGAGCT GACAAGAAAT GCTTACCACA      60
AAAGGAGAAA TGCCAGTCTA GTTAACAGTC AAGGAGAGAA ATCAGGAAGA TTATGTGGGT     120
GGAAGAAGTA GATGATGTGG CTGATGAGTG AGTGAGTGAG CAAGCCTCCC CCCAGCTGAA     180
GAAGGAGTCA GAACTGCCCT TTGTTCCCAA CTATTTGGCG AACCCCAGCC TTCCCTTTTA     240
TCTATACACC CACAGCAGAG GATTCAGCCC AGATGCAGAA TGGGGCCCC TCCACACCCC     300
CTGCATCACC CCCTGCAGAT GGCTCACCTC CATTGCTTCC CCTGGGAAC CTCCCCTGTT     360
AGGGACCTTT CCCCGGGACC ACACCTCTTT GGCACTAGTT CAGAATGGTG ATGTGTCGGC    420
CCCTCTGCCA TACTAGAACA CCAGAAAGAC AAACGGGTGA TGTTTGTCAG CTACAGTGAG    480
TCTAGAGCCG TCCTGTTTTC TTCTGTCCCG TCCCAAGCCA CCATGTCTCT TCGAGCCTCA    540
AAATGGGACG TATGCAGGAC CAGCGCCCAG ATTCCAAGCC ATTTTTCTTC ACTGGAGCAT    600
TTCCATTTAA TATGCAAGAG CTGGTACTCA AGGTGAGAAT TCAGAACCCA TCTCTTCGAC    660
AAAATGATTT CATTGAAATT GAACTGGACC GACAGAGCTC ACCTACCAAG AGTTGCTCAG    720
AGTGTGTTGC TGTGAGCTGG GTGTTAATCC AGATCAAGTG GAGAAGATCA GAAAGTTACC    780
CAATACTCTG TTAAGGAAGG ACAAGGATGT TGCTCGACTC AAGATTTCAG GAGCTGGAAC    840
TGGTTCTGAT GATAGTGAAA ATAATTTTCT GTTCAGAAAT GCTGCATCAC ACTGACTGAA    900
AGGCCTTGCT ATACAGGAGA GCTTCAAAAC TGACTTACTA ATGCAGCAGG GACTTTTATA    960
CTGAGTATAT GACAGTGTGC ATCACCTCTG GGCCAAGGAC AAGCCATGAT CTAAATGCCT   1020
CAGATGCCCG GGCCAGTCTG GTGCACTGCA TAGTATATAC GAACATCATT CTGCCCAAGG   1080
TAGGAAGCCC CATGACCCCC AAGCAGTGGT GTCCACTCTT CCAAGCCTCT TGGTGCACAA   1140
TAAACCTTAT TGCTTGAAGC TTTGAACGAC TGTGAGAATG GTCTGGCGAG GACGAGAACG   1200
TGGAATTATA TGAGTGTCTT TTGTATCCGA GAATGTAGAG AGTTCTCTGA AGACGACGAC   1260
TGAGAGAGAG CGGACGCTAT TTCTAGCCAC TCCTGTTGAC AGTGCACCTG AAGGGCTGGG   1320
ATGCGTTTTT CTTGGTGTTG CATGCTCACA ACTCTGCTGA CATTGGGAAC TTATGAGAGA   1380
GGAAGACTCG GGAAAGCACA GATACTGGAC AGATGGATTC TGGTGTGGGG AAAGCACAGA   1440
TACTGGACAG ATGGTTCTAG TGTGACTTGT GACTGTGAGG TTTCCTATAA CATATTTATA   1500
AATGTTCATC AGGTTCAAAA GTCTATAAGA ATACAGTTCG AGACTGAATT GCTTCGAAAT   1560
ACTTCGATGT TGGGAACCAA AAGAGCTTTC CCTCCCTCAC TTTTTCCTTT GTAACACTCA   1620
TGACTGCTTC TCTGTCTCGA GTCATCTCTG CATTAACTCC CCTTCGTGGT CACTAGAGGG   1680
CTCTCTGATG CTTCTAAGAC ACTGCTTTTT ACATGCCACA CCCACCGCGT AGAGACAGGG   1740
TCTCACTATG TGGCCCAGGC TGGTCTCAAA CTTCTGGCCT TAAGTGATCG TCCTGTCCTT   1800
CGCGCTCGGA AGAAAGTCGT GGGGATTACA GGTGTGAGCC ACCCGCCCAG CCCCTCCCTT   1860
GTGTTTCAAC CAATCGGAAG TGAATTTAAC TAGATGTAGT AACCTTTTTT TTCTTTGACT   1920
TCTAAAAAAG TTACAGTTTA CTAATAAAGT TAAGTCTGGT TCTGTCCTAG AGGAAATAAA   1980
TTCACTATTA ATTCATGTCT TAAGTTACTT GGGTTAAAAC ACTTTCAGCC ACCCAGATTA   2040
ATTAAAGTGG AGCAGTGGAG CCCCTGGCTG GGGAGATGGG CCTCCAGAGG AGCAGCTGCA   2100
GGCATGTTCT GGCTACACAG AGGCAAGCAA GGGACTGGTG TCTCTGGTGA GAGGTGGGTT   2160
TGATGTATCT CTGTCCTATG CTGGTCTCTC TTCTCCTTTA TAAATCCTCC TGTGGTCACT   2220
GACTATCGTA TCGCAGTGAT CAGACTGCAC ATAGTACGGT TAGGCTGAGC TTAATGTCTT   2280
AATCATGTCA TTCGAGAGAA GACACGTTTT GATTCATGCT TTGTGTAATT AATCAATCAA   2340
GGATTCTTTT TTTAGCTTTG TTGACGTGTA ATTCACCCCT CCTCCTCCAC TGCATATTTA   2400
AAGCATGTGT TCACACTGTG TGTATACATT CACTGCGATT TTTTCGTTTG CTGCATTGCT   2460
TGGACTGTTC ATAACATCAC AAGTATTATT CAAATAAAAT ATTAACTGAC CGAAAAAAAA   2520
```

FIG.16S

```
H REG GENE                    5      10     15     20     25     30     35     40     45     50
[ 220 ]     ———————————GA ATTCC TGggC TCAoG TGATC CtCtC otgTC AGtCT CCCAA AGTGC TGGGA>
AD2-283                 GA ACTCC TGACC TCAGG TGATC CGCCC GCCTC AGCCT CCCAA AGTGC TGGGA H REG GENE  55     60     65      70     75     80            85      90     95     100
[ 220 ]     TgACA gGCtT G-AG- CC---A -CCAc ACcAg gcccA -TC— AtCo- G---tT ttToT A-toA>
AD2-283     TTACA AGCGT GCAGA CCGCA CCCAG ACGAT TTTAA TTCTT AACNT GCCAT CCTCT ACCCA H REG GENE  105    110    115    120    125    130    135    140
[ 220 ]     AGoAo AoAoo ACcTT AoooT tgtTA gCAAA tocto tGACA>
AD2-283     AGTAC AGACC ACTTT AGTGT CCCTA TCAAA GGGGG AGACA
```

FIG.17

```
AD2 SP6F    110     115    120    125    130    135    140    145    150
[ 62 ]      ———AA ttC-t C-CtG cCTCA GCCtc gtGog ccGct GGgAT TACAG GcG>
EXON I         AA GCCAA CTCAG ACTCA GCCAA CAGGT AAGTG GCAT TACAG GAG

RAT PTP     605
[ 144 ]     <ACTC
AD2-2 T7    ACTC

RAT PTP     660    655    650    645     640    635    630    625    620    615    610
[ 144 ]     <tcT-o ggoAg oGggg GTTGA C———t tTGCT TTTGA toGoT GGT-c TogT- TTCoc TTttg
AD2-2 T7    AGTGT TTTAT TGCTA GTTGA CAAAG CTGCT TTTGA ATGCT GGTGG TTCTA TTCCT TTGAC RAT PTP     710    705    700    695    690    685    680    675    670    665
[ 144 ]     <oCA-T oCAAt AoTGg oGotA -oooo ToCcA T-A-G GgCAg T—-GA GGcA- AgooT GTTtG
AD2-2 T7    TCATT TCAAA ATTGC TGCCA GTGTT TTCAA TGATG GACAA TCAGA GGGAT ATGCT GTTAG RAT PTP                                                  745 740 735 730 725 720 715
[ 144 ]                                                  <GTg A-Agg toTTT TToTT TooaT gTgco gggTT
AD2-2 T7                                                  GTA ATACT CCTTT TTTCT TCTTT CTTTT TTTTT 5
                        ————————————————FVf cLI I>
HPTPAA                                  FVA SLIK
```

FIG.17A

```
1-9aT7-3  3   140    145    150    155    160    165    170    175    180    185    190    195
[ 206 ]       ACcAC  GCCCc  GCTAA  TLTTT  GTATT  TTTAG  TAGAG  AcaGG  GTTTC  aCCgT  GTTgg  cCAGG>
AD2-283       ACAAC  GCCCA  GCTAA  TATTT  GTATT  TTTAG  TAGAG  ATGGG  GTTTC  TCCAT  GTTCA  TCAGG 1-9a-T72  3   15     20     25     30     35     40     45     50     55     60     65     70
[ 260 ]       CTGGT  cTgoA  ALTCC  TGggC  TgAoG  TGATC  CLCCo  GLCTL  gGCCT  CCCAA  AGTGC  TGGGA>
AD2-283       CTGGT  GTCGA  ACTCC  TGACC  TCAGG  TGATC  CGCCC  GCCTC  AGCCT  CCCAA  AGTGC  TGGGA 1-9a-T72  3   140    145    150    155    160
[ 260 ]       AG-AC  AcA-L  A-Tag  ALTGa  goC-A  goAAA>
AD2-283       AGTAC  AGACC  ACTTT  AGTGT  CCCTA  TCAAA
```

FIG.17B

```
AD16c-SP6                                       5      10     15     20     25     30
[ 344 ]                                   —AGA- TcTCg  CTC-T  G-Tca  CCCAG  GCTGa  AGTGC>
AD2-2 SP6                                  AGAG TTTCA  CTCTT  GCTTG  CCCAG  GCTCG  AGTGC

AD2-2 SP6     35     40     45     50     55     60     65     70     75     80     85
[ 344 ]       AgTGG  CcCAA  TCLcG  GCTCA  CTGCg  AgCTC  C-oCC  TCCCG  gGLTC  AcLLc  oTTCT  CCTGC>
AD2-2 SP6     AATGG  CACAA  TCCTG  GCTCA  CTGCA  ACCTC  CGCCC  TCCCG  AGCTC  AAGAA  CTTCT  CCTGC

AD16c-SP6  100   105    110    115    120    125    130    135    140 145   150    155    160
[ 344 ]       CTCAG  CCTC-  TGAGL  aGCTG  GGAcT  ACAGG  CGCcC  aCCAC  AcGCc  gCTAA  TLTTT  GTATT>
AD2-2 SP6     CTCAG  CCTCG  TGAGC  CGCTG  GGATT  ACAGG  CGCGC  GCCAC  AAGCG  ACTAA  TATTT  GTATT

AD16c-SP6
[ 344 ]       TTTGT  AG>
AD2-2 SP6     TTTGT  AG

AD16c-SP6     140    145    150    155    160    165    170    175    180    185    190    195
[ 206 ]       ACcAC  GCCCc  GCTAA  TLTTT  GTATT  TTTAG  TAGAG  AcaGG  GTTTC  aCCgT  GTTgg  cCAGG>
AD2-283       ACAAC  GCCCA  GCTAA  TATTT  GTATT  TTTAG  TAGAG  ATGGG  GTTTC  TCCAT  GTTCA  TCAGG

AD16c-SP6     200    205    210
[ 206 ]       aTGcT  —CGA   LCTCC  TGA>
AD2-283       CTGGT  GTCGA  ACTCC  TGA
```

FIG.17C

```
H REG GENE     3610  3615   3620 3625 3630      3635 3640 3645 3650 3655 3660
[ 118 ]        ---CC CC-aa  gC-aG tGTta aTcct GG-cT A--CT GtgTG AGcTG AccTC AagcA CaGGt>
AD3-4             CC CCTGT  TCTTG GGTGG GTTTG GGTAT ATTCT GGTTG AGATG ATATC ATTTA CGGGG H REG GENE     3670  3675   3680 3685 3690 3695 3700 3705 3710 3715 3720
[ 118 ]        GAAGG Cagag  aaTcc A-Tcc aCC-T gTTTC TgTTc TCCcT gCtTA gctcc AGGga TgGAA>
AD3-4          GAAGG CGCTT  TGTGA AGTAG GCCTT ATTTC TCTTG TCCTT TCGTA CAGGG AGGAT TTGAA H REG GENE     3725 3730 3735   3740 3745 3750   3755   3760 3765 3770
[ 118 ]        cTgGg Actgg GaT-a gAgga aaG-g TGAAC TC-cT CA-tT aagga aATgG aTG>
AD3-4          GTAGT AGAAC GCTGT TACTC CGGTC TGAAC TCAGT CACGT GGCTT TATCC TTG
```

FIG.18

```
WP03-5 T7         5        15    20    25    30    35    40    45    50
[ 90 ]         GATCC aAGCT acGTA -CgcG TgcAT GCAcg tCaTa gcTcT TCTAT AGTGT CAC>
AD3-4 221      GATCC GAGCT CGGTA CCAAG TTGAT GCATA GCTTG AGTAT TCTAT AGTGT CAC 18-4T7            155  150  145      140  135  130  125  120  115  110  105
[ 362 ]        <gTATg GgCcc gATAg ---c-t TAT-t TAgcC TTTAG AGCAC ACTGG CgGCC GTTAC TAGTG
AD3-4 221      ATATA GACAA TATAA CAATA TATTG TATAC TTTAG ACCAC ACTGG CAGCC GTTAC TAGTG 18-4T7            100   95   90   85   80   75   70   65   60   55   50   45
[ 362 ]        <GATCC GAGCT CGGTA CCAAc TTGAT GCATA GCTTG AGTAT TCTAT AGTGT CACct -aAaT
AD3-4 221      GATCC GAGCT CGGTA CCAAG TTGAT GCATA GCTTG AGTAT TCTAT AGTGT CACTA ATAGT
```

FIG.18A

```
G2A-EP T7              20    25    30    35       40    45    50    55
[ 148 ]         ————————CTT AaTA— gAtAg ctaCT TA—— AAAta AcTTA CaC-A cT—— GTtTt>
AD3-4 SPF               CTT ACTAC CAGAC AACCT TAGCC AAACC ATTTA CCCAA ATAAA GTATA G2A-EP T7  60    65    70    75    80    85    90    95    100   105   110
[ 148 ]    aGaG— T-G—— cTTGA AAaCT atCtg AtcAG AcATA GTAtt GaAAc cAAtG A——At AcATT>
AD3-4 SPF  GGCGA TAGAA ATTGA AACCT GGCGC AATAG ATATA GTACC GCAAG GAAAG ATGAA AAATT G2A-EP T7  115   120   125   130   135
[ 148 ]    AT—At aAAG— —TAA— A—gGa AAGGA —gAA>
AD3-4 SPF  ATAAC CAAGC ATAAT ATAGC AAGGA CTAA AD3-4                         215   210   205       200   195   190 185   180
[ 182 ]         ————————————————<CT ATAaA GgTcG TTG—— TcaaC gaTaA AGCAc GtGAc
H REG GENE                      CT ATAGA GATTG TTGAT TTGCC TCTTA AGCAA GAGAT AD3-4      175   170   165   160   155   150   145   140   135   125
[ 182 ]    <TgAgt tCAG— aCcGg A—Gta aCAG— CgttC TacTA CTTCA —aaTc cTC-C CTGCg aaAgG
H REG GENE TCATT GCAGC TCAGC ATGGC TCAGA CCAGC TCATA CTTCA TGCTG ATCTC CTGCC TGATG AD3-4      120   115   110   105   95    90    85    80    75    70    65    60
[ 182 ]    <caaga Gaaat AagGC CtAct TAAGc gC-CT TccCC cgtAA atgAt atcaT CTcaa CCaGA
H REG GENE TTTCT GTCTC AGAGC CAAGG TAAGA TCTCT TTTCC ACCAA CCAAC TCTTT CTAGC CCTGA AD3-4      55    50    45    40    35    30    25    20    15    10
[ 182 ]    <AtA-T aCcCa aaccC CCCAA GaAcA gGGGa ggAaa aGAAA AAAAA AAAAA
H REG GENE AGACT TCACT CTATC CCCAA GCATA CGGGT CTACT TGAAA AAAAA AAAAA
```

FIG.18B

```
AD2-2 T7                535    530    525    520    515    510    505    500    495
[ 110 ]         ──────────<CAGAA AAcTo GClAc oC-AA lgcAl TGGTC TATcA lglla oAAcg
AD4-4 T7F                CAGAA AAATT GCCAA GCTAA ACTAA TGGTC TATAA AAGCG TAATT AD2-2 T7   490    485    480    475    470    465    460
[ 110 ]    <TGCAT -T--o GoCAc AAA-T ACAoA oocCA TG--A -AocA oGCcA
AD4-4 T7F  TGCAT GTGTG GGCAT AAACT ACAGA GCTCA TGCTA GAGTA TGCAA 1-9a                  145    140    135    130    125    120    115    110
[ 142 ]        ──────────<AA -TTGg gToC- -Cggg cccCc cCTA- gAggT cgAcG gTAT- cGA-T
AD4-4 T7F                AA GTTGA TTGCT TCAAA TTTCT GCTAC TAACT TCAAG CTATG GGAGT 1-9a        105    100    95     90     85     80     75     70     65     60     55     50
[ 142 ]     <ooGcl lGTAl cgAoT TccGG AcTTT gcTT- ----TT gGTTT TCcTT Tcclg TGooA AgGlT
AD4-4 T7F   TTGGC AGTAG TCACT TGAGG ATTTT TTTTC CAATT CGTTT TCATT TTTGT TGTTA AAGCT 1-9a         45     40     35     30     25     20     15     10
[ 142 ]     <gGTll TooAG TGAG- -AlAc AclTT lCC— GlogA ACoAg TGlTC TAT
AD4-4 T7F   CGTAC TTCAG TGAGA CAGAA AAATT GCCAA GCTAA ACTAA TGGTC TAT
```

FIG.19

```
H REG GENE                    5     10    15    20    25    30    35    40    45
[ 278 ]————————————g AATTC CTGGG CTcAA GTGAT CCTCt caTgT caGtC TCCCA AAGTG>
AD16C-T7-A          A AATTC CTGGG CTGAA GTGAT CCTCC AGTCT TGGCC TCCCA AAGTG

H REG GENE    50    55    60    65    70    75    80    85    90    95   100   105
[ 278 ]     CTGGG ATgAC AGGCt TGAGC cACco coCCo gcCCo TcATc AgTtt TToTA tAoaG -oooo>
AD16C-T7-A  CTGGG ATTAC AGGCA TGAGC TACTG AGCCT AGCCT TAATG ATTAA TTTTA GAGTG ATGGC H REG GENE   110   115   120   125   130         140   145   150   155   160
[ 278 ]     ooooA CCT-t A—-oA Attgt TA-gG cooAt AotGA cAAoT TgtAo to-to tottc ttACo>
AD16C-T7-A  TTGTA CCTTC AAGCA ACATA TAGAG TTGAG ACAGA AAATT TCCAT CGTCC CGAGA AAACT H REG GENE 165   170   175   180   185   190   195   200   205   210   215   220
[ 278 ]     tTtCo -gATt tttot ttTtT oooCT GotAA GAott gotTA oTAAo TAoAA tTtoG tAT-->
AD16C-T7-A  GTGCT GCATG GGCCC CGTGT GCCCT GTGAA GATCG CCCTA TTAAC TATAA ATGGG CATTG H REG GENE          225   230   235
[ 278 ]     t-oA- -tcTG t-ctt TToA>
AD16C-T7-A  CACAT GGTTG CCAGC TTCA
```

FIG.20

```
AD16C                                    5    10   15   20
[ 266 ]    ————————————————————————oACgt TtcGA oCCTo tCgTg>
Human-PTP                            TACTG TGTGA GCCTG ACCTC AD16C          25   30   35   40   45   50   55   60   65   70
[ 266 ]    AAG-c -ccGA TTttA GAgtT ootAc -ggGT -gC— ttcAA GggA- ocggg gCToT —go->
Human-PTP  AAGCA CAGGA TTCCA GAAAT GGAAG GATGT GCCTT GTGAA GACAA GTTCT CCTTT GTCTG AD16C          75   80   85   90   95  100  105  110115120  125  130
[ 266 ]    gAAGT -ttlc tACgg GgoGC —oTG GAAAt TttcT GTCTc oAtoT GtgCt tGoAg gTACA>
Human-PTP  CAAGT TCAAA AACTA GAGGC AGCTG GAAAA TACAT GTCTA GAACT GATCC AGCAA TTACA AD16C          135  140  145  150  155  160  165  170  175 180  185  190
[ 266 ]    ACcGt oTCtA AAATT AAtCo tt-oo ggCTo ggCtc ogtAg CTCtg CCTGt -o-oT CcCog>
Human-PTP  ACGGA GTCAA AAATT AAACC GGACC ATCTC TCCAA CTCAA CTCAA CCTGG ACACT CTCTT AD16C          195  200  205   210  215  220  225  230  235  240
[ 266 ]    CoC-t tTcgG gogGC Coo— gAcTg goggA TcocT TcAg- ccCog gAo-t TTcoG AcgCc>
Human-PTP  CTCTG CTGAG TTTGC CTTGT TAATC TTCAA TAGTT TTACC TACCC CAGTC TTTGG AACCT AD16C-T7-A                                             205
[ 33 ]     ————————————————————————————————————————————VPCE Dr>
HPTPAA                                                 VPCE DK RPTP  AA   115  120
[ 33 ]     SgSLf LyKsW D>
Translatio SSSLG LPKCW D
```

FIG.20A

ALIGNMENT OF AD16C-SP6 cDNA WITH AD2-2 SP6 cDNA

```
AD2-2 SP6    40       45        50    55    60    65    70    75    80    85    90
  [ 362 ]   CTtGC  T-TG-  —CCC  AGGCT  GgAGT  GCAaT  GGCoC  AATCc  tGGCT  CACTG  CaAcC  TCCcC>
AD16C-SP6-   CTCGC  TCTGT  CACCC  AGGCT  GAAGT  GCAGT  GGCCC  AATCT  CGGCT  CACTG  CGAGC  TCCAC

AD2-2 SP6  95    100   105   110   115   120   125   130        135   140   145
  [ 362 ]   CTCCC  GaGcT  CAaga  acTTC  TCCTG  CCTCA  —GCC  TC-G-  —TG  AGccG  CTGGG  AtTAC>
AD16C-SP6-   CTCCC  GGGTT  CACTT  CATTC  TCCTG  CCTCA  CTGCC  TCAGC  CTCTG  AGTAG  CTGGG  ACTAC AD2-2 SP6  150   155   160         165   170   175   180   185
  [ 362 ]   AGGCG  CgCgC  CA-CA  oG—  -CgaC  TAA-T  aTTTG  TATTT  TT-GT  AG>
AD16C-SP6-   AGGCG  CCCAC  CACCA  CGTCC  CCTGC  TAATT  TTTTG  TATTT  TTAGT  AG AD2-283       50    55    60    65    70    75    80    85    90    95    100   105
  [ 374 ]   CCaTG  TTcat  CAGGc  TGGTg  TCGAa  CTCCT  GACCT  CGTGA  TCCGC  CCGCC  TcaGC  CtCCC>
AD16C-SP6-   CCGTG  TTGCC  CAGGA  TGGTC  TCGAT  CTCCT  GACCT  CGTGA  TCCGC  CCGCC  TTGGC  CACCC AD2-283    110   115   120   125   130
  [ 374 ]   AAAGt  G-cTG  GGATT  ACAoG  CGTGC>
AD16C-SP6-   AAAGA  GTTTG  GGATT  ACAGG  CGTGC
```

FIG.20B

G2-2Psl-M13F SEQUENCE

Sequence Range: 1 to 251

TGCAG CAATG GCAAC AACGT CTGCA AACTA TTAAC TGGCG AACTA CTTAC TCTAG CTTCC 60
CGGCA ACAAT TAATA GACTG GATGG AGGCG GATAA AGTTG CAGGA CCACT TCTGC GCTCG 120
GCCCT TCCGG CTGGC TGGTT TATTG CTGAT AAATC TGGAG CCGGT CGAGC GTGGG TCTCG 180
CGTAT CATTC GAGCA CTGCG GCCAG ATCGT AAGCC CTCCG TATCG TAGTT ATCTC ACAGC 240
AGGGA GTCAG G                                                       251

FIG.22

G2-2Psl-M13R SEQUENCE

Sequence Range: 1 to 242

TGCAG GAGCG GGGAG GCACG ATGGC CGCTT TGGTC CGGAT CTTTG TGAGG AACCT TACTT 60
CTGTG GTGTG ACATA ATTGG ACAAA CTACC TACAG AGATT TAAAG CTCTA AGGAA ATATA 120
AAATT TTTAA GTGTA TAATG TGTTA AACTA CTGAT TCTAA TTGTT TGTGT ATTTT AGATT 180
CCAAC CCTAT GGAAC CTGAT GAATG GGAGC CAGTG GTGGA ATGCC TTTAA TGAGG AAACC 240
TG                                                                  242

FIG.22A

G2-2Psl1-EcoR1-M13F SEQUENCE

Sequence Range: 1 to 208

TGCAG CAATC TTTCT TATAT ACATG CTTAA TAGAT AGCTA CTTAA AATAA CTTAC ACACG 60
TTTTA GAGTT GCTTG AAAAC TATCT GATCA AGACA TAGTA ATTGA AACCA ATGAA TACAT 120
TATAT AAAGT AAAGG AAAGG AGAAG AGAGG AAAGG GAGGG GAAGA GGAGA GGGAG GGACA 180
AGCGA GAAAG GAAAG GGAAG GGAGA AAA                                    208

FIG.22B

Gen2-2PstI-EcoRI-M13R SEQUENCE

Sequence Range: 1 to 152

```
CTCAC TAAAG GGATC AAGGA ATAAT TTTGA ATTTC AAGTC TTACA TTTAA TAAAT ACATT  60
CATAA GGCTA TAACT ACCAT ACGTT GTGAT TCTC  TGATT AATTT AAAAA TAAAT TAAAA 120
CCTGG AAAGA ATTTT ACCAT TCTAG GAAGC CA                                 152
```

FIG.22C

G2-2PstI-EcoRI-T7 SEQUENCE

Sequence Range: 1 to 338

```
AATCT ATCTT ATATA CATGC TTAAT AGATA GCTAC TTAAA ATAAC TTACA CACGT TTTAG  60
AGTTG CTTGA AAACT ATCTG ATCAA GACAT AGTAA TTGAA ACCAA TGAAT ACATT ATATA 120
AAGTA AGGA  AAGGA GAAGA GAGGA AAGGA GGGGA GAGGA GAGGA GGACA AGCGA GAAAA 180
GGAAG GGAAG GGAGA AAAAG GGGGA AAGGG AGGTA GAGAG AGAGA GAAAA AGTGC TGGTC 240
ATATA GTAAG TGTAC ATTTT AACTT TTTAA GAAAC TACCC TACTC TATTC CAGAG TGATT 300
GTACA TGTGC ATTTT ACTGC ATTAT AGAGA TCATT TTC                          338
```

FIG.22D

G5dPst-M13R SEQUENCE

Sequence Range: 1 to 169

```
TGCAG GAGTG GGGAG GCACG ATGGC CGCTT GGGTC CGGAT CTTTG TGAAG GAACC TTACT  60
TCTGT GTGTC ACATA ATTGG ACAAA CTACC TACAG AGATT TAAAC GTCTA AGGTA AATAT 120
AAAAT TTTTA GTCTA TAGGT TAAAC TACTG ATTCT AATGT TGTGT ATTT             169
```

FIG.22E

G5d Pst-T71 SEQUENCE

Sequence Range: 1 to 209

```
CCCCG GGCTG CAGCA ATGGC AACAA CGTCT GCAAA CTATT AACTG GCGAA CTCAT TCATC  60
TAGCT TCCCG GCAAC AATTA ATGAC TGGAT GGAGG CGGAT AAAGT TGCAG GACCA CTTCT 120
CGCGT GGCCC TTCCG GCTGG CTGGT TTATT GCTGA TAATT GAGCG TGCGA GTGGC TCGCG 180
TATCA TTCGC GACAT GGGCC AGTAG GTAC                                    209
```

FIG.22F

G5dPstI-EcoRI-SP SEQUENCE

Sequence Range: 1 to 272

```
CTTGC CCTTC ATGGA GTCAT ACAGC CGATC AGCAA AATGC AGGGG CTTGT TCTGA ATGCA  60
CTGAA CCAGG TTCAG GAAAG CATTT TCCAG GTCTC CTTTA ACCTC TTTCC TGATG CTTTC 120
CAACA TGTCA TAAGG GCTGT AACTC TTGTA CCTAT CAAAT ACTTT CTGGA GGTGG GGACA 180
CGCTC CGCTC GGTCA TGATG CTGAT CCACT TGGGA ACATC AGTTC TTTCC TCTTC ACTCC 240
AGCTG CATAG AGATC CGAGG ACTCT TGGTC AA                                272
```

FIG.22G

G5dPstI-EcoRI-L7 SEQUENCE

Sequence Range: 1 to 278

```
ACGGC CCAGC TTCCT TCAAA ATGTC TACTG TTCAC GAAAT CCTGT GCAAG CTCAG CTTGG  60
AGGGT GATCA CTCTA CACCC CCAAG TGCAT ATGGG TCTGT CAAAG CCTAT ACTAA CTTTG 120
ATGCT GAGCG GGATG CTTTG AACAT TGAAA CAGCC ATCAA GACCA AAGGT GTGGA TGAGG 180
TCACC ATTGT CAACA TTTTG ACCAA CCGCA GCAAT GACAC GAGAC AGGAT ATTGC CTTCG 240
CCTAC CAGAG AAGGA CCAAA AAAGG AACTT GCATC ACA                         278
```

FIG.22H

ALIGNMENT OF G2-2Pst1 with HUMAN REG GENE (1)

```
H REG GENE      3405  3410   3415  3420  3425  3430  3435   3440  3445  3450  3455
[ 228 ]         —-AG CAATa GCAA- -AgGa aoGgA AAC-A aTAtt ToGC- AA-gg tTTAt TCTtc CTTtg>
G2-2Pst-M13F    AG CAATG GCAAC AACGT CTGCA AACTA TTAAC TGCCG AACTA CTTAC TCTAG CTTCC

H REG GENE            34653470 3475  3480  3485  3490  3495  3500   3505  3510
[ 228 ]               tGtCA gCAtT TctgA GtgTG cAcac AGGCc cAgtg A-TTc CAtG- -tAtT TtTGa G-T-G>
G2-2Pst-M13F          CGGCA ACAAT TAATA GACTG GATGG AGGCC GATAA AGTTG CAGGA CCACT TCTGC GCTCG H REG GEN3515   3520 35253530   3535  3540         3550  3555  3563565        3575  3580
[ 228 ]         aCCac TgCct CTGtC TGG-c ccTTc CccAT AgAaC cGccG CtGGT gGAGC GTGGG TCcCt>
G2-2Pst-M13F    GCCCT TCCGG CTGGC TGGTT TATTG CTGAT AAATC TGGAG CCGGT CGAGC GTGGG TCTCG EXON                                              20    25    30    35    40
[ 124 ]                                       —C TGGca CtGG- aG-ca GTGGG TCcCt>
G2-2Pst-M13F                                   C TGGAG CCGGT CGAGC GTGGG TCTCG H REG GENE      3585  3590  3595  3600   3605  3610  3615   3620  3625  3630
[ 228 ]         gGTcT CcTaC aAGtc CTGGG G-CA- tTGG- -AGCC CcaaG cA—G T-GTT A-aTC ctgGC>
G2-2Pst-M13F    CGTAT CATTC GAG Q CTGGG GCCAG ATGGT AAGCC CTCCG TATCG TAGTT ATCTC ACAGC EXON5           45    50    55    60    65    70    75    80    85    90    95
[ 124 ]         gGTcT CcTaC aAGtc CTGGG G-CA- tTGG- -AGCC CcaaG cA—G T-GTT A-aTC ctgGC>
G2-2Pst-M13F    CGTAT CATTC GAG Q CTGGG GCCAG ATGGT AAGCC CTCCG TATCG TAGTT ATCTC ACAGC H REG GENE3635  3640
[ 228 ]         ActGt GTqAG>
G2-2Pst-M13F    AGGGA GTCAG EXON5           100   105
[ 124 ]         ActGt GTqAG>
G2-2Pst-M13F    AGGGA GTCAG
```

FIG.23

ALIGNMENT OF G2-2Pst with HUMAN REG GENE (2)

```
H REG GENE    3155  3160  3165  3170  3175  3180  3185  3195       3200
[ 194 ]       —AG GAGoc ttGtG GtA-a AaatC tGCTg ctGTa CtGcT CaTT- TG-GG AACCT TA-gT>
G2-2Pst-M13R  AG GAGCG GGGAG GCACG ATGGC CGCTT TGGTC CGGAT CTTTG TGAGG AACCT TACTT H REG GEN3210  3215  3220  3225   3230  3235  3240  3245  3250  3255  3260  3265
[ 194 ]       aTact aaaTa AtATA A-Tat AtcAA CaACt aAtgG tcAgc cAAtG CTaTg ctG-g ATATg>
G2-2Pst-M13R  CTGTG GTGTG ACATA ATTGG ACAAA CTACC TACAG AGATT TAAAG CTCTA AGGAA ATATA H REG GENE    3270  3275   3280  3285  3290  3295  3300  3305       3310  3315  3320
[ 194 ]       AgggT ccT-g GgccA cAAaG acaaA AAaT- CaGga aCcAc TT-TT TaaGT gagaT AcTTT>
G2-2Pst-M13R  AAATT TTTAA GTGTA TAATG TGTTA AACTA CTGAT TCTAA TTGTT TGTGT ATTTT AGATT H REG GEN3325  3330     3335  3340  3345  3350  3355  3360  3365  3370  3375
[ 194 ]       gggtC tCTgT -cAAa tTcAT aAcac ttAtt tctTG GTGGA AToCa gTTAA TGAG>
G2-2Pst-M13R  CCAAC CCTAT GGAAC CTGAT GAATG GGAGC CAGTG GTGGA ATGCC TTTAA TGAG G2-2Pst-M13F          150   155   160      165   170   175   180   185   190   195
[ 130 ]               ——TA aAtCt GgaGC cGG— -TcGA GC-GT GGGTC tCgcG TaTCa TtCgA GcaCT>
EXON5                 TA GAACC GCCGC TGGCA CTGGA GCAGT GGGTC CCTGG TCTCC TACAA GTCCT G2-2Pst-M13F  200    205   210   215   220   225   230   235   240   245   250
[ 130 ]       GGGGC —caG A-tgg tAAGC ccTcc gtATC gTaGt TA-Tc TcacA GCagG gagTC AgG>
EXON5         GGGGC ATTGG AGCCC CAAGC AGTGT TAATC CTGGC TACTG TGTGA GCCTG ACCTC AAG
```

FIG.23A

ALIGNMENT OF G2-2PST-ECOR1-T7 WITH HUMAN REG GENE

```
H REG GENE                         335   340   345   350   355   360   365
[ 132 ]      ———————————————————-AT AGATA tCTAC TTtAt tcgAt TTAoA ttCTG -TTTA>
G2-2PST-ECOR1 T7                     AT AGATA GCTAC TTAAA ATAAC TTACA CACTG TTTTA H REG GENE    370   375   380   385         390   395   400   405   410   415
[ 132 ]      —GTo tTTtA ttA-T ATtTt gTtA- A—T- ccAtT TG-tc CCAAT tcATA tAcT- TAT>
G2A-EP T7    GAGTG CTTGA AAACT ATCTG ATCAG ACATA GTAAT TGAAA CCAAT GAATA CATTA TAT RAT PTP                                                            740   735
[ 82 ]       ———————————————————————————————————————————————<TqAAq qtATT
G2-2PST-ECOR1-M1                                                   TAAAT
ACATT RAT PTP       730   725   720   715         710   705   700   695   690   685
[ 82 ]       <—Ttt otlTA -AAtg tgCA- ggGTT -ocA- ToCoo ToATg gAgoT AAAAA TAcco TAggg
Gen2oEP-Mo   CATAA GGCTA TAACT ACCAT ACGTT GTGAT TTCTC TGATT AATTT AAAAA TAAAT TAAAA RAT PTP      68675 670   665         660   655
[ 82 ]       <CgoGG cAAGA ATgTT ——tg TCTAG GAAG
G2-2PST-ECOR1-M1  CCTGG AAAGA ATTTT ACCAT TCTAG GAAG
```

FIG.23B

```
Human-PTP            270       280  285   290   295   300   305   310   315
[ 166 ]         ——  AcCTG GtGct gTgCT cAC-C cAGgc cgoGG gtgC- cTTtg TgGcC T-cAc tGAtt>
G5dPst-t            AACTG GCGAA CTACT TACTC TAGCT TCCGG CAACA ATTAA TAGAC TGGAT GGAGG Human-PTP  320  325  330  335  340  345  350   355       360   365   370
[ 166 ]    aaG-g AgAGT gGCAt GAtgA CTTCa atG-T CtG-g aTT— GGC— -CTcc aTgAc ccCaa>
G5dPst-t   CGGAT AAAGT TGCAG GACCA CTTCT GCGCT CGGCC CTTCC GGCTG GCTGG TTTAT TGCTG Human-PTP  375  380  385   395  400  405  410  415  420  425   430   435
[ 166 ]    AaAgA aCcGc cGCtG GgGAG CGTGG GTCcC tgGTc TCcTa caAGt cCTGG GG-CA -tTGG>
G5dPst-t   ATAAA TCTGG AGCCG GTGAG CGTGG GTCTC GCGTA TCATT GCAGC ACTGG GGCCA GATGG Human-PTP       440  445  450  455  460  465  470
[ 166 ]    —AGC CCcaa GcA— GTGtT aATCc tggCt ACtGt GtG-A -GcC>
G5dPst-t   TAAGC CCTCC GTATC GTGGT TATCT ACACG ACGGG GAGTA CGGC
```

FIG.23C

```
H REG GENE                        80    85    90       95   100   105   110   115
[ 158 ]    ─────────────── AG GC-Cc ATcaL CagTT T--T- LaLAT aaaga aaAAa aAACC TTAaa>
G5dPsL-M                       AG GCACG ATGGC CGCTT TGGTC CGGaT CTTTG TGAAG GAACC TTACT H REG GENE  120   125   130   135   140   145   150   155   160   165   170   175
[ 158 ]     aLTGT LaGgc AaATA cTaLG ACAAA -TLgL aALAL ALATT cLLAC aTLTc AGaT- -LTLT>
G5dPsL-M    TCTGT GTGTG ACATA ATTGG ACAAA CTACC TACAG AGATT TAAAC GTCTA AGGTA AATAT H REG GENE  180   185   190  1195  200   205   210   215   220
[ 158 ]     ALLLT TTaaA cTGTA TAGaa TLgAL TAaTa AaTaa AAT-T T-aGT ATT>
G5dPsL-M    AAAAT TTTTA GTGTA TAGGT TAAAC TACTG ATTCT AATGT TGTGT ATT G5dPsL-L                125   130   135       140   145   150   155   160   165
[ 118 ]     ───────────TA aALCL GgaGC cGG─── -T-GA GC-GT GGGTC LCgcG TaTCa TLgcA GcaCT>
EXON5                   TA GAACC GCCGC TGGCA CTGGA GCAGT GGGTC CCTGG TCTCC TACAA GTCCT G5dPsL-L    170   175   180   185   190   19S   200   205      210   215   220
[ 118 ]     GGGGC ─caG A-Lgg LAAGC ccTcc gLATC gTGGL TA-Tc T-acA ──cG ACggg gAGLA>
EXON5       GGGGC ATTGG AGCCC CAAGC AGTGT TAATC CTGGC TACTG TGTGA GCCTG ACCTC AAGCA G5dPsL-L
[ 118 ]     C-GG>
EXON5       CAGG
```

FIG.23D

Prot. Gel 18  3/17/94/WB

SEQUENCE LISTING ( 1 ) GENERAL INFORMATION:

( i i i ) NUMBER OF SEQUENCES: 121

( 2 ) INFORMATION FOR SEQ ID NO:1:

( i ) SEQUENCE CHARACTERISTICS:
        ( A ) LENGTH: 21 base pairs
        ( B ) TYPE: nucleic acid
        ( C ) STRANDEDNESS: both
        ( D ) TOPOLOGY: both ( x i ) SEQUENCE DESCRIPTION: SEQ ID NO:1:

CCGATTCCAA CAGACCATCA T                                                        21

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: both
        ( D ) TOPOLOGY: both ( x i ) SEQUENCE DESCRIPTION: SEQ ID NO:2:

CCAACAGACC ATCATTCCAC C                                                        21

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: both
        ( D ) TOPOLOGY: both ( x i ) SEQUENCE DESCRIPTION: SEQ ID NO:3:

CCAAACCGAT TCCAACAGAC C                                                       21

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: both
        ( D ) TOPOLOGY: both ( x i ) SEQUENCE DESCRIPTION: SEQ ID NO:4:

CCTGGGCAAC AAGAGCGAAA ACTCCATCTC                                         30

( 2 ) INFORMATION FOR SEQ ID NO:5:

( i ) SEQUENCE CHARACTERISTICS:
        ( A ) LENGTH: 30 base pairs
        ( B ) TYPE: nucleic acid
        ( C ) STRANDEDNESS: both
        ( D ) TOPOLOGY: both ( x i ) SEQUENCE DESCRIPTION: SEQ ID NO:5:

ATCGCTTGAA CCCGGGAGGC GGAGGTTGCG                                         30

( 2 ) INFORMATION FOR SEQ ID NO:6:

( i ) SEQUENCE CHARACTERISTICS:
        ( A ) LENGTH: 30 base pairs
        ( B ) TYPE: nucleic acid
        ( C ) STRANDEDNESS: both
        ( D ) TOPOLOGY: both ( x i ) SEQUENCE DESCRIPTION: SEQ ID NO:6:

GGGGAGGCTG AGGCAGGAGA ATCGCTTGAA 30

( 2 ) INFORMATION FOR SEQ ID NO:7:

( i ) SEQUENCE CHARACTERISTICS:
        ( A ) LENGTH: 52 base pairs
        ( B ) TYPE: nucleic acid
        ( C ) STRANDEDNESS: both
        ( D ) TOPOLOGY: both ( i x ) FEATURE:
        ( A ) NAME/KEY: misc_feature
        ( C ) OTHER INFORMATION: /label=misc_feature
            / note= Some "N"'s may be absent.

( x i ) SEQUENCE DESCRIPTION: SEQ ID NO:7:

TACTACCAGA CAACCTTAGC CNNNNNNNN NCCGATTCCA ACAGACCATC AT 52

( 2 ) INFORMATION FOR SEQ ID NO:8:

( i ) SEQUENCE CHARACTERISTICS:
        ( A ) LENGTH: 52 base pairs
        ( B ) TYPE: nucleic acid
        ( C ) STRANDEDNESS: both
        ( D ) TOPOLOGY: both ( i x ) FEATURE:
        ( A ) NAME/KEY: misc_feature
        ( C ) OTHER INFORMATION: /label=misc_feature
            / note= Some "N"'s may be absent.

( x i ) SEQUENCE DESCRIPTION: SEQ ID NO:8:

CCGATTCCAA CAGACCATCA TNNNNNNNN NTACTACCAG ACAACCTTAG CC 52

( 2 ) INFORMATION FOR SEQ ID NO:9:

( i ) SEQUENCE CHARACTERISTICS:
        ( A ) LENGTH: 52 base pairs
        ( B ) TYPE: nucleic acid
        ( C ) STRANDEDNESS: both
        ( D ) TOPOLOGY: both ( i x ) FEATURE:
        ( A ) NAME/KEY: misc_feature
        ( C ) OTHER INFORMATION: /label=misc_feature
            / note= Some "N"'s may be absent.

( x i ) SEQUENCE DESCRIPTION: SEQ ID NO:9:

CCACCTTACT ACCAGACAAC CNNNNNNNN NCCAACAGAC CATCATTCCA CC 52

( 2 ) INFORMATION FOR SEQ ID NO:10:

( i ) SEQUENCE CHARACTERISTICS:
        ( A ) LENGTH: 52 base pairs
        ( B ) TYPE: nucleic acid
        ( C ) STRANDEDNESS: both
        ( D ) TOPOLOGY: both ( i x ) FEATURE:
        ( A ) NAME/KEY: misc_feature
        ( C ) OTHER INFORMATION: /label=misc_feature
            / note= Some "N"'s may be absent.

( x i ) SEQUENCE DESCRIPTION: SEQ ID NO:10:

CCAACAGACC ATCATTCCAC CNNNNNNNN NCCACCTTAC TACCAGACAA CC 52

( 2 ) INFORMATION FOR SEQ ID NO:11:

(  i  ) SEQUENCE CHARACTERISTICS:
( A ) LENGTH: 52 base pairs
( B ) TYPE: nucleic acid
( C ) STRANDEDNESS: both
( D ) TOPOLOGY: both (  i x  ) FEATURE:
( A ) NAME/KEY: misc_feature
( C ) OTHER INFORMATION: /label=misc_feature
/ note= Some "N"'s may be absent.

( x i ) SEQUENCE DESCRIPTION: SEQ ID NO:11:

| CCAGACAACC | TTAGCCAAAC | CNNNNNNNN | NCCAAACCGA | TTCCAACAGA | CC | 52 |

( 2 ) INFORMATION FOR SEQ ID NO:12:

(  i  ) SEQUENCE CHARACTERISTICS:
( A ) LENGTH: 52 base pairs
( B ) TYPE: nucleic acid
( C ) STRANDEDNESS: both
( D ) TOPOLOGY: both (  i x  ) FEATURE:
( A ) NAME/KEY: misc_feature
( C ) OTHER INFORMATION: /label=misc_feature
/ note= Some "N"'s may be absent.

( x i ) SEQUENCE DESCRIPTION: SEQ ID NO:12:

| CCAAACCGAT | TCCAACAGAC | CNNNNNNNN | NCCAGACAAC | CTTAGCCAAA | CC | 52 |

( 2 ) INFORMATION FOR SEQ ID NO:13:

(  i  ) SEQUENCE CHARACTERISTICS:
( A ) LENGTH: 1443 base pairs
( B ) TYPE: nucleic acid
( C ) STRANDEDNESS: both
( D ) TOPOLOGY: both ( x i ) SEQUENCE DESCRIPTION: SEQ ID NO:13:

| CGCTGCGCCC | AGGCTGGCTC | TGGAAAGCCT | GTGCGGTCCT | GGCAGGAAGC | CCGGCCCGTG | 60 |
| GAGCAGGTTT | TCGTTCTGCT | TCAGCAATAA | ATAAGGGTGA | CCACAGGGAC | TTTGCTTTTG | 120 |
| GTTTCCTTTC | CTGTGAAAAG | GTTGGTTTTA | AAGTGAGATA | CACTTTTCCG | TAGAACAAGT | 180 |
| GTTCTATCTT | TAAAAACCCA | AATTGCAGCA | CCGTGGATTA | CTGGTCTCAG | AACAACTCAT | 240 |
| TGCGCATCAG | ATTTGACTCT | CTGATTTTCT | GTCTATTGGC | CAAATTGCCC | TTTAACTGCA | 300 |
| CCTGAATCCT | TTGTGTACTG | ATGCCTTTGA | GCTGGGCACC | TTGGGAGAGT | GTTGTGTTGC | 360 |
| TGTTTACGGT | TCTTCCTTCC | CCTTGCTAAT | TACAGTCTCT | GGTGCCCAGC | AAGCCCTTT | 420 |
| GGCTTCCTTC | CGTGACTGGT | CACGTTGTCT | GCCTGGGCTC | AGCGTGGACC | TGCCCCATGC | 480 |
| TGCAGAACCT | GGCCTCACCT | GGACTTTTAC | TAGAATTGCC | AGCTTCTCAA | CTTAGCAGAT | 540 |
| CATCACTCAT | GCGGGCACAA | GCAAAGATCA | ACACTTTCTT | TTTTGGTAAG | CTTGAGTTTT | 600 |
| ACAAGTTATT | TTTTGGTGAT | GCGTAAGACA | TTGCAGTGGG | AAACCATTCA | ACTTGAGTTT | 660 |
| ATTGGAGTTT | GCTGTTGTAG | CAGGTTTTAA | CTCAGGAACA | ACTCTTGTCT | GATCTCTCGC | 720 |
| CCCTCTGCCG | GGACTACATT | ACTGTCTCTC | GGAGCCGGTA | GCGTTGCTGT | CGAGTCCAG | 780 |
| GACTATCTCT | GCAGACTGCT | ATGCTCAGAT | CGAAGTATTT | CACAAGAATA | CTTGTGTTTT | 840 |
| TAACAGCCCT | TCCCCTGGAC | GGTGCGCCAT | GAGGGCCTCA | TGTTACGCAT | TGCCTTTTCT | 900 |
| TTCTGTGGAT | CCAGTATCTT | CCTCGGCTTT | TTAGGGAGCA | GGAAAAATGC | GTCTGAGAGC | 960 |
| AACTCTTTTT | AAAAACCTGC | CCTGTTGTAT | ATAACTGTGT | CTGTTTCACC | GTGTGACCTC | 1020 |
| CAAGGGGGTG | GGAACTTGAT | ATAAACGTTT | AAAGGGGCCA | CGATTTGCCC | GAGGGTTACT | 1080 |

| | | | | | |
|---|---|---|---|---|---|
| CCTTTGCTCT | CACCTTGTAT | GGATGAGGAG | ATGAAGCCAT | TTCTTATCCT | GTAGATGTGA | 1140
| AGCACTTTCA | GTTTTCAGCG | ATGTTGGAAT | GTAGCATCAG | AAGCTCGTTC | CTTCACACTC | 1200
| AGTGGCGTCT | GTGCTTGTCC | ACATGCGCTG | GGCGTCTGGA | CCTTGAATGC | CTGCCCTGGT | 1260
| TGTGTGGACT | CCTTAATGCC | AATCATTTCT | TCACTTCTCT | GGACACCCAG | GGCGCCTGTT | 1320
| GACAAGTGTG | GAGAAACTCC | TAATTAAAT | GTCACAGACA | ATGTCCTAGT | GTTGACTACT | 1380
| ACAATGTTGA | TGCTACACTG | TTGTAATTAT | TAAACTGATT | ATTTTCTTA | TGTCAAAAAA | 1440
| AAA | | | | | | 1443

( 2 ) INFORMATION FOR SEQ ID NO:14:

( i ) SEQUENCE CHARACTERISTICS:
        ( A ) LENGTH: 213 base pairs
        ( B ) TYPE: nucleic acid
        ( C ) STRANDEDNESS: both
        ( D ) TOPOLOGY: both ( x i ) SEQUENCE DESCRIPTION: SEQ ID NO:14:

| | | | | | |
|---|---|---|---|---|---|
| GATCCCGTTT | GACAGGTGTA | CCGCCCCAGT | CAAACTCCCC | ACCTGGCACT | GTCCCCGGAG | 60
| CGGTCGCGCC | CGCGCGACCA | CGGAGCTCTG | GGCGCCAGAA | GCGAGAGCCC | CTCGCTGCCC | 120
| CCCGCCTCAC | CGGGTAGTGA | AAAAACGATG | AGAGTAGTGG | TATTTCACCG | GCGGCCCGCG | 180
| AGGACCCCCG | CCCGACCCAG | TGCGGAACGG | GGG | | | 213

( 2 ) INFORMATION FOR SEQ ID NO:15:

( i ) SEQUENCE CHARACTERISTICS:
        ( A ) LENGTH: 358 base pairs
        ( B ) TYPE: nucleic acid
        ( C ) STRANDEDNESS: both
        ( D ) TOPOLOGY: both ( x i ) SEQUENCE DESCRIPTION: SEQ ID NO:15:

| | | | | | |
|---|---|---|---|---|---|
| CACCGTGGAT | TACTGGTCTC | AGAACAACTC | ATTGCGCATC | AGATTTACTC | TCTGANTTTC | 60
| TGTCTATTGG | CCATTGCCCT | TTAACTGCAC | CTGAATCCTT | TGTGTACTGA | TCCTTTGAGC | 120
| TGGGCACCTT | GGGAGAGTGT | TGTGTTGCTG | TTTACGGTTC | TTCCTTCCCC | TTGCTAATTA | 180
| CAGTCTCTGG | TGCCAGCAAG | CCCCTTTGGC | TTCCTTCCGT | GACTGGTCAC | GTTGTCTGCC | 240
| TGGGCCAGCG | TGGCCCCATG | CTGCAGAACC | TGGCCTCAGG | ACTTTTCACT | AGAATTGCCC | 300
| TTCCTCAACT | TAGCAGATCA | TTCACTCATG | CGGGCACAAG | CAAAGATCAA | CACTTTCT | 358

( 2 ) INFORMATION FOR SEQ ID NO:16:

( i ) SEQUENCE CHARACTERISTICS:
        ( A ) LENGTH: 378 base pairs
        ( B ) TYPE: nucleic acid
        ( C ) STRANDEDNESS: both
        ( D ) TOPOLOGY: both ( x i ) SEQUENCE DESCRIPTION: SEQ ID NO:16:

| | | | | | |
|---|---|---|---|---|---|
| CATTGCAGCT | CAGCATGGCT | CAGACCAGCT | CATACTTCAT | GCTGATCTCC | TGCCTGATGT | 60
| TTCTGTCTCA | GAGCCAAGGC | CAAGAGGCCC | AGACAGAGTT | GCCCCAGGCC | CGGATCAGCT | 120
| GCCCAGAAGG | CACCAATGCC | TATCGCTCCT | ACTGCTACTA | CTTTAATGAA | GACCGTGAGA | 180
| CCTGGGTTGA | TGCAGATCTC | TATTGCCAGA | ACATGAATTC | GGGCAACCTG | GTGTCTGTGC | 240
| TNCCAGGCC | GAGGGTGCCT | TTGTGGCCTC | ACTGATTAAG | GAGAGTGGCA | CTGATGACTT | 300
| CAATGTCTGG | ATTGGCCTCC | ATGACCCCAA | AAAGAACCGC | CGCTGGCACT | GGAGCAGTGG | 360
| GTCCCTGGTC | TCCTACAA | | | | | 378

( 2 ) INFORMATION FOR SEQ ID NO:17:

( i ) SEQUENCE CHARACTERISTICS:
        ( A ) LENGTH: 142 base pairs
        ( B ) TYPE: nucleic acid
        ( C ) STRANDEDNESS: both
        ( D ) TOPOLOGY: both ( x i ) SEQUENCE DESCRIPTION: SEQ ID NO:17:

```
TTTTCCTAGA   ACAAGGGTTC   TATCTTTAAA   AACCCAAATT   GCAGCACCGC   TGGTCTCAGA        60
ACAACTCATT   GCGCATCAGA   TTTACTCTCT   GATTTTTCTG   TCTATTTGGC   CAAATTGCCC       120
TTTTAACTGC   ACCTGAATCT   TT                                                     142
```

( 2 ) INFORMATION FOR SEQ ID NO:18:

( i ) SEQUENCE CHARACTERISTICS:
        ( A ) LENGTH: 151 base pairs
        ( B ) TYPE: nucleic acid
        ( C ) STRANDEDNESS: both
        ( D ) TOPOLOGY: both ( x i ) SEQUENCE DESCRIPTION: SEQ ID NO:18:

```
TTCTCCTATA   GAGATTGTTG   ATTTGCCTCT   TAGCAAGAGA   TTCATTGCAG   CTCAGCATGG        60
CTCAGACCAG   CTCATACTTC   ATGCTGATCT   CCTGCCTGAT   GTTTCTGTCT   CAGAGCCAAG       120
GTAAGATCTC   TTTTCCACCA   ACCAACTCTT   T                                         151
```

( 2 ) INFORMATION FOR SEQ ID NO:19:

( i ) SEQUENCE CHARACTERISTICS:
        ( A ) LENGTH: 75 base pairs
        ( B ) TYPE: nucleic acid
        ( C ) STRANDEDNESS: both
        ( D ) TOPOLOGY: both ( x i ) SEQUENCE DESCRIPTION: SEQ ID NO:19:

```
CACCGTGGAT   TACTGGTCTC   AGAACAACTC   ATTGCGCATC   AGATTACTC   TCTGATTTTT         60
CTGTCTATTG   GCCAA                                                                75
```

( 2 ) INFORMATION FOR SEQ ID NO:20:

( i ) SEQUENCE CHARACTERISTICS:
        ( A ) LENGTH: 77 base pairs
        ( B ) TYPE: nucleic acid
        ( C ) STRANDEDNESS: both
        ( D ) TOPOLOGY: both ( x i ) SEQUENCE DESCRIPTION: SEQ ID NO:20:

```
CATTGCAGCT   CAGCATGGCT   CAGACCAGCT   CATACTTCAT   GCTGATCTCC   TGCCTGATGT        60
TTCTGTCTCA   GAGCCAA                                                              77
```

( 2 ) INFORMATION FOR SEQ ID NO:21:

( i ) SEQUENCE CHARACTERISTICS:
        ( A ) LENGTH: 130 base pairs
        ( B ) TYPE: nucleic acid
        ( C ) STRANDEDNESS: both
        ( D ) TOPOLOGY: both ( x i ) SEQUENCE DESCRIPTION: SEQ ID NO:21:

```
GAATTCCTGG   GCTCAAGTGA   TCCTCTCATG   CAGTCTCCCA   AAGTGCTGGG   ATGACAGGCT        60
TGAGCCACCA   CACCAGGCCC   ATCATCAGTT   TATATAAAGA   AAAAAAAACC   TTAAAATTGT       120
```

| TAGGCAAATA | 1 3 0 |

( 2 ) INFORMATION FOR SEQ ID NO:22:

( i ) SEQUENCE CHARACTERISTICS:
        ( A ) LENGTH: 144 base pairs
        ( B ) TYPE: nucleic acid
        ( C ) STRANDEDNESS: both
        ( D ) TOPOLOGY: both ( x i ) SEQUENCE DESCRIPTION: SEQ ID NO:22:

| GGAGTTTTGT | CATCAGGCCA | GCCTCATCCC | GAGGTCTCCT | CCACCATTGG | CCGTAGCCAG | 6 0 |
| CAGGTTCAGT | GCTCACCGAA | AGTAAAATCC | CCTCCTTCAG | CAAGAATAAA | GCAATATACA | 1 2 0 |
| CCTTAGGTTC | CACTAAGTAA | CATA | | | | 1 4 4 |

( 2 ) INFORMATION FOR SEQ ID NO:23:

( i ) SEQUENCE CHARACTERISTICS:
        ( A ) LENGTH: 96 base pairs
        ( B ) TYPE: nucleic acid
        ( C ) STRANDEDNESS: both
        ( D ) TOPOLOGY: both ( x i ) SEQUENCE DESCRIPTION: SEQ ID NO:23:

| GTTCTGTGAG | TCTCAATTTG | TTCCTTCTTG | GAAGCTGTCT | GGTGAATCTG | TTGGTCCCTC | 6 0 |
| TGTCTGCTAT | TCTGTCTGTC | TGTATGTCTG | TCCATG | | | 9 6 |

( 2 ) INFORMATION FOR SEQ ID NO:24:

( i ) SEQUENCE CHARACTERISTICS:
        ( A ) LENGTH: 105 base pairs
        ( B ) TYPE: nucleic acid
        ( C ) STRANDEDNESS: both
        ( D ) TOPOLOGY: both ( x i ) SEQUENCE DESCRIPTION: SEQ ID NO:24:

| GTTGATTTGC | CTCTTAAGCA | AGAGATTCAT | TGCAGCTCAG | CATGGCTCAG | ACCAGCTCAT | 6 0 |
| ACTTCATGCT | GATCTCCTGC | CTGATGTTTC | TGTCTCAGAG | CCAAG | | 1 0 5 |

( 2 ) INFORMATION FOR SEQ ID NO:25:

( i ) SEQUENCE CHARACTERISTICS:
        ( A ) LENGTH: 215 base pairs
        ( B ) TYPE: nucleic acid
        ( C ) STRANDEDNESS: both
        ( D ) TOPOLOGY: both ( x i ) SEQUENCE DESCRIPTION: SEQ ID NO:25:

| ACTACCAAAC | CTGCATTAAA | AAATTTCGGT | TGGTCGACCT | CGGAGCAGAA | CCCAACCTCC | 6 0 |
| GAGCAGTACA | TGCTAAGACT | TCACCAGTCA | AAGCGAACGT | ACTATACTCA | ATTGATCCAA | 1 2 0 |
| TAACTTGACC | AACGGAACAA | GTTACCCTAT | AACAGCGCAA | TCCTATTCTA | GAGTCCATAT | 1 8 0 |
| CAACAGGGTT | TACGACCTCG | ATGTTGGATC | AGGAC | | | 2 1 5 |

( 2 ) INFORMATION FOR SEQ ID NO:26:

( i ) SEQUENCE CHARACTERISTICS:
        ( A ) LENGTH: 232 base pairs
        ( B ) TYPE: nucleic acid
        ( C ) STRANDEDNESS: both
        ( D ) TOPOLOGY: both ( x i ) SEQUENCE DESCRIPTION: SEQ ID NO:26:

| ACCACGGAGC | TCTGGGCGCC | AGAAGCGAGA | GCCCCTCGCT | GCCCCCCGCC | TCACCGGGTA | 6 0 |

```
GTGAAAAAAC  GATGAGAGTA  GTGGTATTTC  ACCGGCGGCC  CGCGAGGACC  CCCGCCCGAC      120

CCAGTGCGGA  ACGGGGGAGT  AGTCCCGGGG  GCTCACTTAT  TCTACATTAG  TCTCACGTGC      180

AGACTAGAGT  CAAGCTCAAC  AGGGTCTTCT  TTCCCGCTGA  TTCCGCCAAG  TC              232
```

( 2 ) INFORMATION FOR SEQ ID NO:27:

( i ) SEQUENCE CHARACTERISTICS:
        ( A ) LENGTH: 112 base pairs
        ( B ) TYPE: nucleic acid
        ( C ) STRANDEDNESS: both
        ( D ) TOPOLOGY: both ( x i ) SEQUENCE DESCRIPTION: SEQ ID NO:27:

```
AGTTTCACTC  TGTTGCCCAG  GCTGGAGTGC  AATGGCACAA  TCCTGGCTCA  CTGCAACCTC      60

CGCCTCCCGA  GCTCAAGCAA  TTCTCCTGCC  TCAGCCTCGT  GAGCCGCTGG  GA              112
```

( 2 ) INFORMATION FOR SEQ ID NO:28:

( i ) SEQUENCE CHARACTERISTICS:
        ( A ) LENGTH: 120 base pairs
        ( B ) TYPE: nucleic acid
        ( C ) STRANDEDNESS: both
        ( D ) TOPOLOGY: both ( x i ) SEQUENCE DESCRIPTION: SEQ ID NO:28:

```
AGATCTCGCT  CTGTCACCCA  GGCTGAAGTG  CAGTGGCCCA  ATCTCGGCTC  ACTGCGAGCT      60

CCACCTCCCG  GGTTCACTTC  ATTCTCCTGC  CTCACTGCCT  CAGCCTCTGA  GTAGCTGGGA      120
```

( 2 ) INFORMATION FOR SEQ ID NO:29:

( i ) SEQUENCE CHARACTERISTICS:
        ( A ) LENGTH: 594 base pairs
        ( B ) TYPE: nucleic acid
        ( C ) STRANDEDNESS: both
        ( D ) TOPOLOGY: both ( x i ) SEQUENCE DESCRIPTION: SEQ ID NO:29:

```
GAGGCGTATT  ATACCATGCT  CCATCTGCCT  ACGACAAACA  GACCTAAAAT  CGCTCATTGC      60

ATACTCTTCA  ATCAGCCACA  TAGCCCTCGT  AGTAACAGCC  ATTCTCATCC  AAACCCCCTG      120

AAGCTTCACC  GGCGCAGTCA  TTCTCATAAT  CGCCCACGGG  CTTACATCCT  CATTACTATT      180

CTGCCTAGCA  AACTCAAACT  ACGAACGCAC  TCACAGTCGC  ATCATAATCC  TCTCTCAAGG      240

ACTTCAAACT  CTACTCCCAC  TAATAGCTTT  TTGATGACTT  CTAGCAAGCC  TCGCTAACCT      300

CGCCTTACCC  CCCACTATTA  ACCTACTGGG  AGAACTCTCT  GTGCTAGTAA  CCACGTTCTC      360

CTGATCAAAT  ATCACTCTCC  TACTTACAGG  ACTCAACATA  CTAGTCACAG  CCCTATACTC      420

CCTCTACATA  TTTACCACAA  CACAATGGGG  CTCACTCACC  CACCACATTA  ACAACATAAA      480

ACCCTCATTC  ACACGAGAAA  ACACCCTCAT  GTTCATACAC  CTATCCCCCA  TTCTCCTCCT      540

ATCCCTCAAC  CCCGACATCA  TTACCGGGTT  TTCCTCTTAA  AAAAAAAAAA  AAAA            594
```

( 2 ) INFORMATION FOR SEQ ID NO:30:

( i ) SEQUENCE CHARACTERISTICS:
        ( A ) LENGTH: 98 amino acids
        ( B ) TYPE: amino acid
        ( D ) TOPOLOGY: linear ( x i ) SEQUENCE DESCRIPTION: SEQ ID NO:30:

```
Glu  Ala  Tyr  Tyr  Thr  Met  Leu  His  Leu  Pro  Thr  Thr  Asn  Arg  Pro  Lys
 1              5                        10                       15
```

| Ile | Ala | His | Cys | Ile | Leu | Phe | Asn | Gln | Pro | His | Ser | Pro | Arg | Ser | Asn |
|---|---|---|---|---|---|---|---|---|---|---|---|---|---|---|---|
| | | | 20 | | | | | 25 | | | | | 30 | | |

| Ser | His | Ser | His | Pro | Asn | Pro | Leu | Lys | Leu | His | Arg | Arg | Ser | His | Ser |
|---|---|---|---|---|---|---|---|---|---|---|---|---|---|---|---|
| | | 35 | | | | | 40 | | | | | 45 | | | |

| His | Asn | Arg | Pro | Arg | Ala | Tyr | Ile | Leu | Ile | Thr | Ile | Leu | Pro | Ser | Lys |
|---|---|---|---|---|---|---|---|---|---|---|---|---|---|---|---|
| | 50 | | | | | 55 | | | | | 60 | | | | |

| Leu | Lys | Leu | Arg | Thr | His | Ser | Gln | Ser | His | His | Asn | Pro | Leu | Ser | Arg |
|---|---|---|---|---|---|---|---|---|---|---|---|---|---|---|---|
| 65 | | | | | | 70 | | | | | 75 | | | | 80 |

| Thr | Ser | Asn | Ser | Thr | Pro | Thr | Asn | Ser | Phe | Leu | Met | Thr | Ser | Ser | Lys |
|---|---|---|---|---|---|---|---|---|---|---|---|---|---|---|---|
| | | | | 85 | | | | | 90 | | | | | 95 | |

Pro Arg ( 2 ) INFORMATION FOR SEQ ID NO:31:

( i ) SEQUENCE CHARACTERISTICS:
        ( A ) LENGTH: 554 base pairs
        ( B ) TYPE: nucleic acid
        ( C ) STRANDEDNESS: both
        ( D ) TOPOLOGY: both ( x i ) SEQUENCE DESCRIPTION: SEQ ID NO:31:

```
ATACCATGCT CCATCTGCCT ACGACAAACA GACCTAAAAT CGCTCATTGC ATACTCTTCA      60
ATCAGCACAT AGCCCTCGTA GTAACAGCCA TTCTCATCCA AACCCCTGA AGCTTCACCG      120
GCGCAGTCAT TCTCATAATC GCCCACGGGC TTACATCCTC ATTACTATTC TGCCANCAAA     180
CTCAAACTAC GAACGCACTC ACAGTCGCAT CATAATCTCT CTCAAGGACT TCAAACTCTA     240
CTCCCAAGCT TTGTGACTTC TAGCAACCTC GCTAACCTCG CCTTACCCCC ACTATTAACT     300
ACTGGGAGAA TGTGCTAGTA ACCACGTTCT CCTTCAAATA TCACTCTCCT ACTTACAGGA     360
CTCAACATAC TAGTCCAGCC CTATACTCCC TCTACATATT TACCACAACA CAATGGGCTC     420
ACTCACCCAC CACATTAACC ATAAAACCCT CATTCACACG AGAAAACACC CTCATGTTCA     480
TACACCTATC CCCCATTCTT CCTATCCCTC AACCCCGACA TCAACGGGT TTCCTCTTAA      540
AAAAAAAAAA AAAA                                                      554
```

( 2 ) INFORMATION FOR SEQ ID NO:32:

( i ) SEQUENCE CHARACTERISTICS:
        ( A ) LENGTH: 590 base pairs
        ( B ) TYPE: nucleic acid
        ( C ) STRANDEDNESS: both
        ( D ) TOPOLOGY: both ( x i ) SEQUENCE DESCRIPTION: SEQ ID NO:32:

```
ATGCCTATCG CTCCTACTGC TACTACTTTA ATGAAGACCG TGAGACCTGG GTTGATGCAG      60
ATCTCTATTG CCAGAACATG AATTCGGGCA ACCTGGTGTC TGTGCTCACC CAGGCCGAGG     120
GTGCCTTTGT GGCCTCACTG ATTAAGGAGA GTGGCACTGA TGACTTCAAT GTCTGGATTG     180
GCCTCCATGA CCCCAAAAAG AACCGCCGCT GGCACTGGAG CAGTGGGTCC CTGGTCTCCT     240
ACAAGTCCTG GGGCATTGGA GCCCCAAGCA GTGTTAATCC TGGCTACTGT GTGAGCCTGA     300
CCTCAAGCAC AGGATTCCAG AAATGGAAGG ATGTGCCTTG TGAAGACAAG TTCTCCTTTG     360
TCTGCAAGTT CAAAAACTAG AGGCAGCTGG AAAATACATG TCTAGAACTG ATCCAGCAAT     420
TACAACGGAG TCAAAAATTA AACCGGACCA TCTCTCCAAC TCAACTCAAC CTGGACACTC     480
TCTTCTCTGC TGAGTTTGCC TTGTTAATCT TCAATAGTTT TACCTACCCC AGTCTTTGGA     540
ACCTTAAATA ATAAAAATAA ACATGTTTCC ACTAAAAAAA AAAAAAAAA                590
```

( 2 ) INFORMATION FOR SEQ ID NO:33:

( i ) SEQUENCE CHARACTERISTICS:
        ( A ) LENGTH: 466 base pairs
        ( B ) TYPE: nucleic acid
        ( C ) STRANDEDNESS: both
        ( D ) TOPOLOGY: both ( x i ) SEQUENCE DESCRIPTION: SEQ ID NO:33:

```
CTTCTTTTTC  AGGCCAAGAG  GCCCAGACAG  AGTTGCCCCA  GGCCCGGATC  AGCTGCCCAG      60
AAGGCACCAA  CCTATCGCTC  CTACTGCTAC  TACTTTAATG  AAGACCGCGA  GACCTGGGTT     120
GATGCAGTGT  GAGTGAGGAG  AGCGTGTGGG  AAGGGAGACT  CATGAAGGGA  GGGGAAGCTG     180
CCACTCTCCA  GTGTTCAGTG  GCGCAATGAG  ATGAGACTGA  ACCCCTTTAT  ACTATCATCA     240
GCCCCAAACT  TTCCAATCTA  CTTTATCCCA  TTATTCAGCA  CATTCCCAGC  ACAAAGAACC     300
TGGTGGGTGA  CAGCATCATC  ACGGACATTA  CTCTGCTGTC  CTTTTTCACC  CTCCTCTTGG     360
AGGACTCAGT  ATATCCGTCA  CAACCCTCCA  CTGAGTCTCC  ATTTTCTTCT  GCAACAGCTC     420
TATTGCCAGA  ACATGAATTC  GGGCAACCTG  GTGTCTGTGC  TCACCC                    466
```

( 2 ) INFORMATION FOR SEQ ID NO:34:

( i ) SEQUENCE CHARACTERISTICS:
        ( A ) LENGTH: 501 base pairs
        ( B ) TYPE: nucleic acid
        ( C ) STRANDEDNESS: both
        ( D ) TOPOLOGY: both ( x i ) SEQUENCE DESCRIPTION: SEQ ID NO:34:

```
CGTATTATAC  CATGCTCCAT  CTGCCTACGA  CAAACAGACC  TAAAATCGCT  CATTGCATAC      60
TCTTCAATCA  GCCACATAGC  CCTCGTAGTA  ACAGCCATTC  TCATCCAAAC  CCCCTGAAGC     120
TTNCCGGCGC  AGTCATTCTC  ATAATCGCCC  ACGGGCTTAC  ATCCTCATTA  CTATTCTGCC     180
TAGCAAACTC  AAACTACGAA  CGCACTCACA  GTCGCATCAT  AATCCTCTCT  CAAGGACTTC     240
AAACTCTACT  CCCACTAATA  GCTTTTTGAT  GACTTCTAGC  AAGCCTCGCT  AACCTCGCCT     300
TACCCCCCAC  TATTAACCTA  CTGGGAGAAC  TCTCTGTGCT  AGTAACCACG  TTCTCCTGAT     360
CAAATATCAC  TCTCCTACTT  ACAGGACTCA  ACATACTAGT  CACAGCCCTA  TACTCCCTCT     420
ACATATTTAC  CACAACACAA  TGGGGCTCAC  TCACCCACCA  CATTAACAAC  ATAAAACCCT     480
CATTCACACG  AGAAAACACC  C                                                  501
```

( 2 ) INFORMATION FOR SEQ ID NO:35:

( i ) SEQUENCE CHARACTERISTICS:
        ( A ) LENGTH: 372 base pairs
        ( B ) TYPE: nucleic acid
        ( C ) STRANDEDNESS: both
        ( D ) TOPOLOGY: both ( x i ) SEQUENCE DESCRIPTION: SEQ ID NO:35:

```
GTTCTTAGTC  TATCTCTTGT  ACAAACGATG  TGCTTTGAAG  ATGTTAGTGT  ATAACAATTG      60
ATGTTTGTTT  TCTGTTTGAT  TTTAAACAGA  GAAAAAATAA  AAGGGGGTAA  TAGCTCCTTT     120
TTTCTTCTTT  CTTTTTTTTT  TTCATTTCAA  AATTGCTGCC  AGTGTTTTCA  ATGTAGGACA     180
ACAGAGGGAT  ATGCTGTAGA  GTGTTTTTAT  TGCCTAGTTG  ACAAAGCTGC  TTTTGAATGC     240
TGGTGGTTCT  ATTCCTTTGC  ACATCACGAC  ATTTTATAAT  CATAGTTAAA  TCGTATATGA     300
CAAAAATGCT  CTGATCTGAT  GCCAAAGGTC  AATTCAGTGT  ATATAACCTG  AACACACTCA     360
TCCATTGCGT  TT                                                             372
```

(2) INFORMATION FOR SEQ ID NO:36:

(i) SEQUENCE CHARACTERISTICS:
    (A) LENGTH: 68 amino acids
    (B) TYPE: amino acid
    (D) TOPOLOGY: linear (xi) SEQUENCE DESCRIPTION: SEQ ID NO:36:

| Met | Phe | Val | Phe | Cys | Leu | Ile | Leu | Asn | Arg | Glu | Lys | Ile | Lys | Gly | Gly |
|---|---|---|---|---|---|---|---|---|---|---|---|---|---|---|---|
| 1 | | | | 5 | | | | | 10 | | | | | 15 | |

| Asn | Ser | Ser | Phe | Phe | Leu | Leu | Ser | Phe | Phe | Phe | Ser | Phe | Gln | Asn | Cys |
|---|---|---|---|---|---|---|---|---|---|---|---|---|---|---|---|
| | | | 20 | | | | | 25 | | | | | 30 | | |

| Cys | Gln | Cys | Phe | Gln | Cys | Arg | Thr | Thr | Glu | Gly | Tyr | Ala | Val | Glu | Cys |
|---|---|---|---|---|---|---|---|---|---|---|---|---|---|---|---|
| | | 35 | | | | | 40 | | | | | 45 | | | |

| Phe | Tyr | Cys | Leu | Val | Asp | Lys | Ala | Ala | Phe | Glu | Cys | Trp | Trp | Phe | Tyr |
|---|---|---|---|---|---|---|---|---|---|---|---|---|---|---|---|
| | 50 | | | | | 55 | | | | | 60 | | | | |

| Ser | Phe | Asp | Thr |
|---|---|---|---|
| 65 | | | |

(2) INFORMATION FOR SEQ ID NO:37:

(i) SEQUENCE CHARACTERISTICS:
    (A) LENGTH: 377 base pairs
    (B) TYPE: nucleic acid
    (C) STRANDEDNESS: both
    (D) TOPOLOGY: both (xi) SEQUENCE DESCRIPTION: SEQ ID NO:37:

| ACTGTCTCCC | CCTTTGATAG | GGACACTAAA | GTGGTCTGTA | CTTGGGTAGA | GGATGGCANG | 60 |
| TTAAGAATTA | AAATCGTCTG | GGTGCGGTCT | GCACGCTTGT | AATCCCAGCA | CTTTGGGAGG | 120 |
| CTGAGGCGGG | CGGATCACCT | GAGGTCAGGA | GTTCGACACC | AGCCTGATGA | ACATGGAGAA | 180 |
| ACCCCATCTC | TACTAAAAAT | ACAAATATTA | GCTGGGCGTT | GTCGCGCGCC | TGTAATCCCA | 240 |
| GCGGCTCACG | AGGCTGAGGC | AGGAGAATTG | CTTGAGCTCG | GGATGGCGGA | GGTTGCAGTG | 300 |
| AGCCAGGATT | GTGCCATTGC | ACTCCAGCCT | GGGCAACAAG | AGTGAAACTC | TGTCTCAAAA | 360 |
| AAAAAAAAAA | AAAAAAA | | | | | 377 |

(2) INFORMATION FOR SEQ ID NO:38:

(i) SEQUENCE CHARACTERISTICS:
    (A) LENGTH: 1480 base pairs
    (B) TYPE: nucleic acid
    (C) STRANDEDNESS: both
    (D) TOPOLOGY: both (xi) SEQUENCE DESCRIPTION: SEQ ID NO:38:

| GCGTAAACAC | ATTTTTGTTC | TTAGTCTATC | TCTTGTACAA | ACGATGTGCT | TTGAAGATGT | 60 |
| TAGTGTATAA | CAATTGATGT | TTGTTTTCTG | TTTGATTTTA | AACAGAGAAA | AAATAAAAGG | 120 |
| GGGTAATAGC | TCCTTTTTTC | TTCTTTCTTT | GATTTTAAAC | AGAGAAAAA | TAAAAGGGGG | 180 |
| TAATAGCTCC | TTTTTTCTTC | TTTCTTTTTT | TTTTTTCATT | TCAAAATTGC | TGCCAGTGTT | 240 |
| TTCAATGATG | GACAACAGAG | GGATATGCTG | TAGAGTGTTT | TATTGCCTAG | TTGACAAAGC | 300 |
| TGCTTTGAAT | GCTGGTGGTT | CTATTCCTTT | GACACTACGC | ACTTTTATAA | TACATGTTAA | 360 |
| TGCTATAGGA | CAAGATGCTC | TGATTCCTGA | GTGCCAGAGG | TTCAATTCAG | TGTATATAAC | 420 |
| TGAACACACT | CATCCATTTG | TGCTTTTGTT | TTTTTTATGG | TGGCTTAAAG | GTAAAGAGCC | 480 |
| CATCCTTTGC | AAGTCATCCA | TGTTGTTACT | TAGGCATTTT | ATCTTGGCTC | AAATTGTTGG | 540 |

-continued

| | | | | | |
|---|---|---|---|---|---|
| AAGAATGGTG | GCTTGTTTCA | TGGTTTTTGT | ATTTGTGTCT | AATGCACGTT | TTAACATGAT | 600 |
| AGACGCAATG | CATTGTGTAG | CTAGTTTTCT | GGAAAAGTCA | ACTCTTTTAG | GAATTGTTTT | 660 |
| TCAGATCTTC | AATAAATTTT | TTCTTTAAAT | TTCAAAGAAC | AATGTGCTTG | TGTTGATGCC | 720 |
| TTACAAAAAC | CATTGTATAT | TTGTGTATTC | CTTCTTGTAT | TTAGACAGTG | GTTTTTCAGG | 780 |
| TGCGTGCTTT | GTTTCTGGT | ATGGCCTTTA | TGGAATGAGA | CGCTTTAGCT | TTGGTACGTA | 840 |
| GCGCTAATCC | ATAGCAGCTT | TGGCAGTTTC | GTGTCTTGAG | TCTTAGCTAA | AAAGTTAGAA | 900 |
| GTTTACATGA | CTGTTTTTTT | TATTTTCCCT | AAATTATTAC | TTACTCTGAG | CATTAATTAA | 960 |
| GGGCATTTTC | ACCTGTGTAA | AATTATGGTC | AGCTTTTTC | TGTCTATAAT | TGTTTACTTT | 1020 |
| TGTGGGTTTA | CTCTAGAAAC | ATGAGCCAAA | AATGTCAATA | GACAACACAG | TATTAAAATA | 1080 |
| ACCCAAAAGT | TGTAAAGGGC | AACGTTTCTC | CCCTTTGATA | GGGACACTAA | AGTGGTCTGT | 1140 |
| ACTTGGGTAG | AGGATGGCAG | ACGTTAAGAA | TTAAATGCG | TCTGGGTGCG | GTCTCACGCT | 1200 |
| TGTAATCCCA | GCACTTTGGG | AGGCTGAGGC | GGGCGGATCA | CCTGAGGTCA | GGAGTTCGAC | 1260 |
| ACCAGCCTGA | TGAACATGGA | GAAACCCCAT | CTCTACTAAA | AATACAAATA | TTAGCTGGGC | 1320 |
| GTTGTCGCGC | GCCTGTAATC | CCAGCGGCTC | ACGAGGCTGA | GGCAGGAGAA | TTGCTTGAGC | 1380 |
| TCGGGATGGC | GGAGGTTGCA | GTGAGCCAGG | ATTGTGCCAT | TGCACTCCAG | CCTGGGCAAC | 1440 |
| AAGAGTGAAA | CTCTGTCTCA | AAAAAAAAAA | AAAAAAAAA | | | 1480 |

( 2 ) INFORMATION FOR SEQ ID NO:39:

( i ) SEQUENCE CHARACTERISTICS:
        ( A ) LENGTH: 381 base pairs
        ( B ) TYPE: nucleic acid
        ( C ) STRANDEDNESS: both
        ( D ) TOPOLOGY: both ( x i ) SEQUENCE DESCRIPTION: SEQ ID NO:39:

| | | | | | |
|---|---|---|---|---|---|
| TTGGGTGAGG | TGGAATGATG | GTCTGTTGGA | ATCGGTTTGG | TAAATGGGTT | TATTTCATAT | 60 |
| CCGCTATCTT | TAACTTTGGA | CCGCGTTATC | TATATCATGG | CGTTCCTTTC | TACTTTTAA | 120 |
| TATTGGTTCG | TATTATATCG | TTCCTGATTG | GGGATATGGA | AGACGTATTA | CTTAATTGTA | 180 |
| CTTTATTGAA | ACGTTCCTCT | CGGTTTCGAT | TCTGGGGGCT | TTGGTCTGCT | CGATGGATTC | 240 |
| TTGTCGATTT | TCTCGTGTGG | CAGTAACATA | CCGTTTTATC | ACCCTTCTAA | ATATCCCATC | 300 |
| TCCCGCTGTT | TGGTAGGCTC | GGAACACTAT | CGACCAACAG | GTTCTATCTA | GAATCAAGTT | 360 |
| GGAAATTAAA | CGGTGTCTTG | G | | | | 381 |

( 2 ) INFORMATION FOR SEQ ID NO:40:

( i ) SEQUENCE CHARACTERISTICS:
        ( A ) LENGTH: 122 amino acids
        ( B ) TYPE: amino acid
        ( D ) TOPOLOGY: linear ( x i ) SEQUENCE DESCRIPTION: SEQ ID NO:40:

```
Met Met Val Cys Trp Asn Arg Phe Gly Lys Trp Val Tyr Phe Ile Ser
 1               5                  10                  15

Ala Ile Phe Asn Phe Gly Pro Arg Tyr Leu Tyr His Gly Val Pro Phe
                20                  25                  30

Tyr Phe Leu Ile Leu Val Arg Ile Ile Ser Phe Leu Ile Gly Asp Met
            35                  40                  45

Glu Asp Val Leu Leu Asn Cys Thr Leu Leu Lys Arg Ser Ser Arg Phe
        50                  55                  60

Arg Phe Trp Gly Ala Leu Val Cys Ser Met Asp Ser Cys Arg Phe Ser
```

|  | 65 |  |  |  | 70 |  |  |  | 75 |  |  |  | 80 |  |
|---|---|---|---|---|---|---|---|---|---|---|---|---|---|---|
| Arg | Val | Ala | Val | Thr | Tyr | Arg | Phe | Ile | Thr | Leu | Leu | Asn | Ile | Pro | Ser |
|  |  |  |  | 85 |  |  |  |  | 90 |  |  |  |  | 95 |  |
| Pro | Ala | Val | Trp | Met | Ala | Arg | Asn | Thr | Ile | Asp | Gln | Gln | Val | Leu | Ser |
|  |  |  | 100 |  |  |  |  | 105 |  |  |  |  | 110 |  |  |
| Arg | Ile | Lys | Leu | Glu | Ile | Lys | Arg | Cys | Leu |
|  |  |  | 115 |  |  |  |  | 120 |  |

( 2 ) INFORMATION FOR SEQ ID NO:41:

( i ) SEQUENCE CHARACTERISTICS:
        ( A ) LENGTH: 420 base pairs
        ( B ) TYPE: nucleic acid
        ( C ) STRANDEDNESS: both
        ( D ) TOPOLOGY: both ( x i ) SEQUENCE DESCRIPTION: SEQ ID NO:41:

| CCCACAGGTC | CTAAACTACC | AAACCTGCAT | TAAAAAATTT | CGGTTGGTCG | ACCTCGGAGC | 60 |
|---|---|---|---|---|---|---|
| AGAACCCAAC | CTCCGAGCAG | TACATGCTAA | GACTTCACCA | GTCAAAGCGA | ACGTACTATA | 120 |
| CTCAATTGAT | CCAATAACTT | GACCAACGGA | ACAAGTTACC | CTAGGGATAA | CAGCGCAATC | 180 |
| CGATGGTGCA | GCCGCTATTA | AAGGTTCGTT | TGTTCAAACG | ATTAAAGTCC | TCGTGTCTGA | 240 |
| GTTCAGACCG | AAGTAATCCA | GGTCGGTTTC | TATCTTCTTC | AAATTCCTCC | CTGTACCGAA | 300 |
| AGGACTAATG | AGAAATAAGG | CCTACTTCAC | AAAGCGGCCT | TCCCCCGTAA | TGATATCATC | 360 |
| TCAACTTAGT | ATTATACCCA | CACCCACCCA | AGAACAGGTT | TGTTAAAAAA | AAAAAAAAAA | 420 |

( 2 ) INFORMATION FOR SEQ ID NO:42:

( i ) SEQUENCE CHARACTERISTICS:
        ( A ) LENGTH: 381 base pairs
        ( B ) TYPE: nucleic acid
        ( C ) STRANDEDNESS: both
        ( D ) TOPOLOGY: both ( x i ) SEQUENCE DESCRIPTION: SEQ ID NO:42:

| AACCCACTCC | ACCTTACTAC | CAGACAACCT | TAGCCAAACC | ATTTACCCAA | ATAAAGTATA | 60 |
|---|---|---|---|---|---|---|
| GGCGATAGAA | ATTGAAACCT | GGCGCAATAG | ATATAGTACC | GCAAGGAAAG | ATGAAAAATT | 120 |
| ATAACCAAGC | ATAATATAGC | AAGGACTAAC | CCCTATACCT | TCTGCATAAT | GAATTAACAT | 180 |
| GAAATAACTT | TGCAAGGAGA | GCCAAAGCTA | AGACCCCCGA | AACCAGACGA | GCTACCTAAG | 240 |
| AACAGCTAAA | AGAGCACACC | GTCATTGTAT | GGCAAAATAG | TGGGAAGATT | TATAGGGTAG | 300 |
| AGGGCGACAA | ACCATCCGAG | CCTTGTGATA | GCTGGTTGTC | CAAGATAGAT | CTTAGTTCAA | 360 |
| CCTTTAATTT | GCCACAGAAC | C |  |  |  | 381 |

( 2 ) INFORMATION FOR SEQ ID NO:43:

( i ) SEQUENCE CHARACTERISTICS:
        ( A ) LENGTH: 629 base pairs
        ( B ) TYPE: nucleic acid
        ( C ) STRANDEDNESS: both
        ( D ) TOPOLOGY: both ( x i ) SEQUENCE DESCRIPTION: SEQ ID NO:43:

| TTTTTTTTTT | TTTTTAACAA | ACCCTGTTCT | TGGGTGGGTG | TGGGTATAAT | ACTAAGTTGA | 60 |
|---|---|---|---|---|---|---|
| GATGATATCA | TTACGGGGGA | AGGCCGCTTT | GTGAAGTAGG | CCTTATTTCT | CATTAGTCCT | 120 |
| TTCGGTACAG | GGAGGAATTT | GAAGAAGATA | GAAACCGACC | TGGATTACTT | CGGTCTGAAC | 180 |
| TCAGACACGA | GGACTTTAAT | CGTTTGAACA | AACGAACCTT | TAATAGCGGC | TGCACCATCG | 240 |

| | | | | | | |
|---|---|---|---|---|---|---|
| GGATGTCCTG | ATCCAACATC | GAGGTCGTAA | ACCCTATTGT | TGATATGGAC | TCTAGAATAG | 300 |
| GATTGCGCTG | TTATCCCTAG | GGTAACTTGT | TCCGTTGGTC | AAGTTATTGG | ATCAATTGAG | 360 |
| TTTAGTAGTC | CGCTTGGAGT | GGTGAAGTCT | AGAATGTCCT | GTTCGGGGGT | TGGTTTCTGC | 420 |
| TCCCAGGTCG | CCCCAACCGA | ATTTTTTATT | GAAGGTTGGG | TAGTTTAGCA | CCTGTGGGTT | 480 |
| GGTAAGGTAC | TGTTGGAATT | AATAAATTAA | AGCTCCATAG | GGTCTCCTCG | TCTTGTTGTG | 540 |
| TAATGCCCCC | CTCTCCACGG | GAAGGTCAAT | TCCACTGGTT | AAAAGTAAGA | GAAAGCTGAA | 600 |
| CCCTCGGGGA | GCCATCCATA | CAGGTCCCC | | | | 629 |

( 2 ) INFORMATION FOR SEQ ID NO:44:

( i ) SEQUENCE CHARACTERISTICS:
        ( A ) LENGTH: 256 base pairs
        ( B ) TYPE: nucleic acid
        ( C ) STRANDEDNESS: both
        ( D ) TOPOLOGY: both ( x i ) SEQUENCE DESCRIPTION: SEQ ID NO:44:

| | | | | | | |
|---|---|---|---|---|---|---|
| GCGGGTAAAT | TGGTTTGTTA | TTTTTAAAA | AAAACTTGCA | TGTTTAAAAA | AAAGTTGATT | 60 |
| GCTTCAAATT | TCTGCTACTA | ACTTCAAGCT | ATGGGAGTTT | GGCAGTAGTC | ACTTGAGGAT | 120 |
| TTTTTTTCCA | ATTCTTTTCT | TTTTGTTGTT | AAAGCTGTAC | TTCAGTGAAC | AGAAAAATTG | 180 |
| CCAAGCAAAC | TAATGGACTA | TAAAGCGTAA | TTTGACTGTG | TGGGACTAAA | CTACAGAGCC | 240 |
| TACTTGACCA | GTGGAT | | | | | 256 |

( 2 ) INFORMATION FOR SEQ ID NO:45:

( i ) SEQUENCE CHARACTERISTICS:
        ( A ) LENGTH: 270 base pairs
        ( B ) TYPE: nucleic acid
        ( C ) STRANDEDNESS: both
        ( D ) TOPOLOGY: both ( x i ) SEQUENCE DESCRIPTION: SEQ ID NO:45:

| | | | | | | |
|---|---|---|---|---|---|---|
| CATGTTTAAA | AAAAAGTTGA | TTGCTTCAAA | TTACTGCTAC | TAACTTCAAG | CTATGGGAGT | 60 |
| TTGGCAGTAG | TCACTTGAGG | ATTTTTTTTC | CAATTCGTTT | TCATTTTGT | TGTTAAAGCT | 120 |
| CGTACTTCAG | TGAGACAGAA | AAATTGCCAA | GCTAAACTAA | TGGTCTATAA | AAGCGTAATT | 180 |
| TGCATGTGTG | GGCAAAAACT | ACAGAGCCTC | AATTGCCACT | GAGGTATAGT | ACAAAGTTTT | 240 |
| AATACATTTT | GTAAATCAAA | TTGAAAGAAA | | | | 270 |

( 2 ) INFORMATION FOR SEQ ID NO:46:

( i ) SEQUENCE CHARACTERISTICS:
        ( A ) LENGTH: 270 base pairs
        ( B ) TYPE: nucleic acid
        ( C ) STRANDEDNESS: both
        ( D ) TOPOLOGY: both ( x i ) SEQUENCE DESCRIPTION: SEQ ID NO:46:

| | | | | | | |
|---|---|---|---|---|---|---|
| CATGTTTAAA | AAAAAGTTGA | TTGCTTCAAA | TTACTGCTAC | TAACTTCAAG | CTATGGGAGT | 60 |
| TTGGCAGTAG | TCACTTGAGG | ATTTTTTTTC | CAATTCGTTT | TCATTTTGT | TGTTAAAGCT | 120 |
| CGTACTTCAG | TGAGACAGAA | AAATTGCCAA | GCTAAACTAA | TGGTCTATAA | AAGCGTAATT | 180 |
| TGCATGTGTG | GGCAAAAACT | ACAGAGCCTC | AATTGCCACT | GAGGTATAGT | ACAAAGTTTT | 240 |
| AATACATTTT | GTAAATCAAA | TTGAAAGAAA | | | | 270 |

( 2 ) INFORMATION FOR SEQ ID NO:47:

( i ) SEQUENCE CHARACTERISTICS:
     ( A ) LENGTH: 184 base pairs
     ( B ) TYPE: nucleic acid
     ( C ) STRANDEDNESS: both
     ( D ) TOPOLOGY: both ( x i ) SEQUENCE DESCRIPTION: SEQ ID NO:47:

| | | | | |
|---|---|---|---|---|
| TCTGCCCAGG | CTGGTCTGAA | ATTCCTGGGC | TGAAGTGATC | CTCCAGTCTT | GGCCTCCCAA | 60 |
| AGTGCTGGGA | TTACAGGCAT | GAGCTACTGA | GCCTAGCCTT | AATGATTAAT | TTTAGAGTGA | 120 |
| TGGCTTGTAC | CTTCAAGACA | CATATAGATT | GAGACAGAAA | ATTTCCATCG | TCCCCGAGAA | 180 |
| AACT | | | | | | 184 |

( 2 ) INFORMATION FOR SEQ ID NO:48:

( i ) SEQUENCE CHARACTERISTICS:
     ( A ) LENGTH: 75 amino acids
     ( B ) TYPE: amino acid
     ( D ) TOPOLOGY: linear ( x i ) SEQUENCE DESCRIPTION: SEQ ID NO:48:

```
Ser  Ser  Ser  Leu  Gly  Leu  Pro  Lys  Cys  Trp  Asp  Tyr  Arg  His  Glu  Leu
  1              5                        10                       15

Leu  Ser  Leu  Ala  Leu  Met  Ile  Asn  Phe  Arg  Val  Met  Ala  Cys  Thr  Phe
               20                        25                       30

Lys  Gln  His  Ile  Glu  Leu  Arg  Gln  Lys  Ile  Ser  Ile  Val  Pro  Arg  Lys
          35                        40                       45

Leu  Cys  Cys  Met  Gly  Pro  Val  Cys  Pro  Val  Lys  Ile  Ala  Leu  Leu  Thr
     50                        55                       60

Ile  Asn  Gly  His  Cys  Thr  Trp  Leu  Pro  Ala  Ser
 65                       70                       75
```

( 2 ) INFORMATION FOR SEQ ID NO:49:

( i ) SEQUENCE CHARACTERISTICS:
     ( A ) LENGTH: 1381 base pairs
     ( B ) TYPE: nucleic acid
     ( C ) STRANDEDNESS: both
     ( D ) TOPOLOGY: both ( x i ) SEQUENCE DESCRIPTION: SEQ ID NO:49:

| | | | | | |
|---|---|---|---|---|---|
| TTTTTTTTTT | GAGATGGAGT | TTTCGCTCTT | GTTGCCCAGG | CTGGAGTGCA | ATGGCGCAAT | 60 |
| CTCAGCTCAC | CGCAACCTCC | GCCTCCCGGG | TTCAAGCGAT | TCTCCTGCCT | CAGCCTCCCC | 120 |
| AGTAGCTGGG | ATTACAGGCA | TGTGCACCAC | GCTCGGCTAA | TTTTGTATTT | TTTTTAGTA | 180 |
| GAGATGGAGT | TTAACTCCAT | GTTGGTCAGG | CTGGTCTCGA | ACTCCCGACC | TCAGATGATC | 240 |
| TCCCGTCTCG | GCCTGCCCAA | AGTGCTGAGA | TTACAGGCAT | GAGCCACCAT | GCCCGGCCTC | 300 |
| TGCCTGGCTA | ATTTTTGTGG | TAGAAACAGG | GTTTCACTGA | TGTTGCCCAA | GCTGGTCTCC | 360 |
| TGAGCTCAAG | CAGTCCACCT | GCCTCAGCCT | CCCAAAGTGC | TGGGATTACA | GGCGTCAGCC | 420 |
| GTGCCTGGCC | TTTTTATTTT | ATTTTTTTA | AGACACAGGT | GTACCACTCT | TACCCAGGAT | 480 |
| GAAGTGCAGT | GGTGTGATCA | CAGCTCACTG | CAGCCTTCAA | CTCCTGAGAT | CAAGCAATCC | 540 |
| TCCTGCCTCA | GCCTCCCAAG | TAGCTGGGAC | CAAAGACATG | CACCACTACA | CCTGGTAATT | 600 |
| TTTATTTTTA | TTTTTAATTT | TTTGAGACAG | AGTCTCACTC | TGTCACCCAG | GCTGGAGTGC | 660 |
| AGTGGCGCAA | TCTTGGCTCA | CTGCAACCTC | TGCCTCCCGG | GTTCAAGTTA | TTCTCCTGCC | 720 |
| CCAGCCTCCT | GAGTAGCTGG | GACTACAGGC | GCCACCACG | CCTAGCTAAT | TTTTTTGTAT | 780 |
| TTTTAGTAGA | GATGGGGTTT | CACCATGTTC | GCCAGGTTGA | TCTTGATCTC | TTGACCTTGT | 840 |

```
GATCTGCCTG  CCTCGGCCTA  CCCAAAGTGC  TGGGATTACA  GGTCGTGACT  CCACGCCGGC      900

CTATTTTTAA  TTTTTGTTTG  TTTGAAATGG  AATCTCACTC  TGTTACCCAG  GTCGGAGTGC      960

AATGGCAAAT  CTCGGCTACT  CGCAACCTCT  GCCTCCGGG   TCAAGCGATT  CTCCTGTCTC     1020

AGCCTCCCAA  GCAGCTGGGA  TTACGGGACC  TGCACCACAC  CCCGCTAATT  TTTGTATTTT     1080

CATTAGAGGC  GGGTTTACCA  TATTTGTCAG  GCTGGGTCTC  AAACTCCTGA  CCTCAGGTGA     1140

CCCACCTGCC  TCAGCCTTCC  AAAGTGCTGG  GATTACAGGC  GTGAGCCACC  TCACCCAGCC     1200

GGCTAATTTG  GAATAAAAAA  TATGTAGCAA  TGGGGGTCTG  CTATGTTGCC  CAGGCTGGTC     1260

TCAAACTTCT  GGCTTCAGTC  AATCCTTCCA  AATGAGCCAC  AACACCCAGC  CAGTCACATT     1320

TTTTAAACAG  TTACATCTTT  ATTTTAGTAT  ACTAGAAAGT  AATACAATAA  ACATGTCAAA     1380

C                                                                          1381
```

( 2 ) INFORMATION FOR SEQ ID NO:50:

( i ) SEQUENCE CHARACTERISTICS:
        ( A ) LENGTH: 2520 base pairs
        ( B ) TYPE: nucleic acid
        ( C ) STRANDEDNESS: both
        ( D ) TOPOLOGY: both ( x i ) SEQUENCE DESCRIPTION: SEQ ID NO:50:

```
CCATTGTTAG  GTTGTCTCTT  ACCTGTTAAA  ATCAGGAGCT  GACAAGAAAT  GCTTACCACA       60

AAAGGAGAAA  TGCCAGTCTA  GTTAACAGTC  AAGGAGAGAA  ATCAGGAAGA  TTATGTGGGT      120

GGAAGAAGTA  GATGATGTGG  CTGATGAGTG  AGTGAGTGAG  CAAGCCTCCG  CCCAGCTGAA      180

GAAGGAGTCA  GAACTGCCCT  TTGTTCCCAA  CTATTTGGCG  AACCCCAGCC  TTCCCTTTTA      240

TCTATACACC  CACAGCAGAG  GATTCAGCCC  AGATGCAGAA  TGGGGGCCCC  TCCACACCCC      300

CTGCATCACC  CCCTGCAGAT  GGCTCACCTC  CATTGCTTCC  CCCTGGGAAC  CTCCCCTGTT      360

AGGGACCTTT  CCCCGGGACC  ACACCTCTTT  GGCACTAGTT  CAGAATGGTG  ATGTGTCGGC      420

CCCTCTGCCA  TACTAGAACA  CCAGAAAGAC  AAACGGGTGA  TGTTTGTCAG  CTACAGTGAG      480

TCTAGAGCCG  TCCTGTTTTC  TTCTGTCCCG  TCCAAGCCA   CCATGTCTCT  TCGAGCCTCA      540

AAATGGGACG  TATGCAGGAC  CAGCGCCCAG  ATTCCAAGCC  ATTTTCTTC   ACTGGAGCAT      600

TTCCATTTAA  TATGCAAGAG  CTGGTACTCA  AGGTGAGAAT  TCAGAACCCA  TCTCTTCGAG      660

AAAATGATTT  CATTGAAATT  GAACTGGACC  GACAGAGCTC  ACCTACCAAG  AGTTGCTCAG      720

AGTGTGTTGC  TGTGAGCTGG  GTGTTAATCC  AGATCAAGTG  GAGAAGATCA  GAAAGTTACC      780

CAATACTCTG  TTAAGGAAGG  ACAAGGATGT  TGCTCGACTC  AAGATTTCAG  GAGCTGGAAC      840

TGGTTCTGAT  GATAGTGAAA  ATAATTTTCT  GTTCAGAAAT  GCTGCATCAC  ACTGACTGAA      900

AGGCCTTGCT  ATACAGGAGA  GCTTCAAAAC  TGACTTACTA  ATGCAGCAGG  GACTTTTATA      960

CTGAGTATAT  GACAGTGTGC  ATCACCTCTG  GGCCAAGGAC  AAGCCATGAT  CTAAATGCCT     1020

CAGATGCCCG  GGCCAGTCTG  GTGCACTGCA  TAGTATATAC  GAACATCATT  CTGCCCAAGG     1080

TAGGAAGCCC  CATGACCCCC  AAGCAGTGGT  GTCCACTCTT  CCAAGCCTCT  TGGTGCACAA     1140

TAAACCTTAT  TGCTTGAAGC  TTTGAACGAC  TGTGAATG    GTCTGGCGAG  GACGAGAACG     1200

TGGAATTATA  TGAGTGTCTT  TTGTATCCGA  GAATGTAGAG  AGTTCTCTGA  AGACGACGAC     1260

TGAGAGAGAG  CGGACGCTAT  TTCTAGCCAC  TCCTGTTGAC  AGTGCACCTG  AAGGGCTGGG     1320

ATGCGTTTTT  CTTGGTGTTG  CATGCTCACA  ACTCTGCTGA  CATTGGGAAC  TTATGAGAGA     1380

GGAAGACTCG  GGAAAGCACA  GATACTGGAC  AGATGGATTC  TGGTGTGGGG  AAAGCACAGA     1440

TACTGGACAG  ATGGTTCTAG  TGTGACTTGT  GACTGTGAGG  TTTCCTATAA  CATATTTATA     1500
```

| | | | | | |
|---|---|---|---|---|---|
|AATGTTCATC|AGGTTCAAAA|GTCTATAAGA|ATACAGTTCG|AGACTGAATT|GCTTCGAAAT|1560|
|ACTTCGATGT|TGGGAACCAA|AAGAGCTTTC|CCTCCCTCAC|TTTTTCCTTT|GTAACACTCA|1620|
|TGACTGCTTC|TCTGTCTCGA|GTCATCTCTG|CATTAACTCC|CCTTCGTGGT|CACTAGAGGG|1680|
|CTCTCTGATG|CTTCTAAGAC|ACTGCTTTTT|ACATGCCACA|CCCACCGCGT|AGAGACAGGG|1740|
|TCTCACTATG|TGGCCCAGGC|TGGTCTCAAA|CTTCTGGCCT|TAAGTGATCG|TCCTGTCCTT|1800|
|CGCGCTCGGA|AGAAAGTCGT|GGGGATTACA|GGTGTGAGCC|ACCCGCCCAG|CCCCTCCCTT|1860|
|GTGTTTCAAC|CAATCGGAAG|TGAATTTAAC|TAGATGTAGT|AACCTTTTT|TTCTTTGACT|1920|
|TCTAAAAAAG|TTACAGTTTA|CTAATAAAGT|TAAGTCTGGT|TCTGTCCTAG|AGGAAATAAA|1980|
|TTCACTATTA|ATTCATGTCT|TAAGTTACTT|GGGTTAAAAC|ACTTTCAGCC|ACCCAGATTA|2040|
|ATTAAAGTGG|AGCAGTGGAG|CCCCTGGCTG|GGGAGATGGG|CCTCCAGAGG|AGCAGCTGCA|2100|
|GGCATGTTCT|GGCTACACAG|AGGCAAGCAA|GGGACTGGTG|TCTCTGGTGA|GAGGTGGGTT|2160|
|TGATGTATCT|CTGTCCTATG|CTGGTCTCTC|TTCTCCTTTA|TAAATCCTCC|TGTGGTCACT|2220|
|GACTATCGTA|TCGCAGTGAT|CAGACTGCAC|ATAGTACGGT|TAGGCTGAGC|TTAATGTCTT|2280|
|AATCATGTCA|TTCGAGAGAA|GACACGTTTT|GATTCATGCT|TTGTGTAATT|AATCAATCAA|2340|
|GGATTCTTTT|TTTAGCTTTG|TTGACGTGTA|ATTCACCCCT|CCTCCTCCAC|TGCATATTTA|2400|
|AAGCATGTGT|TCACACTGTG|TGTATACATT|CACTGCGATT|TTTTCGTTTG|CTGCATTGCT|2460|
|TGGACTGTTC|ATAACATCAC|AAGTATTATT|CAAATAAAAT|ATTAACTGAC|CGAAAAAAAA|2520|

( 2 ) INFORMATION FOR SEQ ID NO:51:

( i ) SEQUENCE CHARACTERISTICS:
        ( A ) LENGTH: 141 base pairs
        ( B ) TYPE: nucleic acid
        ( C ) STRANDEDNESS: both
        ( D ) TOPOLOGY: both ( x i ) SEQUENCE DESCRIPTION: SEQ ID NO:51:

| | | | | | |
|---|---|---|---|---|---|
|GAATTCCTGG|GCTCAAGTGA|TCCTCTCATG|TCAGTCTCCC|AAAGTGCTGG|GATGACAGGC|60|
|TTGAGCCACC|ACACCAGGCC|CATCATCAGT|TTTTATATAA|AGAAAAAAAA|ACCTTAAAAT|120|
|TGTTAGCAAA|ATACTATGAC|A| | |141|

( 2 ) INFORMATION FOR SEQ ID NO:52:

( i ) SEQUENCE CHARACTERISTICS:
        ( A ) LENGTH: 151 base pairs
        ( B ) TYPE: nucleic acid
        ( C ) STRANDEDNESS: both
        ( D ) TOPOLOGY: both ( x i ) SEQUENCE DESCRIPTION: SEQ ID NO:52:

| | | | | | |
|---|---|---|---|---|---|
|GAACTCCTGA|CCTCAGGTGA|TCCGCCCGCC|TCAGCCTCCC|AAAGTGCTGG|GATTACAAGC|60|
|GTGCAGACCG|CACCCAGACG|ATTTTAATTC|TTAACNTGCC|ATCCTCTACC|CAAGTACAGA|120|
|CCACTTTAGT|GTCCCTATCA|AAGGGGAGAC|A| | |151|

( 2 ) INFORMATION FOR SEQ ID NO:53:

( i ) SEQUENCE CHARACTERISTICS:
        ( A ) LENGTH: 43 base pairs
        ( B ) TYPE: nucleic acid
        ( C ) STRANDEDNESS: both
        ( D ) TOPOLOGY: both ( x i ) SEQUENCE DESCRIPTION: SEQ ID NO:53:

```
AATTCTCCTG CCTCAGCCTC GTGAGCCGCT GGGATTACAG GCG                         43
```

( 2 ) INFORMATION FOR SEQ ID NO:54:

( i ) SEQUENCE CHARACTERISTICS:
        ( A ) LENGTH: 45 base pairs
        ( B ) TYPE: nucleic acid
        ( C ) STRANDEDNESS: both
        ( D ) TOPOLOGY: both ( x i ) SEQUENCE DESCRIPTION: SEQ ID NO:54:

```
AAGCCAACTC AGACTCAGCC AACAGGTAAG TGGGCATTAC AGGAG                       45
```

( 2 ) INFORMATION FOR SEQ ID NO:55:

( i ) SEQUENCE CHARACTERISTICS:
        ( A ) LENGTH: 143 base pairs
        ( B ) TYPE: nucleic acid
        ( C ) STRANDEDNESS: both
        ( D ) TOPOLOGY: both ( x i ) SEQUENCE DESCRIPTION: SEQ ID NO:55:

```
CTCAGTTTTC ACTTTGATCT GGTAGATAGT TTTCGTTTCA GTTGGGGGAG AAGGATCTGT       60

TTGTAAGAAC GGAGTGACGG GATACCATAA AAATAGAGGT AATAACATAC ATTGGGACGT       120

GTAAATTTAT TTTTATGGAA GTG                                               143
```

( 2 ) INFORMATION FOR SEQ ID NO:56:

( i ) SEQUENCE CHARACTERISTICS:
        ( A ) LENGTH: 157 base pairs
        ( B ) TYPE: nucleic acid
        ( C ) STRANDEDNESS: both
        ( D ) TOPOLOGY: both ( x i ) SEQUENCE DESCRIPTION: SEQ ID NO:56:

```
CTCACAGTTT CCTTATCTTG GTGGTCGTAA GTTTTCGTCG AAACAGTTGA TCGTTATTTG       60

TGAGATTGTC GTATAGGGAG ACTAACAGGT AGTAACTTTT GTGACCGTCG TTAAAACTTT       120

ACTTTTTTTT TTCTTTCTTC TTTTTTCCTT CATAATG                                157
```

( 2 ) INFORMATION FOR SEQ ID NO:57:

( i ) SEQUENCE CHARACTERISTICS:
        ( A ) LENGTH: 60 base pairs
        ( B ) TYPE: nucleic acid
        ( C ) STRANDEDNESS: both
        ( D ) TOPOLOGY: both ( x i ) SEQUENCE DESCRIPTION: SEQ ID NO:57:

```
ACCACGCCCC GCTAATTTTT GTATTTTTAG TAGAGACAGG GTTTCACCGT GTTGGCCAGG       60
```

( 2 ) INFORMATION FOR SEQ ID NO:58:

( i ) SEQUENCE CHARACTERISTICS:
        ( A ) LENGTH: 60 base pairs
        ( B ) TYPE: nucleic acid
        ( C ) STRANDEDNESS: both
        ( D ) TOPOLOGY: both ( x i ) SEQUENCE DESCRIPTION: SEQ ID NO:58:

```
ACAACGCCCA GCTAATATTT GTATTTTTAG TAGAGATGGG GTTTCTCCAT GTTCATCAGG       60
```

( 2 ) INFORMATION FOR SEQ ID NO:59:

( i ) SEQUENCE CHARACTERISTICS:
        ( A ) LENGTH: 60 base pairs (B) TYPE: nucleic acid
(C) STRANDEDNESS: both
(D) TOPOLOGY: both (xi) SEQUENCE DESCRIPTION: SEQ ID NO:59:

CTGGTCTGAA ATTCCTGGGC TGAAGTGATC CTCCAGTCTT GGCCTCCCAA AGTGCTGGGA    60

(2) INFORMATION FOR SEQ ID NO:60:

(i) SEQUENCE CHARACTERISTICS:
(A) LENGTH: 60 base pairs
(B) TYPE: nucleic acid
(C) STRANDEDNESS: both
(D) TOPOLOGY: both (xi) SEQUENCE DESCRIPTION: SEQ ID NO:60:

CTGGTGTCGA ACTCCTGACC TCAGGTGATC CGCCCGCCTC AGCCTCCCAA AGTGCTGGGA    60

(2) INFORMATION FOR SEQ ID NO:61:

(i) SEQUENCE CHARACTERISTICS:
(A) LENGTH: 26 base pairs
(B) TYPE: nucleic acid
(C) STRANDEDNESS: both
(D) TOPOLOGY: both (xi) SEQUENCE DESCRIPTION: SEQ ID NO:61:

AGACACATAT AGATTGAGAC AGAAAA    26

(2) INFORMATION FOR SEQ ID NO:62:

(i) SEQUENCE CHARACTERISTICS:
(A) LENGTH: 30 base pairs
(B) TYPE: nucleic acid
(C) STRANDEDNESS: both
(D) TOPOLOGY: both (xi) SEQUENCE DESCRIPTION: SEQ ID NO:62:

AGTACAGACC ACTTTAGTGT CCCTATCAAA    30

(2) INFORMATION FOR SEQ ID NO:63:

(i) SEQUENCE CHARACTERISTICS:
(A) LENGTH: 31 base pairs
(B) TYPE: nucleic acid
(C) STRANDEDNESS: both
(D) TOPOLOGY: both (xi) SEQUENCE DESCRIPTION: SEQ ID NO:63:

AGATCTCGCT CTGTCACCCA GGCTGAAGTG C    31

(2) INFORMATION FOR SEQ ID NO:64:

(i) SEQUENCE CHARACTERISTICS:
(A) LENGTH: 34 base pairs
(B) TYPE: nucleic acid
(C) STRANDEDNESS: both
(D) TOPOLOGY: both (xi) SEQUENCE DESCRIPTION: SEQ ID NO:64:

AGAGTTTCAC TCTTGCTTGC CCAGGCTGGA GTGC    34

(2) INFORMATION FOR SEQ ID NO:65:

(i) SEQUENCE CHARACTERISTICS:
(A) LENGTH: 59 base pairs
(B) TYPE: nucleic acid
(C) STRANDEDNESS: both ( D ) TOPOLOGY: both ( x i ) SEQUENCE DESCRIPTION: SEQ ID NO:65:

AGTGGCCCAA TCTCGGCTCA CTGCGAGCTC CACCTCCCGG GTTCACTTCA TTCTCCTGC    59

( 2 ) INFORMATION FOR SEQ ID NO:66:

( i ) SEQUENCE CHARACTERISTICS:
        ( A ) LENGTH: 60 base pairs
        ( B ) TYPE: nucleic acid
        ( C ) STRANDEDNESS: both
        ( D ) TOPOLOGY: both ( x i ) SEQUENCE DESCRIPTION: SEQ ID NO:66:

AATGGCACAA TCCTGGCTCA CTGCAACCTC CGCCCTCCCG AGCTCAAGAA CTTCTCCTGC    60

( 2 ) INFORMATION FOR SEQ ID NO:67:

( i ) SEQUENCE CHARACTERISTICS:
        ( A ) LENGTH: 66 base pairs
        ( B ) TYPE: nucleic acid
        ( C ) STRANDEDNESS: both
        ( D ) TOPOLOGY: both ( x i ) SEQUENCE DESCRIPTION: SEQ ID NO:67:

CTCAGCCTCT GAGTAGCTGG GACTACAGGC GCCCACCACA AGCCGCTAAT TTTTGTATTT    60

TTGTAG    66

( 2 ) INFORMATION FOR SEQ ID NO:68:

( i ) SEQUENCE CHARACTERISTICS:
        ( A ) LENGTH: 67 base pairs
        ( B ) TYPE: nucleic acid
        ( C ) STRANDEDNESS: both
        ( D ) TOPOLOGY: both ( x i ) SEQUENCE DESCRIPTION: SEQ ID NO:68:

CTCAGCCTCG TGAGCCGCTG GGATTACAGG CGCGCGCCAC AAGCGACTAA TATTTGTATT    60

TTTGTAG    67

( 2 ) INFORMATION FOR SEQ ID NO:69:

( i ) SEQUENCE CHARACTERISTICS:
        ( A ) LENGTH: 76 base pairs
        ( B ) TYPE: nucleic acid
        ( C ) STRANDEDNESS: both
        ( D ) TOPOLOGY: both ( x i ) SEQUENCE DESCRIPTION: SEQ ID NO:69:

ACCACGCCCC GCTAATTTTT GTATTTTTAG TAGAGACAGG GTTTCACCGT GTTGGCCAGG    60

ATGCTCGATC TCCTGA    76

( 2 ) INFORMATION FOR SEQ ID NO:70:

( i ) SEQUENCE CHARACTERISTICS:
        ( A ) LENGTH: 78 base pairs
        ( B ) TYPE: nucleic acid
        ( C ) STRANDEDNESS: both
        ( D ) TOPOLOGY: both ( x i ) SEQUENCE DESCRIPTION: SEQ ID NO:70:

ACAACGCCCA GCTAATATTT GTATTTTTAG TAGAGATGGG GTTTCTCCAT GTTCATCAGG    60

CTGGTGTCGA ACTCCTGA    78

( 2 ) INFORMATION FOR SEQ ID NO:71:

( i ) SEQUENCE CHARACTERISTICS:
        ( A ) LENGTH: 159 base pairs
        ( B ) TYPE: nucleic acid
        ( C ) STRANDEDNESS: both
        ( D ) TOPOLOGY: both ( x i ) SEQUENCE DESCRIPTION: SEQ ID NO:71:

| | | | | | |
|---|---|---|---|---|---|
| CCCCAAGCAG | TGTTAATCCT | GGCTACTGTG | TGAGCTGACC | TCAAGCACAG | GTGAAGGCAG | 60 |
| AGAATCCATC | CACCTGTTTC | TGTTCTCCCT | GCTTAGCTCC | AGGGATGGAA | CTGGGACTGG | 120 |
| GATAGAGGAA | AGGTGAACTC | CTCATTAAGG | AAATGGATG | | | 159 |

( 2 ) INFORMATION FOR SEQ ID NO:72:

( i ) SEQUENCE CHARACTERISTICS:
        ( A ) LENGTH: 170 base pairs
        ( B ) TYPE: nucleic acid
        ( C ) STRANDEDNESS: both
        ( D ) TOPOLOGY: both ( x i ) SEQUENCE DESCRIPTION: SEQ ID NO:72:

| | | | | | |
|---|---|---|---|---|---|
| CCCCTGTTCT | TGGGTGGGTT | TGGGTATATT | CTGGTTGAGA | TGATATCATT | TACGGGGAA | 60 |
| GGCGCTTTGT | GAAGTAGGCC | TTATTTCTCT | TGTCCTTTCG | TACAGGGAGG | ATTTGAAGTA | 120 |
| GTAGAACGCT | GTTACTCCGG | TCTGAACTCA | GTCACGTGGC | TTTATCGTTG | | 170 |

( 2 ) INFORMATION FOR SEQ ID NO:73:

( i ) SEQUENCE CHARACTERISTICS:
        ( A ) LENGTH: 52 base pairs
        ( B ) TYPE: nucleic acid
        ( C ) STRANDEDNESS: both
        ( D ) TOPOLOGY: both ( x i ) SEQUENCE DESCRIPTION: SEQ ID NO:73:

| | | | | |
|---|---|---|---|---|
| GATCCAAGCT | ACGTACGCGT | GCATGCACGT | CATAGCTCTT | CTATAGTGTC | AC | 52 |

( 2 ) INFORMATION FOR SEQ ID NO:74:

( i ) SEQUENCE CHARACTERISTICS:
        ( A ) LENGTH: 53 base pairs
        ( B ) TYPE: nucleic acid
        ( C ) STRANDEDNESS: both
        ( D ) TOPOLOGY: both ( x i ) SEQUENCE DESCRIPTION: SEQ ID NO:74:

| | | | | |
|---|---|---|---|---|
| GATCCGAGCT | CGGTACCAAG | TTGATGCATA | GCTTGAGTAT | TCTATAGTGT | CAC | 53 |

( 2 ) INFORMATION FOR SEQ ID NO:75:

( i ) SEQUENCE CHARACTERISTICS:
        ( A ) LENGTH: 115 base pairs
        ( B ) TYPE: nucleic acid
        ( C ) STRANDEDNESS: both
        ( D ) TOPOLOGY: both ( x i ) SEQUENCE DESCRIPTION: SEQ ID NO:75:

| | | | | | |
|---|---|---|---|---|---|
| GTATGGGCCC | GATAGCTTAT | TTAGCCTTTA | GAGCACACTG | GCGGCCGTTA | CTAGTGGATC | 60 |
| CGAGCTCGGT | ACCAACTTGA | TGCATAGCTT | GAGTATTCTA | TAGTGTCACC | TAAAT | 115 |

( 2 ) INFORMATION FOR SEQ ID NO:76:

( i ) SEQUENCE CHARACTERISTICS:
        ( A ) LENGTH: 120 base pairs
        ( B ) TYPE: nucleic acid (C) STRANDEDNESS: both
(D) TOPOLOGY: both (x i) SEQUENCE DESCRIPTION: SEQ ID NO:76:

| | | | | | |
|---|---|---|---|---|---|
| ATATAGACAA | TATAACAATA | TATTGTATAC | TTTAGAGCAC | ACTGGCAGCC | GTTACTAGTG | 60
| GATCCGAGCT | CGGTACCAAG | TTGATGCATA | GCTTGAGTAT | TCTATAGTGT | CACTAATAGT | 120

(2) INFORMATION FOR SEQ ID NO:77:

(i) SEQUENCE CHARACTERISTICS:
        (A) LENGTH: 117 base pairs
        (B) TYPE: nucleic acid
        (C) STRANDEDNESS: both
        (D) TOPOLOGY: both (x i) SEQUENCE DESCRIPTION: SEQ ID NO:77:

| | | | | | |
|---|---|---|---|---|---|
| CTTAATAGAT | AGCTACTTAA | AATAACTTAC | ACACTGTTTT | AGAGTGCTTG | AAAACTATCT | 60
| GATCAGACAT | AGTATTGAAA | CCAATGAATA | CATTATATAA | AGTAAAGGAA | AGGAGAA | 117

(2) INFORMATION FOR SEQ ID NO:78:

(i) SEQUENCE CHARACTERISTICS:
        (A) LENGTH: 137 base pairs
        (B) TYPE: nucleic acid
        (C) STRANDEDNESS: both
        (D) TOPOLOGY: both (x i) SEQUENCE DESCRIPTION: SEQ ID NO:78:

| | | | | | |
|---|---|---|---|---|---|
| CTTACTACCA | GACAACCTTA | GCCAAACCAT | TTACCCAAAT | AAAGTATAGG | CGATAGAAAT | 60
| TGAAACCTGG | CGCAATAGAT | ATAGTACCGC | AAGGAAAGAT | GAAAATTAT | AACCAAGCAT | 120
| AATATAGCAA | GGACTAA | | | | | 137

(2) INFORMATION FOR SEQ ID NO:79:

(i) SEQUENCE CHARACTERISTICS:
        (A) LENGTH: 198 base pairs
        (B) TYPE: nucleic acid
        (C) STRANDEDNESS: both
        (D) TOPOLOGY: both (x i) SEQUENCE DESCRIPTION: SEQ ID NO:79:

| | | | | | |
|---|---|---|---|---|---|
| CTATAAAGGT | CGTTGTCAAC | GATAAAGCAC | GTGACTGAGT | TCAGACCGGA | GTAACAGCGT | 60
| TCTACTACTT | CAAATCCTCC | CTGCGAAAGG | CAAGAGAAAT | AAGGCCTACT | TAAGCGCCTT | 120
| CCCCCGTAAA | TGATATCATC | TCAACCAGAA | TATACCCAAA | CCCCCCAAGA | ACAGGGGAGG | 180
| AAAAGAAAAA | AAAAAAAA | | | | | 198

(2) INFORMATION FOR SEQ ID NO:80:

(i) SEQUENCE CHARACTERISTICS:
        (A) LENGTH: 200 base pairs
        (B) TYPE: nucleic acid
        (C) STRANDEDNESS: both
        (D) TOPOLOGY: both (x i) SEQUENCE DESCRIPTION: SEQ ID NO:80:

| | | | | | |
|---|---|---|---|---|---|
| CTATAGAGAT | TGTTGATTTG | CCTCTTAAGC | AAGAGATTCA | TTGCAGCTCA | GCATGGCTCA | 60
| GACCAGCTCA | TACTTCATGC | TGATCTCCTG | CCTGATGTTT | CTGTCTCAGA | GCCAAGGTAA | 120
| GATCTCTTTT | CCAACTCTTT | CTAGCCCTGA | AGACTTCACT | CTATCCCCAA | GCATACGGGT | 180
| CTACTTGAAA | AAAAAAAAA | | | | | 200

( 2 ) INFORMATION FOR SEQ ID NO:81:

( i ) SEQUENCE CHARACTERISTICS:
        ( A ) LENGTH: 82 base pairs
        ( B ) TYPE: nucleic acid
        ( C ) STRANDEDNESS: both
        ( D ) TOPOLOGY: both ( x i ) SEQUENCE DESCRIPTION: SEQ ID NO:81:

| | | | | | |
|---|---|---|---|---|---|
| CAGAAAACTA | GCTACACAAT | GCATTGGTCT | ATCATGTTAA | AACGTGCATT | AGACACAAAT | 60 |
| ACAAAAACCA | TGAAACAAGC | CA | | | | 82 |

( 2 ) INFORMATION FOR SEQ ID NO:82:

( i ) SEQUENCE CHARACTERISTICS:
        ( A ) LENGTH: 90 base pairs
        ( B ) TYPE: nucleic acid
        ( C ) STRANDEDNESS: both
        ( D ) TOPOLOGY: both ( x i ) SEQUENCE DESCRIPTION: SEQ ID NO:82:

| | | | | | |
|---|---|---|---|---|---|
| CAGAAAAATT | GCCAAGCTAA | ACTAATGGTC | TATAAAAGCG | TAATTTGCAT | GTGTGGGCAT | 60 |
| AAACTACAGA | GCTCATGCTA | GAGTATGCAA | | | | 90 |

( 2 ) INFORMATION FOR SEQ ID NO:83:

( i ) SEQUENCE CHARACTERISTICS:
        ( A ) LENGTH: 141 base pairs
        ( B ) TYPE: nucleic acid
        ( C ) STRANDEDNESS: both
        ( D ) TOPOLOGY: both ( x i ) SEQUENCE DESCRIPTION: SEQ ID NO:83:

| | | | | | |
|---|---|---|---|---|---|
| AATTGGGTAC | CGGGCCCCCC | CTAGAGGTCG | ACGGTATCGA | TAAGCTTGTA | TCGAATTCCG | 60 |
| GACTTTGCTT | TTGGTTTTCC | TTTCCTGTGA | AAAGGTTGGT | TTTAAAGTGA | GATACACTTT | 120 |
| TCCGTAGAAC | AAGTGTTCTA | T | | | | 141 |

( 2 ) INFORMATION FOR SEQ ID NO:84:

( i ) SEQUENCE CHARACTERISTICS:
        ( A ) LENGTH: 155 base pairs
        ( B ) TYPE: nucleic acid
        ( C ) STRANDEDNESS: both
        ( D ) TOPOLOGY: both ( x i ) SEQUENCE DESCRIPTION: SEQ ID NO:84:

| | | | | | |
|---|---|---|---|---|---|
| AAGTTGATTG | CTTCAAATTT | CTGCTACTAA | CTTCAAGCTA | TGGGAGTTTG | GCAGTAGTCA | 60 |
| CTTGAGGATT | TTTTTTCCAA | TTCGTTTTCA | TTTTTGTTGT | TAAAGCTCGT | ACTTCAGTGA | 120 |
| GACAGAAAAA | TTGCCAAGCT | AAACTAATGG | TCTAT | | | 155 |

( 2 ) INFORMATION FOR SEQ ID NO:85:

( i ) SEQUENCE CHARACTERISTICS:
        ( A ) LENGTH: 232 base pairs
        ( B ) TYPE: nucleic acid
        ( C ) STRANDEDNESS: both
        ( D ) TOPOLOGY: both ( x i ) SEQUENCE DESCRIPTION: SEQ ID NO:85:

| | | | | | |
|---|---|---|---|---|---|
| GAATTCCTGG | GCTCAAGTGA | TCCTCTCATG | TCAGTCTCCC | AAAGTGCTGG | GATGACAGGC | 60 |
| TTGAGCCACC | ACACCAGCCC | ATCATCAGTT | TTTATATAAA | GAAAAAAAAA | CCTTAAAATT | 120 |
| GTTAGGCAAA | TAATGACAAA | TTGTAATATA | TATTCTTACA | TTTCAGATTT | TTATTTTTTA | 180 |

AACTGATAAG AATTGATTAA TAAATAAAAT TTAGTATTAA TCTGTCTTTT AA 232

( 2 ) INFORMATION FOR SEQ ID NO:86:

( i ) SEQUENCE CHARACTERISTICS:
    ( A ) LENGTH: 245 base pairs
    ( B ) TYPE: nucleic acid
    ( C ) STRANDEDNESS: both
    ( D ) TOPOLOGY: both ( x i ) SEQUENCE DESCRIPTION: SEQ ID NO:86:

AAATTCCTGG GCTGAAGTGA TCCTCCAGTC TTGGCCTCCC AAAGTGCTGG GATTACAGGC 60

ATGAGCTACT GAGCCTAGCC TTAATGATTA ATTTTAGAGT GATGGCTTGT ACCTTCAAGC 120

AACATATAGA GTTGAGACAG AAAATTTCCA TCGTCCCGAG AAAACTGTGC TGCATGGGCC 180

CCGTGTGCCC TGTGAAGATC GCCCTATTAA CTATAAATGG GCATTGCACA TGGTTGCCAG 240

CTTCA 245

( 2 ) INFORMATION FOR SEQ ID NO:87:

( i ) SEQUENCE CHARACTERISTICS:
    ( A ) LENGTH: 239 base pairs
    ( B ) TYPE: nucleic acid
    ( C ) STRANDEDNESS: both
    ( D ) TOPOLOGY: both ( x i ) SEQUENCE DESCRIPTION: SEQ ID NO:87:

AACGTTTCGA ACCTATCGTG AAGCCCGATT TTAGAGTTAA TACGGGTGCT TCAAGGGAAC 60

GGGGCTATGA GAAGTTTTCT ACGGGGAGCA TGGAAATTTT CTGTCTCAAT ATGTGCTTGA 120

AGGTACAACC GTATCTAAAA TTAATCATTA AGGCTAGGCT CAGTAGCTCT GCCTGTAATC 180

CCAGCACTTT CGGGAGGCCA AGACTGGAGG ATCACTTCAG CCCAGGAATT TCAGACGCC 239

( 2 ) INFORMATION FOR SEQ ID NO:88:

( i ) SEQUENCE CHARACTERISTICS:
    ( A ) LENGTH: 260 base pairs
    ( B ) TYPE: nucleic acid
    ( C ) STRANDEDNESS: both
    ( D ) TOPOLOGY: both ( x i ) SEQUENCE DESCRIPTION: SEQ ID NO:88:

TACTGTGTGA GCCTGACCTC AAGCACAGGA TTCCAGAAAT GGAAGGATGT GCCTTGTGAA 60

GACAAGTTCT CCTTTGTCTG CAAGTTCAAA AACTAGAGGC AGCTGGAAAA TACATGTCTA 120

GAACTGATCC AGCAATTACA ACGGAGTCAA AAATTAAACC GGACCATCTC TCCAACTCAA 180

CTCAACCTGG ACACTCTCTT CTCTGCTGAG TTTGCCTTGT TAATCTTCAA TAGTTTTACC 240

TACCCCAGTC TTTGGAACCT 260

( 2 ) INFORMATION FOR SEQ ID NO:89:

( i ) SEQUENCE CHARACTERISTICS:
    ( A ) LENGTH: 149 base pairs
    ( B ) TYPE: nucleic acid
    ( C ) STRANDEDNESS: both
    ( D ) TOPOLOGY: both ( x i ) SEQUENCE DESCRIPTION: SEQ ID NO:89:

CTTGCTTGCC CAGGCTGGAG TGCAATGGCA CAATCCTGGC TCACTGCAAC CTCCCCCTCC 60

CGAGCTCAAG AACTTCTCCT GCCTCAGCCT CGTGAGCCGC TGGGATTACA GGCGCGCGCC 120

ACAAGCGACT AATATTTGTA TTTTTGTAG 149

(2) INFORMATION FOR SEQ ID NO:90:

(i) SEQUENCE CHARACTERISTICS:
        (A) LENGTH: 167 base pairs
        (B) TYPE: nucleic acid
        (C) STRANDEDNESS: both
        (D) TOPOLOGY: both (xi) SEQUENCE DESCRIPTION: SEQ ID NO:90:

```
CTCGCTCTGT CACCCAGGCT GAAGTGCAGT GGCCCAATCT CGGCTCACTG CGAGCTCCAC      60
CTCCCGGGTT CACTTCATTC TCCTGCCTCA CTGCCTCAGC CTCTGAGTAG CTGGGACTAC     120
AGGCGCCCAC CACCACGTCC CCTGCTAATT TTTTGTATTT TTAGTAG                  167
```

(2) INFORMATION FOR SEQ ID NO:91:

(i) SEQUENCE CHARACTERISTICS:
        (A) LENGTH: 84 base pairs
        (B) TYPE: nucleic acid
        (C) STRANDEDNESS: both
        (D) TOPOLOGY: both (xi) SEQUENCE DESCRIPTION: SEQ ID NO:91:

```
CCATGTTCAT CAGGCTGGTG TCGAACTCCT GACCTCGTGA TCCGCCCGCC TCAGCCTCCC      60
AAAGTGCTGG GATTACAAGC GTGC                                             84
```

(2) INFORMATION FOR SEQ ID NO:92:

(i) SEQUENCE CHARACTERISTICS:
        (A) LENGTH: 85 base pairs
        (B) TYPE: nucleic acid
        (C) STRANDEDNESS: both
        (D) TOPOLOGY: both (xi) SEQUENCE DESCRIPTION: SEQ ID NO:92:

```
CCGTGTTGGC CAGGATGGTC TCGATCTCCT GACCTCGTGA TCCGCCCGCC TTGGCCACCC      60
AAAGAGTTTG GGATTACAGG CGTGC                                            85
```

(2) INFORMATION FOR SEQ ID NO:93:

(i) SEQUENCE CHARACTERISTICS:
        (A) LENGTH: 251 base pairs
        (B) TYPE: nucleic acid
        (C) STRANDEDNESS: both
        (D) TOPOLOGY: both (xi) SEQUENCE DESCRIPTION: SEQ ID NO:93:

```
TGCAGCAATG GCAACAACGT CTGCAAACTA TTAACTGGCG AACTACTTAC TCTAGCTTCC      60
CGGCAACAAT TAATAGACTG GATGGAGGCG GATAAAGTTG CAGGACCACT TCTGCGCTCG     120
GCCCTTCCGG CTGGCTGGTT TATTGCTGAT AAATCTGGAG CCGGTCGAGC GTGGGTCTCG     180
CGTATCATTC GAGCACTGGG GCCAGATGGT AAGCCCTCCG TATCGTAGTT ATCTCACAGC     240
AGGGAGTCAG G                                                         251
```

(2) INFORMATION FOR SEQ ID NO:94:

(i) SEQUENCE CHARACTERISTICS:
        (A) LENGTH: 242 base pairs
        (B) TYPE: nucleic acid
        (C) STRANDEDNESS: both
        (D) TOPOLOGY: both (xi) SEQUENCE DESCRIPTION: SEQ ID NO:94:

```
TGCAGGAGCG GGGAGGCACG ATGGCCGCTT TGGTCCGGAT CTTTGTGAGG AACCTTACTT      60
```

| CTGTGGTGTG | ACATAATTGG | ACAAACTACC | TACAGAGATT | TAAAGCTCTA | AGGAAATATA | 120 |
| AAATTTTTAA | GTGTATAATG | TGTTAAACTA | CTGATTCTAA | TTGTTTGTGT | ATTTTAGATT | 180 |
| CCAACCCTAT | GGAACCTGAT | GAATGGGAGC | CAGTGGTGGA | ATGCCTTTAA | TGAGGAAACC | 240 |
| TG | | | | | | 242 |

( 2 ) INFORMATION FOR SEQ ID NO:95:

( i ) SEQUENCE CHARACTERISTICS:
        ( A ) LENGTH: 208 base pairs
        ( B ) TYPE: nucleic acid
        ( C ) STRANDEDNESS: both
        ( D ) TOPOLOGY: both ( x i ) SEQUENCE DESCRIPTION: SEQ ID NO:95:

| TGCAGCAATC | TTTCTTATAT | ACATGCTTAA | TAGATAGCTA | CTTAAAATAA | CTTACACACG | 60 |
| TTTTAGAGTT | GCTTGAAAAC | TATCTGATCA | AGACATAGTA | ATTGAAACCA | ATGAATACAT | 120 |
| TATATAAAGT | AAAGGAAAGG | AGAAGAGAGG | AAAGGGAGGG | GAAGAGGAGA | GGGAGGGACA | 180 |
| AGCGAGAAAG | GAAAGGGAAG | GGAGAAAA | | | | 208 |

( 2 ) INFORMATION FOR SEQ ID NO:96:

( i ) SEQUENCE CHARACTERISTICS:
        ( A ) LENGTH: 152 base pairs
        ( B ) TYPE: nucleic acid
        ( C ) STRANDEDNESS: both
        ( D ) TOPOLOGY: both ( x i ) SEQUENCE DESCRIPTION: SEQ ID NO:96:

| CTCACTAAAG | GGATCAAGGA | ATAATTTTGA | ATTTCAAGTC | TTACATTTAA | TAAATACATT | 60 |
| CATAAGGCTA | TAACTACCAT | ACGTTGTGAT | TTCTCTGATT | AATTTAAAAA | TAAATTAAAA | 120 |
| CCTGGAAAGA | ATTTACCAT | TCTAGGAAGC | CA | | | 152 |

( 2 ) INFORMATION FOR SEQ ID NO:97:

( i ) SEQUENCE CHARACTERISTICS:
        ( A ) LENGTH: 338 base pairs
        ( B ) TYPE: nucleic acid
        ( C ) STRANDEDNESS: both
        ( D ) TOPOLOGY: both ( x i ) SEQUENCE DESCRIPTION: SEQ ID NO:97:

| AATCTATCTT | ATATACATGC | TTAATAGATA | GCTACTTAAA | ATAACTTACA | CACGTTTTAG | 60 |
| AGTTGCTTGA | AAACTATCTG | ATCAAGACAT | AGTAATTGAA | ACCAATGAAT | ACATTATATA | 120 |
| AAGTAAAGGA | AAGGAGAAGA | GAGGAAAGGA | GGGGAGAGGA | GAGGAGGACA | AGCGAGAAAA | 180 |
| GGAAGGGAAG | GGAGAAAAAG | GGGGAAAGGG | AGGTAGAGAG | AGAGAGAAAA | AGTGCTGGTC | 240 |
| ATATAGTAAG | TGTACATTTT | AACTTTTTAA | GAAACTACCC | TACTCTATTC | CAGAGTGATT | 300 |
| GTACATGTGC | ATTTTACTGC | ATTATAGAGA | TCATTTTC | | | 338 |

( 2 ) INFORMATION FOR SEQ ID NO:98:

( i ) SEQUENCE CHARACTERISTICS:
        ( A ) LENGTH: 169 base pairs
        ( B ) TYPE: nucleic acid
        ( C ) STRANDEDNESS: both
        ( D ) TOPOLOGY: both ( x i ) SEQUENCE DESCRIPTION: SEQ ID NO:98:

| TGCAGGAGTG | GGGAGGCACG | ATGGCCGCTT | TGGTCCGGAT | CTTTGTGAAG | GAACCTTACT | 60 |

```
TCTGTGTGTG  ACATAATTGG  ACAAACTACC  TACAGAGATT  TAAACGTCTA  AGGTAAATAT      120

AAAATTTTTA  GTGTATAGGT  TAAACTACTG  ATTCTAATGT  TGTGTATTT                   169
```

( 2 ) INFORMATION FOR SEQ ID NO:99:

( i ) SEQUENCE CHARACTERISTICS:
    ( A ) LENGTH: 209 base pairs
    ( B ) TYPE: nucleic acid
    ( C ) STRANDEDNESS: both
    ( D ) TOPOLOGY: both ( x i ) SEQUENCE DESCRIPTION: SEQ ID NO:99:

```
CCCCGGGCTG  CAGCAATGGC  AACAACGTCT  GCAAACTATT  AACTGGCGAA  CTCATTCATC       60

TAGCTTCCCG  GCAACAATTA  ATGACTGGAT  GGAGGCGGAT  AAAGTTGCAG  GACCACTTCT      120

CGCGTGGCCC  TTCCGGCTGG  CTGGTTTATT  GCTGATAATT  GAGCGTGCGA  GTGGCTCGCG      180

TATCATTCGC  GACATGGGCC  AGTAGGTAC                                           209
```

( 2 ) INFORMATION FOR SEQ ID NO:100:

( i ) SEQUENCE CHARACTERISTICS:
    ( A ) LENGTH: 272 base pairs
    ( B ) TYPE: nucleic acid
    ( C ) STRANDEDNESS: both
    ( D ) TOPOLOGY: both ( x i ) SEQUENCE DESCRIPTION: SEQ ID NO:100:

```
CTTGCCCTTC  ATGGAGTCAT  ACAGCCGATC  AGCAAAATGC  AGGGGCTTGT  TCTGAATGCA       60

CTGAACCAGG  TTCAGGAAAG  CATTTTCCAG  GTCTCCTTTA  ACCTCTTTCC  TGATGCTTTC      120

CAACATGTCA  TAAGGGCTGT  AACTCTTGTA  CCTATCAAAT  ACTTTCTGGA  GGTGGGGACA      180

CGCTCGCGTC  GGTCATGATG  CTGATCCACT  TGGGAACATC  AGTTCTTTCC  TCTTCACTCC      240

AGCTGCATAG  AGATCCGAGG  ACTCTTGGTC  AA                                      272
```

( 2 ) INFORMATION FOR SEQ ID NO:101:

( i ) SEQUENCE CHARACTERISTICS:
    ( A ) LENGTH: 278 base pairs
    ( B ) TYPE: nucleic acid
    ( C ) STRANDEDNESS: both
    ( D ) TOPOLOGY: both ( x i ) SEQUENCE DESCRIPTION: SEQ ID NO:101:

```
ACGGCCCAGC  TTCCTTCAAA  ATGTCTACTG  TTCACGAAAT  CCTGTGCAAG  CTCAGCTTGG       60

AGGGTGATCA  CTCTACACCC  CCAAGTGCAT  ATGGGTCTGT  CAAAGCCTAT  ACTAACTTTG      120

ATGCTGAGCG  GGATGCTTTG  AACATTGAAA  CAGCCATCAA  GACCAAAGGT  GTGGATGAGG      180

TCACCATTGT  CAACATTTTG  ACCAACCGCA  GCAATGACAC  GAGACAGGAT  ATTGCCTTCG      240

CCTACCAGAG  AAGGACCAAA  AAAGGAACTT  GCATCACA                                278
```

( 2 ) INFORMATION FOR SEQ ID NO:102:

( i ) SEQUENCE CHARACTERISTICS:
    ( A ) LENGTH: 228 base pairs
    ( B ) TYPE: nucleic acid
    ( C ) STRANDEDNESS: both
    ( D ) TOPOLOGY: both ( x i ) SEQUENCE DESCRIPTION: SEQ ID NO:102:

```
AGCAATAGCA  AAGGAAAGGA  AACAATATTT  AGCAAGGTTT  ATTCTTCCTT  TGTGTCAGCA       60

TTTCTGAGTG  TGCACACAGG  CCCAGTGATT  CCATGTATTT  TTGAGTGACC  ACTGCCTCTG      120
```

```
TCTGGCCCTT  CCCCATAGAA  CCGCCGCTGG  TGGAGCGTGG  GTCCCTGGTC  TCCTACAAGT        180

CCTGGGGCAT  TGGAGCCCCA  AGCAGTGTTA  ATCCTGGCAC  TGTGTNAG                      228
```

( 2 ) INFORMATION FOR SEQ ID NO:103:

( i ) SEQUENCE CHARACTERISTICS:
        ( A ) LENGTH: 246 base pairs
        ( B ) TYPE: nucleic acid
        ( C ) STRANDEDNESS: both
        ( D ) TOPOLOGY: both ( x i ) SEQUENCE DESCRIPTION: SEQ ID NO:103:

```
AGCAATGGCA  ACAACGTCTG  CAAACTATTA  ACTGGCGAAC  TACTTACTCT  TAGCTTCCGG         60

CAACAATTAA  TAGACTGGAT  GGAGGCGGAT  AAAGTTGCAG  GACCACTTCT  GCGCTCGGCC        120

CTTCCGGCTG  GCTGGTTTAT  TGCTGATAAA  TCTGGAGCCG  GTCGAGCGTG  GGTCTCGCGT        180

ATCATTCGAG  NCTGGGGCCA  GATGGTAAGC  CCTCCGTATC  GTAGTTATCT  CACAGCAGGG        240

AGTCAG                                                                         246
```

( 2 ) INFORMATION FOR SEQ ID NO:104:

( i ) SEQUENCE CHARACTERISTICS:
        ( A ) LENGTH: 86 base pairs
        ( B ) TYPE: nucleic acid
        ( C ) STRANDEDNESS: both
        ( D ) TOPOLOGY: both ( x i ) SEQUENCE DESCRIPTION: SEQ ID NO:104:

```
CTGGCACTGG  AGCAGTGGGT  CCCTGGTCTC  CTACAAGTCC  TGGGGCATTG  GAGCCCCAAG         60

CAGTGTTAAT  CCTGGCACTG  TGTGAG                                                  86
```

( 2 ) INFORMATION FOR SEQ ID NO:105:

( i ) SEQUENCE CHARACTERISTICS:
        ( A ) LENGTH: 154 base pairs
        ( B ) TYPE: nucleic acid
        ( C ) STRANDEDNESS: both
        ( D ) TOPOLOGY: both ( x i ) SEQUENCE DESCRIPTION: SEQ ID NO:105:

```
CTGGAGCCGG  TCGAGCGTGG  GTCTCGCGTA  TCATTCGAGN  CTGGGGCCAG  ATGGTAAGCC         60

CTCCGTATCG  TAGTTATCTC  ACAGCCGTAT  CATTCGAGNC  TGGGGCCAGA  TGGTAAGCCC        120

TCCGTATCGT  AGTTATCTCA  CAGCAGGGAG  TCAG                                       154
```

( 2 ) INFORMATION FOR SEQ ID NO:106:

( i ) SEQUENCE CHARACTERISTICS:
        ( A ) LENGTH: 221 base pairs
        ( B ) TYPE: nucleic acid
        ( C ) STRANDEDNESS: both
        ( D ) TOPOLOGY: both ( x i ) SEQUENCE DESCRIPTION: SEQ ID NO:106:

```
AGGAGACTTG  TGGTAAAAAT  CTGCTGCTGT  ACTGCTCATT  TGGGAACCTT  AGTATACTAA         60

ATAATATAAT  ATATCAACAA  CTAATGGTCA  GCCAATGCTA  TGCTGGATAT  GAGGGTCCTG        120

GGCCACAAAG  ACAAAAAATC  AGGAACCACT  TTTTAAGTGA  GATACTTTGG  GTCTCTGTCA        180

AATTCATAAC  ACTTATTTCT  TGGTGGAATA  CAGTTAATGA  G                              221
```

( 2 ) INFORMATION FOR SEQ ID NO:107:

( i ) SEQUENCE CHARACTERISTICS:
  ( A ) LENGTH: 231 base pairs
  ( B ) TYPE: nucleic acid
  ( C ) STRANDEDNESS: both
  ( D ) TOPOLOGY: both ( x i ) SEQUENCE DESCRIPTION: SEQ ID NO:107:

| | | | | | |
|---|---|---|---|---|---|
| AGGAGCGGGG | AGGCACGATG | GCCGCTTTGG | TCCGGATCTT | TGTGAGGAAC | CTTACTTCTG | 60 |
| TGGTGTGACA | TAATTGGACA | AACTACCTAC | AGAGATTTAA | AGCTCTAAGG | AAATATAAAA | 120 |
| TTTTTAAGTG | TATAATGTGT | TAAACTACTG | ATTCTAATTG | TTTGTGTATT | TTAGATTCCA | 180 |
| ACCCTATGGA | ACCTGATGAA | TGGGAGCCAG | TGGTGGAATG | CCTTTAATGA | G | 231 |

( 2 ) INFORMATION FOR SEQ ID NO:108:

( i ) SEQUENCE CHARACTERISTICS:
    ( A ) LENGTH: 102 base pairs
    ( B ) TYPE: nucleic acid
    ( C ) STRANDEDNESS: both
    ( D ) TOPOLOGY: both ( x i ) SEQUENCE DESCRIPTION: SEQ ID NO:108:

| | | | | | |
|---|---|---|---|---|---|
| TAAATCTGGA | GCCGGTCGAG | CGTGGGTCTC | GCGTATCATT | CGAGCACTGG | GGCCAGATGG | 60 |
| TAAGCCCTCC | GTATCGTAGT | TATCTCACAG | CAGGGAGTCA | GG | | 102 |

( 2 ) INFORMATION FOR SEQ ID NO:109:

( i ) SEQUENCE CHARACTERISTICS:
    ( A ) LENGTH: 110 base pairs
    ( B ) TYPE: nucleic acid
    ( C ) STRANDEDNESS: both
    ( D ) TOPOLOGY: both ( x i ) SEQUENCE DESCRIPTION: SEQ ID NO:109:

| | | | | | |
|---|---|---|---|---|---|
| TAGAACCGCC | GCTGGCACTG | GAGCAGTGGG | TCCCTGGTCT | CCTACAAGTC | CTGGGGCATT | 60 |
| GGAGCCCCAA | GCAGTGTTAA | TCCTGGCTAC | TGTGTGAGCC | TGACCTCAAG | | 110 |

( 2 ) INFORMATION FOR SEQ ID NO:110:

( i ) SEQUENCE CHARACTERISTICS:
    ( A ) LENGTH: 85 base pairs
    ( B ) TYPE: nucleic acid
    ( C ) STRANDEDNESS: both
    ( D ) TOPOLOGY: both ( x i ) SEQUENCE DESCRIPTION: SEQ ID NO:110:

| | | | | | |
|---|---|---|---|---|---|
| ATAGATATCT | ACTTTATTCG | ATTTAAATTC | TGTTTAGTAT | TTTATTATAT | TTGTTAATC | 60 |
| CATTTGTCCC | AATTCATATA | CTTAT | | | | 85 |

( 2 ) INFORMATION FOR SEQ ID NO:111:

( i ) SEQUENCE CHARACTERISTICS:
    ( A ) LENGTH: 95 base pairs
    ( B ) TYPE: nucleic acid
    ( C ) STRANDEDNESS: both
    ( D ) TOPOLOGY: both ( x i ) SEQUENCE DESCRIPTION: SEQ ID NO:111:

| | | | | | |
|---|---|---|---|---|---|
| ATAGATAGCT | ACTTAAAATA | ACTTACACAC | TGTTTTAGAG | TGCTTGAAAA | CTATCTGATC | 60 |
| AGACATAGTA | ATTGAAACCA | ATGAATACAT | TATAT | | | 95 |

( 2 ) INFORMATION FOR SEQ ID NO:112:

( i ) SEQUENCE CHARACTERISTICS:

(A) LENGTH: 90 base pairs
(B) TYPE: nucleic acid
(C) STRANDEDNESS: both
(D) TOPOLOGY: both (xi) SEQUENCE DESCRIPTION: SEQ ID NO:112:

GAAGGATCTG TTTGTAAGAA CGGAGCGGGA TACCATAAAA ATAGAGGTAA TAACATACAT  60

TGGGACGTGT AAATTTATTT TTATNNAANT  90

(2) INFORMATION FOR SEQ ID NO:113:

(i) SEQUENCE CHARACTERISTICS:
(A) LENGTH: 94 base pairs
(B) TYPE: nucleic acid
(C) STRANDEDNESS: both
(D) TOPOLOGY: both (xi) SEQUENCE DESCRIPTION: SEQ ID NO:113:

GAAGGATCTT ACCATTTTAA GAAAGGTCCA AAATTAAATA AAAATTTAAT TAGTCTCTTT  60

AGTGTTGCAT ACCATCAATA TCGGAATACT AAAT  94

(2) INFORMATION FOR SEQ ID NO:114:

(i) SEQUENCE CHARACTERISTICS:
(A) LENGTH: 200 base pairs
(B) TYPE: nucleic acid
(C) STRANDEDNESS: both
(D) TOPOLOGY: both (xi) SEQUENCE DESCRIPTION: SEQ ID NO:114:

ACCTGGTGCT GTGCTCACCC AGGCCGAGGG TGCCTTTGTG GCCTCACTGA TTAAGGAGAG  60

TGGCATGATG ACTTCAATGT CTGGATTGGC CTCCATGACC CCAAAAAGAA CCGCCGCTGG  120

GGAGCGTGGG TCCCTGGTCT CCTACAAGTC CTGGGGCATT GGAGCCCCAA GCAGTGTTAA  180

TCCTGGCTAC TGTGTGAGCC  200

(2) INFORMATION FOR SEQ ID NO:115:

(i) SEQUENCE CHARACTERISTICS:
(A) LENGTH: 218 base pairs
(B) TYPE: nucleic acid
(C) STRANDEDNESS: both
(D) TOPOLOGY: both (xi) SEQUENCE DESCRIPTION: SEQ ID NO:115:

AACTGGCGAA CTACTTACTC TAGCTTCCGG CAACAATTAA TAGACTGGAT GGAGGCGGAT  60

AAAGTTGCAG GACCACTTCT GCGCTCGGCC CTTCCGGCTG GCTGGTTTAT TGCTGATAAA  120

TCTGGAGCCG GTGAGCGTGG GTCTCGCGTA TCATTGCAGC ACTGGGGCCA GATGGTAAGC  180

CCTCCGTATC GTGGTTATCT ACACGACGGG GAGTACGC  218

(2) INFORMATION FOR SEQ ID NO:116:

(i) SEQUENCE CHARACTERISTICS:
(A) LENGTH: 146 base pairs
(B) TYPE: nucleic acid
(C) STRANDEDNESS: both
(D) TOPOLOGY: both (xi) SEQUENCE DESCRIPTION: SEQ ID NO:116:

AGGCCCATCA TCAGTTTTTA TATAAAGAAA AAAAAACCTT AAAATTGTTA GGCAAATACT  60

ATGACAAATT GTAATATATA TTCTTACATT TCAGATTTTT ATTTTTAAA CTGTATAGAA  120

TTGATTAATA AATAAAATTT AGTATT  146

( 2 ) INFORMATION FOR SEQ ID NO:117:

( i ) SEQUENCE CHARACTERISTICS:
        ( A ) LENGTH: 155 base pairs
        ( B ) TYPE: nucleic acid
        ( C ) STRANDEDNESS: both
        ( D ) TOPOLOGY: both ( x i ) SEQUENCE DESCRIPTION: SEQ ID NO:117:

```
AGGCACGATG  GCCGCTTTGG  TCCGGATCTT  TGTGAAGGAA  CCTTACTTCT  GTGTGTGACA        60

TAATTGGACA  AACTACCTAC  AGAGATTTAA  ACGTCTAAGG  TAAATATAAA  ATTTTTAGTG       120

TATAGGTTAA  ACTACTGATT  CTAATGTTGT  GTATT                                    155
```

( 2 ) INFORMATION FOR SEQ ID NO:118:

( i ) SEQUENCE CHARACTERISTICS:
        ( A ) LENGTH: 102 base pairs
        ( B ) TYPE: nucleic acid
        ( C ) STRANDEDNESS: both
        ( D ) TOPOLOGY: both ( x i ) SEQUENCE DESCRIPTION: SEQ ID NO:118:

```
TAAATCTGGA  GCCGGTGAGC  GTGGGTCTCG  CGTATCATTG  CAGCACTGGG  GCCAGATGGT        60

AAGCCCTCCG  TATCGTGGTT  ATCTACACGA  CGGGGAGTAC  GG                           102
```

( 2 ) INFORMATION FOR SEQ ID NO:119:

( i ) SEQUENCE CHARACTERISTICS:
        ( A ) LENGTH: 116 base pairs
        ( B ) TYPE: nucleic acid
        ( C ) STRANDEDNESS: both
        ( D ) TOPOLOGY: both ( x i ) SEQUENCE DESCRIPTION: SEQ ID NO:119:

```
TAGAACCGCC  GCTGGCACTG  GAGCAGTGGG  TCCCTGGTCT  CCTACAAGTC  CTGGGGCATT        60

GGAGCCCCAA  GCAGTGTTAA  TCCTGGCTAC  TGTGTGAGCC  TGACCTCAAG  CACAGG           116
```

( 2 ) INFORMATION FOR SEQ ID NO:120:

( i ) SEQUENCE CHARACTERISTICS:
        ( A ) LENGTH: 1442 base pairs
        ( B ) TYPE: nucleic acid
        ( C ) STRANDEDNESS: double
        ( D ) TOPOLOGY: both ( i i ) MOLECULE TYPE: cDNA ( i x ) FEATURE:
        ( A ) NAME/KEY: CDS
        ( B ) LOCATION: 15..1139

( x i ) SEQUENCE DESCRIPTION: SEQ ID NO:120:

```
TTTTTTTTT  TGAG  ATG  GAG  TTT  TCG  CTC  TTG  TTG  CCC  AGG  CTG  GAG  TGC         50
                 Met  Glu  Phe  Ser  Leu  Leu  Leu  Pro  Arg  Leu  Glu  Cys
                  1              5                       10

AAT  GGC  GCA  ATC  TCA  GCT  CAC  CGC  AAC  CTC  CGC  CTC  CCG  GGT  TCA  AGC       98
Asn  Gly  Ala  Ile  Ser  Ala  His  Arg  Asn  Leu  Arg  Leu  Pro  Gly  Ser  Ser
              15                  20                   25

GAT  TCT  CCT  GCC  TCA  GCC  TCC  CCA  GTA  GCT  GGG  ATT  ACA  GGC  ATG  TGC      146
Asp  Ser  Pro  Ala  Ser  Ala  Ser  Pro  Val  Ala  Gly  Ile  Thr  Gly  Met  Cys
         30                  35                   40

ACC  CAC  GCT  CGG  CTA  ATT  TTG  TAT  TTT  TTT  TTA  GTA  GAG  ATG  GAG  TTT      194
Thr  His  Ala  Arg  Leu  Ile  Leu  Tyr  Phe  Phe  Leu  Val  Glu  Met  Glu  Phe
 45                 50                   55                   60
```

| | | | | | | | | | | | | | | | | |
|---|---|---|---|---|---|---|---|---|---|---|---|---|---|---|---|---|
| CTC | CAT | GTT | GGT | CAG | GCT | GGT | CTC | GAA | CTC | CCG | ACC | TCA | GAT | GAT | CCC | 242 |
| Leu | His | Val | Gly | Gln | Ala | Gly | Leu | Glu | Leu | Pro | Thr | Ser | Asp | Asp | Pro | |
| | | | 65 | | | | 70 | | | | | | | 75 | | |
| TCC | GTC | TCG | GCC | TCC | CAA | AGT | GCT | AGA | TAC | AGG | ACT | GGC | CAC | CAT | GCC | 290 |
| Ser | Val | Ser | Ala | Ser | Gln | Ser | Ala | Arg | Tyr | Arg | Thr | Gly | His | His | Ala | |
| | | | 80 | | | | | 85 | | | | | 90 | | | |
| CGG | CTC | TGC | CTG | GCT | AAT | TTT | TGT | GGT | AGA | AAC | AGG | GTT | TCA | CTG | ATG | 338 |
| Arg | Leu | Cys | Leu | Ala | Asn | Phe | Cys | Gly | Arg | Asn | Arg | Val | Ser | Leu | Met | |
| | | 95 | | | | | 100 | | | | | 105 | | | | |
| TGC | CCA | AGC | TGG | TCT | CCT | GAG | CTC | AAG | CAG | TCC | ACC | TGC | CTC | AGC | CTC | 386 |
| Cys | Pro | Ser | Trp | Ser | Pro | Glu | Leu | Lys | Gln | Ser | Thr | Cys | Leu | Ser | Leu | |
| | 110 | | | | 115 | | | | | 120 | | | | | | |
| CCA | AAG | TGC | TGG | GAT | TAC | AGG | CGT | GCA | GCC | GTG | CCT | GGC | CTT | TTT | ATT | 434 |
| Pro | Lys | Cys | Trp | Asp | Tyr | Arg | Arg | Ala | Ala | Val | Pro | Gly | Leu | Phe | Ile | |
| 125 | | | | 130 | | | | | 135 | | | | | 140 | | |
| TTA | TTT | TTT | TTA | AGA | CAC | AGG | TGT | CCC | ACT | CTT | ACC | CAG | GAT | GAA | GTG | 482 |
| Leu | Phe | Phe | Leu | Arg | His | Arg | Cys | Pro | Thr | Leu | Thr | Gln | Asp | Glu | Val | |
| | | | | 145 | | | | 150 | | | | | 155 | | | |
| CAG | TGG | TGT | GAT | CAC | AGC | TCA | CTG | CAG | CCT | TCA | ACT | CCT | GAG | ATC | AAG | 530 |
| Gln | Trp | Cys | Asp | His | Ser | Ser | Leu | Gln | Pro | Ser | Thr | Pro | Glu | Ile | Lys | |
| 160 | | | | 165 | | | | | 170 | | | | | | | |
| CAT | CCT | CCT | GCC | TCA | GCC | TCC | CAA | GTA | GCT | GGG | ACC | AAA | GAC | ATG | CAC | 578 |
| His | Pro | Pro | Ala | Ser | Ala | Ser | Gln | Val | Ala | Gly | Thr | Lys | Asp | Met | His | |
| | | 175 | | | | | 180 | | | | | 185 | | | | |
| CAC | TAC | ACC | TGG | CTA | ATT | TTT | ATT | TTT | ATT | TTT | AAT | TTT | TTG | AGA | CAG | 626 |
| His | Tyr | Thr | Trp | Leu | Ile | Phe | Ile | Phe | Ile | Phe | Asn | Phe | Leu | Arg | Gln | |
| | 190 | | | | | 195 | | | | | 200 | | | | | |
| AGT | CTC | AAC | TCT | GTC | ACC | CAG | GCT | GGA | GTG | CAG | TGG | CGC | AAT | CTT | GGC | 674 |
| Ser | Leu | Asn | Ser | Val | Thr | Gln | Ala | Gly | Val | Gln | Trp | Arg | Asn | Leu | Gly | |
| 205 | | | | | 210 | | | | | 215 | | | | | 220 | |
| TCA | CTG | CAA | CCT | CTG | CCT | CCC | GGG | TTC | AAG | TTA | TTC | TCC | TGC | CCC | AGC | 722 |
| Ser | Leu | Gln | Pro | Leu | Pro | Pro | Gly | Phe | Lys | Leu | Phe | Ser | Cys | Pro | Ser | |
| | | | | 225 | | | | | 230 | | | | | 235 | | |
| CTC | CTG | AGT | AGC | TGG | GAC | TAC | AGG | CGC | CCA | CCA | CGC | CTA | GCT | AAT | TTT | 770 |
| Leu | Leu | Ser | Ser | Trp | Asp | Tyr | Arg | Arg | Pro | Pro | Arg | Leu | Ala | Asn | Phe | |
| | | | 240 | | | | | 245 | | | | | 250 | | | |
| TTT | GTA | TTT | TTA | GTA | GAG | ATG | GGG | TTC | ACC | ATG | TTC | GCC | AGG | TTG | ATC | 818 |
| Phe | Val | Phe | Leu | Val | Glu | Met | Gly | Phe | Thr | Met | Phe | Ala | Arg | Leu | Ile | |
| | | 255 | | | | | 260 | | | | | 265 | | | | |
| TTG | ATC | TCT | GGA | CCT | TGT | GAT | CTG | CCT | GCC | TCG | GCC | TCC | CAA | AGT | GCT | 866 |
| Leu | Ile | Ser | Gly | Pro | Cys | Asp | Leu | Pro | Ala | Ser | Ala | Ser | Gln | Ser | Ala | |
| | 270 | | | | | 275 | | | | | 280 | | | | | |
| GGG | ATT | ACA | GGC | GTG | AGC | CAC | CAC | GCC | CGG | CTT | ATT | TTT | AAT | TTT | TGT | 914 |
| Gly | Ile | Thr | Gly | Val | Ser | His | His | Ala | Arg | Leu | Ile | Phe | Asn | Phe | Cys | |
| 285 | | | | | 290 | | | | | 295 | | | | | 300 | |
| TTG | TTT | GAA | ATG | GAA | TCT | CAC | TCT | GTT | ACC | CAG | GCT | GGA | GTG | CAA | TGG | 962 |
| Leu | Phe | Glu | Met | Glu | Ser | His | Ser | Val | Thr | Gln | Ala | Gly | Val | Gln | Trp | |
| | | | | 305 | | | | | 310 | | | | | 315 | | |
| CCA | AAT | CTC | GGC | TCA | CTG | CAA | CCT | CTG | CCT | CCC | GGG | CTC | AAG | CGA | TTC | 1010 |
| Pro | Asn | Leu | Gly | Ser | Leu | Gln | Pro | Leu | Pro | Pro | Gly | Leu | Lys | Arg | Phe | |
| | | | 320 | | | | | 325 | | | | | 330 | | | |
| TCC | TGT | CTC | AGC | CTC | CCA | AGC | AGC | TGG | GAT | TAC | GGG | CAC | CTG | CCA | CCA | 1058 |
| Ser | Cys | Leu | Ser | Leu | Pro | Ser | Ser | Trp | Asp | Tyr | Gly | His | Leu | Pro | Pro | |
| | | 335 | | | | | 340 | | | | | 345 | | | | |
| CAC | CCC | GCT | AAT | TTT | TGT | ATT | TTC | ATT | AGA | GGC | GGG | GTT | TCA | CCA | TAT | 1106 |
| His | Pro | Ala | Asn | Phe | Cys | Ile | Phe | Ile | Arg | Gly | Gly | Val | Ser | Pro | Tyr | |
| | 350 | | | | | 355 | | | | | 360 | | | | | |
| TTG | TCA | GGC | TGG | TCT | CAA | ACT | CCT | GAC | CTC | AGG | TGACCCACCT | GCCTCAGCCT | | | | 1159 |
| Leu | Ser | Gly | Trp | Ser | Gln | Thr | Pro | Asp | Leu | Arg | | | | | | |
| 365 | | | | | 370 | | | | | 375 | | | | | | |

|  |  |  |  |  |  |
|---|---|---|---|---|---|
| TCCAAAGTGC | TGGGATTACA | GGCGTGAGCC | ACCTCACCCA | GCCGGCTAAT | TTAGATAAAA | 1219 |
| AAATATGTAG | CAATGGGGGG | TCTTGCTATG | TTGCCCAGGC | TGGTCTCAAA | CTTCTGGCTT | 1279 |
| CATGCAATCC | TTCCAAATGA | GCCACAACAC | CCAGCCAGTC | ACATTTTTA | AACAGTTACA | 1339 |
| TCTTTATTTT | AGTATACTAG | AAAGTAATAC | AATAAACATG | TCAAACCTGC | AAATTCAGTA | 1399 |
| GTAACAGAGT | TCTTTTATAA | CTTTTAAACA | AAGCTTTAGA GCA |  |  | 1442 |

( 2 ) INFORMATION FOR SEQ ID NO:121:

( i ) SEQUENCE CHARACTERISTICS:
( A ) LENGTH: 375 amino acids
( B ) TYPE: amino acid
( D ) TOPOLOGY: linear ( i i ) MOLECULE TYPE: protein ( x i ) SEQUENCE DESCRIPTION: SEQ ID NO:121:

```
Met Glu Phe Ser Leu Leu Leu Pro Arg Leu Glu Cys Asn Gly Ala Ile
 1               5                  10                  15

Ser Ala His Arg Asn Leu Arg Leu Pro Gly Ser Ser Asp Ser Pro Ala
            20                  25                  30

Ser Ala Ser Pro Val Ala Gly Ile Thr Gly Met Cys Thr His Ala Arg
        35                  40                  45

Leu Ile Leu Tyr Phe Phe Leu Val Glu Met Glu Phe Leu His Val Gly
    50                  55                  60

Gln Ala Gly Leu Glu Leu Pro Thr Ser Asp Asp Pro Ser Val Ser Ala
 65                  70                  75                  80

Ser Gln Ser Ala Arg Tyr Arg Thr Gly His His Ala Arg Leu Cys Leu
                85                  90                  95

Ala Asn Phe Cys Gly Arg Asn Arg Val Ser Leu Met Cys Pro Ser Trp
            100                 105                 110

Ser Pro Glu Leu Lys Gln Ser Thr Cys Leu Ser Leu Pro Lys Cys Trp
        115                 120                 125

Asp Tyr Arg Arg Ala Ala Val Pro Gly Leu Phe Ile Leu Phe Phe Leu
    130                 135                 140

Arg His Arg Cys Pro Thr Leu Thr Gln Asp Glu Val Gln Trp Cys Asp
145                 150                 155                 160

His Ser Ser Leu Gln Pro Ser Thr Pro Glu Ile Lys His Pro Pro Ala
                165                 170                 175

Ser Ala Ser Gln Val Ala Gly Thr Lys Asp Met His His Tyr Thr Trp
            180                 185                 190

Leu Ile Phe Ile Phe Ile Phe Asn Phe Leu Arg Gln Ser Leu Asn Ser
        195                 200                 205

Val Thr Gln Ala Gly Val Gln Trp Arg Asn Leu Gly Ser Leu Gln Pro
    210                 215                 220

Leu Pro Pro Gly Phe Lys Leu Phe Ser Cys Pro Ser Leu Leu Ser Ser
225                 230                 235                 240

Trp Asp Tyr Arg Arg Pro Pro Arg Leu Ala Asn Phe Phe Val Phe Leu
                245                 250                 255

Val Glu Met Gly Phe Thr Met Phe Ala Arg Leu Ile Leu Ile Ser Gly
            260                 265                 270

Pro Cys Asp Leu Pro Ala Ser Ala Ser Gln Ser Ala Gly Ile Thr Gly
        275                 280                 285

Val Ser His His Ala Arg Leu Ile Phe Asn Phe Cys Leu Phe Glu Met
    290                 295                 300
```

-continued

| Glu 305 | Ser | His | Ser | Val | Thr 310 | Gln | Ala | Gly | Val | Gln 315 | Trp | Pro | Asn | Leu | Gly 320 |
|---|---|---|---|---|---|---|---|---|---|---|---|---|---|---|---|
| Ser | Leu | Gln | Pro | Leu 325 | Pro | Pro | Gly | Leu | Lys 330 | Arg | Phe | Ser | Cys | Leu 335 | Ser |
| Leu | Pro | Ser | Ser 340 | Trp | Asp | Tyr | Gly | His 345 | Leu | Pro | Pro | His | Pro 350 | Ala | Asn |
| Phe | Cys | Ile 355 | Phe | Ile | Arg | Gly | Gly 360 | Val | Ser | Pro | Tyr | Leu 365 | Ser | Gly | Trp |
| Ser | Gln 370 | Thr | Pro | Asp | Leu | Arg 375 | | | | | | | | | |

NEURAL THREAD PROTEIN GENE EXPRESSION AND DETECTION OF ALZHEIMER'S DISEASE

CROSS REFERENCE TO RELATED APPLICATIONS

This application is a divisional of U.S. application Ser. No. 08/340,426 filed Nov. 14, 1994 which is a continuation-in-part of U.S. application Ser. No. 08/230,139 filed Apr. 20, 1994, now abandoned and U.S. application Ser. No. 08/055,778 filed May 3, 1993 U.S. application Ser. No. 08/230,139 is a continuation-in-part of U.S. application Ser. No. 08/050,559 filed Apr. 20, 1993, now abandoned. U.S. application Ser. No. 08/055,778 is a continuation of U.S. application Ser. No. 07/451,975 filed Dec. 20, 1989, now abandoned which is a continuation-in-part of U.S. application Ser. No. 07/287, 207 filed Dec. 21, 1988, now abandoned.

STATEMENT AS TO RIGHTS TO INVENTIONS MADE UNDER FEDERALLY-SPONSORED RESEARCH AND DEVELOPMENT

The present invention was made with U.S. government support. Therefore, the U.S. government has certain rights in the invention.

FIELD OF THE INVENTION

The present invention is in the field of genetic engineering and molecular biology. This invention is directed to recombinant hosts expressing novel proteins associated with Alzheimer's Disease, neuroectodermal tumors, malignant astrocytomas, and glioblastomas. This invention is specifically directed to the recombinant hosts and vectors which contain the genes coding for the neuronal thread proteins. This invention is also directed to substantially pure neural thread proteins, immunodiagnostic and molecular diagnostic methods to detect the presence of neural thread proteins, and the use of nucleic acid sequences which code for neural thread proteins in gene therapy.

BACKGROUND OF THE INVENTION

Alzheimer's Disease

Alzheimer's Disease (AD) is the most frequent cause of dementia in the United States, affecting over two million individuals each year. It is a degenerative brain disorder characterized clinically by loss of memory, confusion, and gradual physical deterioration. It is the fourth most common cause of death. The etiology of the disease is virtually unknown but has been attributed to various viruses, toxins, heavy metals, as well as genetic defects. The disease is at present incurable.

Until quite recently, AD was thought to account for relatively few of the cases generally classified as senile dementia. Other factors can lead to such a condition, including repetitious mild strokes, thyroid disorders, alcoholism, and deficiencies of certain vitamins, many of which are potentially treatable. It can be appreciated, then, that a diagnostic test specific for AD would be very useful for the clinical diagnosis and proper clinical treatment of subjects presenting with symptoms common to all of these conditions.

The brains of individuals with AD exhibit characteristic pathological accumulations of congophilic fibrous material which occurs as neurofibrillary tangles within neuronal cell bodies, and neuritic (or senile) plaques. Neurofibrillary tangles may also be found in the walls of certain cerebral blood vessels. The major organized structural components of neurofibrillary tangles are paired helical filaments. Qualitatively indistinguishable amyloid deposits also occur in normal aged brains but in much smaller numbers with restricted topographical distribution.

There has been considerable recent investigative activity regarding the characterization of proteins found in neuritic plaques and neurofibrillary tangles of AD and other neurologic diseases. One of the amyloid proteins initially described by Glenner et al. has been cloned and sequenced (Glenner et al., Biochem. Biophys. Res. Commun. 120:1131–1135 (1984); U.S. Pat. No. 4,666,829). The A4 amyloid protein found in neuritic plaques and blood vessels has been determined to be a component of a 695 amino acid precursor; a protein postulated to function as a glycosylated cell surface receptor (Masters et al., Proc. Natl. Acad. Sci. USA 82:4245–4249 (1985), Kang et al., Nature 325:733–736 (1987)). In addition, the amyloid protein has been postulated to function as a cell adhesion molecule and as a calcium ion channel protein (Hooper, J. NIH Res. 4:48–54 (1992); Rensberger, Wayward Protein Molecule May Be Elusive Killer of Brain Cells, The Washington Post, Jan. 25, 1993, §1, at A3 (1993)). The gene coding for A4 is located on chromosome 21 (Kang et al., ibid.; Goldgaber et al., Science 235:877–880 (1987); Tanzi et al., Science 235:880–885 (1987); St. George-Hyslop et al., Science 235:885–889 (1987)) but apparently is not linked to the familial form of the disease (Van Broekhoven et al., Nature 329:153–155 (1987)). There appears to be little, if any, protein sequence homology between amyloid A4 and β protein, their higher molecular weight precursor, and pancreatic thread protein (PTP) (Gross et al., J. Clin. Invest. 76:2115–2126 (1985)).

A number of other proteins thought to be associated with the disease have been described, including Ubiquitin, ALZ-50, microtubular-associated proteins τ and MAP2, and neurofilament protein (see, for example, Manetto et al., Proc. Natl. Acad. Sci. USA 85:4502–4505 (1988); Wolozin et al., Science 232:648–651 (1986); Selkoe, Neurobiol. Aging 7:425–432 (1986); Perry et al., in: Alterations of the Neuronal Cytoskeleton in Alzheimer's Disease, Plenum, New York, pp 137–149 (1987)). More recently, a serine protease inhibitor called $\alpha_1$-anti-chymotrypsin has been found in AD amyloid deposits (Abraham et al., Cell 52:487–501 (1988)).

There is currently no useful diagnostic test for AD being practiced clinically. A definitive diagnosis is possible only postmortem, or during life through a brain biopsy, to reveal the presence of the characteristic plaques, tangles, paired helical filaments, and other cerebrovascular deposits which characterize the disorder. Such an invasive surgical procedure is inherently dangerous and is therefore rarely utilized. As a result, the clinical misdiagnosis of AD is estimated to be approximately 20%–30%.

Thread Proteins

The prototype thread protein molecule is pancreatic thread protein (PTP) which bears the unusual physical property of forming insoluble fibrils at neutral pH, but is highly soluble at acid or alkaline pH (Gross et al., supra). PTP is highly abundant, synthesized by pancreatic acinar cells, and secreted into pancreatic juice in concentrations exceeding 1 mg/ml (Id.). An increased thread protein immunoreactivity has been demonstrated in brains with AD lesions, using monoclonal antibodies to PTP (Ozturk et al., Proc. Natl. Acad. Sci. USA 86:419–423 (1989)). In addition, a highly sensitive forward sandwich immunoradiometric assay was used to demonstrate that at least three distinct antigenic epitopes were shared between PTP and the related protein in the brain (Id.) Despite similarities, the pancreatic and neuronal forms of the thread protein are almost certainly distinct since the MnRNA molecules and proteins differ in size, and many of the antigenic epitopes which are present in the pancreatic thread protein are not detectable in brain tissue (de la Monte et. al., *J. Clin. Invest.* 86:1004–1013 (1990); de la Monte et. al., *J. Neurol. Sci.* 113:152–164 (1992); de la Monte et al., *Ann. Neurol.* 32:733–742 (1992)).

The central nervous system form of the thread protein, designated hereafter as "neural thread protein" (NTP), has been identified in AD and Down's Syndrome brain tissue (Wands et al., International Application Publication No. WO90/06993). NTP has been found in all AD brains studied where characteristic neuropathologic changes of the disease exist (Id.). The saline-extractable soluble immunoreactivity shares has a molecular weight of approximately 17 to 20 kD (Id.).

Quantitative measurements of NTP immunoreactivity in various regions of AD brains revealed levels varying from 12 to 295 ng/gm tissue (Mean=116 ng/gm tissue) compared to 1–11 ng/gm tissue (Mean=5 ng/gm tissue) in comparable ares of control brains (Id.).

Immunocytochemistry performed with monoclonal antibodies directed against the pancreatic form of PTP demonstrated that NTP is localized within cells, within fine processes within the neuropil, or is extracellular in both AD and Down's Syndrome brains (Id.). Two types of cell contain NTP: neurons and astrocytes (Id.). The affected neurons are the large pyramidal type which typically contain the neurofibrillary tangles well known in AD brain (Id.).

That NTP accumulation within neurons is intrinsically important or integrally related to the evolution of AD lesions is corroborated by the presence of identical patterns of immunolabeling for NTP in Down's Syndrome brains, but not in control brains (Id.). It is important to note that the same structural abnormalities of AD occur in brains of all middle-age individuals with Down's syndrome, whether or not they are demented. There is also a higher incidence of AD in family members of Down's Syndrome patients. Moreover, the regional differences in the densities of NTP-containing neurons parallels the density distributions of neurofibrillary AD and Down's Syndrome. This provides further evidence that NTP is germane to the pathophysiology of AD. Whether NTP accumulates within neuronal perikarya, as a result of aberrant cellular metabolism or transport is not yet known.

SUMMARY OF THE INVENTION

A need exists for a definitive diagnostic test which can be performed on individuals suspected of having, or being at risk for AD. The present invention satisfies such needs and provides further advantages.

The manner in which these and other objects are realized by the present invention will be apparent from the summary and detailed description set forth below.

Unless defined otherwise, various terms used herein have the same meaning as is well understood in the art to which the invention belongs. All cited publications are incorporated herein by reference.

This invention is directed to recombinant hosts expressing novel proteins associated with Alzheimer's Disease, neuroectodermal tumors, malignant astrocytomas, and glioblastomas. This invention is specifically directed to the recombinant hosts and vectors which contain the genes coding for the neuronal thread proteins (NTP) having molecular weights of about 8 kDa, 14 kDa, 17 kDa, 21 kDa, 26 kDa or 42 kDa. This invention is also directed to the substantially pure neural thread proteins, immunodiagnostic and molecular diagnostic methods to detect the presence of neural thread proteins, and the use of nucleic acid sequences which code for neural thread proteins in gene therapy.

In particular, the invention includes a method for detecting and quantitating an NTP in a human subject, comprising:
  (a) contacting a biological sample from a human subject that is suspected of containing detectable levels of an NTP with a molecule capable of binding to the NTP; and
  (b) detecting the molecule bound to the NTP.

The invention additionally includes the method as above, wherein the binding molecule is selected from the group consisting of:
  (a) an antibody substantially free of natural impurities;
  (b) a monoclonal antibody; and
  (c) a fragment of (a) or (b).

The invention additionally includes the method as above, wherein the detecting molecule is detectably labeled and where a combination of such binding molecules is used.

The invention additionally includes a method for detecting the presence of a genetic sequence coding for an NTP in a biological sample using a polynucleotide probe derived from a recombinant human NTP of this invention.

The invention additionally includes a method for determining the presence of a condition in a human subject, said condition including, but not limited to, the group consisting of Alzheimer's Disease, the presence of neuroectodermal tumors, the presence of malignant astrocytomas, and the presence of gliomas.

The invention additionally includes a method of diagnosing the presence of AD in a human subject suspected of having AD which comprises:
  (a) incubating a biological sample from said subject suspected of containing an NTP with a molecule capable of identifying an NTP; and
  (b) detecting the molecule which is bound in the sample, wherein the detection indicates that the subject has AD.

The invention additionally includes a method of diagnosing the presence of neuroectodermal tumors in a human subject suspected of having neuroectodermal tumors which comprises:
  (a) incubating a biological sample from said subject suspected of containing an NTP with a molecule capable of identifying an NTP; and
  (b) detecting the molecule which is bound in the sample, wherein the detection indicates that the subject has neuroectodermal tumors.

The invention additionally includes a method of diagnosing the presence of a malignant astrocytoma in a human subject suspected of having a malignant astrocytoma which comprises:
  (a) incubating a biological sample from said subject, which is suspected of containing an NTP, in the presence of a binding molecule capable of identifying an NTP; and
  (b) detecting molecule which is bound in the sample, wherein the detection indicates that the subject has a malignant astrocytoma.

The invention additionally includes a method of diagnosing the presence of a glioblastoma in a human subject suspected of having a glioblastoma which comprises:
  (a) incubating a biological sample from said subject, which is suspected of containing an NTP, in the presence of a binding molecule capable of identifying an NTP; and (b) detecting molecule which is bound in the sample, wherein the detection indicates that the subject has a glioblastoma.

The invention additionally includes the methods as above, wherein a biological sample is removed a human subject prior to contacting the sample with the molecule.

The invention additionally includes the methods as above, wherein detecting any of the molecules bound to the protein is performed by in situ imaging.

The invention additionally includes the methods as above, wherein detecting of any of the molecule bound to the protein is performed by in vivo imaging.

The invention additionally includes the methods as above, wherein the biological sample is reacted with the binding molecule in a manner and under such conditions sufficient to determine the presence and the distribution of the protein.

The invention additionally includes the methods as above, wherein a detectably labeled binding molecule of an. NTP is administered to a human subject.

The invention additionally includes the methods as above, wherein the binding molecule is bound to the protein in vivo.

The invention additionally involves an NTP substantially free of any natural impurities and having a molecular weight of about 42 kDa.

The invention additionally involves an NTP substantially free of any natural impurities and having a molecular weight of about 26 kDa.

The invention additionally includes an NTP substantially free of any natural impurities and having a molecular weight of about 21 kDa.

The invention additionally includes an NTP substantially free of any natural impurities and having a molecular weight of about 17 kDa.

The invention additionally includes an NTP substantially free of any natural impurities and having a molecular weight of about 14 kDa.

The invention additionally includes an NTP substantially free of any natural impurities and having a molecular weight of about 8 kDa.

The present invention also particularly relates to the diagnostic methods recited above, wherein the immunoassay comprises two different antibodies bound to a solid phase support combined with a third different detectably labeled antibody in solution.

The invention is also directed to a method of producing an NTP, said method comprising:

(a) culturing a recombinant host comprising a human gene coding for said NTP; and (b) isolating said NTP from said host.

Additionally, the invention is directed to a substantially pure NTP obtained by the such a process.

The invention is also directed to an 15- to 30-mer antisense oligonucleotide which is complementary to an NTP nucleic acid sequence and which is nonhomologous to PTP nucleic acid sequences, as well as pharmaceutical compositions comprising such oligonucleotides and a pharmaceutically acceptable carrier.

The invention is also directed to ribozymes comprising a target sequence which is complementary to an NTP sequence and nonhomologous to PTP nucleic acid sequences, as well as pharmaceutical compositions comprising such ribozymes and a pharmaceutically acceptable carrier.

The invention is also directed to a method of achieving pharmaceutical delivery of NTP molecules to the brain through acceptable carriers or expression vectors.

The invention is also directed to oligodeoxynucleotides that form triple stranded regions with the various NTP genes (nucleic acid sequences) and which are nonhomologous to PTP nucleic acid sequences, as well as pharmaceutical compositions comprising such oligodeoxynucleotides and a pharmaceutically acceptable carrier.

The invention is also directed to the therapeutic use of NTP-derived molecules or fragments thereof to modify or improve dementias of the Alzheimer's type of neuronal degeneration.

The invention is also directed to methods for the differential diagnosis of sporadic and familial Alzheimer's disease.

BRIEF DESCRIPTION OF THE DRAWINGS

FIGS. 1A–1J show neural thread protein immunoreactivity in CNS-derived tumors.

FIG. 9 shows the 1–9a partial cDNA sequence, and FIG. 9A shows a partial sequence of the second 5' anchor PCR product corresponding to the 5' region of the 1–9a cDNA (WP5' Sequence).

FIG. 10 shows alignment of partial sequences between 1–9a and human PTP and the Reg gene (the nucleic acid sequence corresponding to the genomic clone of human PTP).

FIG. 10A shows alignment between 1–9a and Exon 2 of the human Reg gene, and between the first 5' anchor PCR product of 1–9a (WP03-417) and Exon 2 and Reg.

FIG. 10B shows alignment between the 1–9a and its second 5' anchor PCR product (WP5') and AD 3-4 and AD 2-2 cDNAs.

FIG. 11A shows the partial nucleic acid and deduced amino acid sequences of the HB4 cDNA. FIGS. 11B and 11C show a protein hydrophilicity window plot. Hydrophilicity Window Size=7; scale=Kyte-Doolittle.

FIG. 11D shows alignment between HB4 and human PTP.

FIG. 11E shows alignment between HB4 and human Reg gene.

FIG. 13B demonstrates four different transcripts with greater abundance of the lower molecular size mRNAs in AD compared with aged controls.

FIG. 14A is a longer exposure of FIG. 14B. FIG. 14C shows hybridization of the same blot using the O18 rat PTP probe.

FIGS. 16A, 16D and 16E show the partial nucleic acid sequences of the AD 2-2 cDNAs isolated from the AD brain library. FIGS. 16B and 16C show a hydrophilicity window plot of AD2-2 T7. Hydrophilicity Window Size=7; scale=Kyte-Doolittle.

FIGS. 16F, 16I, 16J and 16K show the partial nucleic acid sequences of the AD 3-4 cDNAs isolated from the AD brain library.

FIGS. 16L, 16M and 16N show the partial nucleic acid sequences of the AD 4-4 cDNAs isolated from the AD brain library.

FIG. 16O shows the partial nucleic acid sequences of the AD 16c (also called AD 10-7) cDNAs isolated from the AD brain library. FIGS. 16P and 16Q show a hydrophilicity window plot of AD16c-T7. Hydrophilicity Window Size=7; scale=Kyte-Doolittle.

FIG. 16R shows the complete nucleotide sequence of the AD10-7 cDNA clone that was isolated from an AD library.

FIG. 16S shows the complete nucleotide sequence of the AD16c cDNA clone that was isolated from the AD brain library.

FIG. 17 shows alignment of partial sequences between AD 2-2 and human Reg gene.

FIG. 17A shows alignment of partial sequences between AD 2-2 and Exon 1 of Reg and rat PTP.

FIG. 17B shows alignment of partial sequences between AD 2-2 and 1–9a.

FIG. 17C shows alignment of partial sequences between AD 2-2 and AD 16c.

FIG. 18 shows alignment of partial sequences between AD 3-4 (also called AD 5-3) and the Reg gene.

FIG. 18A shows alignment of partial sequences between AD 3-4 and the 5' anchor PCR products of the 1-9a mRNA, termed WPO3-5 and 18-4.

FIG. 18B shows alignment of partial sequences between AD 3-4 and the G2a-a EcoRI|PstI genomic clone.

FIG. 19 shows alignment of partial sequences between AD 4-4 and AD 2-2 and 1-9a (also called SE-4 corresponding to the PCR clone which is identical to 1–9a).

FIG. 20 shows alignment of partial sequences between AD 16c and Reg gene.

FIG. 20A shows alignment of partial sequences between AD 16c and human PTP.

FIG. 20B shows alignment of partial sequences between AD 16c and AD 2-2.

FIG. 21B shows a similar pattern of hybridization on a genomic Southern using AD 2-2 as a probe. FIGS. 21A–21D show a Northern blot analysis of neuroectodermal tumor cell lines using AD 3-4 as a probe. The four cell lines that exhibit AD 3-4 transcripts are neuronal in phenotype; C6 glioma cell mRNA did not hybridize with the AD 3-4 probe. FIG. 21D shows a Northern analysis of human AD and aged control brain temporal lobe tissue using the AD 3-4 probe, and demonstrates over-expression of the corresponding gene in AD (lanes labeled A) compared with aged control brains (lanes labeled C).

FIGS. 22, 22A, 22B, 22C, 22D, 22E, 22F, 22G and 22H show partial sequences of four genomic clones (isolated using both the 1-9a cDNA and rat PTP 0-18 cDNA as probes.

FIGS. 23 and 23A show the alignment of the G2a-2 PstI partial sequence with the Reg gene.

FIG. 23B shows alignment of the G2a-2 PstI-EcoRI sequence and the Reg gene and the rat PTP.

FIGS. 23C and 23D show the alignment of the G5d-1 PstI sequence and the Reg gene.

FIGS. 24C and 24D show negative expression by the G5d-1 EcoRI/PstI genomic clone, and pBluescript which lacks a cloned insert, respectively.

DEFINITIONS

Figure 2:
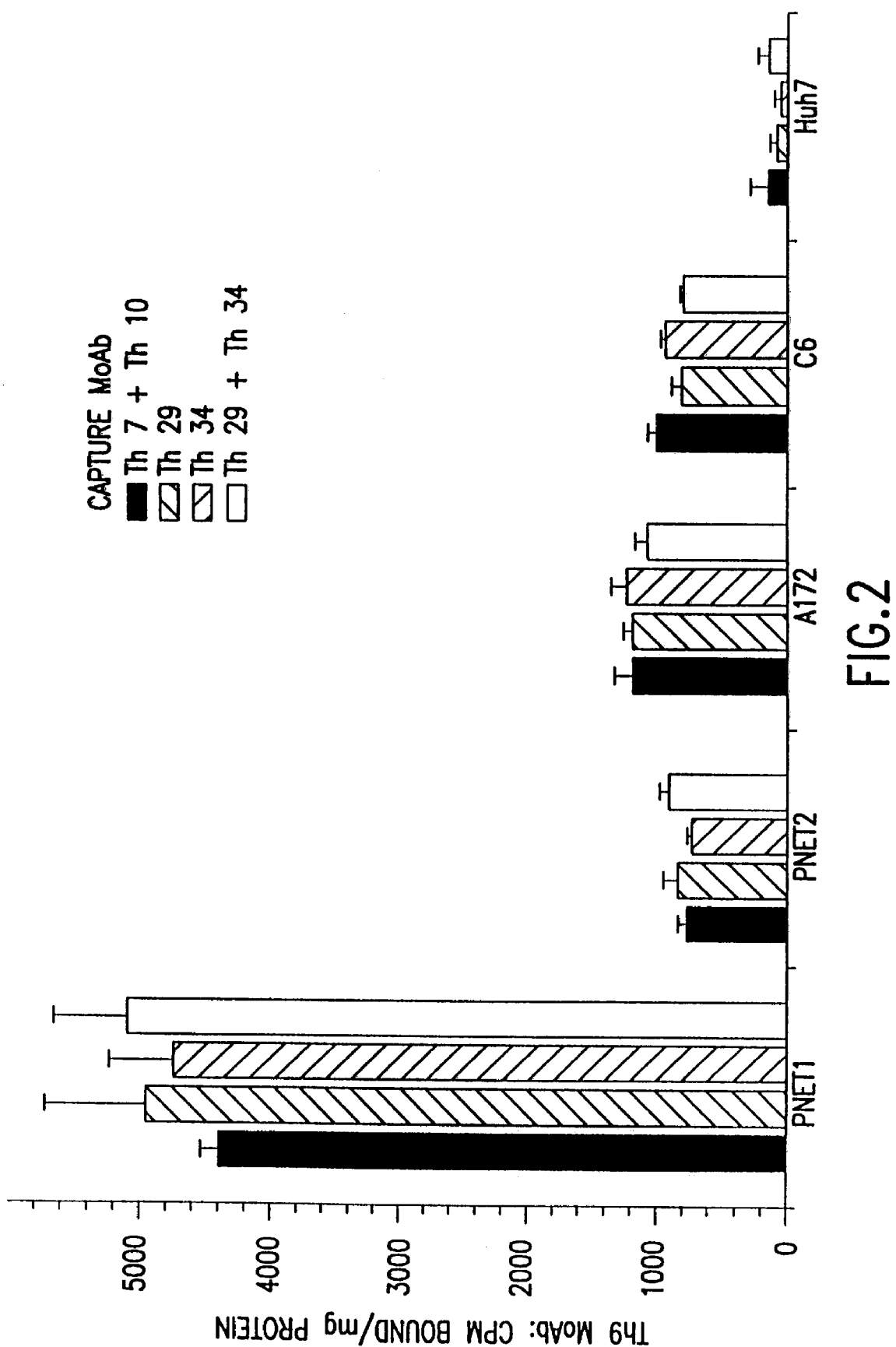
FIG. 2 depicts a graph showing neural thread protein levels in PNET1, PNET2, A172, C6, and Huh7 hepatocellular carcinoma cells measured by a forward sandwich monoclonal antibody-based immunoradiometric assay (M-IRMA).

In the description that follows, a number of terms used in recombinant DNA technology are utilized extensively. In order to provide a clear and consistent understanding of the specification and claims, including the scope to be given such terms, the following definitions are provided.

Cloning vector. A plasmid or phage DNA or other DNA sequence which is able to replicate autonomously in a host cell, and which is characterized by one or a small number of restriction endonuclease recognition sites at which such DNA sequences may be cut in a determinable fashion without loss of an essential biological function of the vector, and into which a DNA fragment may be spliced in order to bring about its replication and cloning. The cloning vector may further contain a marker suitable for use in the identification of cells transformed with the cloning vector. Markers, for example, provide tetracycline resistance or ampicillin resistance.

Expression vector. A vector similar to a cloning vector but which is capable of enhancing the expression of a gene which has been cloned into it, after transformation into a host. The cloned gene is usually placed under the control of (i.e., operably linked to) certain control sequences such as promoter sequences. Promoter sequences may be either constitutive or inducible.

Substantially pure. As used herein means that the desired purified protein is essentially free from contaminating cellular components, said components being associated with the desired protein in nature, as evidenced by a single band following polyacrylamide-sodium dodecyl sulfate gel electrophoresis. Contaminating cellular components may include, but are not limited to, proteinaceous, carbohydrate, or lipid impurities.

The term "substantially pure" is further meant to describe a molecule which is homogeneous by one or more purity or homogeneity characteristics used by those of skill in the art. For example, a substantially pure NTP will show constant and reproducible characteristics within standard experimental deviations for parameters such as the following: molecular weight, chromatographic migration, amino acid composition, amino acid sequence, blocked or unblocked N-terminus, HPLC elution profile, biological activity, and other such parameters. The term, however, is not meant to exclude artificial or synthetic mixtures of the factor with other compounds. In addition, the term is not meant to exclude NTP fusion proteins isolated from a recombinant host.

Recombinant Host. According to the invention, a recombinant host may be any prokaryotic or eukaryotic cell which contains the desired cloned genes on an expression vector or cloning vector. This term is also meant to include those prokaryotic or eukaryotic cells that have been genetically engineered to contain the desired gene(s) in the chromosome or genome of that organism.

Recombinant vector. Any cloning vector or expression vector which contains the desired cloned gene(s).

Host. Any prokaryotic or eukaryotic cell that is the recipient of a replicable expression vector or cloning vector. A "host," as the term is used herein, also includes prokaryotic or eukaryotic cells that can be genetically engineered by well known techniques to contain desired gene(s) on its chromosome or genome. For examples of such hosts, see Sambrook et al., *Molecular Cloning: A Laboratory Manual*, Second Edition, Cold Spring Harbor Laboratory, Cold Spring Harbor, N.Y. (1989).

Promoter. A DNA sequence generally described as the 5' region of a gene, located proximal to the start codon. The transcription of an adjacent gene(s) is initiated at the promoter region. If a promoter is an inducible promoter, then the rate of transcription increases in response to an inducing agent. In contrast, the rate of transcription is not regulated by an inducing agent if the promoter is a constitutive promoter.

Gene. A DNA sequence that contains information needed for expressing a polypeptide or protein.

Structural gene. A DNA sequence that is transcribed into messenger RNA (mRNA) that is then translated into a sequence of amino acids characteristic of a specific polypeptide.

Antisense RNA gene/Antisense RNA. In eukaryotes, mRNA is transcribed by RNA polymerase II. However, it is also known that one may construct a gene containing a RNA polymerase II template wherein a RNA sequence is transcribed which has a sequence complementary to that of a specific mRNA but is not normally translated. Such a gene construct is herein termed an "antisense RNA gene" and such a RNA transcript is termed an "antisense RNA." Antisense RNAs are not normally translatable due to the presence of translation stop codons in the antisense RNA sequence.

Antisense oligonucleotide. A DNA or RNA molecule containing a nucleotide sequence which is complementary to that of a specific mRNA. An antisense oligonucleotide binds to the complementary sequence in a specific mRNA and inhibits translation of the mRNA.

Antisense Therapy. A method of treatment wherein antisense oligonucleotides are administered to a patient in order to inhibit the expression of the corresponding protein.

Complementary DNA (cDNA). A "complementary DNA," or "cDNA" gene includes recombinant genes synthesized by reverse transcription of mRNA and from which intervening sequences (introns) have been removed.

Expression. Expression is the process by which a polypeptide is produced from a structural gene. The process involves transcription of the gene into mRNA and the translation of such mRNA into polypeptide(s).

Homologous/Nonhomologous. Two nucleic acid molecules are considered to be "homologous" if their nucleotide sequences share a similarity of greater than 50%, as determined by HASH-coding algorithms (Wilber, W. J. and Lipman, D. J., *Proc. Natl. Acad. Sci.* 80:726–730 (1983)). Two nucleic acid molecules are considered to be "nonhomologous" if their nucleotide sequences share a similarity of less than 50%.

Ribozyme. A ribozyme is an RNA molecule that contains a catalytic center. The term includes RNA enzymes, self-splicing RNAs, and self-cleaving RNAs.

Ribozyme Therapy. A method of treatment wherein ribozyme is administered to a patient in order to inhibit the translation of the target mRNA.

Fragment. A "fragment" of a molecule such as NTP is meant to refer to any polypeptide subset of that molecule.

Functional Derivative. The term "functional derivatives" is intended to include the "variants," "analogues," or "chemical derivatives" of the molecule. A "variant" of a molecule such as NTP is meant to refer to a naturally occurring molecule substantially similar to either the entire molecule, or a fragment thereof. An "analogue" of a molecule such as NTP is meant to refer to a non-natural molecule substantially similar to either the entire molecule or a fragment thereof.

A molecule is said to be "substantially similar" to another molecule if the sequence of amino acids in both molecules is substantially the same, and if both molecules possess a similar biological activity. Thus, provided that two molecules possess a similar activity, they are considered variants as that term is used herein even if one of the molecules contains additional amino acid residues not found in the other, or if the sequence of amino acid residues is not identical.

As used herein, a molecule is said to be a "chemical derivative" of another molecule when it contains additional chemical moieties not normally a part of the molecule. Such moieties may improve the molecule's solubility, absorption, biological half-life, etc. The moieties may alternatively decrease the toxicity of the molecule, eliminate or attenuate any undesirable side effect of the molecule, etc. Examples of moieties capable of mediating such effects are disclosed in *Remington's Pharmaceutical Sciences* (1980) and will be apparent to those of ordinary skill in the art.

NTP. The term "NTP" refers to a family of neural thread proteins. The NTP family includes proteins with molecular weights of about 8 kDa, 14 kDa, 17 kDa, 21 kDa, 26 kDa and 42 kDa, as described herein.

Immuno-Polymerase Chain Reaction. A method for the detection of antigens using specific antibody-DNA conjugates. According to this method, a linker molecule with bispecific binding affinity for DNA and antibodies is used to attach a DNA molecule specifically to an antigen-antibody complex. As a result, a specific antigen-antibody-DNA conjugate is formed. The attached DNA can be amplified by the polymerase chain reaction (PCR) using appropriate oligonucleotide primers. The presence of specific PCR products demonstrates that DNA molecules are attached specifically to antigen-antibody complexes, thus indicating the presence of antigen. (Sano et al., *Science* 258:120–122 (1992)).

For example, Sano et al., supra, constructed a streptavidin-protein A chimera that possesses specific binding affinity for biotin and immunoglobulin G. This chimera (i.e., the "linker molecule") was used to attach a biotinylated DNA specifically to antigen-monoclonal antibody complexes that had been immobilized on microtiter plate wells. A segment of the attached DNA was subsequently amplified by PCR.

DETAILED DESCRIPTION OF THE INVENTION

This invention is directed to neural thread proteins (NTP), genetic sequences coding for an NTP mRNA or antisense mRNA, expression vectors containing the genetic sequences, recombinant hosts transformed therewith, and NTP and antisense RNA produced by such transformed recombinant host expression. This invention further relates to NTP ribozymes, and recombinant DNA molecules which code for NTP ribozymes and NTP antisense oligonucleotides. This invention further relates to antibodies directed against an NTP, as well as the use of NTP antibodies and NTP nucleic acid sequences for detection of the presence of an NTP in biological samples. The invention further relates to the use of NTP coding sequences in gene therapy.

I. Isolation of DNA Sequences Coding for Neuronal Thread Proteins

DNA sequences coding for an NTP are derived from a variety of sources. These sources include genomic DNA, cDNA, synthetic DNA, and combinations thereof.

Human NTP genomic DNA can be extracted and purified from any human cell or tissue, by means well known in the art (for example, see Sambrook et al., *Molecular Cloning: A Laboratory Manual*, Second Edition, Cold Spring Harbor Laboratory Press, 1989). The NTP genomic DNA of the invention may or may not include naturally occurring introns. Moreover, such genomic DNA may be obtained in association with the 5' promoter region of the NTP gene sequences and/or with the 3' translational termination region. Further, such genomic DNA may be obtained in association with DNA sequences which encode the 5' non-translated region of the NTP mRNA and/or with the genetic sequences which encode the 3' nontranslated region. To the extent that a host cell can recognize the transcriptional and/or translational regulatory signals associated with the expression of the mRNA and protein, then the 5' and/or 3' nontranscribed regions of the native gene, and/or, the 5' and/or 3' nontranslated regions of the mRNA, may be retained and employed for transcriptional and translational regulation.

Alternatively, an NTP mRNA can be isolated from any cell which expresses an NTP, and used to produce cDNA by means well known in the art (for example, see Sambrook et al., supra). Preferably, the mRNA preparation used will be enriched in mRNA coding for an NTP, either naturally, by isolation from cells which produce large amounts of an NTP, or in vitro, by techniques commonly used to enrich mRNA preparations for specific sequences, such as sucrose gradient centrifugation, or both. An NTP mRNA may be obtained from mammalian neuronal tissue, or from cell lines derived therefrom. Preferably, human cDNA libraries are constructed from 17-18 week old fetal brain, 2 year old temporal lobe neocortex, end-stage AD cerebral cortex, or from cell lines derived from human neuronal tissue. Such cell lines may include, but are not limited to, central nervous system primitive neuroectodermal tumor cells (such as PNET1 or PNET2, as described herein), neuroblastoma cells (such as SH-Sy5y, as described herein), or human glioma cells (such as A172; ATCC CRL 1620). Alternatively, a rat cDNA library can be prepared from mRNA isolated from rat glioma cells, for example, C6 rat glioma cells (ATCC CCL107).

For cloning into a vector, suitable DNA preparations (either genomic or cDNA) are randomly sheared or enzymatically cleaved, respectively, and ligated into appropriate vectors to form a recombinant gene (either genomic or cDNA) library. A DNA sequence encoding an NTP may be inserted into a vector in accordance with conventional techniques, including blunt-ending or staggered-ending termini for ligation, restriction enzyme digestion to provide appropriate termini, filling in of cohesive ends as appropriate, alkaline phosphatase treatment to avoid undesirable joining, and ligation with appropriate ligases. Techniques for such manipulation are disclosed by Sambrook et al., supra, and are well known in the art.

Libraries containing NTP clones may be screened and the NTP clones identified by any means which specifically selects for NTP DNA such as, for example: 1) by hybridization with an appropriate nucleic acid probe(s) containing a sequence specific for the DNA of this protein; or, 2) by hybridization-selected translational analysis in which native mRNA hybridizes to the clone in question, is translated in vitro, and the translation products are further characterized; or, 3) if the cloned DNA sequences are themselves capable of expressing mRNA, by immunoprecipitation of a translated NTP product produced by the host containing the clone.

Oligonucleotide probes specific for an NTP which can be used to identify clones to this protein can be designed from knowledge of the amino acid sequence of the corresponding NTP, or homologous regions of the PTP. Alternatively, oligonucleotide probes can be designed from knowledge of the nucleotide sequence of PTP (de la Monte et al., *J. Clin. Invest.* 86:1004–1013 (1990)).

The suitable oligonucleotide, or set of oligonucleotides, which is capable of encoding a fragment of the NTP gene (or which is complementary to such an oligonucleotide, or set of oligonucleotides) may be synthesized by means well known in the art (for example, see Sambrook et al., supra). Techniques of nucleic acid hybridization and clone identification are disclosed by Sambrook et al., supra. Those members of the above-described gene library which are found to be capable of such hybridization are then analyzed to determine the extent and nature of the NTP encoding sequences which they contain.

To facilitate the detection of the desired NTP coding sequence, the above-described DNA probe is labeled with a detectable group. Such detectable group can be any material having a detectable physical or chemical property. Such materials have been well-developed in the field of nucleic acid hybridization and in general most any label useful in such methods can be applied to the present invention. Particularly useful are radioactive labels including $^{32}P$, $^{3}H$, $^{14}C$, $^{125}I$, or the like. Any radioactive label may be employed which provides for an adequate signal and has sufficient half-life. The DNA probe may be labeled, for example, by nick-translation, by T4 DNA polymerase replacement synthesis, or by random priming, among other methods well known in the art (see Sambrook et al. supra).

Alternatively, DNA probes can be labeled with non-radioactive markers such as biotin, an enzyme, or fluorescent group.

In an alternative method of cloning NTP DNA sequences, NTP cDNAs are obtained by direct cloning of cDNAs from cell lines and brain tissue, using the 3' - and 5' -RACE methods, as described herein. Preferably, a human neuroectodermal tumor cell line or AD brain tissue is used as a source of mRNA.

II. Expressing the Gene Coding for NTP

The above-discussed methods are, therefore, capable of identifying DNA sequences which are code for an NTP or fragments thereof. In order to further characterize such DNA sequences, and in order to produce the recombinant protein, it is desirable to express the proteins which the DNA sequences encode.

To express an NTP, transcriptional and translational signals recognizable by an appropriate host are necessary. The cloned NTP DNA sequences, obtained through the methods described above, and preferably in double-stranded form, may be "operably linked" to sequences controlling transcriptional expression in an expression vector, and introduced into a host cell, either prokaryotic or eukaryotic, to produce recombinant NTP. Depending upon which strand of the NTP coding sequence is operably linked to the sequences controlling transcriptional expression, it is also possible to express an NTP antisense RNA.

Expression of the NTP in different hosts may result in different post-translational modifications which may alter the properties of the NTP. Preferably, the present invention encompasses the expression of an NTP in eukaryotic cells, and especially mammalian, insect, and yeast cells. Especially preferred eukaryotic hosts are mammalian cells. Mammalian cells provide post-translational modifications to recombinant NTP which include folding and/or phosphorylation. Most preferably, mammalian host cells include human CNS primitive neuroectodermal tumor cells, human neuroblastoma cells, human glioma cells, or rat glioma cells. Especially preferred primitive neuroectodermal tumor cells include PNET1 and PNET2, especially preferred human glioblastoma cells include Hg16 and Hg17, especially preferred human glioma cells include A172, and especially preferred rat glioma cells include C6 (see Example 1).

Alternatively, an NTP may be expressed by prokaryotic host cells. Preferably, a recombinant NTP is expressed by such cells as a fusion protein, as described herein. An especially preferred prokaryotic host is E. coli. Preferred strains of E. coli include Y1088, Y1089, CSH18, ER1451, and ER1647 (see, for example, *Molecular Biology LabFax*, Brown, T. A., Ed., Academic Press, New York (1991)). An alternative preferred host is *Bacillus subtilus*, including such strains as BR151, YB886, MI119, M1120, and B170 (see, for example, Hardy, "Bacillus Cloning Methods," in DNA *Cloning: A Practical Approach*, IRL Press, Washington, D.C. (1985)).

A nucleic acid molecule, such as DNA, is said to be "capable of expressing" a polypeptide if it contains expression control sequences which in turn contain transcriptional regulatory information and such sequences are "operably linked" to the nucleotide sequence which encodes the protein.

Two sequences of a nucleic acid molecule are said to be operably linked when they are linked to each other in a manner which either permits both sequences to be transcribed onto the same RNA transcript, or permits an RNA transcript, begun in one sequence to be extended into the second sequence. Thus, two sequences, such as a promoter sequence and any other "second" sequence of DNA or RNA are operably linked if transcription commencing in the promoter sequence will produce an RNA transcript of the operably linked second sequence. In order to be operably linked it is not necessary that two sequences be immediately adjacent to one another.

The promoter sequences of the present invention may be either prokaryotic, eukaryotic or viral. Suitable promoters are repressible, constitutive, or inducible. Examples of suitable prokaryotic promoters include promoters capable of recognizing the T4 polymerases (Malik et al.,*J. Biol. Chem.* 263:1174–1181 (1984); Rosenberg et al., *Gene* 59:191–200 (1987); Shinedling et al., *J. Molec. Biol.* 195:471–480 (1987); Hu et al., *Gene* 42:21–30 (1986)), T3, Sp6, T7 (Chamberlin et al., *Nature* 228:227–231 (1970); Bailey et al., *Proc. Natl. Acad. Sci.* (U.S.A.) 80:2814–2818 (1983); Davanloo et al., *Proc. Natl. Acad. Sci.* (U.S.A.) 81:2035–2039 (1984)); the $P_R$ and $P_L$ promoters of bacteriophage lambda (The Bacteriophage Lambda, Hershey, A.D., Ed., Cold Spring Harbor Press, Cold Spring Harbor, N.Y. (1973); Lambda II, Hendrix, R. W., Ed., Cold Spring Harbor Press, Cold Spring Harbor, N.Y. (1980)); the trp, recA, heat shock, and lacZ promoters of *E. coli*; the α-amylase (Ulmanen et al., *J. Bacteriol.* 162:176–182 (1985)) and the delta-28-specific promoters of *B. subtilis* (Gilman et al., *Gene* 32:11–20 (1984)); the promoters of the bacteriophages of Bacillus (Gryczan, In: *The Molecular Biology of the Bacilli*, Academic Press, Inc., N.Y. (1982)); Streptomyces promoters (Ward et al., *Mol. Gen. Genet.* 203:468–478 (1986)); the int promoter of bacteriophage lambda; the bla promoter of the β-lactamase gene of pBR322, and the CAT promoter of the chloramphenicol acetyl transferase gene of pBR325, etc. Prokaryotic promoters are reviewed by Glick, *J. Ind. Microbiol.* 1:277–282 (1987); Cenatiempo, *Biochimie* 68:505–516 (1986); Watson et al., In: *Molecular Biology of the Gene*, Fourth Edition, Benjamin Cummins, Menlo Park, Calif. (1987); Gottesman, *Ann. Rev. Genet.* 18:415–442 (1984); and Sambrook et al., supra.

Preferred eukaryotic promoters include the promoter of the mouse metallothionein I gene (Hamer et al.,*J. Mol. Appl. Gen.* 1:273–288 (1982)); the TK promoter of Herpes virus (McKnight, *Cell* 31:355–365 (1982)); the SV40 early promoter (Benoist, et al., *Nature* (London) 290:304–310 (1981)); and the yeast gal4 gene promoter (Johnston, et al., *Proc. Natl. Acad. Sci.* (USA) 79:6971–6975 (1982); Silver, et al., *Proc. Natl. Acad. Sci.* (USA) 81:5951–5955 (1984)). All of the above listed references are incorporated by reference herein.

Strong promoters are the most preferred promoters of the present invention. Examples of such preferred promoters are those which recognize the T3, SP6 and T7 polymerase promoters; the $P_L$ promoter of bacteriophage lambda; the recA promoter and the promoter of the mouse metallothionein I gene. The most preferred promoter for expression in prokaryotic cells is one which is capable of recognizing the T7 polymerase promoter. The sequences of such polymerase recognition sequences are disclosed by Watson, et al. (In: *Molecular Biology of the Gene*, Fourth Edition, Benjamin Cummins, Menlo Park, Calif. (1987)). The most preferred promoter for expression in mammalian cells is SV40 (Gorman, "High Efficiency Gene Transfer into Mammalian cells," in *DNA Cloning: A Practical Approach*, Volume II, IRL Press, Washington, D.C., pp. 143–190 (1985)).

III. Methods of Detecting NTP

This invention is directed towards methods of detecting neurological disease in a human subject, utilizing the nucleic acid probes hybridizable to NTP genes or transcripts, or antibodies specific for an NTP. By "neurological disease" is meant Alzheimer's Disease (AD), or other neurodegenerative disorders with the Alzheimer's type pathogenic changes (for example, Parkinson's disease with AD-type neurodegeneration), as well as neuroectodermal tumors, malignant astrocytomas, and glioblastomas. By "human subject" is meant any human being or any developmental form thereof, such as a human embryo or fetus, prior to birth. The diagnostic methods of the present invention do not require invasive removal of neural tissue.

The present invention additionally pertains to assays, both nucleic acid hybridization assays and immunoassays, for detecting the presence of NTP in cells or in the biological fluids of a human subject using light or electron microscopic histology, imaging, radioactive or enzyme based assays, and the like.

A. Nucleic Acid Hybridization Assays

In testing a tissue sample for an NTP using a nucleic acid hybridization assay, RNA can be isolated from tissue by sectioning on a cryostat and lysing the sections with a detergent such as SDS and a chelating agent such as EDTA, optionally with overnight digestion with proteinase K (50 $\mu$g/ml). Such tissue is obtained by autopsy and biopsy. A preferred quantity of tissue is in the range of 1–10 milligrams. Protein is removed by phenol and chloroform extractions, and nucleic acids are precipitated with ethanol. RNA is isolated by chromatography on an oligo dT column and then eluted therefrom. Further fractionation can also be carried out, according to methods well known to those of ordinary skill in the art.

A number of techniques for molecular hybridization are used for the detection of DNA or RNA sequences in tissues; each has certain advantages and disadvantages. When large amounts of tissue are available, analysis of hybridization kinetics provides the opportunity to accurately quantitate the amount of DNA or RNA present, as well as to distinguish sequences that are closely related but not identical to the probe, and determine the percent homology.

Reactions are run under conditions of hybridization (Tm-25° C.) in which the rate of reassociation of the probe is optimal (Wetmur et al., *J. Mol. Biol.* 31:349–370 (1968)). The kinetics of the reaction are second- order when the sequences in the tissue are identical to those of the probe; however, the reaction exhibits complex kinetics when probe sequences have partial homology to those in the tissue (Sharp et al., *J. Mol. Biol.* 86:709–726 (1974)).

The ratio of probe to cell RNA is determined by the sensitivity desired. To detect one transcript per cell would require about 100 pg of probe per tg of total cellular DNA or RNA. The nucleic acids are mixed, denatured, brought to the appropriate salt concentration and temperature, and allowed to hybridize for various periods of time. The rate of reassociation can be determined by quantitating the amount of probe hybridized either by hydroxy apatite chromatography (Britten et al., *Science* 161:529–540 (1968)) or S1 nuclease digestion (Sutton, *Biochim. Biophys.* Acta 240:522–531 (1971)).

A more flexible method of hybridization is the northern blot technique. This technique offers variability in the stringency of the hybridization reaction, as well as determination of the state of the retroviral sequences in the specimen under analysis. Northern analysis can be performed as described herein.

A major consideration associated with hybridization analysis of DNA or RNA sequences is the degree of relatedness the probe has with the sequences present in the specimen under study. This is important with the blotting technique, since a moderate degree of sequence homology under nonstringent conditions of hybridization can yield a strong signal even though the probe and sequences in the sample represent non-homologous genes.

The particular hybridization technique is not essential to the invention, any technique commonly used in the art being within the scope of the present invention. Typical probe technology is described in U.S. Pat. No. 4,358,535 to Falkow et al., incorporated by reference herein. For example, hybridization can be carried out in a solution containing 6×SSC (10×SSC: 1.5 M sodium chloride, 0.15 M sodium citrate, pH 7.0), 5×Denhardt's (1 Denhardt's: 0.2% bovine serum albumin, 0.2% polyvinylpyrrolidone, 0.02% Ficoll 400), 10 mM EDTA, 0.5% SDS and about $10^7$ cpm of nick-translated DNA for 16 hours at 65° C.

The labeled probes, as described above, provide a general diagnostic method for detection of an NTP in tissue. The method is reasonably rapid, has a simple protocol, has reagents which can be standardized and provided as commercial kits, and allows for rapid screening of large numbers of samples.

In one method for carrying out the procedure, a clinical isolate containing RNA transcripts is fixed to a support. The affixed nucleic acid is contacted with a labeled polynucleotide having a base sequence complementary or homologous to the coding strand of the NTP gene.

The hybridization assays of the present invention are particularly well suited for preparation and commercialization in kit form, the kit comprising a carrier means compartmentalized to receive one or more container means (vial, test tube, etc.) in close confinement, each of said container means comprising one of the separate elements to be used in hybridization assay.

For example, there may be a container means containing NTP cDNA molecules suitable for labeling by "nick translation" (see, for example, Sambrook et al., supra, for standard methodology), or labeled NTP cDNA or RNA molecules. Further container means may contain standard solutions for nick translation of NTP cDNA comprising DNA polymerase I/DNase I and unlabeled deoxyribonucleotides (i.e., dCTP, dTTP, dGTP, and dATP).

The presence of NTP RNA is determined by the variation in the appearance and/or quantity of probe-related RNA in tested tissue.

The DNA probes of this invention can also be used for differential diagnosis of hereditary or familial AD and non-hereditary or sporadic AD. The familial form of AD often occurs at an earlier age and is associated with Down's syndrome in the family. Thus, a genetic test for familial AD allows for genetic counseling of families. While much effort has been directed toward characterizing a genetic marker for familial AD (Gusella, *FASEB J* 3:2036–2041 (1989); Hooper, *J NIH Res.* 4:48–54 (1992)), genetic linkage analysis only identifies a genetic marker sequence without providing the knowledge of the function of the genomic sequence. In contrast, the cDNA probes described herein and obtained from individuals with sporadic AD encode a known protein of known function which is over-expressed in brain tissue of patients with AD.

Most cases of the AD disorder appear to be the sporadic form, although there are well-documented familial cases (Gusella, supra; *Harrison's Principles of Internal Medicine*, Braunwald et al., Eds., Eleventh Edition, Mc-Graw-Hill Book Company, New York, pp. 2012–2013 (1987)). A patient with familial AD, unlike a patient with sporadic AD, inherited the predisposing mutation through the germ cells. Some of the familial cases have been shown to follow an autosomal dominant pattern of inheritance (Id.). Thus, the DNA of a patient with familial AD will contain the inherited genetic alteration which is absent from the DNA of a patient with sporadic AD.

A method of differentiating between sporadic and familial AD in a human subject involves obtaining a biological sample from the human subject who is suspected of having Alzheimer's Disease. Then, DNA is purified from the biological sample. Finally, the DNA is contacted with a NTP DNA probe under conditions of hybridization. Familial AD is indicated by the detection of a hybrid of the probe and the DNA, whereas sporadic AD is indicated by the absence of detection of hybridization.

For example, the biological sample can be a blood sample which is subjected to differential centrifugation to enrich for white blood cells within three days of collection (Park, "PCR in the Diagnosis of Retinoblastoma," in *PCR Protocols*, Innis et al., Eds., Academic Press, Inc., New York, pp. 407–415 (1990)). The DNA sample can be prepared using the sodium N-lauroylsarcosine-Proteinase K, phenol, and RNase method (Sambrook et al., supra). DNA analysis can be performed by digesting the DNA sample, preferably 5 micrograms, with a restriction endonuclease (such as HindIII). Digested DNA is then fractionated using agarose gel electrophoresis, preferably, a 1% horizontal agarose gel, for 18 hours in a buffer preferably containing 89 mM Tris-Hcl (pH 8), 89 mM sodium borate and 2 mM EDTA (Gusella et al., *Nature* 306:234–238 (1983)). Southern analysis can be performed using conventional techniques (Sambrook et al., supra), and the labelled AD cDNA probes can be hybridized under conditions described above. The preferred DNA probes for this differential diagnosis method include 1-9a, AD3-4, AD4-4 and G2-2 PstI.

B. Immunoassays

Antibodies directed against an NTP can be used, as taught by the present invention, to detect and diagnose AD. Various histological staining methods, including immunohistochemical staining methods, may also be used effectively according to the teaching of the invention. Silver stain is but one method of visualizing NTP. Other staining methods useful in the present invention will be obvious to the artisan, the determination of which would not involve undue experimentation (see generally, for example, *A Textbook of Histology*, Eds. Bloom and Fawcett, W.B. Saunders Co., Philadelphia (1964)).

One screening method for determining whether a given compound is an NTP functional derivative comprises, for example, immunoassays employing radioimmunoassay (RIA) or enzyme-linked immunosorbant assay (ELISA) methodologies, based on the production of specific antibodies (monoclonal or polyclonal) to an NTP. For these assays, biological samples are obtained by venepuncture (blood), spinal tap (cerebral spinal fluid (CSF)), urine and other body secretions such as sweat and tears. For example, in one form of RIA, the substance under test is mixed with diluted antiserum in the presence of radiolabelled antigen. In this method, the concentration of the test substance will be inversely proportional to the amount of labeled antigen bound to the specific antibody and directly related to the amount of free labeled antigen. Other suitable screening methods will be readily apparent to those of skill in the art.

The present invention also relates to methods of detecting an NTP or functional derivatives in a sample or subject. For example, antibodies specific for an NTP, or a functional derivative, may be detectably labeled with any appropriate marker, for example, a radioisotope, an enzyme, a fluorescent label, a paramagnetic label, or a free radical.

Alternatively, antibodies specific for an NTP, or a functional derivative, may be detectably labeled with DNA by the technique of immunopolymerase chain reaction (Sano et al., *Science* 258:120–122 (1992)). The polymerase chain reaction (PCR) procedure amplifies specific nucleic acid sequences through a series of manipulations including denaturation, annealing of oligonucleotide primers, and extension of the primers with DNA polymerase (see, for example, Mullis et al., U.S. Pat. No. 4,683,202; Mullis et al., U.S. Pat. No. 4,683,195; Loh et al., *Science* 243:217 (1988)). The steps can be repeated many times, resulting in a large amplification of the number of copies of the original specific sequence. As little as a single copy of a DNA sequence can be amplified to produce hundreds of nanograms of product (Li et al., *Nature* 335:414 (1988)). Other known nucleic acid amplification procedures include transcription-based amplification systems (Kwoh et al., *Proc. Natl. Acad. Sci. USA* 86:1173 (1989); Gingeras et al., WO 88/10315), and the "ligase chain reaction" in which two (or more) oligonucleotides are ligated in the presence of a nucleic acid target having the sequence of the resulting "di-oligonucleotide" thereby amplifying the di-oligonucleotide (Wu et al., *Genomics* 4:560 (1989); Backman et al., EP 320,308; Wallace, EP 336,731; Orgel, WO 89/09835).

For example, the immuno-PCR assay can be carried out by immobilizing various amounts of the test material on the surface of microtiter wells (see Sanzo et al., supra, page 122, footnote 7). The wells are subsequently incubated with an NTP monoclonal antibody, washed, and then incubated with biotinylated with biotinylated NTP DNA molecules which have been conjugated to streptavidin-protein chimera (Id.). This chimera binds biotin (via the streptavidin moiety) and the Fc portion of an immunoglobulin G molecule (via the protein A moiety) (Id., at 120; Sanzo et al., *Bio/Technology* 9:1378 (1991)). The wells are then washed to remove unbound conjugates. Any NTP present in the test material will be bound by the NTP monoclonal antibody, which in turn, is bound by the protein A moiety of the biotinylated NTP DNA— streptavidin-protein A conjugate. Then, the NTP DNA sequences are amplified using PCR. Briefly, the microtiter wells are incubated with deoxyribonucleoside triphosphates, NTP oligonucleotide primers, and Taq DNA polymerase (see Sanzo et al., supra, page 122, footnote 11). An automated thermal cycler (such as the PTC-100-96 Thermal Cycler, MJ Research, Inc.) can be used to perform PCR under standard conditions (Id.). The PCR products are then analyzed by agarose gel electrophoresis after staining with ethidium bromide.

Methods of making and detecting such detectably labeled antibodies or their functional derivatives are well known to those of ordinary skill in the art, and are described in more detail below. Standard reference works setting forth the general principles of immunology include the work of Klein (*Immunology: The Science of Self-Nonself Discrimination*, John Wiley & Sons, New York (1982)); Kennett et al. (*Monoclonal Antibodies and Hybridomas: A New Dimension in Biological Analyses*, Plenum Press, New York (1980)); Campbell ("Monoclonal Antibody Technology," In: *Laboratory Techniques in Biochemistry and Molecular Biology*, Volume 13 (Burdon, R., et al., eds.), Elsevier, Amsterdam (1984)); and Eisen (In: *Microbiology*, 3rd Ed. (Davis, et al., Harper & Row, Philadelphia (1980)).

The term "antibody" refers both to monoclonal antibodies which are a substantially homogeneous population and to polyclonal antibodies which are heterogeneous populations. Polyclonal antibodies are derived from the sera of animals immunized with an antigen. Monoclonal antibodies (mAbs) to specific antigens may be obtained by methods known to those skilled in the art. See, for example, Kohler and Milstein, *Nature* 256:495–497 (1975) and U.S. Pat. No. 4,376,110. Such antibodies may be of any immunoglobulin class including IgG, IgM, IgE, IgA, IgD and any subclass thereof.

The monoclonal antibodies, particularly iabs Th7, Th9, and Th10 used in the present invention, may be prepared as previously described (Gross et al., *J. Clin. Invest.* 76:2115–2126 (1985); Ozturk et al., *Proc. Natl. Acad. Sci. USA* 86:419–423 (1989); de la Monte et. al., *J. Clin. Invest.* 86:1004–1013 (1990); de la Monte et. al., *J. Neurol. Sci.* 113:152–164 (1992); de la Monte et al., *Ann. Neurol.* 32:733–742 (1992)). The Th monoclonal antibodies were generated against the purified pancreatic form of thread protein (Id.). NTP-specific polyclonal and monoclonal antibodies can also be generated against a substantially pure NTP isolated from recombinant hosts (for example, see Carroll et al., "Production and Purification of Polyclonal Antibodies to the Foreign Segment of β-Galactosidase Fusion Proteins," in *DNA Cloning: A Practical Approach*, Volume III, IRL Press, Washington, D.C., pp. 89–111 (1987); Mole et al., "Production of Monoclonal Antibodies Against Fusion Proteins Produced in *Escherichia coli*," in *DNA Cloning: A Practical Approach*, Volume III, IRL Press, Washington, D.C., pp. 113–1139 (1987)). Alternatively, NTP-specific polyclonal and monoclonal antibodies can be generated against a substantially pure NTP isolated from biological material such as brain tissue and cell lines, by using well known techniques.

For example, monoclonal antibodies specific for the various NTP molecules of approximately, 8, 14, 17, 21, 26 kDa and 42 kDa molecular weights may be prepared from recombinant-derived proteins, which are expressed, isolated and purified from the cDNA (i.e., 1-9a), genomic clones (G2-2 PstI) and AD-NTP 3-4 cDNA clones. These NTP molecules are derived from the above cDNA's and genomic clones, inserted and produced in suitable expression vectors (see FIGS. 2A and 2B). Since there are regions of 60–70% homology in the 5' ends of the 1-9a NTP cDNA and PTP, one can obtain monoclonal antibodies that bind specifically to the NTP recombinant proteins and not to the pancreatic form by performing routine differential screening (see, for example, de la Monte et al., *J. Clin. Invest.* 86:1004–1013 (1990)). Although there will be monoclonal antibodies that bind to both NTP and PTP, it will be possible to generate NTP-specific monoclonal antibodies because there is a substantial sequence divergence between NTP molecules of various forms (e.g., 8, 14, 17, 21, 26 and 42 kDa) and because an epitope may be defined by as few as 6-8 amino acids.

The term "antibody" is also meant to include both intact molecules as well as fragments thereof, such as, for example, Fab and F(ab')$_2$, which are capable of binding antigen. Fab and F(ab')$_2$ fragments lack the Fc fragment of intact antibody, clear more rapidly from the circulation, and may have less non-specific tissue binding than an intact antibody (Wahl et al., *J. Nucl. Med.* 24:316–325 (1983)).

It will be appreciated that Fab and F(ab')$_2$ and other fragments of the antibodies useful in the present invention may be used for the detection and quantitation of an NTP according to the methods disclosed herein in order to detect and diagnose AD in the same manner as an intact antibody. Such fragments are typically produced by proteolytic cleavage, using enzymes such as papain (to produce Fab fragments) or pepsin (to produce F(ab')$_2$ fragments).

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopic determinants usually consist of chemically active surface groupings of molecules such as amino acids or sugar side chains and have specific three dimensional structural characteristics as well as specific charge characteristics.

An "antigen" is a molecule capable of being bound by an antibody which is additionally capable of inducing an animal to produce antibody capable of binding to an epitope of that antigen. An antigen may have one, or more than one epitope. The specific reaction referred to above is meant to indicate that the antigen will react, in a highly selective manner, with its corresponding antibody and not with the multitude of other antibodies which may be evoked by other antigens.

The antibodies, or fragments of antibodies, useful in the present invention may be used to quantitatively or qualitatively detect the presence of cells which contain the NTP antigens. Thus, the antibodies (or fragments thereof) useful in the present invention may be employed histologically to detect or visualize the presence of an NTP.

Such an assay for an NTP typically comprises incubating a biological sample from said subject suspected of having such a condition in the presence of a detectably labeled binding molecule (e.g., antibody) capable of identifying an NTP, and detecting said binding molecule which is bound in a sample.

Thus, in this aspect of the invention, a biological sample may be treated with nitrocellulose, or other solid support which is capable of immobilizing cells, cell particles or soluble proteins. The support maybe then be washed with suitable buffers followed by treatment with the detectably labeled NTP-specific antibody. The solid phase support may then be washed with the buffer a second time to remove unbound antibody. The amount of bound label on said solid support may then be detected by conventional means.

By "solid phase support" is intended any support capable of binding antigen or antibodies. Well-known supports, or carriers, include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will note many other suitable carriers for binding monoclonal antibody or antigen, or will be able to ascertain the same by use of routine experimentation.

One embodiment for carrying out the diagnostic assay of the present invention on a biological sample containing an NTP, comprises:

(a) contacting a detectably labeled NTP-specific antibody with a solid support to effect immobilization of said NTP-specific antibody or a fragment thereof;

(b) contacting a sample suspected of containing an NTP with said solid support;

(c) incubating said detectably labeled NTP-specific antibody with said support for a time sufficient to allow the immobilized NTP-specific antibody to bind to the NTP;

(d) separating the solid phase support from the incubation mixture obtained in step (c); and (e) detecting the bound label and thereby detecting and quantifying NTP.

Alternatively, labeled NTP-specific antibody/NTP complexes in a sample may be separated from a reaction mixture by contacting the complex with an immobilized antibody or protein which is specific for an immunoglobulin, e.g., Staphylococcus protein A, Staphylococcus protein G, anti-IgM or anti-IgG antibodies. Such anti-immunoglobulin antibodies may be polyclonal, but are preferably monoclonal. The solid support may then be washed with a suitable buffer to give an immobilized NTP/labeled NTP-specific antibody complex. The label may then be detected to give a measure of an NTP.

This aspect of the invention relates to a method for detecting an NTP or a fragment thereof in a sample comprising:

(a) contacting a sample suspected of containing an NTP with an NTP-specific antibody or fragment thereof which binds to NTP; and (b) detecting whether a complex is formed.

The invention also relates to a method of detecting an NTP in a sample, further comprising:

(c) contacting the mixture obtained in step (a) with an Fc binding molecule, such as an antibody, Staphylococcus protein A, or Staphylococcus protein G, which is immobilized on a solid phase support and is specific for the NTP-specific antibody to give a NTP/NTP-specific antibody immobilized antibody complex;

(d) washing the solid phase support obtained in step (c) to remove unbound NTP/NTP-specific antibody complex;

(e) and detecting the label bound to said solid support.

Of course, the specific concentrations of detectably labeled antibody and NTP, the temperature and time of incubation, as well as other assay conditions may be varied, depending on various factors including the concentration of an NTP in the sample, the nature of the sample, and the like. The binding activity of a given lot of anti-NTP antibody may be determined according to well known methods. Those skilled in the art will be able to determine operative and optimal assay conditions for each determination by employing routine experimentation.

Other such steps as washing, stirring, shaking, filtering and the like may be added to the assays as is customary or necessary for the particular situation.

One of the ways in which the NTP-specific antibody can be detectably labeled is by linking the same to an enzyme. This enzyme, in turn, when later exposed to its substrate, will react with the substrate in such a manner as to produce a chemical moiety which can be detected, for example, by spectrophotometric, fluorometric or by visual means. Enzymes which can be used to detectably label the NTP-specific antibody include, but are not limited to, malate dehydrogenase, staphylococcal nuclease, delta-V-steroid isomerase, yeast alcohol dehydrogenase, a-glycerophosphate dehydrogenase, triose phosphate isomerase, horseradish peroxidase, alkaline phosphatase, asparaginase, glucose oxidase, β-galactosidase, ribonuclease, urease, catalase, glucose-VI-phosphate dehydrogenase, glucoamylase and acetylcholinesterase.

Detection may be accomplished using any of a variety of immunoassays. For example, by radioactively labeling the NTP-specific antibodies or antibody fragments, it is possible to detect NTP through the use of radioimmune assays. A good description of a radioimmune assay may be found in *Laboratory Techniques and Biochemistry in Molecular Biology*, by Work, et al., North Holland Publishing Company, N.Y. (1978), with particular reference to the chapter entitled "An Introduction to Radioimmune Assay and Related Techniques" by Chard, incorporated by reference herein.

The radioactive isotope can be detected by such means as the use of a gamma counter or a scintillation counter or by autoradiography. Isotopes which are particularly useful for the purpose of the present invention are: $^3H$, $^{125}I$, $^{131}I$, $^{35}S$, $^{14}C$, and preferably $^{125}I$.

It is also possible to label the NTP-specific antibody with a fluorescent compound. When the fluorescently labeled antibody is exposed to light of the proper wave length, its presence can then be detected due to fluorescence. Among the most commonly used fluorescent labelling compounds are fluorescein isothiocyanate, rhodamine, phycoerytherin, phycocyanin, allophycocyanin, o-phthaldehyde and fluorescamine.

The NTP-specific antibody can also be detectably labeled using fluorescence emitting metals such as $^{152}Eu$, or others of the lanthanide series. These metals can be attached to the NTP-specific antibody using such metal chelating groups as diethylenetriaminepentaacetic acid (DTPA) or ethylenediaminetetraacetic acid (EDTA).

The NTP-specific antibody also can be detectably labeled by coupling it to a chemiluminescent compound. The presence of the chemiluminescent-tagged NTP-specific antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

The NTP-specific antibody may also be labeled with biotin and then reacted with avidin. A biotin-labeled DNA fragment will be linked to the NTP-biotinylated monoclonal antibody by an avidin bridge. NTP molecules are then detected by polymerase chain reaction (PCR) amplification of the DNA fragment with specific primers (Sano et al., *Science* 258:120–122 (1992)).

Likewise, a bioluminescent compound may be used to label the NTP-specific antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Detection of the NTP-specific antibody may be accomplished by a scintillation counter, for example, if the detectable label is a radioactive gamma emitter, or by a fluorometer, for example, if the label is a fluorescent material. In the case of an enzyme label, the detection can be accomplished by colorimetric methods which employ a substrate for the enzyme. Detection may also be accomplished by visual comparison of the extent of enzymatic reaction of a substrate in comparison with similarly prepared standards.

The detection of foci of such detectably labeled antibodies is indicative of a disease or dysfunctional state as previously described. For the purposes of the present invention, the NTP which is detected by this assay may be present in a biological sample. Any sample containing an NTP can be used. However, one of the benefits of the present diagnostic invention is that invasive tissue removal may be avoided. Therefore, preferably, the sample is a biological solution such as, for example, cerebrospinal fluid, amniotic fluid, blood, serum, urine and the like. However, the invention is not limited to assays using only these samples, it being possible for one of ordinary skill in the art to determine suitable conditions which allow the use of other samples.

For example, the three-site monoclonal antibody-based immunoradiometric assays (M-IRMA) may be used to measure NTP levels in a biological fluid, such as CSF. It is possible to obtain, by spinal tap, on a routine basis, CSF from individuals suspected of having AD. Thus, the diagnosis of AD can be established by a simple, non-invasive immunoassay which reveals NTP levels greatly increased over normal levels.

In one embodiment, as described above, this examination for AD is accomplished by removing samples of biological fluid and incubating such samples in the presence of detectably labeled antibodies (or antibody fragments). In a preferred embodiment, this technique is accomplished in a non-invasive manner through the use of magnetic imaging, fluorography, etc.

Preferably, the detection of cells which express an NTP may be accomplished by in vivo imaging techniques, in which the labeled antibodies (or fragments thereof) are provided to a subject, and the presence of the NTP is detected without the prior removal of any tissue sample. Such in vivo detection procedures have the advantage of being less invasive than other detection methods, and are, moreover, capable of detecting the presence of NTP in tissue which cannot be easily removed from the patient, such as brain tissue.

Using in vivo imaging techniques, it will be possible to differentiate between AD and a brain tumor because NTP will be detected throughout the brain in an AD patient, while NTP will be localized in discrete deposits in the case of brain tumors. For example, in brains of AD patients, NTP will be found in the temporal, parietal and frontal cortices as well as the amygdala and hippocampus. Favored cites for astrocytomas include the cerebrum, cerebellum, thalamus, optic chiasma, and pons (*Harrison's Principles of Internal Medicine*, Petersdorf et al., Eds., Tenth Edition, McGraw-Hill Book Company, New York, p.2076 (1983)), and glioblastoma multiform is predominantly cerebral in location (Id. at 2075).

There are many different in vivo labels and methods of labeling known to those of ordinary skill in the art. Examples of the types of labels which can be used in the present invention include radioactive isotopes and paramagnetic isotopes. Those of ordinary skill in the art will know of other suitable labels for binding to the antibodies used in the invention, or will be able to ascertain such, using routine experimentation. Furthermore, the binding of these labels to the antibodies can be done using standard techniques common to those of ordinary skill in the art.

An important factor in selecting a radionuclide for in vivo diagnosis is that the half-life of a radionuclide be long enough so that it is still detectable at the time of maximum uptake by the target, but short enough so that deleterious radiation upon the host is minimized. Ideally, a radionuclide used for in vivo imaging will lack a particulate emission, but produce a large number of photons in the 140–200 keV range, which maybe readily detected by conventional gamma cameras.

For in vivo diagnosis radionuclides may be bound to antibody either directly or indirectly by using an intermediary functional group. Intermediary functional groups which are often used in binding radioisotopes which exist as metallic ions to immunoglobulins are DTPA and EDTA. Typical examples of ions which can be bound to immunoglobulins are $^{99m}$Tc, $^{123}$I, $^{111}$In, $^{131}$I, $^{97}$Ru, $^{67}$Cu, $^{67}$Ga, $^{125}$I, $^{68}$Ga, $^{72}$As, $^{89}$Zr, and $^{201}$T1.

For diagnostic in vivo imaging, the type of detection instrument available is a major factor in selecting a given radionuclide. The radionuclide chosen must have a type of decay which is detectable for a given type of instrument. In general, any conventional method for visualizing diagnostic imaging can be utilized in accordance with this invention. For example, PET, gamma, beta, and MRI detectors can be used to visualize diagnostic imagining.

The antibodies useful in the invention can also be labeled with paramagnetic isotopes for purposes of in vivo diagnosis. Elements which are particularly useful, as in Magnetic Resonance Imaging (MRI), include $^{157}$Gd, $^{55}$Mn, $^{62}$Dy, and $^{56}$Fe.

The antibodies (or fragments thereof) useful in the present invention are also particularly suited for use in vitro immunoassays to detect the presence of an NTP in body tissue, fluids (such as CSF), or cellular extracts. In such immunoassays, the antibodies (or antibody fragments) may be utilized in liquid phase or, preferably, bound to a solid-phase carrier, as described above.

Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy, et al. (*Clin. Chim. Acta* 70:1–31 (1976)) and Schurs, et al. (*Clin. Chim. Acta* 81:1–40 (1977)). Coupling techniques mentioned in the latter are the glutaraldehyde method, the periodate method, the dimaleimide method, the m-maleimidobenzyl-N-hydroxy-succinimide ester method, all of which methods are incorporated by reference herein.

In situ detection may be accomplished by removing a histological specimen from a patient, and providing the combination of labeled antibodies of the present invention to such a specimen. The antibody (or fragment) is preferably provided by applying or by overlaying the labeled antibody (or fragment) to a biological sample. Through the use of such a procedure, it is possible to determine not only the presence of an NTP, but also the distribution of an NTP on the examined tissue. Using the present invention, those of ordinary skill will readily perceive that any of a wide variety of histological methods (such as staining procedures) can be modified in order to achieve such in situ detection.

The binding molecules of the present invention may be adapted for utilization in an immunometric assay, also known as a "two-site" or "sandwich" assay. In a typical immunometric assay, a quantity of unlabeled antibody (or fragment of antibody) is bound to a solid support that is insoluble in the fluid being tested (i.e., CSF) and a quantity of detectably labeled soluble antibody is added to permit detection and/or quantitation of the ternary complex formed between solid-phase antibody, antigen, and labeled antibody.

Typical, and preferred, immunometric assays include "forward" assays in which the antibody bound to the solid phase is first contacted with the sample being tested to extract the antigen from the sample by formation of a binary solid phase antibody-antigen complex. After a suitable incubation period, the solid support is washed to remove the residue of the fluid sample, including unreacted antigen, if any, and then contacted with the solution containing an unknown quantity of labeled antibody (which functions as a "reporter molecule"). After a second incubation period to permit the labeled antibody to complex with the antigen bound to the solid support through the unlabeled antibody, the solid support is washed a second time to remove the unreacted labeled antibody. This type of forward sandwich assay may be a simple "yes/no" assay to determine whether antigen is present or may be made quantitative by comparing the measure of labeled antibody with that obtained for a standard sample containing known quantities of antigen. Such "two-site" or "sandwich" assays are described by Wide at pages 199–206 of *Radioimmune Assay Method*, edited by Kirkham and Hunter, E. & S. Livingstone, Edinburgh, 1970.

In another type of "sandwich" assay, which may also be useful with the antigens of the present invention, the so-called "simultaneous" and "reverse" assays are used. A simultaneous assay involves a single incubation step as the antibody bound to the solid support and labeled antibody are both added to the sample being tested at the same time. After the incubation is completed, the solid support is washed to remove the residue of fluid sample and uncomplexed labeled antibody. The presence of labeled antibody associated with the solid support is then determined as it would be in a conventional "forward" sandwich assay.

In the "reverse" assay, stepwise addition first of a solution of labeled antibody to the fluid sample followed by the addition of unlabeled antibody bound to a solid support after a suitable incubation period is utilized. After a second incubation, the solid phase is washed in conventional fashion to free it of the residue of the sample being tested and the solution of unreacted labeled antibody. The determination of labeled antibody associated with a solid support is then determined as in the "simultaneous" and "forward" assays.

The above-described in vitro or in vivo detection methods may be used in the detection and diagnosis of AD without the necessity of removing tissue. Such detection methods may be used to assist in the determination of the stage of neurological deterioration in AD by evaluating and comparing the concentration of an NTP in the biological sample.

As used herein, an effective amount of a diagnostic reagent (such as an antibody or antibody fragment) is one capable of achieving the desired diagnostic discrimination and will vary depending on such factors as age, condition, sex, the extent of disease of the subject, counterindications, if any, and other variables to be adjusted by the physician. The amount of such materials which are typically used in a diagnostic test are generally between 0.1 to 5 mg, and preferably between 0.1 to 0.5 mg.

The assay of the present invention is also ideally suited for the preparation of a kit. Such a kit may comprise a carrier means being compartmentalized to receive in close confinement therewith one or more container means such as vials, tubes and the like, each of said container means comprising the separate elements of the immunoassay.

For example, there may be a container means containing a first antibody immobilized on a solid phase support, and a further container means containing a second detectably labeled antibody in solution. Further container means may contain standard solutions comprising serial dilutions of the NTP to be detected. The standard solutions of an NTP may be used to prepare a standard curve with the concentration of NTP plotted on the abscissa and the detection signal on the ordinate. The results obtained from a sample containing an NTP may be interpolated from such a plot to give the concentration of the NTP.

IV. Isolation of NTP

The NTP proteins or fragments of this invention may be obtained by expression from recombinant DNA as described above. Alternatively, an NTP may be purified from biological material.

For purposes of the present invention, one method of purification which is illustrative, without being limiting, consists of the following steps.

A first step in the purification of an NTP includes extraction of the NTP fraction from a biological sample, such as brain tissue or CSF, in buffers, with or without solubilizing agents such as urea, formic acid, detergent, or thiocyanate.

A second step includes subjecting the solubilized material to ionexchange chromatography on Mono-Q or Mono-S columns (Pharmacia LKB Biotechnology, Inc; Piscataway, N.J.). Similarly, the solubilized material may be separated by any other process wherein molecules can be separated according to charge density, charge distribution and molecular size, for example. Elution of the NTP from the ion-exchange resin are monitored by an immunoassay, such as M-IRMA, on each fraction. Immunoreactive peaks would are then dialyzed, lyophilized, and subjected to molecular sieve, or gel chromatography.

Molecular sieve or gel chromatography is a type of partition chromatography in which separation is based on molecular size. Dextran, polyacrylamide, and agarose gels are commonly used for this type of separation. One useful gel for the present invention is Sepharose 12 (Pharmacia LKB Biotechnology, Inc.). However, other methods, known to those of skill in the art may be used to effectively separate molecules based on size.

A fourth step in a purification protocol for an NTP includes analyzing the immunoreactive peaks by sodium dodecyl sulfate-polyacrylamide gel electrophoresis (SDS-PAGE), a further gel chromatographic purification step, and staining, such as, for example, silver staining.

A fifth step in a purification method includes subjecting the NTP obtained after SDS-PAGE to affinity chromatography, or any other procedure based upon affinity between a substance to be isolated and a molecule to which it can specifically bind. For further purification of an NTP, affinity chromatography on Sepharose conjugated to anti-NTP mAbs (such as Th9, or specific mABs generated against substantially pure NTP) can be used. Alternative methods, such as reverse-phase HPLC, or any other method characterized by rapid separation with good peak resolution are useful.

Another method to purify an NTP is to use concentrated CSF obtained from patients with AD. For this procedure, 30–40 milliliters are concentrated by lyophilization or Amicon filtration or the like, and subjected to two dimensional gel electrophoresis. Proteins are separated in one direction by charge in a pH gradient and then, subjected to molecular sieve chromatography in the other direction by polyacrylamide gel electrophoresis. NTP-immunoreactive proteins are identified as spots by the Th monoclonal antibodies (for example, Th 9) using Western blot analysis. The gel is cut and NTP proteins are eluted from the gel. NTP purified in this manner can be sequenced or used to make new monoclonal antibodies.

It will be appreciated that other purification steps may be substituted for the preferred method described above. Those of skill in the art will be able to devise alternate purification schemes without undue experimentation.

V. Gene Therapy Using Antisense Oligonucleotides and Ribozymes

Antisense oligonucleotides have been described as naturally occurring biological inhibitors of gene expression in both prokaryotes (Mizuno et al., *Proc. Natl. Acad. Sci. USA* 81:1966–1970 (1984)) and eukaryotes (Heywood, *Nucleic Acids Res.* 14:6771–6772 (1986)), and these sequences presumably function by hybridizing to complementary mRNA sequences, resulting in hybridization arrest of translation (Paterson, et al., *Proc. Natl. Acad. Sci. USA*, 74:4370–4374 (1987)).

Antisense oligonucleotides are short synthetic DNA or RNA nucleotide molecules formulated to be complementary to a specific gene or RNA message. Through the binding of these oligomers to a target DNA or mRNA sequence, transcription or translation of the gene can be selectively blocked and the disease process generated by that gene can be halted (see, for example, Jack Cohen, *Oligodeoxynucleotides, Antisense Inhibitors of Gene Expression*, CRC Press (1989)). The cytoplasmic location of mRNA provides a target considered to be readily accessible to antisense oligodeoxynucleotides entering the cell; hence much of the work in the field has focused on RNA as a target. Currently, the use of antisense oligodeoxynucleotides provides a useful tool for exploring regulation of gene expression in vitro and in tissue culture (Rothenberg, et al., *J. Natl. Cancer Inst.* 81:1539–1544 (1989)).

Antisense therapy is the administration of exogenous oligonucleotides which bind to a target polynucleotide located within the cells. For example, antisense oligonucleotides may be administered systemically for anticancer therapy (Smith, International Application Publication No. WO 90/09180). As described herein, NTP-related proteins are produced by neuroectodermal tumor cells, malignant astrocytoma cells, glioblastoma cells, and in relatively high concentrations (i.e, relative to controls) in brain tissue of AD patients. Thus, NTP antisense oligonucleotides of the present invention may be active in treatment against AD, as well as neuroectodermal tumors, malignant astrocytomas, and glioblastomas.

The NTP antisense oligonucleotides of the present invention include derivatives such as S-oligonucleotides (phosphorothioate derivatives or S-oligos, see, Jack Cohen, supra). S-oligos (nucleoside phosphorothioat) are isoelectronic analogs of an oligonucleotide (O-oligo) in which a nonbridging oxygen atom of the phosphate group is replaced by a sulfur atom. The S-oligos of the present invention may be prepared by treatment of the corresponding O-oligos with 3H-1,2-benzodithiol-3-one-1,1-dioxide which is a sulfur transfer reagent. See Iyer et al., *J. Org. Chem.* 55:4693–4698 (1990); and Iyer et al., *J. Am. Chem. Soc.* 112:1253–1254 (1990), the disclosures of which are fully incorporated by reference herein.

As described herein, sequence analysis of an NTP cDNA clone shows that NTP contains sequences which are non-homologous to PTP DNA sequences (see FIG. 9). Thus, the NTP antisense oligonucleotides of the present invention may be RNA or DNA which is complementary to and stably hybridizes with such sequences which are specific for an NTP. Use of an oligonucleotide complementary to this region allows for the selective hybridization to NTP mRNA and not to mRNA specifying PTP. Preferably, the NTP antisense oligonucleotides of the present invention are a 15 to 30-mer fragment of the antisense DNA molecule coding for the nonhomologous sequences of the AD 3-4 cDNA, such as:

1. 5'-CCGATTCCAACAGACCATCAT-3' [SEQ ID NO:1];
2. 5'-CCAACAGACCATCATTCCACC-3' [SEQ ID NO:2]; and
3. 5'-CCAAACCGATTCCAACAGACC-3' [SEQ ID NO:3].

Preferred antisense oligonucleotides bind to the 5'-end of the AD10-7 mRNA. Such antisense oligonucleotides may be used to down regulate or inhibit expression of the NTP gene. Examples of such antisense oligonucleotides (30-mers) include:

1. 5'-CCTGGGCAACAAGAGCGAAAACTCCATCTC-3' [SEQ ID NO:4];
2. 5'-ATCGCTTGAACCCGGGAGGCGGAGGTTGCG-3' [SEQ ID NO:5]; and
3. 5'-GGGGAGGCTGAGGCAGGAGAATCGCTTGAA-3' [SEQ ID NO:6].

Included as well in the present invention are pharmaceutical compositions comprising an effective amount of at least one of the NTP antisense oligonucleotides of the invention in combination with a pharmaceutically acceptable carrier. In one embodiment, a single NTP antisense oligonucleotide is utilized. In another embodiment, two NTP antisense oligonucleotides are utilized which are complementary to adjacent regions of the NTP genome. Administration of two NTP antisense oligonucleotides which are complementary to adjacent regions of the genome or corresponding mRNA may allow for more efficient inhibition of NTP genomic transcription or mRNA translation, resulting in more effective inhibition of NTP production.

Preferably, the NTP antisense oligonucleotide is coadministered with an agent which enhances the uptake of the antisense molecule by the cells. For example, the NTP antisense oligonucleotide may be combined with a lipophilic cationic compound which may be in the form of liposomes. The use of liposomes to introduce nucleotides into cells is taught, for example, in U.S. Pat. Nos. 4,897,355 and 4,394,448, the disclosures of which are incorporated by reference in their entirety. See also U.S. Pat. Nos. 4,235,871, 4,231,877, 4,224,179, 4,753,788, 4,673,567, 4,247,411, 4,814,270 for general methods of preparing liposomes comprising biological materials.

Alternatively, the NTP antisense oligonucleotide may be combined with a lipophilic carrier such as any one of a number of sterols including cholesterol, cholate and deoxycholic acid. A preferred sterol is cholesterol.

In addition, the NTP antisense oligonucleotide may be conjugated to a peptide that is ingested by cells. Examples of useful peptides include peptide hormones, antigens or antibodies, and peptide toxins. By choosing a peptide that is selectively taken up by the neoplastic cells, specific delivery of the antisense agent may be effected. The NTP antisense oligonucleotide may be covalently bound via the 5'OH group by formation of an activated aminoalkyl derivative. The peptide of choice may then be covalently attached to the activated NTP antisense oligonucleotide via an amino and sulfhydryl reactive hetero bifunctional reagent. The latter is bound to a cysteine residue present in the peptide. Upon exposure of cells to the NTP antisense oligonucleotide bound to the peptide, the peptidyl antisense agent is endocytosed and the NTP antisense oligonucleotide binds to the target NTP mRNA to inhibit translation (Haralambid et al., WO 8903849; Lebleu et al., EP 0263740).

The NTP antisense oligonucleotides and the pharmaceutical compositions of the present invention may be administered by any means that achieve their intended purpose. For example, administration may be by parenteral, subcutaneous, intravenous, intramuscular, intra-peritoneal, or transdermal routes. The dosage administered will be dependent upon the age, health, and weight of the recipient, kind of concurrent treatment, if any, frequency of treatment, and the nature of the effect desired.

Compositions within the scope of this invention include all compositions wherein the NTP antisense oligonucleotide is contained in an amount effective to achieve inhibition of proliferation and/or stimulate differentiation of the subject cancer cells, or alleviate AD. While individual needs vary, determination of optimal ranges of effective amounts of each component is with the skill of the art. Typically, the NTP antisense oligonucleotide may be administered to mammals, e.g. humans, at a dose of 0.005 to 1 mg/kg/day, or an equivalent amount of the pharmaceutically acceptable salt thereof, per day of the body weight of the mammal being treated.

Alternatively, antisense oligonucleotides can be prepared which are designed to interfere with transcription of the NTP gene by binding transcribed regions of duplex DNA (including introns, exons, or both) and forming triple helices (Froehler et al., WO 91/06626; Toole, WO 92/10590). Preferred oligonucleotides for triple helix formation are oligonucleotides which have inverted polarities for at least two regions of the oligonucleotide (Id.). Such oligonucleotides comprise tandem sequences of opposite polarity such as 3'---5'-L-5'---3', or 5'---3'-L-3'---5', wherein L represents a 0–10 base oligonucleotide linkage between oligonucleotides. The inverted polarity form stabilizes single-stranded oligonucleotides to exonuclease degradation (Froehler et al., supra). Preferred triple helix-forming oligonucleotides are based upon SEQ ID NOs1–3:

1. 3'-TACTACCAGACAACCTTAGCC-5'-L-5'-CCGATTCCAACAGACCATCAT-3' [SEQ ID NO:7];
2. 5'-CCGATTCCAACAGACCATCAT-3'-L-3'-TACTACCAGACAACCTTAGCC-5' [SEQ ID NO:8];
3. 3'-CCACCTTACTACCAGACAACC-5'-L-5'-CCAACAGACCATCATTCCACC-3' [SEQ ID NO:9];
4. 5'-CCAACAGACCATCATTCCACC-3'-L-3'-CCACCTTACTACCAGACAACC-5' [SEQ ID NO:10];
5. 3'-CCAGACAACCTTAGCCAAACC-5'-L-5'-CCAAACCGATTCCAACAGACC-3' [SEQ ID NO:11]; and
6. 5'-CCAAACCGATTCCAACAGACC-3'-L-3'-CCAGACAACCTTAGCCAAACC-5' [SEQ ID NO:12].

Thus, triple helix-forming oligonucleotides 1 and 2 are represented as 3'[SEQ ID NO:1]5'-L-5'[SEQ ID NO:1]3' and 5'[SEQ ID NO:1]3'-L-3'[SEQ ID NO:1]5', respectively. Triple helix-forming oligonucleotides 3 and 4 are represented as 3'[SEQ ID NO:2]5'-L-5'[SEQ ID NO:2]3' and 5'[SEQ ID NO:2]3'-L-3'[SEQ ID NO:2]5', respectively. Triple helix-forming oligonucleotides 5 and 6 are represented as 3'[SEQ ID NO:3]5'-L-5'[SEQ ID NO:3]3' and 5'[SEQ ID NO:3]3'-L-3'[SEQ ID NO:3]5', respectively. Of course, similar triple helix-forming oligonucleotide may be prepared with SEQ ID NOs. 4–6, or fragments thereof.

In therapeutic application, the triple helix-forming oligonucleotides can be formulated in pharmaceutical preparations for a variety of modes of administration, including systemic or localized administration, as described above.

The antisense oligonucleotides of the present invention may be prepared according to any of the methods that are well known to those of ordinary skill in the art, as described above.

Ribozymes provide an alternative method to inhibit mRNA function. Ribozymes may be RNA enzymes, self-splicing RNAs, and self-cleaving RNAs (Cech et al., *Journal of Biological Chemistry* 267:17479–17482 (1992)). It is possible to construct de novo ribozymes which have an endonuclease activity directed in trans to a certain target sequence. Since these ribozymes can act on various sequences, ribozymes can be designed for virtually any RNA substrate. Thus, ribozymes are very flexible tools for inhibiting the expression of specific genes and provide an alternative to antisense constructs.

A ribozyme against chloramphenicol acetyltransferase mRNA has been successfully constructed (Haseloff et al., *Nature* 334:585–591 (1988); Uhlenbeck et al., *Nature* 328:596–600 (1987)). The ribozyme contains three structural domains: 1) a highly conserved region of nucleotides which flank the cleavage site in the 5' direction; 2) the highly conserved sequences contained in naturally occurring cleavage domains of ribozymes, forming a base-paired stem; and 3) the regions which flank the cleavage site on both sides and ensure the exact arrangement of the ribozyme in relation to the cleavage site and the cohesion of the substrate and enzyme. RNA enzymes constructed according to this model have already proved suitable in vitro for the specific cleaving of RNA sequences (Haseloff et al., supra).

Alternatively, hairpin ribozymes may be used in which the active site is derived from the minus strand of the satellite RNA of tobacco ring spot virus (Hampel et al., *Biochemistry* 28:4929–4933 (1989)). Recently, a hairpin ribozyme was designed which cleaves human immunodeficiency virus type 1 RNA (Ojwang et al., *Proc. Natl. Acad. Sci. USA* 89:10802–10806 (1992)). Other self-cleaving RNA activities are associated with hepatitis delta virus (Kuo et al., *J. Virol.* 62:4429–4444 (1988)).

As discussed above, preferred targets for NTP ribozymes are the nucleotide sequences which are not homologous with PTP sequences. Preferably, the NTP ribozyme molecule of the present invention is designed based upon the chloramphenicol acetyltransferase ribozyme or hairpin ribozymes, described above. Alternatively, NTP ribozyme molecules are designed as described by Eckstein et al. (International Publication No. WO 92/07065) who disclose catalytically active ribozyme constructions which have increased stability against chemical and enzymatic degradation, and thus are useful as therapeutic agents.

In an alternative approach, an external guide sequence (EGS) can be constructed for directing the endogenous ribozyme, RNase P, to intracellular NTP mRNA, which is subsequently cleaved by the cellular ribozyme (Altman et al., U.S. Pat. No. 5,168,053). Preferably, the NTP EGS comprises a ten to fifteen nucleotide sequence complementary to an NTP mRNA and a 3'-NCCA nucleotide sequence, wherein N is preferably a purine (Id.). After NTP EGS molecules are delivered to cells, as described below, the molecules bind to the targeted NTP mRNA species by forming base pairs between the NTP mRNA and the complementary NTP EGS sequences, thus promoting cleavage of NTP mRNA by RNase P at the nucleotide at the 5' side of the base-paired region (Id.).

Included as well in the present invention are pharmaceutical compositions comprising an effective amount of at least one NTP ribozyme or NTP EGS of the invention in combination with a pharmaceutically acceptable carrier. Preferably, the NTP ribozyme or NTP EGS is coadministered with an agent which enhances the uptake of the ribozyme or NTP EGS molecule by the cells. For example, the NTP ribozyme or NTP EGS may be combined with a lipophilic cationic compound which may be in the form of liposomes, as described above. Alternatively, the NTP ribozyme or NTP EGS may be combined with a lipophilic carrier such as any one of a number of sterols including cholesterol, cholate and deoxycholic acid. A preferred sterol is cholesterol.

The NTP ribozyme or NTP EGS, and the pharmaceutical compositions of the present invention may be administered by any means that achieve their intended purpose. For example, administration may be by parenteral, subcutaneous, intravenous, intramuscular, intra-peritoneal, or transdermal routes. The dosage administered will be dependent upon the age, health, and weight of the recipient, kind of concurrent treatment, if any, frequency of treatment, and the nature of the effect desired. For example, as much as 700 milligrams of antisense oligodeoxynucleotide has been administered intravenously to a patient over a course of 10 days (i.e., 0.05 mg/kg/hour) without signs of toxicity (Sterling, "Systemic Antisense Treatment Reported," *Genetic Engineering News* 12(12):1, 28 (1992)).

Compositions within the scope of this invention include all compositions wherein the NTP ribozyme or NTP EGS is contained in an amount which is effective to achieve inhibition of proliferation and/or stimulate differentiation of the subject cancer cells, or alleviate AD. While individual needs vary, determination of optimal ranges of effective amounts of each component is with the skill of the art.

In addition to administering the NTP antisense oligonucleotides, ribozymes, or NTP EGS as a raw chemical in solution, the therapeutic molecules may be administered as part of a pharmaceutical preparation containing suitable pharmaceutically acceptable carriers comprising excipients and auxiliaries which facilitate processing of the NTP antisense oligonucleotide, ribozyme, or NTP EGS into preparations which can be used pharmaceutically.

Suitable formulations for parenteral administration include aqueous solutions of the NTP antisense oligonucleotides, ribozymes, NTP EGS in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers.

Alternatively, NTP antisense RNA molecules, NTP ribozymes, and NTP EGS can be coded by DNA constructs which are administered in the form of virions, which are preferably incapable of replicating in vivo (see, for example, Taylor, WO 92/06693). For example, such DNA constructs may be administered using herpes-based viruses (Gage et al., U.S. Pat. No. 5,082,670). Alternatively, NTP antisense RNA sequences, NTP ribozymes, and NTP EGS can be coded by RNA constructs which are administered in the form of virions, such as retroviruses. The preparation of retroviral vectors is well known in the art (see, for example, Brown et al., "Retroviral Vectors," in DNA Cloning: *A Practical Approach*, Volume 3, IRL Press, Washington, D.C. (1987)).

Specificity for gene expression in the central nervous system can be conferred by using appropriate cell-specific regulatory sequences, such as cell-specific enhancers and promoters. For example, such sequences include the sequences that regulate the oligodendroglial-specific expression of JC virus, glial-specific expression of the proteolipid protein, and the glial fibrillary acidic protein genes (Gage et al., supra). Since protein phosphorylation is critical for neuronal regulation (Kennedy, "Second Messengers and Neuronal Function," in *An Introduction to Molecular Neurobiology*, Hall, Ed., Sinauer Associates, Inc. (1992)), protein kinase promoter sequences can be used to achieve sufficient levels of NTP gene expression.

Thus, gene therapy can be used to alleviate AD by inhibiting the inappropriate expression of a particular form of NTP. Moreover, gene therapy can be used to alleviate AD by providing the appropriate expression level of a particular form of NTP. In this case, particular NTP nucleic acid sequences may be coded by DNA or RNA constructs which are administered in the form of viruses, as described above. Alternatively, "donor cells" may be modified in vitro using viral or retroviral vectors containing NTP sequences, or using other well known techniques of introducing foreign DNA into cells (see, for example, Sambrook et al., supra). Such donor cells include fibroblast cells, neuronal cells, glial cells, and connective tissue cells (Gage et al., supra). Following genetic manipulation, the donor cells are grafted into the central nervous system and thus, the genetically-modified cells provide the therapeutic form of NTP (Id.).

Moreover, such virions may be introduced into the blood stream for delivery to the brain. This is accomplished through the osmotic disruption of the blood brain barrier prior to administration of the virions (see, for example, Neuwelt, U.S. Pat. No. 4,866,042). The blood brain barrier may be disrupted by administration of a pharmaceutically effective, nontoxic hypertonic solution, such as mannitol, arabinose, or glycerol (Id.).

The following clones in *E. coli* were deposited according to the Budapest Treaty with the American Type Culture Collection (10801 University Boulevard, Manassas, Va., 20110-2209): G2-2 PstI-DH5 (ATCC No. 69257); G5d-PstI-DH5 (ATCC No. 69258); 1-9a-LX-1 blue (ATCC No. 69259); AD3-4-DH1 (ATCC No. 69260); HB4-XL-blue (ATCC No. 69261); AD10-7-DH1 (ATCC No. 69262); Ad2-2-DH1- (ATCC No. 69263); G5d-1PstI-EcoRI-DH5 (ATCC No. 69264); and G2-2PstI-EcoRI-DH5 (ATCC No. 69265), on Mar. 16, 1993.

Having now generally described the invention, the same will be more readily understood through reference to the following Examples which are provided by way of illustration, and are not intended to be limiting of the present invention, unless specified.

EXAMPLE 1

Expression of NTP Immunoreactivity in Cell Lines

Seven cell lines of central nervous system origin were identified that express thread protein immunoreactivity using the Th9 monoclonal antibody which was generated to the pancreatic form of the protein (Gross et al., *J. Clin. Invest.* 76:2115–2126 (1985)), but cross-reacts with thread proteins present in brain tissue and cerebrospinal fluid (Ozturk et al., *Proc. Natl. Acad. Sci. USA* 86:419–423 (1989); de la Monte et. al., *J. Clin. Invest.* 86:1004–1013 (1990); de la Monte et. al., *J. Neurol. Sci.* 113:152–164 (1992); de la Monte et al., *Ann. Neurol.* 32:733–742 (1992)). Among them were the following: two primitive neuroectodermal tumor (PNET) cell lines designated PNET1 and PNET2; three glioblastoma cell lines Hg1 16, Hg1 17, and C6; the A172 glial cell line; and the SH-Sy5y neuroblastoma cell line. The glioblastoma cell lines and the A172 cells were obtained from the American Type Culture Collection (ATCC). SH-Sy5y cells were obtained from Dr. Biedler at Sloan-Kettering Memorial Hospital. The PNET cell lines have been described previously (The et al., *Nature genetics* 3:62–66 (1993)), and were obtained from Dr. Rene' Bernards at the MGH Cancer Center. All cell lines were maintained in Earl's Modified Eagle Medium supplemented with 10% fetal calf serum, and without antibiotics.

To examine the cells for thread protein and other immunoreactivities, the cultures were harvested in phosphate buffered saline (PBS) (137 mM NaCl, 2.7 mM KCl, 4.3 mM $Na_2HPO4$, 1.4 mM $KH_2PO_4$, pH 7.3) containing 2 mM EDTA, and cytospin preparations were made using $10^5$ cells per slide. The cytospin preparations were fixed immediately in 100% methanol (−20° C.), air-dried, and then stored at −80° C. until used. Prior to immunostaining, the slides were equilibrated to room temperature and hydrated in PBS. Nonspecific antibody binding was blocked with 3% nonimmune horse serum. Replicate cytospin preparations from the same cultures were incubated overnight at 4° C. with 5 or 10 μg/ml of primary antibody. Immunoreactivity was revealed by the avidin-biotin horseradish peroxidase method using the Vectastain Elite kit (Vector Laboratories, Burlingame, Calif.) according to the manufacturer's protocol, and with 3-3' diaminobenzidine (0.5 mg/ml plus 0.03% hydrogen peroxide) as the chromogen. The cells then were counterstained with hematoxylin, dehydrated in graded alcohol solutions, cleared in xylenes, and preserved under coverglass with Permount (Fisher Scientific).

Cytospin preparations of each cell line were immunostained with the thread protein monoclonal antibodies Th9, Th7, Th10, Th29, Th34, TH46, Th67, and Th90. In addition, replicate slides were immunostained with positive (neurofilament, glial fibrillary acidic protein (GFAP), and vimentin) and negative (desmin, Hepatitis B surface antigen-5C3) control monoclonal antibodies. Except for 5C3 which was generated in the inventor's laboratory (Fujita et al., *Gastroenterology* 91:1357–1363 (1986)), the control antibodies were purchased (Boehringer-Mannheim). All serological reagents were diluted in PBS containing 1% bovine serum albumin (BSA), and all incubations except the one with primary antibody were carried out at room temperature in humidified chambers. The slides were washed in 3 changes of PBS between each step.

Both PNET1 and PNET2 cells expressed high and middle molecular weight neurofilament proteins and little or no glial fibrillary acidic protein or vimentin. The PNET1, PNET2, and SH-Sy5y cells expressed GAP-43, an abundant calmodulin-binding phosphoprotein that is highly expressed in immature neurons and in neurons undergoing regenerative cell growth (Benowitz et al., *J. Neurosci.* 3:2153–2163 (1983); DeGraan et al., *Neurosci. Lett.* 61:235–241 (1985); Kalil et al., *J. Neurosci.* 6:2563–2570 (1986)). The A172 and C6 cells expressed GFAP and vimentin. However, A172 also exhibited neurofilament immunoreactivity, raising doubt about its purely glial cell nature. None of the cell lines manifested immunoreactivity with monoclonal antibodies to desmin or to Hepatitis B surface antigen. As a negative control cell line, the Huh7 hepatocellular carcinoma cell line was similarly immunostained, and found not to exhibit any immunoreactivity with the above antibodies. However, the Huh cells were immunoreactive with monoclonal antibodies to the insulin receptor substrate protein, IRS-1 (data not shown) which was used as a positive control for this cell line (Sasaki et al., *J. Biol. Chem.* 268:1–4 (1993)).

Using the Th9 monoclonal antibody, thread protein immunoreactivity was detected in primary PNET (A), primary glioblastoma (F), PNET1 (B), and C6 cells (G), but not in hepatocellular carcinoma cell lines (FIGS. 1A–1J). In addition, Th9 immunoreactivity was detected in histological sections from 8 of the 9 primary human CNS PNETs, and from all 5 of the primary human glioblastomas studied (FIGS. 1A–1J). Although all 5 cell lines exhibited intense immunoreactivity with the Th9 monoclonal antibody, they differed with respect to immunoreactivity for other Th monoclonal antibodies. The immunostaining reaction generated with the Th10 (C,H), Th7 (D,I), or Th46 monoclonal antibodies was either low-level (C,D) or absent (H,I,E,J) in PNET1 (C–E) and C6 (H–J). PNET2 cells exhibited only low levels of immunoreactivity with Th7 and Th29, and they manifested no immunostaining with the other Th monoclonal antibodies. A172, C6, and SH-Sy5y cells displayed little or no immunoreactivity with Th monoclonal antibodies other than Th9. Huh7 cells exhibited no immunoreactivity with any of the thread protein monoclonal antibodies employed, whereas human pancreatic tissue was immunoreactive with all of the Th antibodies, which had been generated against the purified pancreatic form of thread protein (Gross et al., *J. Clin. Invest.* 76:2115–2126 (1985)).

EXAMPLE 2

Analysis of Thread Proteins by Monoclonal Antibody-Based Immunoradiometric Assay (M-IRMA)

Cultured cells were washed in PBS and recovered in PBS containing 2 mM EDTA. The cells were pelleted by centrifugation at 1000 × g for 15 min, and then resuspended in lysis buffer containing 50 mM Tris-HCl (pH 7.5), 1% Triton X-100, 2 mM EGTA, 10 mM EDTA, 100 mM NaF, 1 mM $Na_4P_2O_7$, 2 mM $Na_3VO_4$, 100 μg/ml phenylmethylsulfonyl fluoride, 1 μg/ml aprotinin, 1 μg/ml pepstatin A, and 1 μg/ml leupeptin. The supernatant fractions obtained by centrifugation of the lysates at 14,000 × g for 10 min were used for the Western blot analysis, immunoprecipitation studies, and M-IRMA. Protein concentration was determined by the Lowry colorimetric assay. The samples were stored at −40° C.

M-IRMA is a highly sensitive two- or three-site forward sandwich assay which permits quantitation of picomolar NTP in cell lysates, tissue culture medium, tissue homogenates, and body fluids (Ozturk et al., *Proc. Natl. Acad. Sci. USA* 86:419–423 (1989); de la Monte et. al., *J. Clin. Invest.* 86:1004–1013 (1990); de la Monte et. al., *J. Neurol. Sci.* 113:152–164 (1992); de la Monte et al., *Ann. Neurol.* 32:733–742 (1992); Gross et al., *J. Clin. Invest.* 76:2115–2126 (1985)). In addition, when combined with SDS-PAGE, M-IRMA can be used to determine molecular size of thread proteins and related species (Ozturk et al., *Proc. Natl. Acad. Sci. USA* 86:419–423 (1989); de la Monte et. al., *J. Clin. Invest.* 86:1004–1013 (1990); de la Monte et. al., *J. Neurol. Sci.* 113:152–164 (1992); de la Monte et al., *Ann. Neurol.* 32:733–742 (1992)). M-IRMA involves capturing the immunoreactive thread proteins present in biological samples using monoclonal antibodies Th7 and Th10 affixed to a solid-phase matrix, and then detecting the captured antigen with a third radiolabelled tracer monoclonal antibody (Th9) to the same protein. Briefly, ¼" polystyrene beads (Precision Ball, Inc) were coated with one or two monoclonal antibodies to thread proteins (usually Th7+Th10 ). Cell lysates or supernatant fractions of tissue homogenates (Ozturk et al., *Proc. Natl. Acad. Sci. USA* 86:419–423 (1989); de la Monte et. al., *J. Clin. Invest.* 86:1004–1013 (1990); de la Monte et. al., *J. Neurol. Sci.* 113:152–164 (1992); de la Monte et al., *Ann. Neurol.* 32:733–742 (1992)) were incubated over night with the coated beads to capture thread proteins present in the samples. The beads were washed 5x in PBS, and then incubated with $^{125}xI$ labeled Th9 as a tracer to detect the captured thread proteins. The concentration of thread protein in the lysate or tissue homogenate was determined from a standard curve generated with known quantities of purified thread protein. This highly sensitive assay can detect as little as 10 pmol of thread protein in solution. To assay for thread proteins fractionated by SDS-PAGE, the wet gels were sliced at 2 mm intervals, and the proteins were eluted from each fraction into 0.5 ml of PBS by shaking for 24 hours at room temperature. The eluates were assayed directly for thread proteins by M-IRMA.

Corresponding with the widespread immunocytochemical staining of PNET1 cells with Th7, Th10, Th34, and Th29, thread protein immunoreactivity was readily measured in these cells by M-IRMA. In other words, with Th7, Th10, Th34, and Th29 monoclonal antibodies (MoAb) used as capture antibodies, either singularly or with two of them together, and $^{125}$xI labeled Th9 was used as the tracer, similarly high levels of thread protein were measured (FIG. 2). In contrast, in PNET2, C6, and A172 cells, which exhibited intense immunoreactivity with Th9, but little or no immunocytochemical staining with the Th monoclonal antibodies that were used to capture antigen, the levels of thread protein detected by M-IRMA were much lower than those measured in the PNET1 cells (FIG. 2). Similarly, Huh7 cells, which manifested no immunocytochemical staining with any of the thread protein monoclonal antibodies, had virtually nondetectable levels of thread proteins in the cellular lysates by M-IRMA. The concentrations of thread protein in the cell lysates were computed from a standard curve generated with purified PTP using Th7 and Th10 as capture antibodies. The results expressed as mean S.D. pg/mg of total protein were as follows: PNET1-13.1±0.39; PNET2-2.06±0.10; A172-3.38±0.37; C6-2.52±0.22; and Huh7-0.34±0.05.

EXAMPLE 3

Characterization of Neural Thread Proteins in Tumor Cell Lines

In Western Blot analysis, samples containing 100 µg of protein were fractionated by SDS-PAGE, along with pre-labeled molecular weight standards. The proteins were blotted onto nylon membranes (Immobilon-P transfer membrane, Millipore) using a semi-dry transfer apparatus (Integrated Systems). The membranes were washed in Tris buffered saline (TBS; 10 mM Tris, 0.85% sodium chloride, pH 7.5), and then blocked with TBS containing 3% BSA. The blots were incubated overnight at 4° C. with $^{125}$-I labeled Th9 monoclonal antibody. Unspecifically bound probe was removed by washing the membranes at room temperature in TBS-BSA 3×15 min, and 1×30 min. The results were analyzed by autoradiography using Kodak XAR film.

To prepare samples for immunoprecipitation studies, one milliliter samples of cell lysate containing approximately 1 mg/ml of protein were used for immunoprecipitation studies. The lysates were initially pre-cleared with non-relevant antibody (5C3 or antidesmin), and then with Protein A sepharose. Thread proteins were immunoprecipitated using 5–10 µg of Th9 and Protein A sepharose (Sasaki et al., *J. Biol. Chem.* 268:1–4 (1993)). The immune complexes collected by centrifugation were resuspended in buffer containing 2% SDS and 10 mM β-mercaptoethanol, and then subjected to SDS-PAGE under denaturing and reducing conditions (Id.). Crude cellular lysates (100 µg protein) were analyzed simultaneously. The proteins were blotted onto Immobilon-P membranes and probed with $^{125}$-I labeled (Id.) Th9 to detect thread proteins and related molecules. Negative control experiments were performed simultaneously using either monoclonal antibodies to Hepatitis B surface antigen (5C3) or to desmin.

Metabolic labeling experiments were performed using monolayers of cells cultured in 100 mm² petri dishes. Prior to labeling, the cells were exposed to methionine- and cysteine-free medium for 2 h. The medium was then replaced with 3 ml of DMEM containing 300 µCi each of [$^{35}$S] methionine or [$^{35}$S] cysteine. After labeling for 3 hours, the cells were incubated for various intervals with complete medium devoid radiolabelled amino acids and supplemented with 10 mM methionine. Cell lysates were prepared as described above. Thread proteins were immunoprecipitated using the Th9 monoclonal antibody and protein A sepharose, and the immunoprecipitation products were analyzed by SDS-PAGE and film autoradiography.

For the in vivo phosphorylation studies, cells cultured as described for metabolic labeling studies were washed twice with TBS and incubated for 2 h with phosphate-free Dulbecco's MEM containing 10% dialyzed fetal calf serum. Then the cells were washed with TBS and incubated for 3 h with the same medium containing 400 µCi/ml of [$^{32}$P] orthophosphoric acid. The cell lysates were analyzed by immunoprecipitation with thread protein, and both positive (p36) and negative (desmin) control monoclonal antibodies, followed by SDS-PAGE.

In order to study the glycosylation state of neural thread proteins, cell culture lysates containing approximately 100 µg or protein were subjected to SDS-PAGE, and the fractionated proteins were transferred to Immobilon-P membranes (Millipore). O- and N-glycans were detected by periodate oxidation followed by biotinylation, and then Western blot analysis with a Streptavidin-alkaline phosphatase probe and NBT/BCIP as the colorimetric substrate. The assays were performed using the GlycoTrack Kit (Oxford Glycosystems, Rosedale, N.Y.) according to the protocol provided by the manufacturer.

Figure 3:
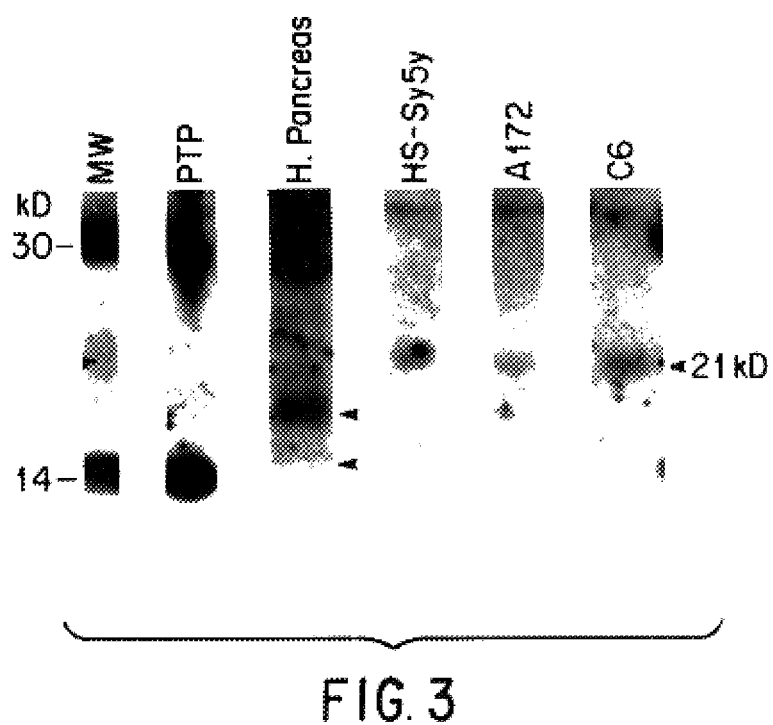
FIG. 3 shows molecular size of neural thread proteins in SH-Sy5y, A172, and C6 cells demonstrated by immunoprecipitation and Western blot analysis using the Th9 monoclonal antibody.

Th9-immunoreactive proteins were detected in lysates of PNET1, PNET2, SH-Sy5y, C6, and A172 cells by four different methods: Western blot analysis, immunoprecipitation followed by Western blot analysis, metabolic labeling followed by immunoprecipitation, and SDS-PAGE combined with M-IRMA. Western blot analysis of crude cellular lysates using $^{125}$I-labeled Th9 demonstrated ~21 kDa bands in the above cell lines (as indicated by the arrow in FIG. 3), but the signal intensity was low. In contrast, in lysates of human pancreatic tissue, the expected 17 kDa uncleaved and 14 kDa cleaved forms of pancreatic thread protein were readily detected by Western blot analysis (FIG. 3). Thread proteins were not detected in lysates of human hepatocellular carcinoma cell lines. The strikingly greater abundance of thread proteins in pancreatic tissue compared with neuronal and glial cell lines is consistent with a previous finding of 10⁶-fold higher levels of thread proteins in pancreas and pancreatic juice compared with brain tissue and cerebrospinal fluid (Ozturk et al., *Proc. Natl. Acad. Sci. USA* 86:419–423 (1989); de la Monte et. al., *J. Clin. Invest.* 86:1004–1013 (1990); de la Monte et. al., *J. Neurol. Sci.* 113:152–164 (1992); de la Monte et al., *Ann. Neurol.* 32:733–742 (1992)). Although one would expect that thread proteins synthesized by PNET and glial cells are secreted as is the case for PTP and NTP, thread proteins were not detected in the tissue culture medium by Western blot analysis, even after concentrating the medium four- or five-fold by lyophilization.

Th9-immunoreactive thread proteins were more readily detected in PNET and glial cell lines by first immunoprecipitating from the lysates with either Th7+Th10 or Th9, and then performing Western blot analysis using $^{125}$I-labeled Th9 (direct) (FIG. 3), or unlabeled Th9 with $^{125}$I-labeled Protein A (indirect). Both methods demonstrated 21 kDa thread protein-related species, similar to those detected by Western blot analysis. In addition, ~17 kDa bands were also observed in both PNET and glial cells, but the signal was inconsistent and low-level, as determined by Western blot analysis. As negative controls, the Huh7, HepG2, and FOCUS (Lun et al., *In Vitro (Rockville)* 20:493–504 (1984)) human hepatocellular carcinoma cell lines were studied simultaneously under identical conditions, and Th9-immunoreactive proteins were not detected in the cellular lysates.

Figure 4A:
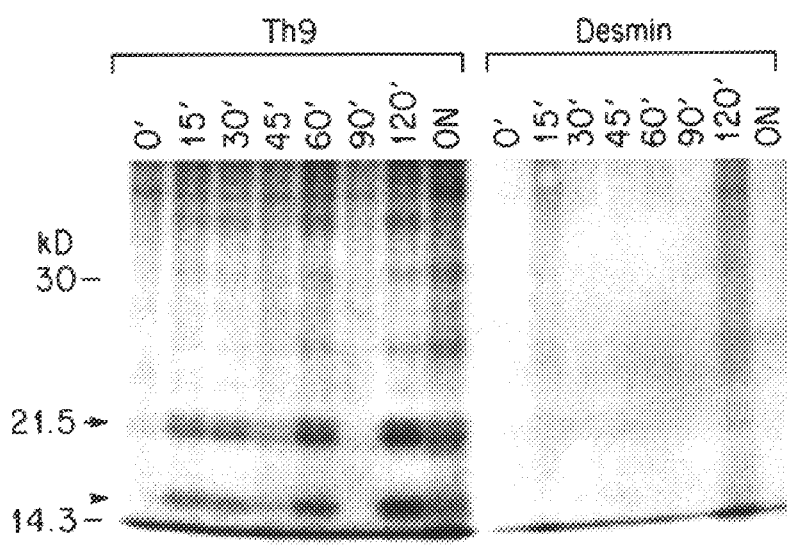
FIG. 4A and 4B shows molecular sizes of neural thread proteins in PNET1 cells (a) and C6 glioblastoma cells (b) demonstrated by pulse-chase metabolic labeling with $^{35}$S-methionine, and immunoprecipitation with Th9 monoclonal antibody (FIG. 4A). The molecular weights are 8, 14, 17, 21, 26 and 42 kDa (arrows).
Figure 4B:
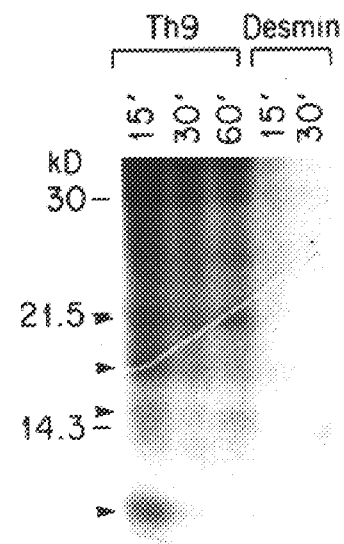
Figure 5A:
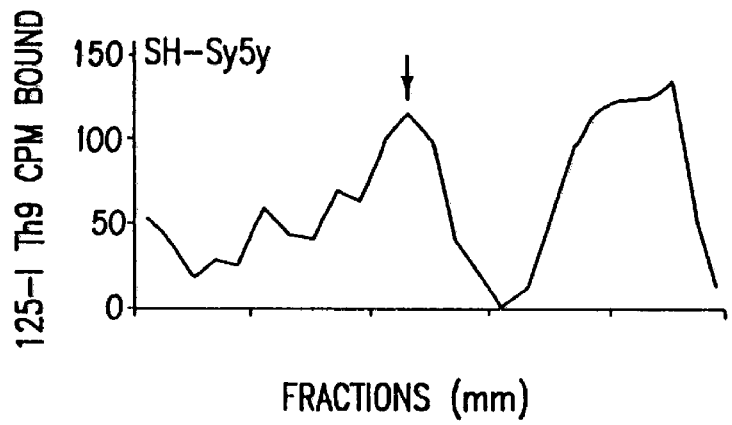
FIGS. 5A–5E depict a series of five graphs showing the 21 kDa and 17 kDa neural thread proteins in SH-Sy5y, PNET1, A172, and C6 cells and the absence thereof in Huh7 cells by SDS-PAGE/M-IRMA.
Figure 5B:
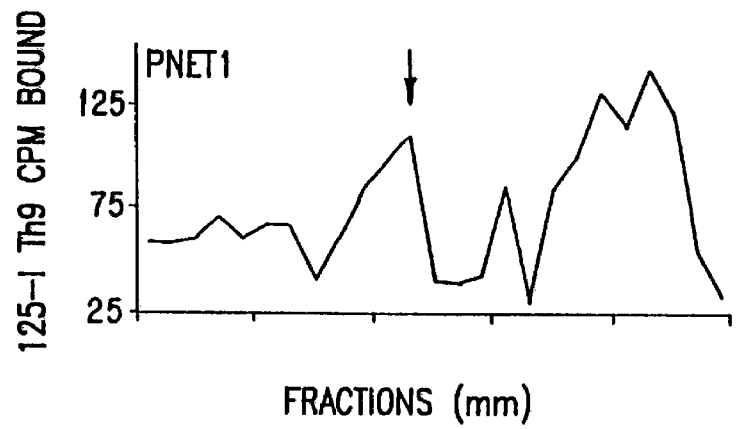
Figure 5C:
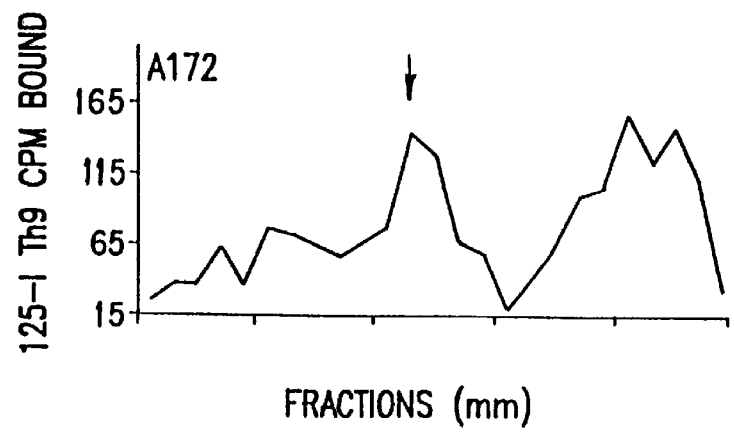
Figure 5D:
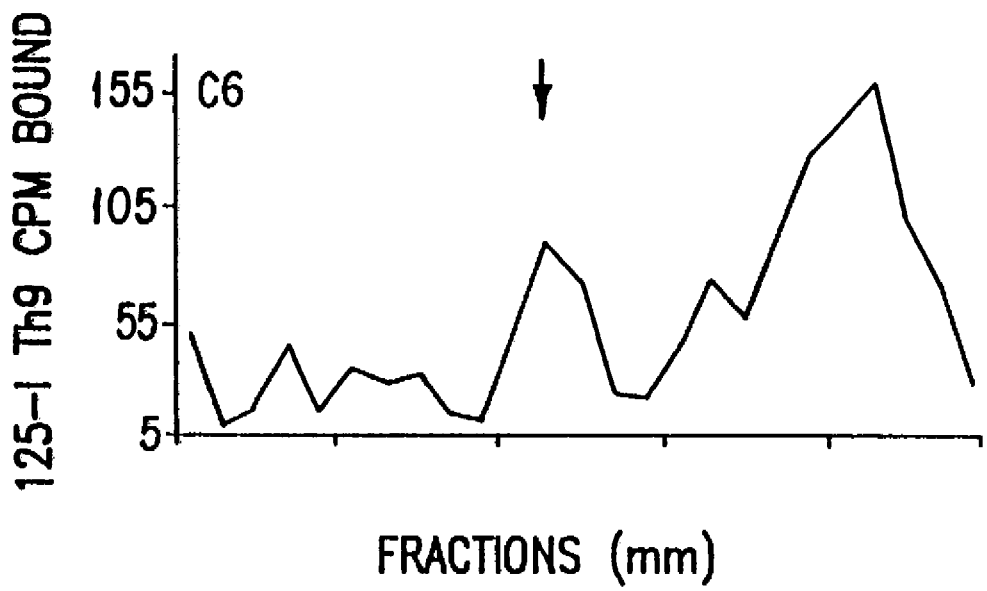
Figure 5E:
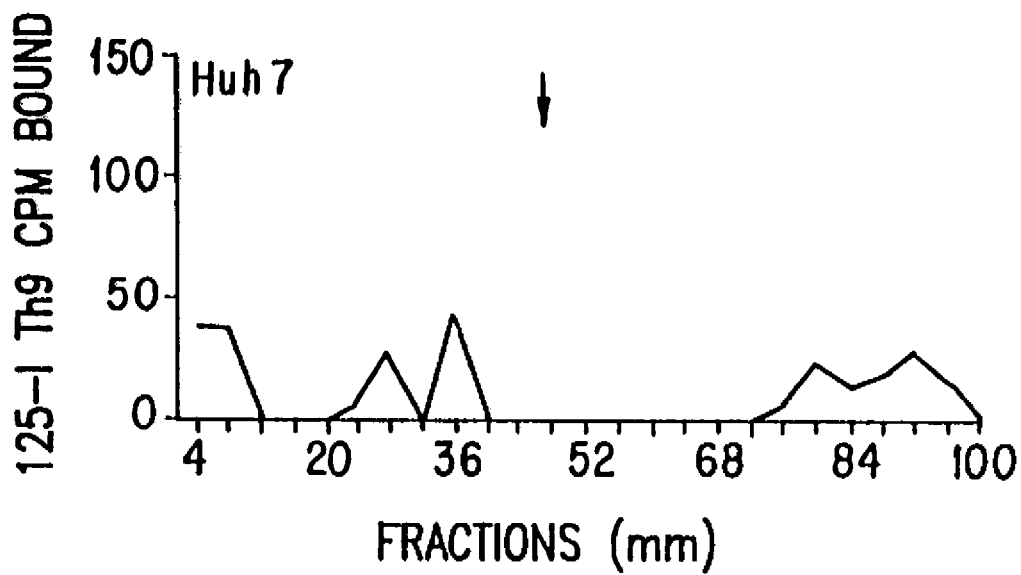

The molecular sizes of thread proteins present in PNET and glial cells were most prominently demonstrated by metabolical labeling with $^{35}$S-methionine or $^{35}$S-cysteine, followed by immunoprecipitation using Th9 monoclonal antibody. Monoclonal antibodies to desmin or to hepatitis B surface antigen (5C3) were used as negative controls for immunoprecipitation. In both PNET and glial cell lines, ~26 and ~21 kDa Th9-immunoreactive proteins were detected by SDS-PAGE analysis of the immunoprecipitated products (FIG. 4B). In PNET1 cells, the 21 kDa band appeared as a doublet (FIG. 4A); the accompanying slightly higher molecular weight species appeared to be less abundant than the dominant band at ~21 kDa. In addition, in both PNET and glial cell lines, there were also ~17 kDa Th9-immunoreactive proteins associated with bands of nearly the same intensity as the ~21 kDa bands. In C6 cells, there were also ~26 kDa, ~14–15 kDa and ~8 kDa Th9-immunoreactive proteins which were not detected in PNET cells (FIGS. 4A and 4B, arrows).

The 21 kDa and 17 kDa thread proteins in SH-Sy5y, PNET1, A172, and C6 cells, and their absence in hepatocellular carcinoma cells were also demonstrated by SDS-PAGE/M-IRMA (FIGS. 5A–5E). Cellular proteins fractionated by SDS-PAGE were eluted from the gels sliced at 2 mm intervals, and assayed directly for thread protein immunoreactivity by M-IRMA using Th7+Th10 as capture antibodies, and $^{125}$I-labeled Th9 as the tracer. Despite low levels, two distinct peaks were evident in all neuroectodermal cell lines, but not in Huh7 hepatocellular carcinoma cells assayed simultaneously and in the same manner. The resolution of these gels did not permit distinction of ~17 kDa from ~14–15 kDa proteins which might have been present.

Figure 6:
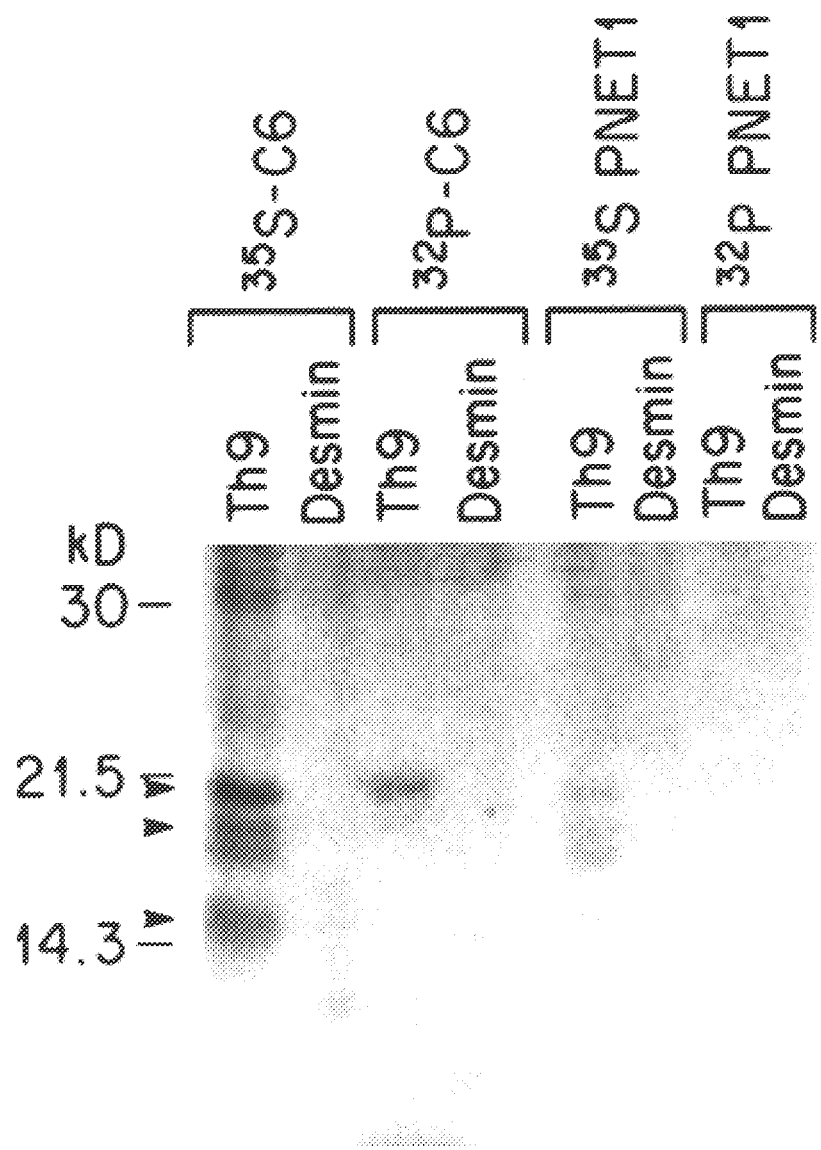
FIG. 6 depicts a gel showing that the 21 kDa neural thread protein in C6 glioblastoma cells is phosphorylated.

PNET1 and C6 cells were metabolically labeled with $^{32}$P or $^{35}$S-methionine, and thread proteins were immunoprecipitated from the lysates using Th9 monoclonal antibody (FIG. 6). As a negative control, immunoprecipitation studies were conducted using an equal portion of the cellular lysate and monoclonal antibodies to desmin protein (FIG. 6, right panel). In the cells labeled with $^{35}$S methionine, Th9-immunoreactive bands were detected at ~26 kDa and ~21 kDa (upper arrows), ~17 kDa (lower arrows), and also at ~14-15 kDa (FIG. 6). After $^{32}$P labeling, only the 21 kDa band was observed by immunoprecipitation with Th9 monoclonal antibody; the other molecular weight species did not appear to be phosphorylated (FIG. 6). Phosphorylated Th9-immunoreactive proteins were detected in C6 cells, but not in PNET1 cells, but this might be due to less efficient labeling since PNET1 cells grow slower than C6 cells. No bands in the 14 kDa to 26 kDa range were detected using monoclonal antibodies to desmin for immunoprecipitation (FIG. 6). Carbohydrate moieties were not detected in Th9 immunoprecipitated proteins (data not shown).

Figure 7:
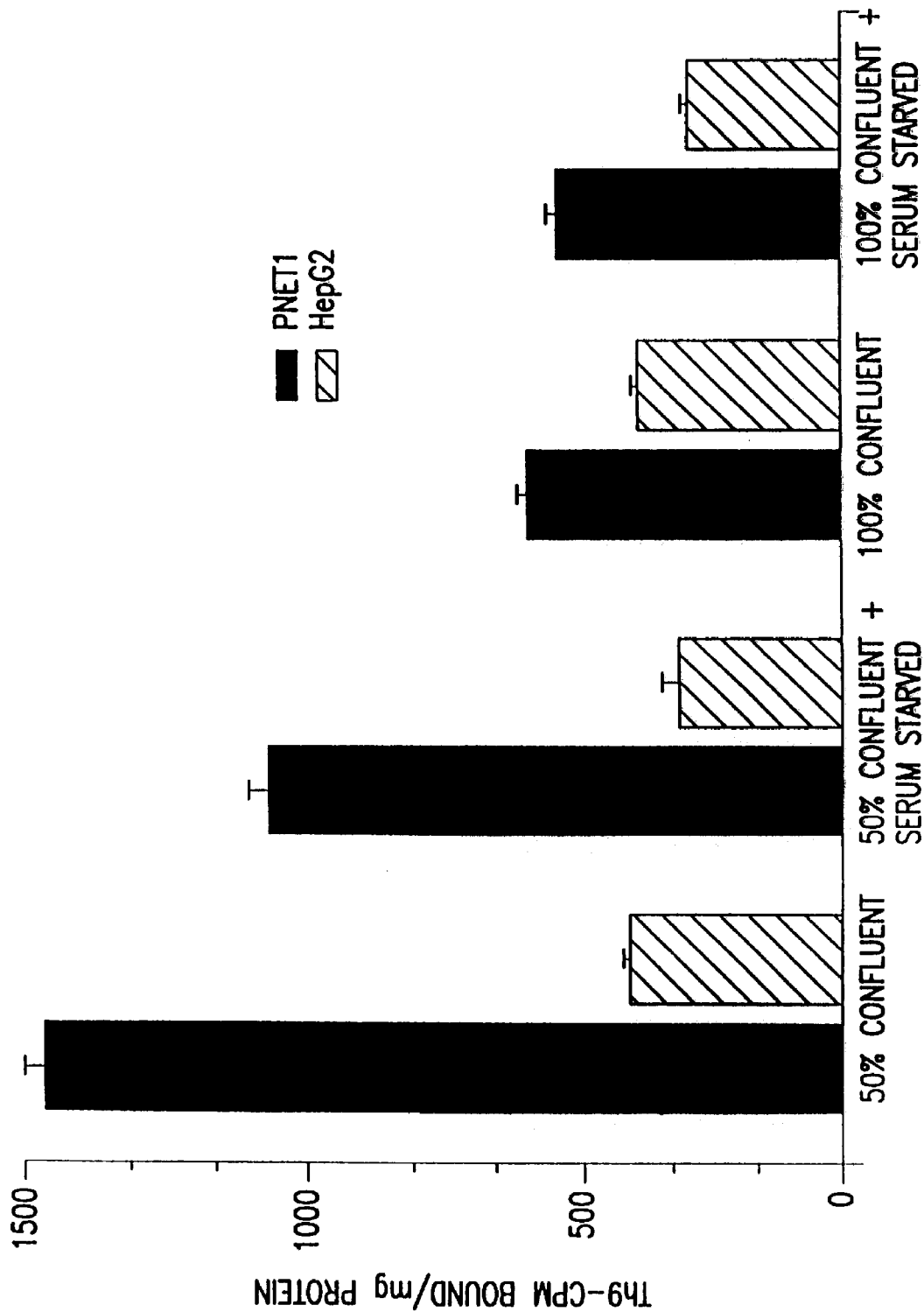
FIG. 7 depicts a bar graph showing altered neural thread protein expression in PNET1 cells with growth phase.
Figure 8A:
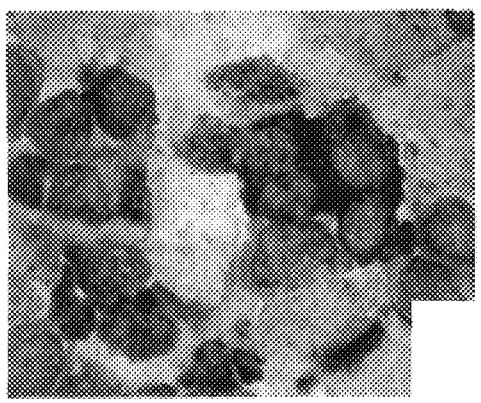
FIGS. 8A–8F show altered phenotype of PNET1 cells with cessation of cell growth and overnight serum starvation.
Figure 8B:
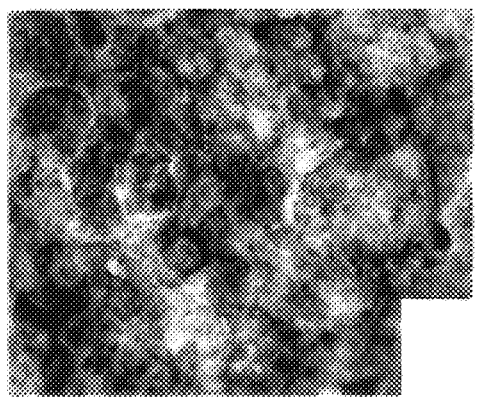
Figure 8C:
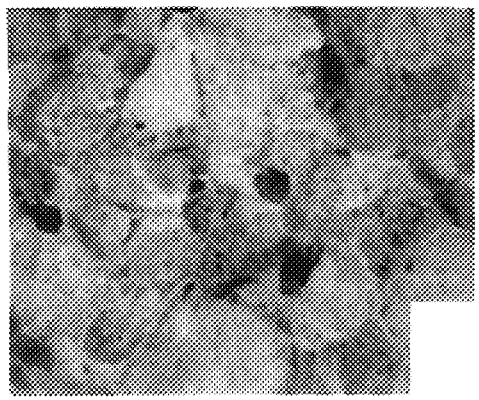
Figure 8D:
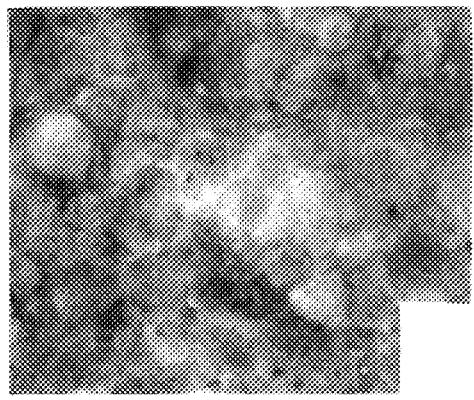
Figure 8E:
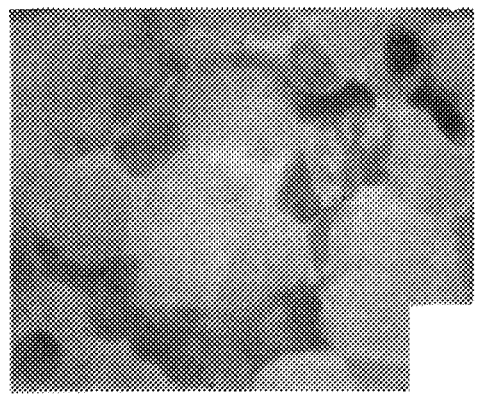
Figure 8F:
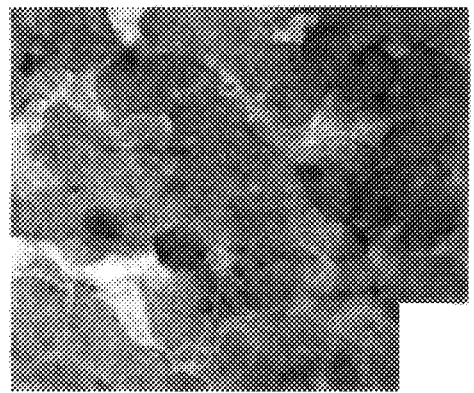

The highest concentrations of thread protein were measured in subconfluent cultures of PNET1 cells, i.e. during the log phase of growth, and the lowest concentrations in overnight serum-starved cultures (growth arrest) (FIG. 7). Cultures that were 100% confluent also had lower levels of thread protein expression compared with proliferating cultures. Huh7 hepatocellular carcinoma cells (negative control) were simultaneously studied using identical culture conditions, but the levels of thread protein remained low throughout.

Surprisingly, there was no change in the degree of thread protein immunocytochemical staining of PNET cells cultured under these various conditions. However, the degree to which the levels of thread proteins changed by M-IRMA measurement may not have been detectable by immunocytochemistry. Nevertheless, the reduction in cellular thread protein content induced by serum starvation was associated with a change in the phenotype of the cells. When the cells achieved 100% confluence or after they had been subjected to overnight serum starvation, the cell bodies reduced in size, and they exhibited striking changes in the degree and distribution of immunoreactivity for neurofilament protein, GAP-43, and GFAP (FIG. 8). In PNET cultures that were 50% confluent, the cells exhibited punctate and often a polar distribution of neurofilament and GAP-43 immunoreactivity, whereas 100% confluent and serum-starved PNET cultures exhibited diffuse perikaryal immunoreactivity for both neurofilament and GAP-43. The punctate immunoreactivity may have corresponded with distribution of neurofilament and GAP-43 in neurites. In contrast, 50% confluent PNET cultures were devoid of GFAP immunoreactivity, while 100% confluent and serum-starved cultures contained conspicuous proportions of GFAP-positive cells. Moreover, the proportion of GFAP-immunoreactive cells was greatest in 100% confluent serum-starved cultures, followed by 50% confluent serumstarved cultures, and then 100% confluent cultures with medium containing 10% fetal calf serum. Therefore, the reduction in thread protein levels measured in PNET cells subjected to overnight serum starvation may have been due to differentiation of the cells toward an astrocytic phenotype. C6 cells and other glioblastoma cell lines exhibited intense immunoreactivity with the Th9 monoclonal antibody, but the levels of thread protein measured by M-IRMA were often low, possibly due to low-level immunoreactivity with other thread protein antibodies, including Th7 and TH10 (see FIGS. 1A–1J).

EXAMPLE 4

Cloning of Thread Proteins from Human cDNA Libraries

Human brain cDNA libraries made from 17–18 week old fetal brain (Stratagene, Inc., La Jolla, Calif.), 2 year-old temporal lobe neocortex (Stratagene), and end-stage Alzheimer's disease cerebral cortex (In Vitrogen; San Diego, Calif.) were screened using probes generated from a 416 bp DNA fragment corresponding to nucleotides 235–650 of the rat PTP cDNA. The rat PTP cDNA, designated O18, was isolated from a rat pancreatic cDNA library using synthetic 60mer DNA probes corresponding to nucleotides 45–104 and 345–404 of the published sequence (Terazono et al., *J. Biol. Chem.* 263:2111–2114 (1988); Watanabe et al., *J. Biol. Chem.* 265:7432–7439 (1990)). Approximately $2\times10^6$ plaques or colonies from each library were screened with low-stringency hybridization using standard techniques (see Sambrook et al., supra). Putative clones were plaque/colony purified, and the DNA inserts were sequenced by the dideoxynucleotide chain termination method using T7 polymerase (USB Sequenase; United States Biochemical Corp., Cleveland, Ohio). The sequences were compared with the Genebank database, and aligned with the nucleic acid sequences of other thread protein cDNAs.

a. CNS Neural Thread Protein cDNA Isolated from Human Fetal Brain Library

Figure 12A:
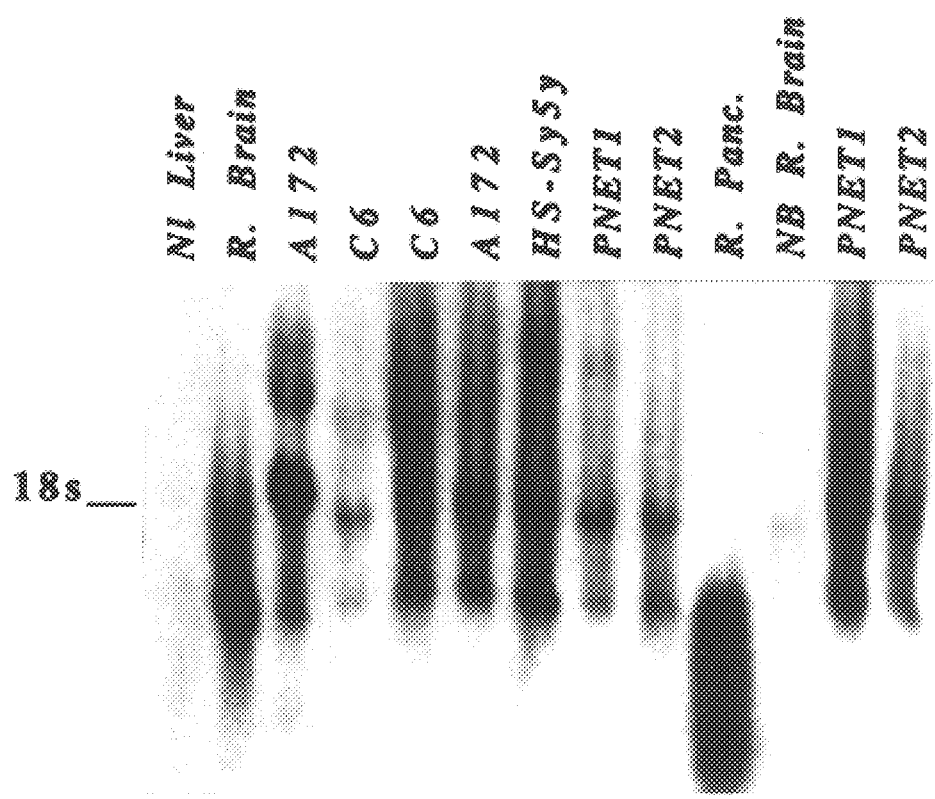
FIGS. 12A–12C show the expression of mRNA molecules corresponding to the 1-9a CNS neural thread protein cDNA sequence in neuroectodermal tumor cell lines and in rat pancreas.
Figure 12B:
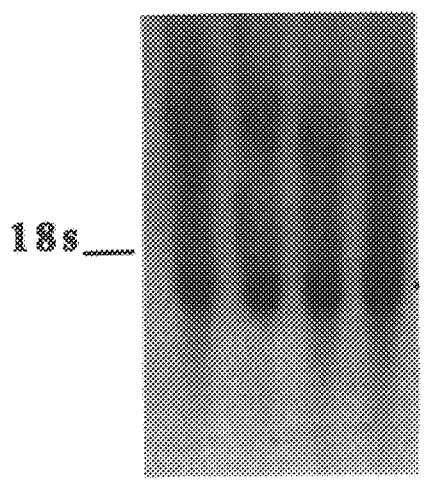
Figure 12C:
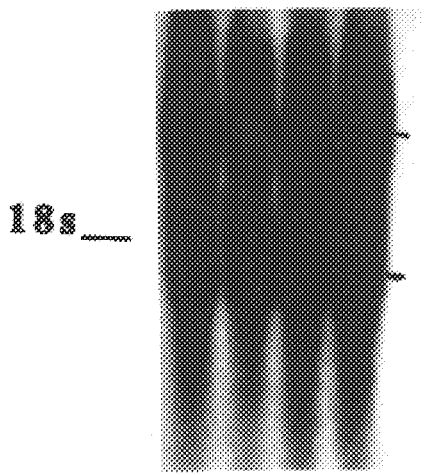

A 1.35 kilobase (KY) 1-9a CNS thread protein partial cDNA was isolated in which only a small segment corresponds to an open reading frame, and the remainder, to a 3' untranslated region (FIG. 9). The sequence of an additional 150 nucleotides was obtained from 5' anchor PCR amplification products. A second round of 5' anchor PCR amplification yielded a further upstream 600 bp product (FIG. 9A). A portion of the 1-9a cDNA sequence shares significant homology with the 5' end of the human PTP cDNA and the Reg gene (FIG. 10). In addition, the initial 5' anchor PCR product has 60% homology with the 5' end of the Reg gene, and 63% homology with Exon 2 of the human Reg gene (FIG. 10A). Moreover, probes generated from the 590 bp 5'-end fragment of 1-9a cDNA hybridized with human brain and pancreas mRNA (FIGS. 12A–12C). The 1-9a sequence is also homologous with the AD2-2 and AD3-4 cDNAs in that at one end of their completed sequences, the overlaps are substantial (FIG. 10B).

b. CNS Neural Thread Protein cDNA Isolated from a Two-Year Old Temporal Cortex Library The HB4 clone is a 593 base pair partial cDNA that was isolated from a 2-year old temporal cortex library. This cDNA contains an open reading frame at its 5' end and terminates at nucleotide 275. There is a polyadenylation signal beginning at nucleotide 475, and the sequence ends with a poly-A tail (FIG. 11A). The deduced amino acid sequence of the partial HB4 clone predicts a protein with a molecular weight of 10.4 kDa, and a pI of 12.1. The HB4 cDNA exhibits 50% overall nucleic acid homology with the human PTP cDNA (FIG. 11D), a segment of the human Reg gene (FIG. 11E).

C. Isolation of Neural Thread Protein cDNAs from an Alzheimer's Disease Library

Figure 16G:
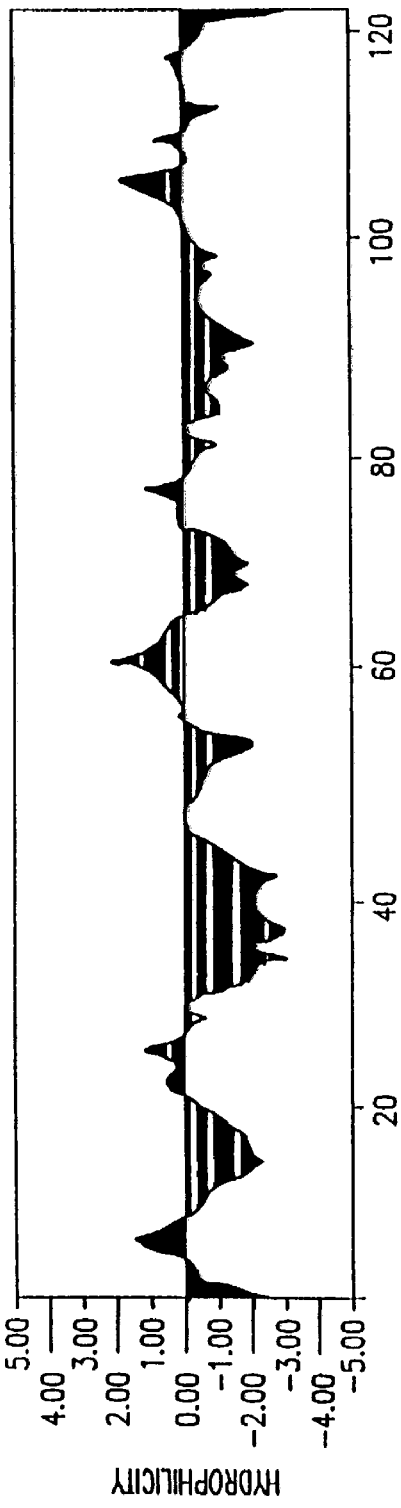
FIGS. 16G and 16H show a hydrophilicity window plot of AD3-4. Hydrophilicity Window Size=7; scale=Kyte-Doolittle.
Figure 16H:
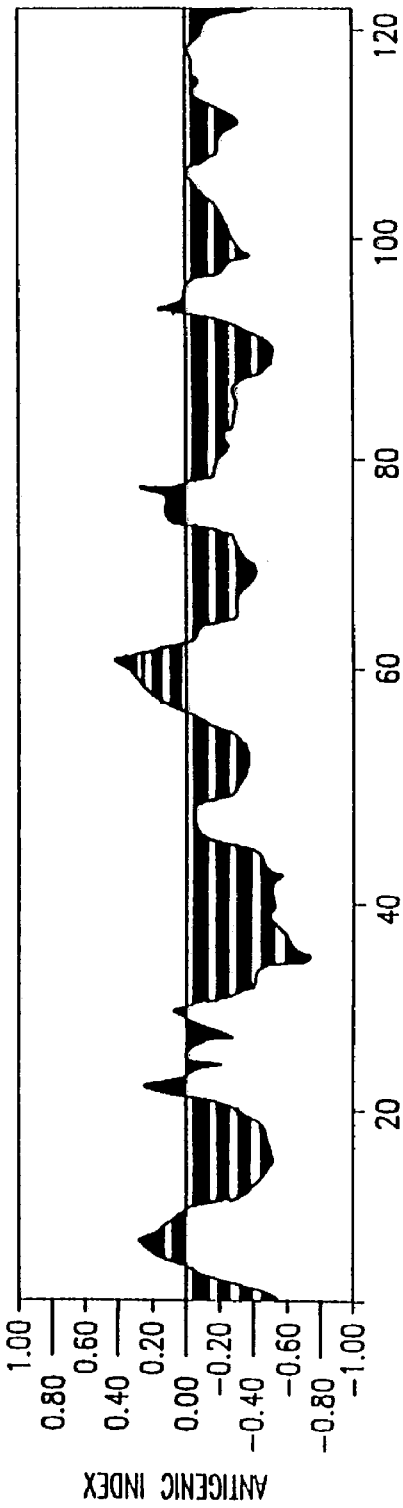

Using the 018 rat PTP cDNA probe, four related cDNAs were isolated from an AD brain library. These clones were designated: AD2-2, AD3-4, AD4-4 and AD16c (also called AD10-7) (FIGS. 16A–16S).

The AD 2-2 cDNA is approximately 1.2 kb and it shares significant homology with the 1-9a cDNA, AD16c, rat PTP cDNA, and Exon 1 of the human Reg gene (FIG. 17). The AD2-2 probe generates a genomic Southern blot pattern similar to that obtained with the AD3-4 probe. FIG. 16E depicts the complete nucleotide sequence of the AD2-2 cDNA clone that was isolated from an AD brain library. Random primer generated probes based on this sequence hybridized with human brain and neuronal samples but not with glial cell lines of with pancreatic RNA.

FIGS. 16F, 16I, 16J and 16K depict partial nucleotide sequences of the AD3-4 cDNA clones that were isolated from an AD brain library. Rnadom primer generated AD3-4 probes yielded two mRNA transcripts, 1.6 kB and 3.4 kB. These mRNA species are over-expressed in AD brains, with an average of two-fold elevation compared with aged matched controls (N=8).

The AD3-4 cDNA 1.6 kb clone is identical to another clone isolated at the same time (AD5-3) (FIG. 18A). The AD3-4/AD5-3 cDNA exhibits substantial homology with the 1-9a 5' anchor PCR products (FIG. 18B), as well as with the human Reg gene and the Gen2a-EP genomic clone (FIG. 18B). Southern blot analysis of human genomic DNA with the AD 3-4 probe revealed a pattern similar to that obtained with the AD 2-2 probe.

FIGS. 16L and 16M depict the partial nucleotide sequence of AD4-4 which is a 0.8 kb partial cDNA clone which is identical to another cDNA isolated at the same time (AD3-5). This AD4-4 clone shares substantial sequence homology with AD2-2 and 1-9a cDNAs (FIG. 19). FIG. 16N depicts the complete nucleotide sequence of a partial cDNA clone isolated from an AD brain library. This cDNA hybridized with brain and neuronal cell line mRNA, yielding a single 1.4 kB transcript.

FIG. 16O depicts the nucleotide sequence of the 0.5 kb partial cDNA clone AD 16c (also called AD10-7) that is 72% homologous with AD2-2, and also aligns with human PTP and the human Reg gene sequences (FIGS. 20A and 20B).

FIG. 16R depicts the complete nucleotide sequence of the AD10-7 clone that was isolated from an AD brain library. Hybridization of Northern blots using either antisense cRNA probes or random primer generated DNA probes detected 2.6, 1.9. 1.4 and 0.9 kB mRNA transcripts in neuronal cells. Neuronal cell lines expressed only the two largest transcripts, while mature adult human brains expressed predominantly the two smallest transcripts, and either very low or nondetectable levels of the 2.6 kB and 1.9 kB transcripts. Using an AD10-7 probe, Northern blot analysis of RNA obtained from human liver, ovary, fallopian tube, colon, stomach, spleen, rectum, thyroid, 12 week placenta and kidney was negative.

FIG. 16S depicts the complete nucleotide sequence of the AD16c cDNA clone that was isolated from an AD brain library. Hybridization of Northern blots using random primer generated DNA probes yielded the same results as obtained with the AD10-7 cDNA clone. The AD16c clone shares a 650 bp segment of near identity with AD10-7. In addition, elevated levels of AD16c mRNA were detected in AD brains compared with aged control brains by Northern blot analysis.

EXAMPLE 5

Analysis of Brain Thread Protein Gene Expression

Thread protein mRNA expression was examined in the following neuroectodermal tumor derived cell lines: central nervous system primitive neuroectodermal tumor cells designated PNET1 and PNET2; HGL-16 and HGL-17 human glioblastoma cells; A172 human glioma cells; C6 rat glioma cells; and SH-Sy5y neuroblastoma cells. In addition, human brain tissue from patients with Alzheimer's disease or no neurological disease (aged controls), and embryonic and postnatally developing rat brain were assayed for thread protein mRNA expression. RNA extracted from human and rat pancreas served as positive controls.

RNA was extracted in 5 M guanidinium isothiocyanate, and then isolated by centrifugation through a cesium chloride step gradient (see Sambrook et al., supra). RNA was quantified by measuring the absorbance at 260 nm and 280 nm. The thread protein mRNA transcript sizes were assessed by northern blot analysis, and the levels of expression were evaluated by RNA dot blot hybridization. Northern blot analysis was performed by electrophoresing samples containing 15 µg of total cellular RNA through 1% agarose-formaldehyde gels. The RNA was transferred to nylon membrane, cross-linked with ultraviolet light, and hybridized with probes generated from a 600 bp fragment of the 1-9A cDNA clone. The fragment used for hybridization studies contained the regions most homologous with the human PTP cDNA. The probes were labeled with [$^{32}$P] α-dCTP by the random primer method (Amersham Corporation; Arlington Heights, Ill). The blots were hybridized overnight at 42° C. with 2×10$^6$ dpm /ml of probe in buffer containing 50% formamide, 5×SSPE, 10×Denhardt's (100× Denhardt's is 2% Ficoll, 2% bovine serum albumin, 2% polyvinylpyrollidine), 0.5% SDS (sodium dodecyl sulfate), and 100 μg/ml of sheared denatured salmon sperm DNA. The membranes were washed in SSPE containing 0.25% SDS using standard methods. Autoradiograms were generated by exposing the membranes to Kodak XAR film at −80° C. The membranes were subsequently stripped of probe and then rehybridized with a synthetic 30mer corresponding to 18s RNA to evaluate sample loading.

Northern analysis of total cellular RNA using probes made from the 1-9a cDNA disclosed two dominant transcripts in central nervous system (CNS) tumor cell lines: one transcript was 1.6 kb, and the other was 0.9 kb (FIG. 12A). In addition, in the SH-Sy5y neuroblastoma and PNET1 cell lines, a larger 4.2 kb mRNA transcript was also detected. The 4.2 kb transcript may represent preprocessed mRNA. The same size transcripts were detected in adult (R. Brain) and newborn (NB) rat, but the 0.9 kb transcript was more abundant in the adult brain whereas the 1.6 kb transcript was more abundant in the newborn rat brain. In rat pancreas (R. Panc.), only a 0.9 kB transcript was detected, corresponding to the size of rat PTP mRNA (Terazono et al., *J. Biol. Chem.* 263:2111–2114 (1988); Watanabe et al., *J. Biol. Chem.* 265:7432–7439 (1990)). mRNA transcripts were not detected in normal liver (Ni Liver). Using a probe generated from the 3' region of the 1-9a cDNA, the 1.6 kb, but not the 0.9 kb transcript was revealed (FIG. 12B). Using a 30-mer probe corresponding to the most 5'-end of the 1-9a cDNA, the higher molecular weight mRNA transcripts were detected (FIG. 12C). The 0.9 kb transcript was also evident with longer exposure of the blot.

Figure 13A:
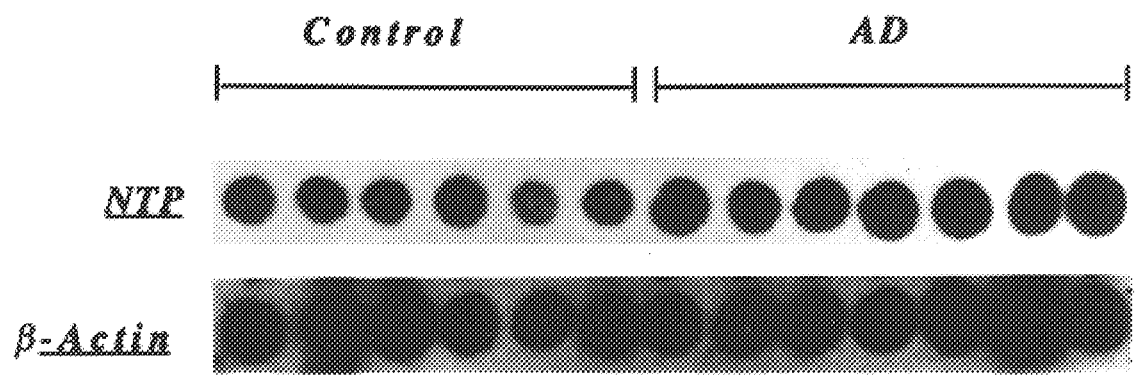
FIGS. 13A and 13B show mRNA transcripts corresponding to the 1-9a CNS neural thread protein cDNA sequence in human brain. This figure also demonstrates higher levels of 1-9a CNS neural thread protein-related mRNAs in AD brains compared with aged-matched controls (FIG. 13A).
Figure 13B:
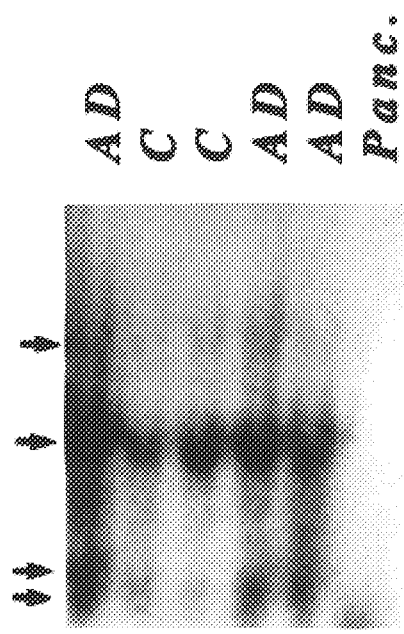

Northern analysis of human brain RNA disclosed a dominant 1.6 kb transcript, but also two and sometimes three smaller transcripts of 1.2 kb, 0.9 kb, and 0.8 kb (FIG. 13B). In contrast to the findings in cell lines, the 4.2 kb mRNA transcript was seldom observed in adult human brain. Hybridization with human pancreas disclosed a 0.8 kb transcript, corresponding with the size of PTP mRNA. The transcripts detected in human brain and pancreas using 1-9a probes were identical in size to the transcripts observed using PTP cDNA probes.

Dot blot RNA hybridization to 5 μg of total RNA using the 600 bp fragment of the 1-9a cDNA (NTP) demonstrated higher levels of expression in AD, compared with aged control brains (FIG. 13A). Rehybridization of the same membrane with a cDNA corresponding to β-actin demonstrated similar loading of RNA in each dot. The observation of elevated levels of 1-9a-related mRNA in AD brain tissue is similar to that reported previously using 60mer probes corresponding to human PTP cDNA (de la Monte et. al., *J. Clin. Invest.* 86:1004–1013 (1990)). The differences between AD and control brains appeared to be due to differences in the levels of the 1.6 kb, 0.9 kb and 0.8 kb transcripts, as shown in FIGS. 13A and 13B.

Figure 21A:
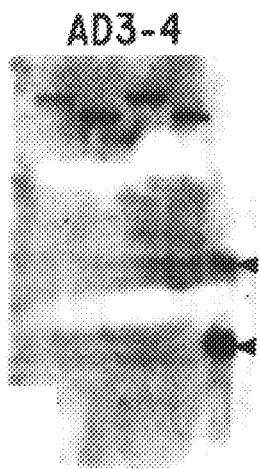
FIGS. 21A–21D show a genomic Southern blot analysis using the AD 3-4 as a probe.
Figure 21B:
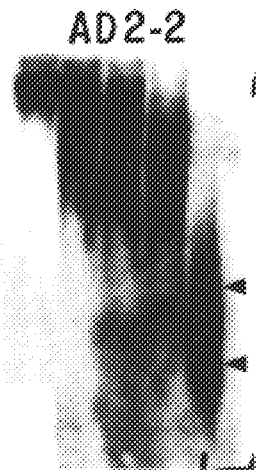
Figure 21C:
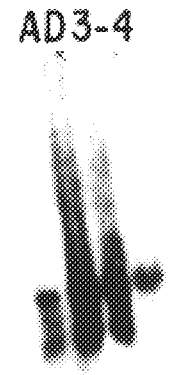
Figure 21D:
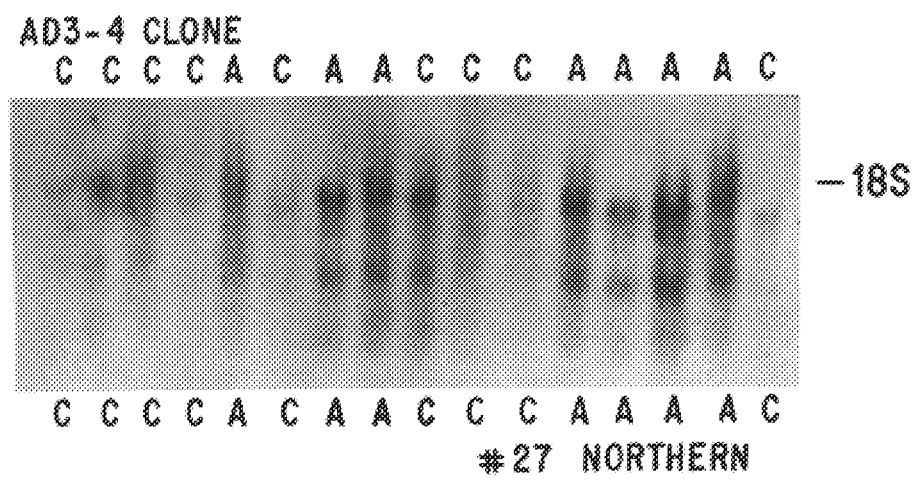
Figure 24A:
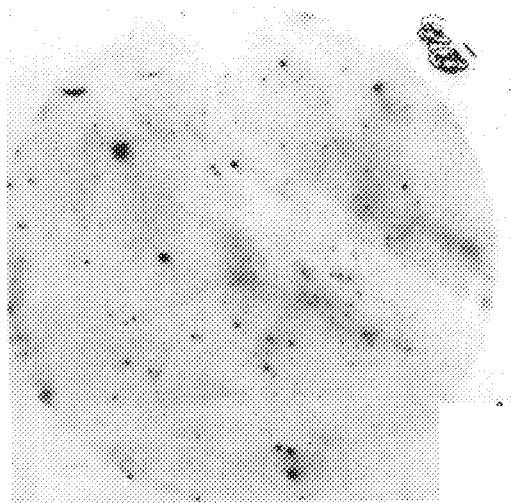
FIGS. 24A–24D show neural thread protein expression by the 1-9a cDNA (FIG. 24A) and the G2a-2 PstI genomic clone (FIG. 24B).
Figure 24B:
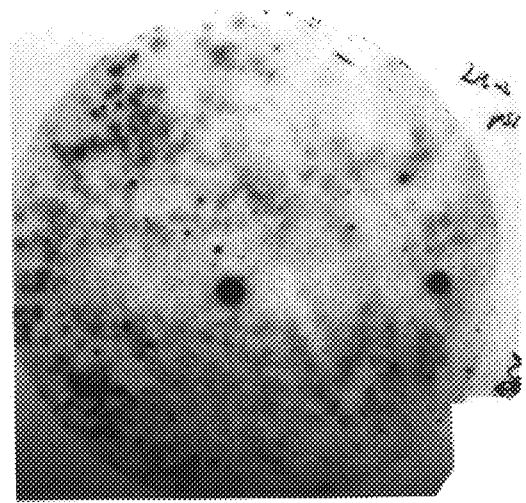
Figure 24C:
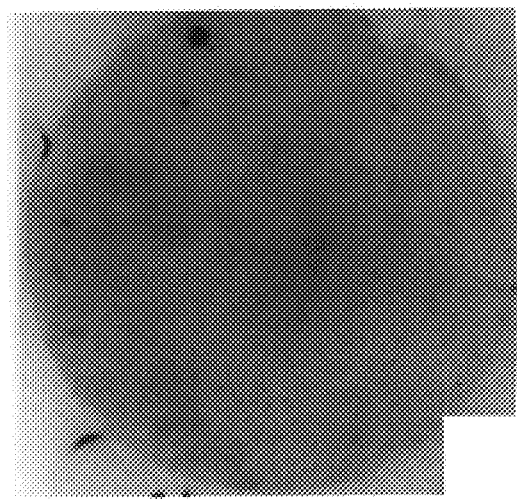
Figure 24D:
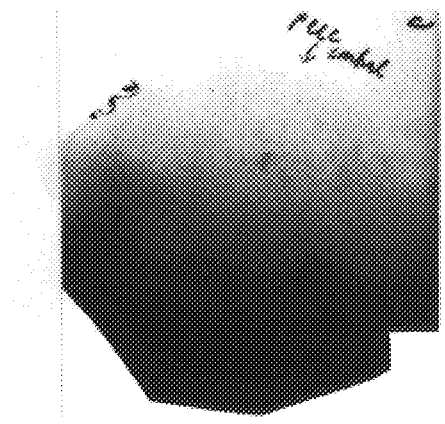

The AD-NTP 3-4 cDNA, isolated from the AD library, hybridizes with RNA from neuronal-derived neuroectodermal tumor cell lines, and human brain tissue. In the cell lines, 1.6 kb and 0.9 kb transcripts as observed with the 1-9a probe were detected (FIG. 21C). However, in human brain, ~4 kb, 1.6 kb, and 0.9 kb transcripts were detected, and the levels of expression for all three transcripts were higher in AD compared with aged control brains (FIG. 21D).

AD4-4 cDNA probe hybridized only with a 0.9 kb transcript, and only in neuronal cell lines.

EXAMPLE 6

Direct Cloning and Sequencing of Thread Protein cDNAs from Neuroectodermal Tumor Cell Lines and Alzheimer's Disease Brain Thread protein cDNAs were cloned directly from PNET1, PNET2, SH-Sy5y, and A172 cells, and from Alzheimer's disease and aged control brain RNA using the 3'- and 5'-RACE methods (Frohman et al., *Proc. Natl. Acad. Sci. USA* 85:8998 (1988); Ohara et al., *Proc. Natl. Acad. Sci. USA* 86:5673 (1989); Loh et al., *Science* 243:217 (1989)). Briefly, RNA was reverse transcribed using oligo-dT primers. For the 5'-RACE reaction, the cDNAs were amplified by polymerase chain reaction (PCR) using a specific 17-mer corresponding to a 5'-region of the 1-9a sequence, and a 17 dT primer. The resulting PCR products were subjected to another round of amplification using another internal but overlapping 5'-end primer, and a specific 3'-17-mer corresponding to a 3' region of the 1-9a sequence. For the 3'-RACE reactions, the cDNAs were first tailed with dCTP using terminal deoxynucleotide transferase, and then they were amplified using a specific 17-mer corresponding to nucleotides 781–797 of the 1-9a clone and dG (17mer). A second nested PCR amplification was performed using a specific 17mer corresponding to nucleotides 766–792 at the 3' end, and dGTP (17mer) for the 5' end. The PCR products were subjected to Southern blot analysis using probes generated from an internal DNA fragment of the 1-9a cDNA clone, and from the 018 rat PTP cDNA clone. The PCR products were gel purified and ligated into pAmpl vectors using uracil deoxytransferase. The subcloned DNA inserts were sequenced by the dideoxynucleotide chain termination method using T7 DNA polymerase.

Figure 14A:
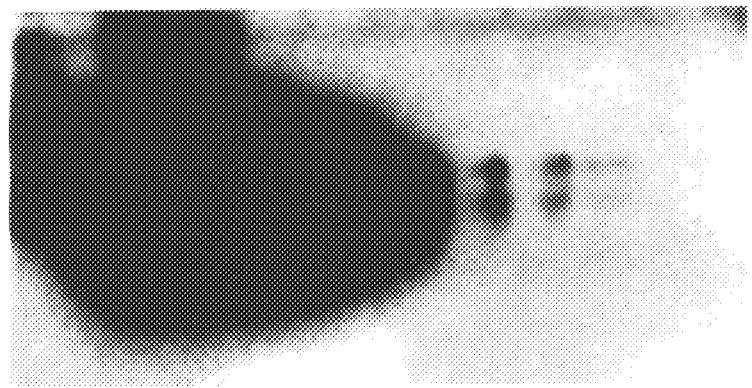
FIGS. 14A–14C show 1-9a Southern blot analysis of RT/PCR-derived cDNAs in neuroectodermal cell lines. A- and B-PCR amplification of 1-9a mRNA sequences in neuroectodermal cell lines, and using mRNA from newborn rat (NB) brain, AD brain, and aged control brain.
Figure 14B:
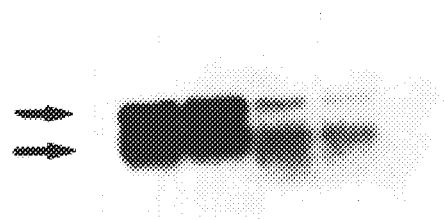

CNS thread protein transcripts were detected in neuroectodermal tumor cell lines and in AD human brain tissue by reverse transcription followed by PCR using specific primers corresponding to the 5' and 3' regions of the 1-9a cDNA sequence. Southern blot analysis of the PCR products demonstrated two dominant cross-hybridizing species, 0.8 kb and 1.0 kb (FIGS. 14A and 14B). In addition, in the SH-Sy5y cells, a larger 1.8 kb PCR product was also detected. In the PNET1, PNET2, SH-Sy5y, and A172 cells, a 0.4 kb PCR product that hybridized with the 1-9a probe was observed. Corresponding with the higher levels of thread protein mRNAs in Alzheimer's disease brains, the hybridization signal was more intense in AD samples compared with aged control samples.

Figure 14C:
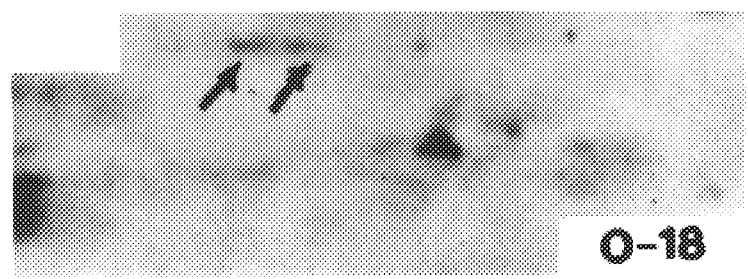
Figure 15A:
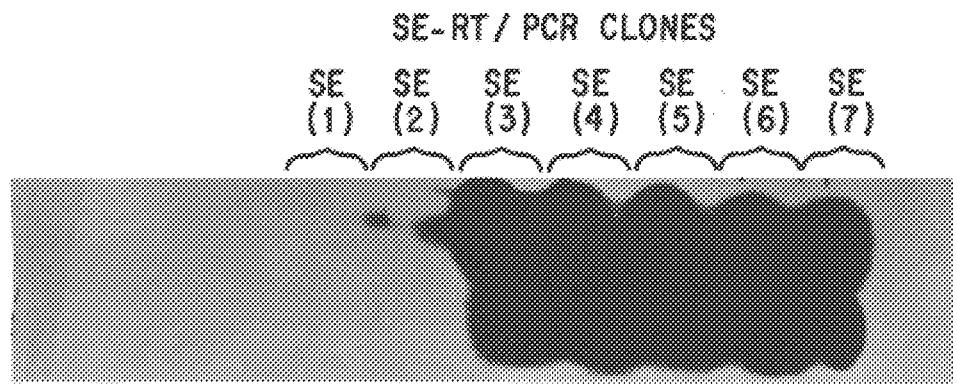
FIGS. 15A and 15B (SE-RT/PCR) show hybridization of the 1-9a and O18 probes with several clones isolated from SH-Sy5y cells by reverse transcribing mRNA and amplifying with primers corresponding to the known sequence of the 1-9a partial cDNA.
Figure 15B:
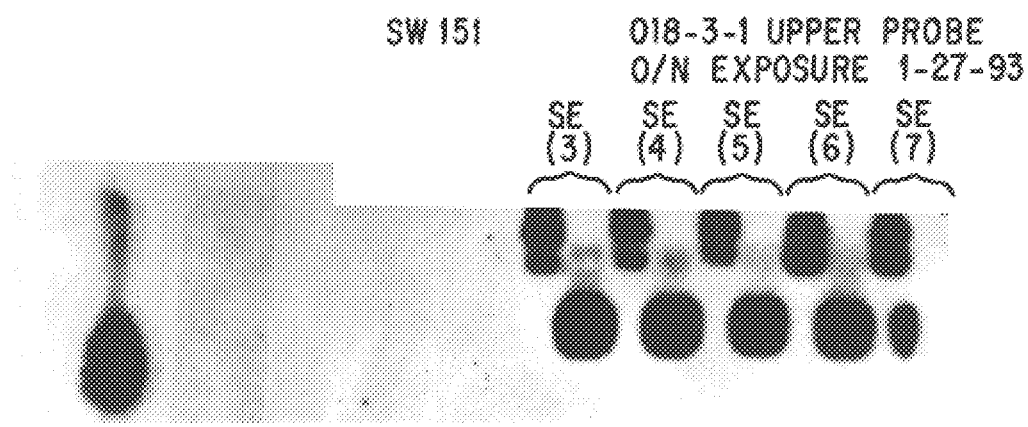

The PCR products generated from the SH-Sy5y cells were subcloned and sequenced. Southern analysis of the cloned fragments exhibited intense hybridization with the 1-9a cDNA, and less intense but definite hybridization with the 018 cDNA (rat PTP) (FIG. 14C). The nucleic acid sequence of the SH-Sy5y PCR clone (Sy-NTP) was identical to the 1-9a cDNA sequence.

EXAMPLE 7

Isolation of Genomic Clones Coding for Human Brain Thread Proteins

A human genomic DNA library was screened using probes made with a 600 bp fragment of the 1-9a human brain thread protein cDNA that was isolated from the two year-old temporal cortex library. The 1-9a cDNA fragment contained a region with 60% nucleic acid sequence homology with human PTP. After colony purification, the putative genomic clones were checked for cross-hybridization with the O18 rat PTP cDNA fragment. EcoRI, PstI, and EcoRI/PstI restriction fragments that hybridized with both the 1-9a and 018 probes were subcloned into pBluescript II vectors (Promega, Inc., Madison, Wis.) and then sequenced by the dideoxynucleotide chain termination method using either T7 polymerase (USB Sequenase) or polymerase chain reaction amplification and Vent polymerase.

Four genomic fragments designated G2-2 PstI, G2-2 PstI-EcoRI, G5d-1 PstI, and G5d-1 PstI-EcoRI were isolated from a human genomic DNA library (FIGS. 22A–22D). These genomic fragments all hybridized with both the 1-9a and O18 cDNA probes, and they ranged in size between 1.5 kb and 3 kb. Partial nucleic acid sequence information demonstrated homology between G2-2PstI and the human Reg gene and human and rat PTP cDNAs (FIG. 23A); between G2-2 PstI-EcoRI and both the Reg gene and rat PTP cDNA (FIG. 23B), and also with AD2-2, AD3-4, and the 1-9a cDNAs (data not shown); between G5d-1 PstI and the Reg gene and human PTP (FIG. 23C); and between G5d-1 PstI-EcoRI and Reg gene, human PTP, 1-9a, and AD4-4.

EXAMPLE 8

In vitro Expression of the LacZ Fusion Protein and Demonstration of its Relatedness to Thread Proteins Fusion protein expression in bacteria containing the 1-9a cDNA clone, or one of the four genomic clones was induced with isopropylthio-β-D-galactoside (IPTG) using standard techniques (Sambrook et al., supra). Crude bacterial lysates from induced and uninduced cultures were subjected to SDS-PAGE and Western blot analysis using the Th9 monoclonal antibody to thread protein (Sasaki et al., *J. Biol. Chem.* 268:1–4 (1993)), and $^{125}$-I labeled protein A to detect the bound antibody. In addition, bacterial lawns containing cloned DNA were induced to express the fusion protein with IPTG, and replica filters were probed directly with Th9 monoclonal antibody followed by $^{125}$-I labeled protein A.

Thread protein immunoreactivity was demonstrated in the bacterial fusion proteins by direct antibody binding to the IPTG-induced colonies (FIGS. 24A–24D). Thread protein immunoreactivity was detected using a cocktail of Th9, Th7, and Th10 monoclonal antibodies to PTP (Sasaki et al., *J. Biol. Chem.* 268:1–4 (1993), and $^{125}$-I labeled Protein A.

EXAMPLE 9

Relative Levels of AD16c mRNA in AD and Aged Control Brains

Figure 25A:
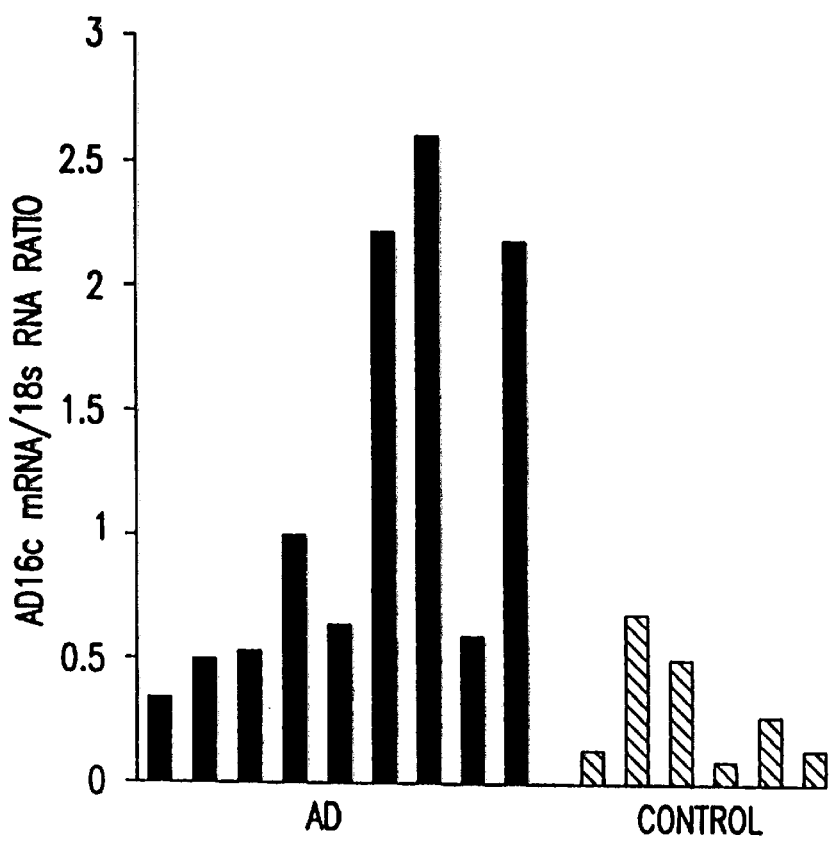
FIGS. 25A and 25B depict a Northern blot analysis of AD 16c mRNA in AD and aged control brains. The data shows elevated levels of AD16c mRNA expression in 6 of 9 AD compared to 1 of 6 age-matched controls.
Figure 25B:
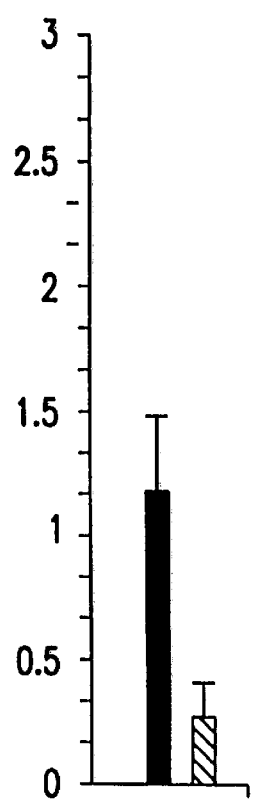

Northern blot analysis was performed using an AD16 cDNA probe. The blots were re-probed to detect 18s ribosomal RNA to evaluate loading of RNA in each lane. The unsaturated autoradiograms were subjected to densitometric analysis using a Molecular Dynamics Image Analyzer. The ratios of the AD16c and 18s RNA hybridization signals were plotted for each case, and the results are depicted graphically in FIGS. 25A and 25B. The mean ratios (relative levels of AD16c) with standard errors are depicted in the smaller right hand graph. The findings confirm that there are elevated levels of AD16c mRNA expression in 6 of 9 AD brains compared to 1 of 6 age-matched controls. The difference between the mean levels is highly statistically significant (P<0.005). Similar results were obtained using AD10-7 probes. Theses results demonstrate that there is a statistically significant increase in levels of expression in AD brains compared to control brains.

EXAMPLE 10

Figure 26:
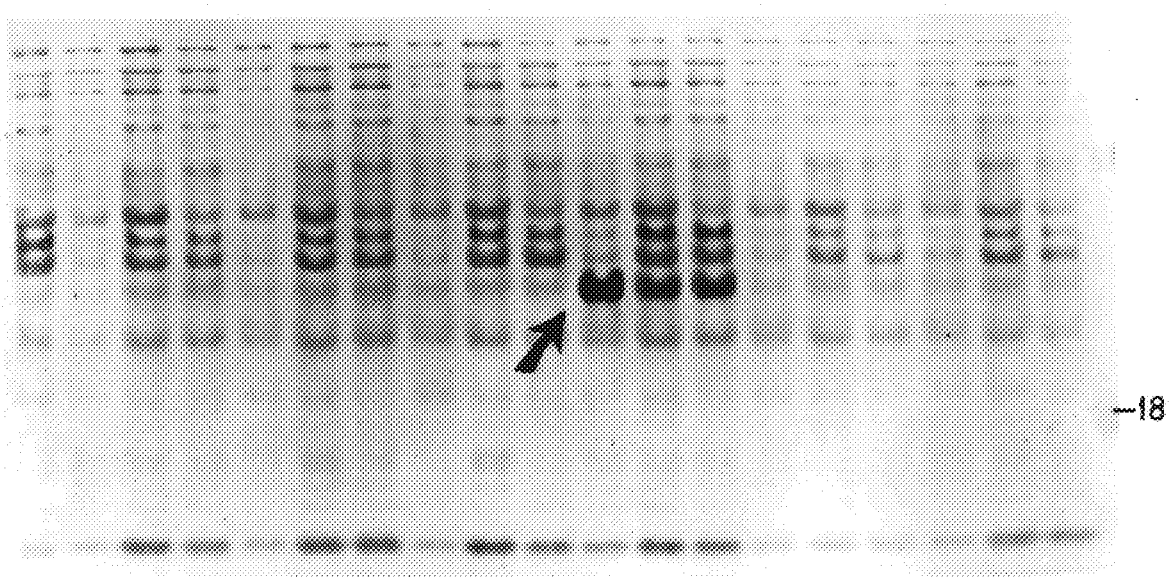
FIG. 26 depicts a Western blot analysis of AD10-7 fusion proteins using monoclonal antibodies against the expressed tag protein (T7-tag mouse monoclonal antibodies.

Preparation of Recombinant AD10-7 Fusion Protein and Detection Thereof With Monoclonal Antibodies AD10-7 cDNA was ligated into pTrcHIS vectors (In Vitrogen, San Diego) in three different reading frames (two incorrect-A and B, and one correct-C). Bacteria transformed with one of the three plasmids were induced with IPTG and bacterial lysates were examined for protein expression 0, 1 and 5 hours later. The proteins were fractionated by SDS-PAGE, and Western blot analysis was performed using monoclonal antibodies against the expressed tag protein (T7-tag mouse monoclonal antibodies; Novogen). The blots were developed using the avidin-biotin, horseradish peroxidase method, with diaminobenzidine as the chromogen (FIG. 26). A band corresponding to ~45 kDA was detected in bacteria that had been transformed with plasmid DNA which contained AD10-7 ligated only in the correct reading frame (C) (arrow). The same size protein was observed by in vitro translation of the AD10-7 cDNA in a rabbit reticulocyte lysate assay system. In both systems, the fusion partner peptide was ~3 kDA, indicating that the cDNA encodes a protein of about ~42 kDA. A ~42 kDA NPT species is routinely detected by Western Blot analysis of neuronal cell lines and of human brain tissue.

EXAMPLE 11

Figure 27A:
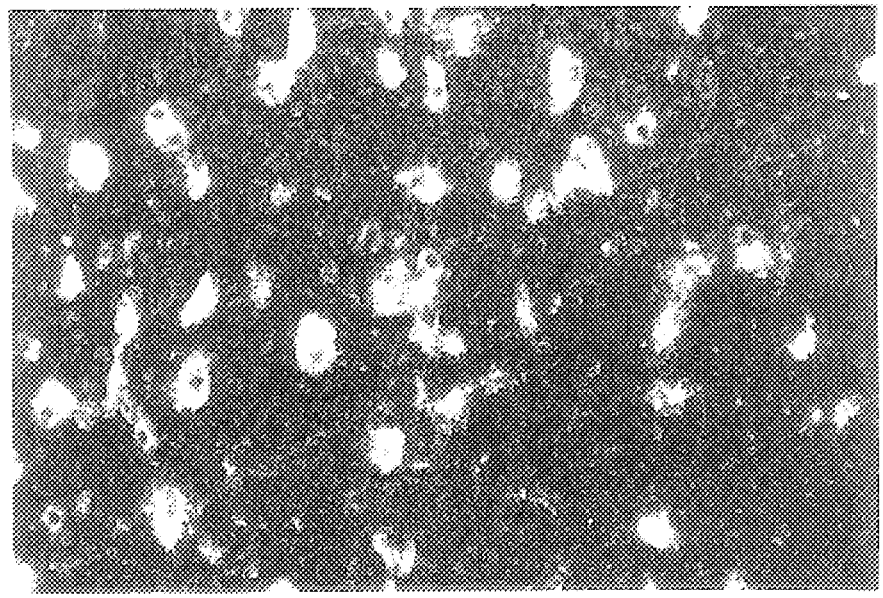
FIGS. 27A and 27B depict brightfield and darkfield microscopic analysis of the in situ hybridization of sense and antisense cRNA probes to human brain tissue sections of early AD.
Figure 27B:
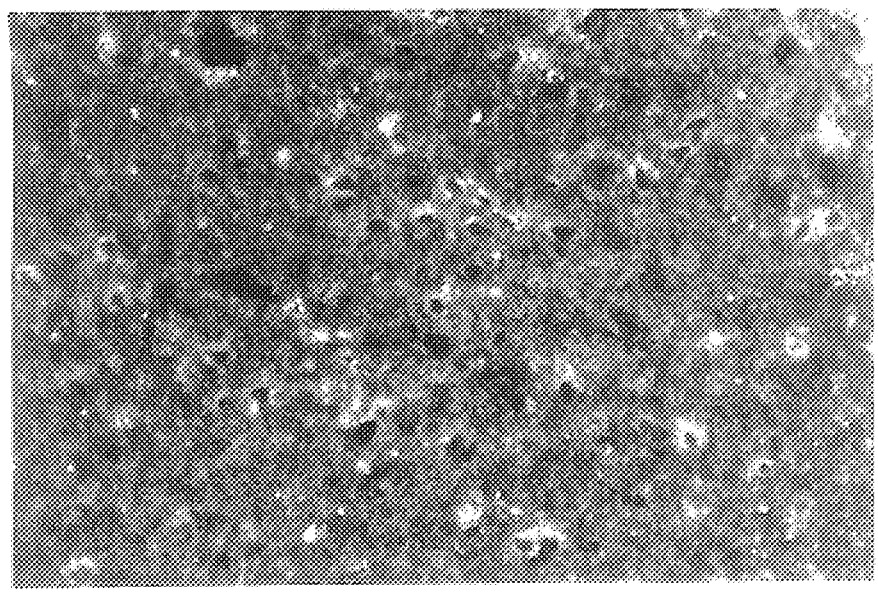

Demonstration of Neuronal Localization of AD10-7 mRNA Expression by In Situ Hybridization Sense and antisense cRNA probes were generated from linearized AD10-7 plasmid DNA using SP6 or T7 DNA-dependent RNA polymerase, respectively. The antisense probes hybridized with neuronal cell line mRNA as described above for this clone. The cRNA sense probes, on the other hand, failed to hybridize with RNA by Northern blot analysis. cRNA probes labeled with digoxigenin-UTP were hybridized with human brain tissue sections from early AD. After washing the sections extensively (de la Monte et al., *J. Clin. Invest.* 86:1004–1013 (1990)), the hybridized probes were detected using peroxidase or alkaline phosphatase conjugated monoclonal antibodies to digoxigenin, and the colorimetric reactions were revealed using standard methods. Examination of the sections by brightfield and darkfield microscopy demonstrated hybridization of AD10-7 only in neurons (FIG. 27; dense aggregates of white grains over cell bodies in (FIG. 27A)). In contrast, and similar to the findings by Northern blot analysis, the sense AD 10-7 cRNA probes failed to hybridize with brain tissue (FIG. 27B).

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following Claims.

EXAMPLE 12

Levels of NTP Expression in AD and Other Neurodegenerative Diseases a. Cellular localization and accumulation of NTP immunoreactivity in AD brains demonstrated by immunohistochemistry NTP immunoreactivity was detected in histological sections with the high affinity Th9 monoclonal antibody to PTP, the pancreatic form of thread protein. Although the PTP MoAbs cross-react with NTP, NTP is distinct since it differs in molecular mass, and many antigenic epitopes present in PTP are not shared with NTP. Moreover, hybridization studies demonstrated NTP mRNA transcripts in neurons, indicating that NTP is synthesized in brain. NTP immunoreactivity is localized in neuronal perikarya, and in neuropil and white matter fibers. In AD, the density of NTP immunoreactive neurons, and intensity of immunoreactive staining are increased relative to intact aged control brains. Increased neuronal labeling in AD was detected in the cerebral cortex and subcortical nuclei. Within the neocortex, NTP immunoreactivity was primarily distributed in Layers III, V, and VI. Although NTP immunoreactivity was detected in neurons with neurofibrillary tangles or granuole vacuolar degeneration, numerous neurons without overt neurodegenerative changes also expressed high levels of NTP. NTP immunoreactivity was not distributed in plaques or extracellular neurofibrillary tangles, and dystrophic neurites were not selectively labeled (de la Monte & Wands, *J. Neurol. Sci.* 113:152–164 (1992); Ozturk, M. et al., *Proc. Natl. Acad. Sci.* 82:5627–5631 (1985)).

b. Semiquantitative estimates of NTP expression in AD and other neurodegenerative diseases A detailed quantitative immunohistochemical analysis of NTP expression was performed using matched paraffin-embedded blocks of different brain regions from patients with AD (N=25), AD plus Parkinson's disease (PD) (N=8), PD, AD plus Down's syndrome (AD+DS) (N=6), or no neurological disease (aged controls) (N=21). In addition, brains with Huntington's disease (N=5) and multi-infarct dementia (N=2) were studied as disease controls. The highest mean densities of NTP immunoreactive neurons were observed in AD and AD+DS, followed by AD+PD, then PD. The AD+PD brains had less severe AD lesions compared with AD, and PD had relatively few AD lesions. In contrast to neurofibrillary tangles and plaques which showed striking regional variation, the densities of NTP immunoreactive neurons were relatively uniform in different neocortical regions. Elevated levels of NTP immunoreactive expression were detected in PD dementia, but the levels were much lower than in AD or AD+PD (de la Monte & Wands, *J. Neurol. Sci.* 113:152–164 (1992)). The finding of high densities of neurofilament immunoreactive dystrophic dendrites in PD dementia, similar to AD, suggested that AD histopathological lesions may have been evolving at the time of death, and thus account for the modestly elevated levels of NTP in these cases. Specificity of the elevated NTP gene expression in AD was corroborated by the absence of increased NTP immunoreactivity in brains with Huntington's disease or multi-infarct dementia. However, in the vicinity of subacute cerebral infarction in both control and diseased brains, NTP immunoreactivity was strikingly increased in viable appearing neurons, while in the setting of healed infarction, NTP immunoreactive expression was not elevated. Thus, NTP gene expression can be modulated by neuronal injury with attendant reparative or regenerative sprouting.

C. Demonstration of elevated NTP levels in AD brain tissue by a quantitative radioimmunoassay A highly sensitive three-site monoclonal antibody-based immunoradiometric assay (M-IRMA) was developed to measure NTP concentrations in biological fluids and tissue homogenates. The M-IRMA was developed using the Th7, Th9, and Th10 MoAbs to PTP, which are cross-reactive with NTP in tissue sections and brain homogenates. Briefly, the Th7 and Th10 antibodies, bound to polystyrene beads, were used to capture NTP in brain homogenates or biological fluids. The captured antigens were detected using $^{125}$I-labeled Th9 high affinity MoAb. The concentrations of NTP present in the samples were computed from a standard curve generated with different amounts of purified PTP. This highly sensitive assay detected as little as 10 pmol of thread proteins.

Homogenates of fresh frozen brain tissue sampled immediately adjacent to the blocks taken for histological and immunohistochemical staining, were used to measure NTP concentrations. The tissue was homogenized in phosphate buffered saline (0.85% NaCl, 10 mM phosphate, pH 7.4) plus protease inhibitors. The supernatant fractions obtained after centrifugation at 12,000 × g was used to measure NTP concentration by M-IRMA. Note that this gentle extraction procedure excluded membrane bound and insoluble NTP which may have been present in the tissue. However, the Th MoAbs bind to conformational rather than linear epitopes, and immunoreactivity was lost to unpredictable degrees in specimens that had been extracted with denaturing or reducing reagents. Using M-IRMA, significantly high levels of NTP were detected in AD cerebral tissue compared with corresponding regions of intact aged control brains. In addition, the concentrations of NTP in AD+DS and AD+PD were significantly elevated relative to control and PD. In AD, elevated levels of NTP were detected in all regions of cerebral cortex and in subcortical nuclei, and the degree of increased expression was correlated more with the patterns of NTP immunohistochemical staining in neurons than with the distribution of neurofibrillary tangles and plaques (de la Monte & Wands, *J. Neurol. Sci.* 113:152–164 (1992)).

d. Detection of NTP in cerebrospinal fluid

NTP immunoreactivity was also detected in choroid plexus and ependymal epithelial cells, although corresponding mRNA expression has not been observed. NTP was assayed directly in cerebrospinal fluid (CSF) samples using M-IRMA. To determine the molecular mass of NTP present in CSF and demonstrate its distinctiveness from PTP, which is present in high concentrations in blood, CSF samples containing 100 μg of protein were fractionated by SDS-PAGE, and proteins eluted from the gel fractions were assayed for NTP by M-IRMA as described above. Unlike brain tissue in which several different size NTP-related molecules may be expressed, the only species of NTP detected in clear CSF samples had an Mr of ~21 kD. In contrast, hemorrhagic samples contained a dominant 21 kD peak, and another 14 kD peak, probably corresponding to PTP. In several samples of AD CSF or ventricular fluid, 21 kD NTP molecules could also be detected by immunoprecipitation followed by Western blot analysis using monoclonal or polyclonal Th antibodies.

e. Demonstration of elevated levels of NTP in AD CSF

NTP concentrations were measured in paired postmortem samples of clear ventricular fluid (VF) and temporal lobe neocortex using M-IRMA. The concentrations of NTP in postmortem ventricular fluid from patients with histopathologically proven AD were significantly elevated compared with the levels in similar specimens from aged control patients. In addition, the concentrations of NTP measured in ventricular fluid were positively correlated with the levels of NTP in cerebral tissue, such that the mean values were nearly identical. Intact aged control and PD brain and VF samples contained low levels of NTP. As observed in histological sections, in the setting of subacute cerebral infarction or non-specific injury, during an interval when regenerative neuronal sprouting would be expected, the levels of NTP measured in both cerebral tissue and VF were also elevated. However, in specimens from patients with remote cerebral infarcts and multi-infarct dementia, no elevation of NTP was detected in either brain tissue homogenates or VF samples (de la Monte, S.M. et al., *Ann. Neurol.* 32:733–742 (1992)).

f. Detection of elevated levels of NTP early in the course of AD dementia

A large clinically-based study was conducted to determine whether the concentrations of NTP in CSF of patients with early manifestations of AD were significantly elevated compared with neurological disease (PD, Multiple sclerosis-MS) and non-demented control patients (back pain, cervical spondylosis, depression, headache, psychosis). NTP concentrations were measured by M-IRMA, and the assays and data analysis were conducted under code. In patients with clinically diagnosed AD, with confirmed follow-up 6 to 10 years later, the concentrations of NTP were significantly elevated compared with both the non-demented and neurological disease control patients (Table 1) (de la Monte, S. M. et al., Ann. Neurol. 32:733–742 (1992)). Comparison of antemortem early AD CSF levels with postmortem temporal neocortex and ventricular fluid end-stage AD levels demonstrated striking increases in mean NTP concentration with progression of disease, as opposed to no significant change over the same intervals in aged control samples. Moreover, in paired samples from 9 patients with AD, the concentrations of NTP in postmortem brain and CSF were 5- to 50-fold higher than in corresponding antemortem CSF samples obtained approximately 6 years earlier. These findings demonstrated that NTP levels were significantly elevated in CSF of individuals with AD, and that NTP levels in CSF may increase strikingly with progression of dementia and neuronal degeneration. Thus, elevated concentrations of NTP in CSF can serve as an in vivo marker for AD neuronal degeneration.

TABLE 1

Elevated NTP Levels in Antemortem CSF in Early AD Dementia

|  | AD | PD | MS | Control | P-value |
|---|---|---|---|---|---|
| No. of Patients | 84 | 45 | 73 | 73 |  |
| Age (years) | 76 | 61 | 41 | 55 | <0.01 |
| Blessed Score | 15 | 5 | ND | ND | <0.001 |
| CSF NTP (ng/ml) | 4.2 | 1.9 | 1.6 | 1.3 | <0.001 |

EXAMPLE 13

Cloning of the human brain cDNA encoding NTP
a. Strategy for Isolating NTP cDNAs Using probes prepared with a rat PTP cDNA, a single 1.4 kB mRNA transcript was detected in AD and DS brains (de la Monte, S. M. et al., J. Clin. Invest. 86:1004–1013 (1990)). However, low stringency hybridization with either rat or bovine PTP cDNA probes revealed 4 distinct cross-hybridizing NTP transcripts in human brain. To isolate NTP cDNAs, several human brain cDNA libraries were screened using probes derived from the 3' half of the rat PTP cDNA. Clones were selected for further study based upon positive Southern blot analysis with probes derived from the 5' half of rat PTP. In addition to nucleic acid sequence analysis, final clone selection was based upon detection of the appropriate size mRNA transcripts in pancreas and human brain. An incomplete probable NTP cDNA initially isolated from an AD brain library, was then used to re-screen the AD brain, as well as a 17 week human fetal brain library to obtain full-length and other related cDNA clones.
b. Characteristics of the AD7c-NTP cDNA isolated from an AD brain library The AD7C-NTP clone is a 1.39 kB complete CDNA that encodes a protein with a predicted Mr of 39 kDa (SEQ ID NO:120 and 121, nucleotide and amino acid sequence, respectively). The cDNA contains an AUG start codon, 1140 bp of continuous open reading frame, and a 250 bp 3' untranslated segment, followed by an AATAAA poly adenylation signal. One unusual feature of the AD7c-NTP cDNA is that it contains a tandemly repeated head-to-tail dimer of a 570 bp sequence within the coding region. The deduced amino acid sequence of the 570 bp sequence is 45% homologous with human PTP. Importantly, there is conservation of the positions of 5 of the 7 Cys residues, a feature that appears to be characteristic of thread proteins (Lasserre, C. et al., Cancer Res. 52:5089–5095 (1992)). The AD7c-NTP protein contains a hydrophobic leader sequence with a potential cleavage at amino acid residue #15, and multiple Ser and Thr phosphorylation motifs. Correspondingly, several NTP molecules expressed in primitive neuroectodermal tumor cell lines (PNET1 and PNET2), and in SH-Sy5y neuroblastoma cells are phosphorylated by insulin stimulation or by activation protein kinase C (see below). The translated AD7c-NTP protein also has numerous hydrophilic domains.
c. Tissue distribution of AD7c-NTP mRNA by Northern blot analysis Northern blot analysis was performed using 15 µg samples of total RNA extracted from adult human brain, kidney, liver, spleen, gastrointestinal tract (various regions) ovaries, fallopian tubes, uterus, thyroid, lung, skeletal muscle, and pancreas, and from adult rat brain, kidney, liver, spleen, gastrointestinal tract (various regions), testis, thymus, lung, skeletal muscle, and pancreas. Random primer generated [32P]dCTP-labeled DNA probes, prepared with the AD7c-NTP cloned insert as the template, hybridized under highly stringent conditions with RNA from human and rat brain and pancreas. Cross-hybridization signals were not detected in the other organs and tissues. In the pancreas, the AD7c-NTP probes hybridized with 0.9 kB transcripts, corresponding with the size of PTP. In adult human brain, the AD7c-NTP hybridized with 1.4 kB and 0.9 kB mRNA transcripts. In adult rat brain, the AD7c-NTP probes hybridized with 0.8 kB transcripts.
d. Expression of mature and fetal brain forms of AD7c-NTP-related mRNA transcripts Northern blot analysis demonstrated 5 distinct AD7c-NTP-related mRNA transcripts. Two of the mRNA transcripts (3.2 kB and 1.9 kB) were mainly expressed in fetal brain and neoplastic neuronal cells, e.g. primitive neuroectodermal tumors cell lines, while the other three (1.4 kB, 1.2 kB, and 0.8 kB) were primarily expressed in postnatal developing and mature brains. With increasing age, there was a progressive decline in the steady-state levels of all AD7c-NTP-related mRNA transcripts, and a shift toward exclusive, very low-level expression of the 0.8 kB transcript in the adult rat brain. The major decline in postnatal NTP gene expression was between days 1 and 8, coincident with the reduction in development-associated cortical neuritic sprouting.
e. Demonstration of AD7c-NTP mRNA up-regulated expression in AD brains AD7c-NTP mRNA expression was examined in AD and aged control brains by Northern blot analysis. RNA was extracted from matched samples of frontal lobe neocortex (Brodmann Area 11), and 15 µg of total RNA were fractionated. Using random primer generated DNA probes, two AD7c-NTP-related mRNA transcripts, 1.4 kB and 0.9 kB were detected in both AD and control brains. Quantitative assessment of the levels of expression was made by volume densitometric analysis of unsaturated autoradiograms. After correcting for differences in sample loading, based upon corresponding 18s ribosomal RNA hybridization signals (obtained by re-probing the blots with a 30mer corresponding to 18s RNA), it was determined that the steady state levels of both the 0.9 kB and 1.4 kB AD7C-NTP mRNA transcripts were elevated in most of the AD brain samples. In addition, the mean level of AD7c-NTP mRNA in AD brains was two-fold higher than in aged control brains (P<0.01).

f. Cellular localization of AD7c-NTP mRNA expression by in situ hybridization

In situ hybridization was used to demonstrate cellular localization of AD7c-NTP-related mRNA transcripts. Antisense and sense cRNA probes were prepared from linearized AD7c-NTP cDNA template, and purified from polyacrylamide gel. cRNA probes labeled with [$^{32}$P]-UTP were used in Northern blot analysis to demonstrate specificity of hybridization with antisense, and absence of hybridization with sense probes. In situ cRNA probes were labeled with digoxigenin-UTP. Hybridized probes were detected with alkaline phosphatase- or horseradish peroxidase-conjugated anti-digoxigenin antibodies, and BCIP/NBT substrate. AD7c-NTP gene expression was detected in cortical neurons of both AD and control frontal (Brodmann Area 11) and temporal (Area 21) neocortex using antisense cRNA probes. Hybridization signals were not detected in white matter or glial cells, nor in tissue hybridized with sense cRNA probes (negative control).

g. In vitro translation and expression of the AD7c-NTP clone

Sense and antisense RNA transcripts were incorporated into rabbit reticulocyte lysate in vitro translation assays, and the products analyzed by SDS-PAGE. A single 39 kD protein was generated by translation of sense strand cRNAs. SDS-PAGE analysis of AD7c-NTP recombinant fusion proteins generated in a pTrcHis expression vector (InVitrogen) also demonstrated the translated product to be ~39 kD. Western blot analysis of AD7c-NTP recombinant proteins demonstrated positive immunoreactivity with polyclonal antibodies to PTP, under non-reducing conditions.

h. Polyclonal antibodies to AD7c-NTP are immunoreactive with PTP, and polyclonal anti-PTP is immunoreactive with recombinant AD7c-NTP protein Rabbit polyclonal antibodies were generated to the AD7c-NTP-pTrcHis recombinant protein. The immunoglobulin fraction was precipitated with ammonium sulfate and dialyzed against PBS. In a radioimmunoassay, the polyclonal antibodies were specifically immunoreactive with the recombinant AD7c-NTP at greater than a 1:100,000 dilution of serum. Western blot analysis was performed under non-reducing conditions since the antibodies may recognize both conformational and linear epitopes. Both anti-AD7c-NTP and anti-PTP exhibited positive immunoreactivity with recombinant AD7c-NTP protein and purified PTP. However, the intensity of cross-reactivity was comparatively low-level for each antibody.

i. Tissue and cellular distribution of anti-AD7c-NTP immunoreactivity

Western blot analysis demonstrated binding of anti-AD7c-NTP with pancreas and brain. The protein recognized in the rat pancreas was 17 kD, the same as detected with anti-PTP. Several low intensity AD7c-NTP-immunoreactive bands were detected in adult rat brain, but the dominant species was ~39 kD. All other rat organs were negative. The same distribution of immunoreactivity was observed with polyclonal anti-PTP, but with brain, the binding intensity was low-level, and most of the bands detected with the AD7c-NTP antibodies were not observed with the PTP antibodies. Immunocytochemical staining demonstrated positive immunoreactivity in PNET cells of neuronal phenotype, and in neurons, neuropil fibers, and axons of mature human brain. Glial cells were not immunoreactive with anti-AD7c-NTP.

j. AD7c-NTP immunoreactivity in AD brain

Studies using postmortem brain tissue demonstrated more abundant and greater intensities of cortical neuron labeling in AD (N=5) compared with intact aged control (N=5) brains. Studies were conducted to examine the molecular sizes of AD7c-NTP-related proteins expressed in AD and aged control brains by either direct Western blot analysis, and by immunoprecipitation followed by Western blot analysis with the same antibodies. 21 kD, 26 kD, and 39 kD AD7c-NTP-related molecules were found in AD (N=6), control (N=7), and infant Down' syndrome (N=1) brains, but higher levels of the 21 kD NTP protein were found in AD relative to control. Although the same size bands were detected with polyclonal anti-PTP, the sensitivity was low, and the relative intensities of the bands were different. For example, the 21 kD and 39 kD NTP molecules were more clearly detected with the AD7c-NTP antibodies. In addition, these studies demonstrated abnormal size AD7c-NTP-related bands in several AD brains.

k. Characteristics of the large library of MoAbs generated to recombinant AD7c-NTP protein 150 mouse MoAbs were generated to the AD7c-NTP recombinant protein. The hybridoma supernatants were screened by western blot analysis and immunohistochemistry using AD and control brain, and radioimmunoassay of recombinant AD7c-NTP. With another radioimmunoassay, the MoAbs were also screened against PTP. The objectives of these studies were to do the following: 1) select high affinity antibodies that recognize AD7c-NTP-related proteins (NTP), but not PTP; 2) identify antibodies that recognize or bind to neurons in AD brains to a greater extent than in control brains; and 3) determine which antibodies bind to molecules in brain tissue or CSF that are the same size as recombinant AD7c-NTP. These reagents enable specific detection of elevated levels of NTP in brain tissue, and also in CSF. Analysis of 25 representative MoAbs demonstrated several with cross-reactivity between PTP and AD7c-NTP, but most with strong binding only to AD7c-NTP. Western blot analysis confirmed high level binding of all 25 MoAbs with recombinant AD7c-NTP. In addition, 6 antibodies were identified that recognized precisely the same size molecules in brain as detected in the fusion protein, 6 others that recognized slightly high molecular weight molecules in brain, and 10 with low-level or absent binding in brain. The three remaining antibodies recognized completely different size bands in brain compared with AD7c-NTP itself. Immunohistochemical staining studies demonstrated 5 MoAbs with similar high-level binding in AD and control brains, 3 with more intense and widely distributed immunoreactivity in AD brains, 6 with low-level binding in both AD and control brains, and 11 with little or no binding to histological sections of brain. The degree of binding by immunohistochemistry correlated with the findings by Western blot analysis.

l. A radioimmunoassay to measure levels of AD7c-NTP-related proteins in brain tissue and biological fluids (CSF, serum, urine)

A M-IRMA has been developed to specifically measure AD7c-NTP concentrations in brain, CSF, and blood. Empirical studies have been performed with a large matrix of MoAbs linked to a solid phase support to determine which antibodies were suitable for capture of AD7c-NTP antigen in biological fluids. MoAbs were then selected for their high binding capability to recombinant AD7c-NTP bound to a solid phase support after labeling with $^{125}$I. MoAbs #2 and #5, used in the M-IRMA, were selected from a panel of 25 MoAbs because of the following characteristics: 1) the antibodies were highly reactive to recombinant AD7c-NTP and not PTP when bound to a solid phase support; 2) the MoAbs specifically stained neurons in AD brains; 3) the MoAbs reacted with a 42 kD species in cell lysates of AD brain by Western blot analysis; and 4) the MoAbs were of the IgG1 isotype, and therefore suitable for labeling with $^{125}$I. Finally, competitive inhibition experiments were performed to demonstrate that the MoAbs recognized separate and distinct antigenic determinants on AD7c-NTP molecules.

m. Isolation of AD7c-related cDNAs from an AD brain library

In addition to the AD7c-NTP clone, five related but distinct cDNAs (AD12-1, AD16b, AD19-1, AD11D, AD16c) were isolated from the AD brain library. All 5 cDNAs share either an identical or nearly identical 570 bp sequence with the AD7c-NTP clone. Each of the cDNAs has been subcloned into pTrc-His expression vectors for analysis of the corresponding fusion proteins by SDS-PAGE, Western blot, and M-IRMA. Each of these fusion proteins was immunoreactive with polyclonal AD7c-NTP antibodies. Unique DNA and antibody reagents are made to distinguish expression of the corresponding mRNAs and proteins in neuronal cells and brain tissue. The same reagents are used to analyze function and evaluate expression of distinct NTP genes in normal and pathological states.

n. Isolation of AD7c-NTP-related cDNAs from a human fetal brain library

Five AD7c-NTP-related cDNA clones (FB1-3c, FB1-6C1, FB2-3C2, FB2-6C1, FB8-3B2) were isolated from a 17 week human fetal brain library. These cDNAs have been partially characterized, and like the AD clones, they also contain an identical or nearly identical 570 bp sequence as described for AD7c-NTP. The 5 FB cDNAs all hybridized to 3.2 kB and 1.9 kB mRNA transcripts in developing rat brains and PNET cell lines. However, the cDNAs exhibited different degrees (intensities) of hybridization with mature brain, and variability with respect to the number (between 1 and 3) of low molecular weight (0.8–1.2 kB) mRNA transcripts detected in immature brain and PNET cells. Sequence data analysis suggests that each of the five FB clones corresponds with at least one of the cDNAs isolated from the AD brain library.

EXAMPLE 14

The biological functions of NTP with respect to developmental regulation and cell growth in the CNS a. NTP expression is developmentally regulated Studies with human brain tissue suggested that NTP expression was developmentally regulated. Using the Th9 MoAb to PTP, and [$^{35}$S]UTP-labeled cRNA probes generated with the rat PTP cDNA, NTP gene expression was examined in developing and mature rat brains. By in situ hybridization, NTP mRNA expression was detected throughout the CNS at embryonic day 13 (E13). The density of hybridization grains (levels of mRNA expression) increased throughout development and peaked on postnatal day 8 (P8). By P16, NTP mRNA expression was low-level and similar to adult brains. With regard to NTP immunoreactivity, faint widespread labeling of neuropil fibers, and intense focal labeling of ependymal lining cells were observed in E13 brains. Thereafter, was a rostral-to-caudal wave of neuronal perikaryal NTP gene expression, such that olfactory structures were mainly labeled in E15 and E17 brains, while cerebellar cortical neurons were primarily labeled in P8 and P16 brains. Young adult and aged (>15 mos.) rat brains exhibited low, virtually non-detectable levels of NTP immunoreactivity in scattered cerebral cortex neurons.

b. Quantitative assessment of NTP expression in developing rat brain using AD7c-NTP polyclonal antibodies Immunohistochemical staining studies using AD7c-NTP polyclonal antibodies yielded results similar to those obtained with PTP polyclonal antibodies. The greater specificity of AD7c-NTP antibodies for brain permitted Western blot analysis and quantitation of NTP expression. Western blot analysis disclosed 6 different size NTP-related proteins in rat brain: 15 kD, 17 kD, 21 kD, 26 kD, 39 kD, and 42 kD. Densitometric scanning of the autoradiographs revealed progressive declines in the levels of several NTP proteins with increasing age. Importantly, like human brain, the 21 kD NTP molecules were expressed at high levels during development, and at low levels in the mature brain. The same was true for the 17 kD and 39 kD species. In contrast, levels of the 26 kD NTP molecules increased with age, while expression of the 42 kD species did not appear to be developmentally regulated.

c. Aberrantly increased NTP expression in Down syndrome occurs prior to the establishment of AD histopathology and dementia In both control and Down syndrome 19–36 week fetus and infant brains, NTP immunoreactivity was widely distributed in neurons, neuropil fibers, and axons. In control brains, the density of NTP-immunoreactive neurons and the intensity of neuropil fiber labeling reduced substantially within the first decade, generally by 5 or 6 years of age. Thereafter, NTP immunoreactive expression remained low-level in all age groups. Adjacent histological sections were immunostained with a cocktail of MoAbs to neurofilament (SMI31+SMI32+SMI34) to delineate the frequency of AD lesions. None of the control brains had neurofibrillary tangles or dystrophic dendrites, but one elderly control had scattered neurofilament immunoreactive plaques. In Down syndrome, neurofilament immunoreactive superficial cortical dystrophic neurites (dendrites) developed and proliferated during early childhood, probably representing one of the earliest histopathological manifestations of AD neuronal degeneration. Neurofibrillary tangles were first detected between ages 10 and 20 years, while neurofilament-immunoreactive plaques were initially detected in the fourth decade of life.

In developing Down syndrome brains, NTP immunoreactive expression in neuronal perikarya and neuropil fibers increased along with the large-scale proliferation of superficial neurofilament-immunoreactive dystrophic dendrites, and the appearance of neurofibrillary tangles. With increasing age and evolution of AD lesions, NTP expression further increased in Down syndrome. The increased NTP immunoreactivity was not restricted to neurons with neurofibrillary tangles or granuole vacuolar degeneration, nor was it localized in plaques. Increased NTP gene expression in Down syndrome brains begins at least two decades prior to the establishment of clinical and histopathological AD. Thus NTP up-regulated gene expression is an early marker of AD neuronal degeneration, age and development of AD lesions.

d. Demonstration of distinct NTP molecules in developing and mature human brains The molecular sizes of the NTP molecules expressed in brain were determined by SDS-PAGE fractionation of 100 μg samples of protein, followed by radioimmunoassay (M-IRMA) of proteins eluted from gel slices. The results were graphed with respect to distances migrated by simultaneously analyzed molecular weight standards. Regardless of age, the dominant NTP species detected in brain was 21 kDa. In AD, with or without underlying Down syndrome, small 39 kDa and 26 kDa NTP peaks were also detected. In both control and Down syndrome infant brains, a prominent 17 kD NTP peak was also detected.

e. Development of an in vitro model to examine NTP expression during growth and differentiation Of the human primitive neuroectodermal tumor (PNET) cell lines— PNET1, PNET2, and SH-Sy5y—PNET1 and PNET2 were of CNS PNET origin, while SH-Sy5y cells were derived from a neuroblastoma. All primary human PNET brain tumors have been found to express NTP. The 3 PNET cell lines used were demonstrated to have neurofilament, synaptophysin, and GAP-43 immunoreactivities, confirming their neuronal phenotypes. In addition, PNET2 and SH-Sy5y cells undergo neuronal differentiation with neuritic sprouting, increased synaptophysin expression, and decreased vimentin expression following treatment with retinoic acid, insulin, or phorbol esther myristate (PMA). In contrast, the PNET1 cells are highly primitive, and fail to exhibit growth factor mediated cell growth or differentiation.

f. Characterization of NTP expression in PNET cells

In all three PNET cell lines, five different NTP species with Mr's of 39-42 kD, 26 kD, 21 kD, 18 kD, and 15 kD were detected by (1) direct Western blot analysis, (2) metabolic labeling followed by immunoprecipitation, or (3) radioimmunoassay (M-IRMA). NTP gene expression was detected using Th polyclonal or monoclonal antibodies to PTP. Unlike adult human brain where the dominant NTP species detected was 21 kD, in PNET cells, the 39 kD, 18 kD, and 15 kD NTP molecules were most abundant, while the 21 kD and 26 kD were expressed at low or non-detectable levels. Pulse-chase and metabolic labeling studies demonstrated that the 18 kD and 26 kD species were probably derived from other NTP molecules. Additional studies demonstrated phosphorylation of the 39 kD, 26 kD, 21 kD, and 18 kD NTP molecules. Moreover, tyrosyl phosphorylated residues were detected in the 39 kD and 18 kD NTP molecules by Western blot analysis of the immunoprecipitated proteins. Finally, after stimulation with either PMA or insulin, a rapid supershifts in NTP molecular mass from 15 kD to 18 kD with incorporation of $[^{32}P]$ orthophosphate as observed in SH-Sy5y and PNET2 cells. Glycosylation of NTP has not been detected. Therefore, at least some of the NTP molecules are likely to be phosphoproteins.

$^{35}$S-Met-labeled NTP molecules were immunoprecipitated using PTP Th MoAbs. Rapid labeling of the 39 kD, 21 kD, and 15 kD proteins, with subsequent appearance (within 10–30 min) of 26 kD, and 18 kD NTP species occurred. Thus some NTP molecules can be derived rather than synthesized de novo.

g. Insulin modulation of NTP expression

Insulin is an important mediator of growth and differentiation in CNS neurons. Insulin stimulated differentiation of PNET2 cells was associated with rapid (within 10 minutes) but transient increases in the levels of the 39 kD, 18 kD and 15 kD NTP species, followed by sustained increases in synthesis and steady state levels of all five NTP species. In contrast, the failure of insulin to induce differentiation of PNET1 cells was associated with absent insulin modulation of NTP. Analysis of the signal transduction pathways demonstrated that the insulin-induced up-regulation of NTP molecules in PNET2 cells was mediated through phosphorylation of the insulin receptor substrate-1 (IRS-1) and the insulin receptor β subunit (IRβs) itself. In PNET1 cells, the lack of insulin responsiveness was associated with impaired insulin-mediated tyrosyl phosphorylation of IRS-1, but normal insulin receptor phosphorylation. Correspondingly, the insulin-stimulated association between PI3 kinase and phosphorylated IRS-1 was also impaired in PNET1 cells. In essence, impaired insulin-mediated tyrosyl phosphorylation of IRS-1 in PNET1 cells halted activation of the insulin signal transduction cascade, and subsequent events leading to modulated gene (NTP) expression. PNET1 cells lacked insulin responsiveness and failed to phosphorylate IRS-1, but insulin receptor levels and tyrosyl phosphorylation (PY) of the β-subunit were intact. PNET2 cells responded to insulin stimulation with phosphorylation of IRS-1, up-regulation of NTP, and neuronal differentiation. The results were confirmed by absent association between PI3 kinase and IRS-1-PY in PNET1 cells after insulin stimulation.

h. Phorbol esther myristate (PMA) and retinoic acid (RA) modulate NTP expression and neuronal differentiation PMA and RA induced PNET2 and SH-Sy5y cells to differentiate into neurofilament-positive, GAP-43-positive, vimentin-negative cells with fine interconnecting neuritic processes. Following PMA stimulation, there was immediate phosphorylation of the 15 kD NTP species, with a supershift in molecular mass to 18 kD. After 12 hours of PMA or RA stimulation, synthesis of the 21 kD and 26 kD NTP species increased four- to five-fold, followed by intracellular accumulation of these same molecules. At the same time, housekeeping gene expression, e.g. GAPDH, was not affected. PMA and RA treatment also resulted in a shift from the perikarya to neuritic process localization of NTP immunoreactivity. Since the effects of PMA stimulation were mimicked by phosphatidylserine plus diolein treatment, and blocked by inhibitors of protein kinase C, expression of the 21 kD and 26 kD NTP species can be modulated through the protein kinase C cascade.

i. In vitro stimulation studies

Neuritic sprouting and neuronal differentiation were induced in PNET2 and SH-Sy5y cells by insulin, PMA, or RA stimulation. Insulin-mediated neuritic growth was associated with increased expression of the fetal brain and PNET-dominant forms of NTP (15 kD and 18 kD). In contrast, the PMA- and RA-induced neuritic sprouting modulated expression of the 21 kD and 26 kD NTP species, which are primarily expressed in the mature brain, and accumulated in AD brains. Thus, expression of the immature or fetal forms of NTP are regulated by mechanisms and growth factors distinct from those involved in modulating expression of the 21 kD and 26 kD NTP molecules. Therefore, expression of fetal NTP molecules/genes can be mediated through the IRS-1 cascade, whereas expression of adult brain/AD-associated NTP genes can be regulated mainly through protein kinase C pathways.

EXAMPLE 15

AD7c-NTP gene expression in postmortem brain tissue from a large number of patients with AD, other neurodegenerative diseases, e.g. Parkinson's Disease, and no neurological disease (aged controls)

a. Source of tissue

Matched snap-frozen, and adjacent formalin-fixed paraffin-embedded blocks of cerebral tissue from different brain regions (Table 2) is used to analyze AD7c-NTP gene expression. All specimens are obtained from the Alzheimer's Disease Research Center (ADRC) Brain Bank located at the Massachusetts General Hospital (MGH). Additional fresh tissue is continually harvested by the ADRC Brain Bank. The histopathological sections are reviewed for all cases. Routine neuropathological evaluation includes luxol fast blue-hematoxylin and eosin, Bielchowsky silver, and Congo red staining, and ubiquitin and neurofilament immunostaining to detect neurodegenerative lesions in paraffin-embedded sections.

TABLE 2

Postmortem Samples for AD7c-NTP Gene Expression Studies

| Diagnosis | Total Number of Cases | | |
|---|---|---|---|
| | Frozen Tissue* | Paraffin Blocks** | Ventricular Fluid |
| AD | 50 | 50 | 50 |
| PD | 10 | 10 | 5 |
| DLBD | 8 | 10 | 0 |
| Pick's | 4 | 8 | 2 |
| ALS | 0 | 4 | 0 |
| Down + AD | 7 | 8 | 4 |
| Aged control | 50 | 50 | 50 |

| Frozen Tissue Ventricular Fluid Assays | Paraffin Tissue Section Studies |
|---|---|
| RNAse Protection or RT/PCR | In situ hybridization |
| Western blot analysis | Immunohistochemistry |
| M-IRMA | |

*Brodmann Areas: 21, 11, 40, 17; amydgala; midbrain, striatum, cerebellar cortex, s. cord.
**Brodmann Areas: 21, 11, 24, 40, 17; amygdala, hippocampus, midbrain, cerebellum, s. cord.

b. Tissue Processing

Frozen tissue blocks (approximately 2×2×0.5 cm) are divided for RNA and protein extraction. RNA is extracted by the Chomczynski-Sacchi one-step guanidinium isothiocyanate/phenol method (Chomczynski & Sacchi, Anal. Biochem. 162:156–159 (1987)) using a commercially available reagents, e.g. RNAzol or TRIzol. The integrity of RNA is assessed by Northern blot analysis using glyceraldehyde-3-phosphate dehydrogenase (GAPDH) cDNA, and 18s synthetic 30mer (Enoch, T. et al., Mol. Cell. Biol. 6:801–810 (1986)) probes. Completely degraded samples are not used. Protein assays are performed with tissue homogenates prepared in 5 volumes of PBS plus protease inhibitors (Sasaki, Y. et al., J. Biol. Chem. 268:3805–3808 (1993)). The supernatant fractions obtained by centrifugation at 12,000 × g for 30 minutes at 4° C., and pelleted proteins solubilized in 1% SDS-containing buffer are used for Western blot analysis and M-IRMA. Previous studies demonstrated that a substantial portion of thread proteins can be contained in the pellet fractions due to reduced solubility, particularly in AD brains. Protein content is determined by the Lowry (Lowry, O. H. et al., J. Biol. Chem. 193:265–275 (1951)) or BioRad calorimetric assay. Paraffin-embedded histological sections of tissue adjacent to the blocks processed for the quantitative RNA and protein studies, are used for immunohistochemistry and in situ hybridization studies.

c. Western blot analysis

Western blot analysis is employed to determine the size and relative abundance of the AD7c-NTP proteins present in brain homogenates. Polyclonal AD7c-NTP antibodies is utilized in these studies in order to simultaneously detect all NTP species. Both supernatant (soluble) and pellet (insoluble) fractions are analyzed. 100 µg samples of protein is fractionated in Laemmli SDS-PAGE gels, transferred to Imobilon (nylon) or ECL Hybond membranes, and probed for AD7c-NTP expression using rabbit polyclonal antibodies generated to the recombinant fusion protein (Harlow & Lane, Antibodies. A Laboratory Manual, Cold Spring Harbor Laboratory (1988) Cold Spring Harbor, N.Y.). Antibody binding is detected with horseradish peroxidase conjugated goat anti-rabbit IgG, and enhanced chemiluminescence reagents (Amersham). Pre-stained molecular weight standards is included on each gel. In addition, Western blots generated with different amounts (between 0.1 µg and 10 µg) of purified recombinant AD7c-NTP protein in each lane, is probed simultaneously to provide a basis for normalizing data among different experiments. The autoradiograms are subjected to volume densitometric scanning to quantitate the steady-state levels of AD7c-NTP protein expressed.

d. Immunohistochemical Staining

Paraffin sections (Table 2) are de-waxed in xylenes and re-hydrated through graded alcohol solutions. AD7c-NTP immunoreactivity is assessed using rabbit polyclonal antibodies generated to the recombinant fusion protein. Antibody binding is detected by the avidin-biotin horseradish peroxidase complex (ABC) method using the Vectastain-Elite kit according to the manufacturer's protocol. Immunoreactivity is revealed with diaminobenzidine. The sections are counterstained with hematoxylin, dehydrated through graded alcohols, cleared in xylenes, and preserved under coverglass with permount. The sections are processed in large groups, adhering rigidly to the incubation conditions. The results are analyzed under code to determine the presence and distribution of AD7c-NTP immunoreactivity.

e. In situ hybridization

Cellular localization of AD7c-NTP gene expression is assessed by in situ hybridization using paraffin-embedded tissue (Table 2). The sections are prepared and prehybridized. Antisense and sense (negative control) digoxigenin-UTP labeled cRNA probes are generated from AD7c-NTP plasmid linearized with Kpn1 or Xho1, using T7 or SP6 DNA-dependent RNA polymerase, respectively. The probes are gel purified to remove free nucleotides. The sections are hybridized overnight at 50° C. with 200 ng/ml of probe (Lee, M.-E. et al., J. Clin. Invest. 86:141–147 (1990). After extensive washing and RNAse A digestion to destroy single-stranded RNA, hybridized probes are detected with alkaline phosphatase conjugated anti-digoxigenin, and the antibody binding are revealed with a suitable chromogen, e.g. BCIP/NBT. Sections counterstained with hematoxylin and preserved with aqueous mounting medium are examined and photographed by brightfield and darkfield microscopy. Adjacent sections are evaluated for intactness of RNA by performing in situ hybridization with cRNA probes corresponding to GAPDH.

f. RNAse Protection Assay

RNAse protection assays are used to examine levels of AD7c-NTP mRNA expression because, compared with Northern blot analysis, this technique is relatively insensitive to the small degrees of RNA degradation which frequently exist in postmortem tissue. Samples of 5 or 10 µg of total RNA are hybridized with gel purified antisense [$^{32}$P] UTP-labeled cRNA probes (Current Protocols in Molecular Biology. Ausubel et al. Eds., John Wiley & Sons, New York, 1994) corresponding to nucleotides 670 to 910 of the AD7c-NTP cDNA. As a positive control, the same samples are simultaneous hybridized (in the same assay tubes) with identically labeled 316 bp antisense cRNA probes corresponding to exons 5–8 of the GAPDH gene (Sabath, D. et al., Gene 91:185–191 (1990)). After hybridization, single-stranded RNA are digested with RNAse A and RNAse T1 (Current Protocols in Molecular Biology. Ausubel et al. Eds., John Wiley & Sons, New York, 1994, and the protected probe fragments analyzed on denaturing polyacrylamide gels. tRNA and human infant brain RNA are used as negative and positive controls, respectively. Non-saturated autoradiograms are subjected to volume densitometric analysis to quantitate the hybridization signals.

g. Alternative method for examining levels of AD7c-NTP mRNA Expression

Reverse transcription/polymerase chain reaction amplification of RNA has been successfully used to study gene expression. The advantage of RT/PCR over RNAse protection is that multiple genes can be studied simultaneously, utilizing only 1 µg of total RNA as starting material. Low yields of RNA have been problematic in the past, particularly with respect to AD brain tissue. RNAse protection assays are performed on samples with abundant RNA yields, and RT/PCR are performed with all samples. Messenger RNA are reverse transcribed using oligo-dT and random oligonucleotide primers. The cDNAs are amplified with primers that flank the sequences contained between nucleotides 670 and 910 of AD7c-NTP. The results are analyzed using 1–3% Nusieve agarose gels and ethidium bromide staining. In addition, to confirm the authenticity of PCR products, Southern blot analysis is performed using either [$^{32}$P]dATP or [fluorescein]dATP end-labeled oligonucleotide probes corresponding to internal sequences of the amplified DNA segment. The minimum number of PCR cycles required to detect AD7c-NTP is determined to ensure the amplified products do not reach saturation.

h. Construction of a two- or three-site monoclonal antibody based immunoradiometric assay (M-IRMA) to measure AD7c-NTP concentration Two- or three-site forward sandwich M-IRMAs are used to measure AD7c-NTP concentrations. An assay using the #5 and #2 antibodies which specifically recognize NTP (not PTP) exhibits greater degrees of binding to AD compared with aged control brains by immunohistochemical staining. The configuration of the prototype two-site M-IRMA is as follows: the #2 MoAb serves as the capture antibody bound to a solid-phase support (0.25" polystyrene beads). After incubating the coated beads with brain tissue homogenates or CSF, the captured AD7c-NTP proteins are detected with $^{25}$I-labeled #5 MoAb, which serves as a tracer. The radioactivity remaining on the beads after extensive washing is measured in a gamma counter. The signal-to-noise ratios are calculated, and the concentrations of AD7c-NTP in the samples, determined from a linear standard curve constructed with different amounts of recombinant AD7c-NTP protein. Immunoreactivity is measured in 200 µl volumes of diluted tissue extract, CSF, or serum. The lower limit of sensitivity is between 1 and 10 pg per ml of purified recombinant AD7c-NTP protein.

Brain protein extracts corresponding to the supernatant (soluble) and pellet (insoluble) fractions, and samples of postmortem ventricular fluid are assayed in quadruplicate at 1:10, 1:50, and 1:100 dilutions to generate S:N ratios within the linear range of the standard curve. The AD7c-NTP protein concentrations are measured in brain tissue by M-IRMA, using the forward sandwich assay described. Other configurations with one- or two-site MoAb capture are also used.

i. Characterization of additional anti-AD7c-NTP MoAbs

The M-IRMA is optimized in terms of sensitivity and specificity for detecting NTP molecules that accumulate in AD brain tissue. The hybridomas are screened by evaluating the extent of immunoreactive binding in solid phase support immunoassays, Western blot analysis, immunohistochemical staining, as described above with the first 25 AD7c-NTP MoAbs. For the solid phase support immunoassay, 50 ng of recombinant AD7c-NTP protein are bound to polypropylene surfaces in 96-well plates. Hybridoma supernatant are reacted, and antibody binding detected using $^{125}$I-labeled goat anti-mouse IgG. Specificity for AD7c-NTP is assessed by demonstrating absent binding to purified PTP, and significant binding above background levels generated with nonrelevant hybridoma supernatant. Indirect Western blot analysis are performed using recombinant AD7c-NTP protein and human AD brain homogenates, and immunoreactivity is detected with ECL reagents. Western blot analysis permits rapid comparison of the relative sizes of the recombinant protein with the AD7c-NTP-related molecules expressed in brain. Immunohistochemical staining of Brodmann Area 11 in the frontal lobe using neet hybridoma supernatant is performed to demonstrate the distributions and relative levels of AD7c-NTP MoAb immunoreactivity in corresponding sections of AD and control brains. Immunohistochemical screening permits the identification of AD7c-NTP MoAbs with specific immunoreactivity in neurons, and greater degrees of binding in AD compared with aged control brains.

EXAMPLE 16

Use of M-IRMA to compare the levels of AD7c-NTP protein in AD, aged control, and neurological disease control samples of postmortem ventricular fluid and antemortem CSF a. Source of specimens Postmortem ventricular fluid samples from patients with AD, PD, Down syndrome, and normal aging have been obtained from the ADRC-MGH brain bank (Table 2). Approximately 400 clinical cerebrospinal fluid (CSF) samples (Table 3) from patients with AD, PD, multiple sclerosis, non-dementing psychiatric disease (controls), minor neurological ailments, e.g. back pain (controls), or multi-infarct dementia have also been banked. These samples represent discarded clinical material from previously approved studies, or samples obtained for diagnostic purposes. The AD and PD samples were obtained from patients enrolled in the ADRC, and therefore long-term clinical follow-up, including autopsy in many instances, is available. The psychiatric case samples were obtained from patients hospitalized at the Bedford VA Hospital. These samples also represent discarded specimens from previously approved clinical studies, and long-term clinical follow-up data has already been obtained and incorporated into a computerized database.

TABLE 3

Clinical CSF Samples for M-IRMA

| Diagnosis | No. of Cases | Dementia |
|---|---|---|
| AD | 154 | Yes |
| PD | 56 | Yes |
| Multiple Sclerosis | 75 | No |
| Multi-infarct dementia | 5 | Yes |
| Psychiatric | 28 | No |
| Control | 94 | No | b. M-IRMA Assay to measure AD7c-NTP in ventricularfluid and CSF samples

The samples are diluted 1:10, 1:50, and 1:100 in PBS/BSA, and assayed in quadruplicate for AD7c-NTP as described above. Samples yielding results with signal:noise (S:N) ratios that do not fall within the linear range of the standard curve generated with purified recombinant AD7c-NTP protein are re-assayed at higher or lower dilutions as required. Results are expressed with respect to volume and protein concentration.

c. Analysis of the size of AD7c-NTP present in ventricular fluid and CSF

The molecular size of the AD7c-NTP molecules present in CSF or ventricular fluid is determined by Western blot analysis. These studies determine whether the levels of the 21 kD or another NTP species are increased in AD compared with aged control CSF and ventricular fluid specimens. Samples containing 100 μg of protein are fractionated in Laemmli SDS-PAGE gels with molecular weight standards. For comparison with results obtained using polyclonal antibodies, the Western blots are re-probed with the tracer (detection) AD7c-NTP MoAb used in the M-IRMA. Additional planned efforts to generate MoAbs that bind to specific and unique NTP molecules will abrogate the need to perform Western blot analysis, in order to interpret abnormally elevated levels of AD7c-NTP. Complete analysis of samples will be possible with a series of rapid and simple M-IRMAs.

EXAMPLE 17

Analysis of levels of AD7c-NTP in serum of AD

Approximately 100 AD antemortem serum samples, representing discarded specimens from previously approved clinical studies, are available. In addition, approximately 250 samples of serum from normal individuals, obtained from previously approved, unrelated studies are also available. Finally, postmortem serum from patients with confirmed AD has been banked by the ADRC-MGH, and is available. Studies are conducted to determine whether AD7c-NTP molecules are detectable in serum by Western blot analysis. Although some of MoAbs generated to recombinant AD7c-NTP cross-react with PTP, which is abundantly present in serum, the antibodies selected for M-IRMA exhibit no detectable binding to purified PTP at concentrations as high as 1 mg/ml. The objective is to determine whether AD7c-NTP can be measured in serum samples, and whether elevated levels of AD7c-NTP detected in postmortem ventricular fluid, brain tissue, or CSF are detectable in paired serum samples from the same individuals. Another objective is to determine whether the levels of AD7c-NTP are elevated in sera from probable and definite AD patients for whom CSF samples are not available. Sera diluted 1:10, 1:50, 1:100, and 1:250 in PBS/BSA are assayed for AD7c-NTP by M-IRMA.

EXAMPLE 18

Additional AD and fetal brain NTP cDNAs

Data suggest that the NTP molecules expressed in such non-AD related diseases, are 15 kD or 17 kD, rather than 21 kD in size. A family of NTP cDNAs was isolated from AD brain, and 17 week human fetal brain (FB) libraries. Analysis of the nucleic acid sequences indicates clear regions of extreme homology or identity, as well as unique domains in each clone.

Both strands of each clone are sequenced by the dideoxy-nucleotide chain termination method using T7 polymerase and custom oligonucleotide primers, with incorporation of deazo-G analogue nucleotides to help circumvent compression artifacts. The nucleic acid and amino acid sequences are compared with the AD7c-NTP cDNA, and with the published sequences of non-neural thread proteins (PTP and HIP).

mRNA expression of the different NTP cDNAs is examined using RT/PCR technology with primers designed to amplify 200 to 500 bp unique sequences contained within each cDNA. cDNA fragments amplified from plasmid templates are directionally subcloned into pGEM vectors to generate digoxigenin-labeled cRNA probes for in situ hybridization studies. To quickly assess potential function, RT/PCR and in situ hybridizations are conducted on a battery of test samples (Table 4). NTP gene expression is quantitated by Southern blot analysis of PCR products, relative to the levels of simultaneously amplified GAPDH.

TABLE 4

Samples for Surveying Expression of Different NTP Genes

| Mature Brain | Developing Brain | PNET2 and SH-Sy5y cells |
|---|---|---|
| 1. AD (N = 4) | 1. 2nd trimester fetus (N = 2) | 1. overnight serum starved |
| 2. normal aging (N = 4) | 2. 3rd trimester fetus (N = 2) | 2. proliferating |
| 3. Acute stroke + intact tissue (N = 3) | 3. infant (N = 2) | 3. retinoic acid-induced differential |
| 4. Remote stroke + intact tissue (N = 2) | 4. 5 year old (N = 2) | 4. vehicle-treated negative control |
|  | 5. 16 year old (N = 1) |  |

Methods to Examine NTP Gene Expression:

RNA Studies

In situ hybridization
RT-PCR or RNAse Protection
Protein Methods

Immunocytochemistry
Western Blot analysis
Metabolic Labeling/Immunoprecipitation (cell culture studies only)

The PCR amplified cDNA fragments are subcloned into pTrc-His vectors (InVitrogen) to generate recombinant proteins for immunization and analysis of immunoreactivity. The recombinant proteins are purified by metal chelate affinity chromatography. The purified and concentrated (Centricon filter) recombinant fusion proteins are used to generate monoclonal and polyclonal antibodies for examining protein expression in brain and PNET cell lines.

DNA sequence analysis suggests a need to generate polyclonal and MoAbs to 3 or 4 distinct recombinant truncated fusion proteins to distinguish among the different NTP molecules expressed in brain and PNET cell lines. Polyclonal antibodies are generated first and used to study gene expression. Rabbits are immunized with purified AD-NTP or FB-NTP truncated proteins (described above) (Harlow & Lane, *Antibodies. A Laboratory Manual*, Cold Spring Harbor Laboratory (1988) Cold Spring Harbor, N.Y.). Pre-immune serum, and serum obtained after the second boost are assayed for NTP-specific immunoreactivity by Western blot analysis and solid phase immunoassay using different amounts of recombinant protein, and with AD7c-NTP, as well as the other NTP truncated proteins as negative controls. The resulting polyclonal antibodies are used to examine the levels and cellular and tissue distributions of immunoreactivity by Western blot analysis and immunocytochemistry using a battery of testing materials (Table 4).

All publications and patent applications mentioned in this specification are indicative of the level of skill of those in the art to which the invention pertains. All publications and patent applications are herein incorporated by reference to the same extent as if each individual publication or patent application was specifically and individually indicated to be incorporated by reference in their entirety.

What is claimed is:

1. A method of diagnosing the presence of Alzheimer's Disease in a human subject suspected of having Alzheimer's Disease which comprises:
   (a) incubating a biological sample from said subject which is suspected of containing neural thread protein (NTP) having a molecular weight observed by SDS-PAGE of about 8 kDa, about 14 kDa, about 17 kDa, about 21 kDa, about 26 kDa or about 42 kDa, in the presence of at least one antibody that specifically binds said NTP and does not cross-react with pancreatic thread protein; and
   (b) detecting said antibody which is bound in said sample, wherein detection of elevated levels of NTP indicates that said subject has Alzheimer's Disease.

2. The diagnostic method of claim 1, wherein said detection is by immunometric assay.

3. The diagnostic method of claim 2, wherein said immunometric assay is a monoclonal antibody-based immunometric assay.

4. The diagnostic method of claim 1, wherein said method comprises:
   (a) incubating said biological sample with two different monoclonal antibodies specific for NTP, said monoclonal antibodies bound to a solid phase support; and
   (b) detecting NTP bound to said monoclonal antibodies with a third different detectably labeled NTP monoclonal antibody in solution.

5. The diagnostic method of claim 1, wherein said incubating step further includes adding a known quantity of labeled Neural Thread Protein whereby a competitive immunoassay is established.

6. The diagnostic method of claim 1, wherein said detection is by immuno-polymerase chain reaction.

7. A method for detecting the presence of Neural Thread Protein (NTP) having a molecular weight observed by SDS PAGE of about 8 kDa, about 14 kDa, about 17 kDa, about 21 kDa, about 26 kDa or about 42 kDa, in a human subject, said method comprising:
   (a) contacting a biological sample from said human subject that is suspected of containing said NTP with at least one antibody that specifically binds said protein and does not cross-react with pancreatic thread protein; and
   (b) detecting any of said antibody bound to said protein.

8. The method of claim 7, wherein the detecting of any of said antibody bound to said protein is performed by in situ imaging.

9. The method of claim 7, wherein the detecting of any of said antibody bound to said protein is performed by in vitro imaging.

10. The method of claim 7, wherein said antibody is administered to said human subject.

11. The method of claim 7, wherein said NTP has a molecular weight of about 42 kDa.

12. The method of claim 7, wherein said NTP is identical to that encoded by the DNA molecule present in the DH1 E. coli cells that are on deposit at the American Type Culture Collection, Manassas, Va., under accession number 69262.

13. The method of claim 7, wherein the NTP has a molecular weight of about 26 kDa.

14. The method of claim 7, wherein the NTP has a molecular weight of about 21 kDa.

15. The method of claim 7, wherein the NTP has a molecular weight of about 17 kDa.

16. The method of claim 7, wherein the NTP has a molecular weight of about 14 kDa.

17. The method of claim 7, wherein the NTP has a molecular weight of about 8 kDa.

18. A method for detecting the presence of Neural Thread Protein (NTP) identical to that coded for by the DNA molecule present in the DH5 E. coli cells that are on deposit at the American Type Culture Collection, Manassas, Va., under accession number 69257, in a human subject, said method comprising:
   (a) contacting a biological sample from said human subject that is suspected of containing said NTP with at least one antibody that specifically binds said protein and does not cross-react with pancreatic thread protein; and
   (b) detecting any of said antibody bound to said protein.

19. A method for detecting the presence of Neural Thread Protein (NTP) identical to that coded for by the DNA molecule present in the DH5 E. coli cells that are on deposit at the American Type Culture Collection, Manassas, Va., under accession number 69258, in a human subject, said method comprising:
   (a) contacting a biological sample from said human subject that is suspected of containing said NTP with at least one antibody that specifically binds said protein and does not cross-react with pancreatic thread protein; and
   (b) detecting any of said antibody bound to said protein.

20. A method for detecting the presence of Neural Thread Protein (NTP) identical to that coded for by the DNA molecule present in the E. coli cells that are on deposit at the American Type Culture Collection, Manassas, Va., under accession number 69259, in a human subject, said method comprising:
   (a) contacting a biological sample from said human subject that is suspected of containing said NTP with at least one antibody that specifically binds said protein and does not cross-react with pancreatic thread protein; and (b) detecting any of said antibody bound to said protein.

21. A method for detecting the presence of Neural Thread Protein (NTP) identical to that coded for by the DNA molecule present in the DH1 *E. coli* cells that are on deposit at the American Type Culture Collection, Manassas, Va., under accession number 69260, in a human subject, said method comprising:
   (a) contacting a biological sample from said human subject that is suspected of containing said NTP with at least one antibody that specifically binds said protein and does not cross-react with pancreatic thread protein; and
   (b) detecting any of said antibody bound to said protein.

22. A method for detecting the presence of Neural Thread Protein (NTP) identical to that coded for by the DNA molecule present in the *E. coli* cells that are on deposit at the American Type Culture Collection, Manassas, Va., under accession number 69261, in a human subject, said method comprising:
   (a) contacting a biological sample from said human subject that is suspected of containing said NTP with at least one antibody that specifically binds said protein and does not cross-react with pancreatic thread protein; and
   (b) detecting any of said antibody bound to said protein.

23. A method for detecting the presence of Neural Thread Protein (NTP) identical to that coded for by the DNA molecule present in the DH1 *E. coli* cells that are on deposit at the American Type Culture Collection, Manassas, Va., under accession number 69263, in a human subject, said method comprising:
   (a) contacting a biological sample from said human subject that is suspected of containing said NTP with at least one antibody that specifically binds to said protein and does not cross-react with pancreatic thread protein; and
   (b) detecting any of said antibody bound to said protein.

24. A method for detecting the presence of Neural Thread Protein (NTP) identical to that coded for by the DNA molecule present in the DH5 *E. coli* cells that are on deposit at the American Type Culture Collection, Manassas, Va., under accession number 69264, in a human subject, said method comprising:
   (a) contacting a biological sample from said human subject that is suspected of containing said NTP with at least one antibody that specifically binds said protein and does not cross-react with pancreatic thread protein; and
   (b) detecting any of said antibody bound to said protein.

25. A method for detecting the presence of Neural Thread Protein (NTP) identical to that coded for by the DNA molecule present in the DH5 *E. coli* cells that are on deposit at the American Type Culture Collection, Manassas, Va., under accession number 69265, in a human subject, said method comprising:
   (a) contacting a biological sample from said human subject that is suspected of containing said NTP with at least one antibody that specifically binds said protein and does not cross-react with pancreatic thread protein; and
   (b) detecting any of said antibody bound to said protein.

* * * * *